US006333403B1

(12) United States Patent
Tavtigian et al.

(10) Patent No.: US 6,333,403 B1
(45) Date of Patent: Dec. 25, 2001

(54) CHROMOSOME 17P-LINKED PROSTATE CANCER SUSCEPTIBILITY GENE AND A PARALOG AND ORTHOLOGOUS GENES

(75) Inventors: Sean V. Tavtigian; David H. F. Teng, both of Salt Lake City, UT (US); Jacques Simard, St. Augustin de DesMaures; Johanna M. Rommens, Toronto, both of (CA)

(73) Assignees: Myriad Genetics, Inc., Salt Lake City, UT (US); The Hospital for Sick Children (CA)

( * ) Notice: Subject to any disclaimer, the term of this patent is extended or adjusted under 35 U.S.C. 154(b) by 0 days.

(21) Appl. No.: 09/564,805

(22) Filed: May 5, 2000

Related U.S. Application Data

(63) Continuation-in-part of application No. 09/434,382, filed on Nov. 5, 1999
(60) Provisional application No. 60/107,468, filed on Nov. 6, 1998.

(51) Int. Cl.$^7$ .................................................. C07H 21/04
(52) U.S. Cl. .................... 536/23.5; 536/23.1; 536/24.31; 536/24.33; 435/325; 435/320.1; 435/183; 435/6
(58) Field of Search .................................. 536/23.1, 23.5

(56) References Cited

PUBLICATIONS

Vesprini, D, et al, 2001, HPC2 variants and screen–detected prostate cancer, American Journal of Human Genetics, vol. 68, pp. 912–917.*
Rebbeck, TR, et al, 2000, Association of HPC2/ELAC2 genotypes and prostate cancer, American Journal of Human Genetics, vol. 67, pp. 1014–1019.*
Peters, MA, et al, 2001, Prostate cancer: simplicity to complexity, Nature Genetics, vol. 27, pp. 134–135.*
Tavtigian, SV, et al, 2001, A candidate prostate cancer susceptibility gene at chromosome 17p, Nature Genetics, vol. 27, pp. 172–180.*
Borg, A, 2001, Hereditary prostate cancer: a new piece of the puzzle, Nature Medicine, vol. 7, No. 2, pp. 153–155.*
Barbeyron, T. et al. "Arylsulphatase from *Alteromonas carrageenovora*", Microbiology, 1995; 141:2897–2904.
Chanfreau, G. et al. "Essential Yeast Protein with Unexpected Similarity to Subunits of Mammalian Cleavage and Polyadenylation Specificity Factor (CPSF)", Science, Nov. 29, 1996; 274:1511–1514.
Haase, E. et al. "Molecular cloning of SNM1, a yeast gene responsible for a specific step in the repair of cross–linked DNA", *Mol. Gen. Genet.*, 1989; 218:64–71.
Henriques, J.A.P. et al. "Role of PSO genes in the repair of photoinduced interstrand cross–links and photooxidative damage in the DNA of the yeast *Saccharomyces cerevisiae*", *J. Photochem. Photobiol.*, B: Biol. 39, 1997; 185–196.
Jenny, A. et al. "Characterization of Cleavage and Polyadenylation Specificity Factor and Cloning of Its 100–Kilodalton Subunit", *Molecular and Cellular Biology*, Dec. 1994; 14(12):8183–8190.

Jenny, A. et al. "Sequence Similarity Between the 73–Kilodalton Protein of Mammalian CPSF and a Subunit of Yeast Polyadenylation Factor I", *Science*, Nov. 29, 1996; 274:1514–1517.
Meniel, V. et al. "Preferential repair in *Sacharomyces cerevisiae rad* mutants after induction of interstrand cross–links by 8–methoxypsoralen plus UVA", *Mutagenesis*, Nov. 1995; 10(6):543–8.
Niegemann, E. et al. "A single amino acid change in SNM1–encoded protein leads to thermoconditional deficiency for DNA cross–link repair in *Saccharomyces cerevisiae*", Mutation Research, DNA Repair 315, 1994; 275–279.
Richter, D. et al. "Molecular structure of the DNA cross–linked repair gene SNM1 (PSO2) of the yeast *Saccharomyces cerevisiae*", *Mol. Gen. Genet.*, 1992; 231:194–200.
Marra, M. et al. "The WashU–HHMI Mouse EST Project"; GenBank Accession No. AA174437; Feb. 16, 1997; 2 pp.
Marra, M. et al. "The WashU–HHMI Mouse EST Project"; GenBank Accession No. AA518169; Jul. 16, 1997; 2 pp.
Marra, M. et al. "The WashU–HHMI Mouse EST Project"; GenBank Accession No. Al132016; Sep. 14, 1998; 2 pp.
Marra, M. et al. "The WashU–HHMI Mouse EST Project"; GenBank Accession No. AA184645; Feb. 19, 1997; 2 pp.
Marra, M. et al. "The WashU–HHMI Mouse EST Project"; GenBank Accession No. AA563096; Aug. 18, 1997; 2 pp.
Pohl, T.M. et al. GenBank Accession No. Z28304 Y13137; Aug. 11, 1997; 3 pp.

* cited by examiner

*Primary Examiner*—Donna Wortman
*Assistant Examiner*—Stephen L. Rawlings
(74) *Attorney, Agent, or Firm*—Rothwell, Figg, Ernst & Manbeck

(57) ABSTRACT

The present invention relates generally to the field of human genetics. Specifically, the present invention relates to methods and materials used to isolate and detect a human prostate cancer predisposing gene (HPC2), some alleles of which cause susceptibility to cancer, in particular prostate cancer. More specifically, the present invention relates to germline mutations in the HPC2 gene and their use in the diagnosis of predisposition to prostate cancer. The invention also relates to presymptomatic therapy of individuals who carry deleterious alleles of the HPC2 gene. The invention further relates to somatic mutations in the HPC2 gene in human prostate cancer and their use in the diagnosis and prognosis of human prostate cancer. Additionally, the invention relates to somatic mutations in the HPC2 gene in other human cancers and their use in the diagnosis and prognosis of human cancers. The invention also relates to the therapy of human cancers which have a mutation in the HPC2 gene, (including gene therapy, protein replacement therapy, protein mimetics, and inhibitors). The invention further relates to the screening of drugs for cancer therapy. The invention also relates to the screening of the HPC2 gene for mutations, which are useful for diagnosing the predisposition to prostate cancer. In addition, the invention relates to a paralog of human HPC2, the paralog being named ELAC1, and to orthologs of human HPC2, these being mouse Elac2, chimpanzee Elac2 and gorilla Elac2.

1 Claim, 18 Drawing Sheets

```
Hs.HPC2.exon1        cgcgggcgtaggtgaccggcggctttctcagttttggtggagacgggcgc
Hs.HPC2.exon1.pep
Mm.HPC2.exon2        tggcggcgtgaggggtctggctgccttgtcagcctggtgtggtcgggtgc
Mm.HPC2.exon1.pep
                     |---------|---------|---------|---------|---------
                     1        11        21        31        41

Hs.HPC2.exon1        ATGTGGGCGCTTTGCTCGCTGCTGCGGTCCGCGGCCGGACGCACCATGTC
Hs.HPC2.exon1.pep    M--W--A--L--C--S--L--L--R--S--A--A--G--R--T--M--S-
Mm.HPC2.exon2        ATGTGGGCGCTCCGCTCACTGTTGCGTCCCCTTGGCCTGCGCACCATGTC
Mm.HPC2.exon1.pep    M--W--A--L--R--S--L--L--R--P--L--G--L--R--T--M--S-
                     |---------|---------|---------|---------|---------
                     51       61        71        81        91

Hs.HPC2.exon1        GCAGGGACGCACCATATCGCAGGCACCCGCCCGCCGCGAGCGGCCGCGCA
Hs.HPC2.exon1.pep    -Q--G--R--T--I--S--Q--A--P--A--R--R--E--R--P--R--K
Mm.HPC2.exon2        GCAGGGT-----------------TCGGCTCGTCGGCCGCGGCCACCCA
Mm.HPC2.exon1.pep    -Q--G--------------------S--A--R--R--P--R--P--P--K
                     |---------|---------|---------|---------|---------
                     101      111       121       131       141

Hs.HPC2.exon1        AGGACCCGCTGCGGCACCTGCGCACGCGAGAGAAGCGCGGACCGTCGGGG
Hs.HPC2.exon1.pep    --D--P--L--R--H--L--R--T--R--E--K--R--G--P--S--G--
Mm.HPC2.exon2        AAGACCCACTGCGACACCTGCGTACGCGGGAGAAGCGCGGCCCGGGT---
Mm.HPC2.exon1.pep    --D--P--L--R--H--L--R--T--R--E--K--R--G--P--G-----
                     |---------|---------|---------|---------|---------
                     151      161       171       181       191

Hs.HPC2.exon1        TGCTCCGGCGGCCCAAACACCGTGTACCTGCAGGTGGTGGCAGCGGGTAG
Hs.HPC2.exon1.pep    C--S--G--G--P--N--T--V--Y--L--Q--V--V--A--A--G--S-
Mm.HPC2.exon2        ---CCCGGGGGCCCGAACACCGTGTACCTGCAGGTGGTGGCGGCGGGCGG
Mm.HPC2.exon1.pep    ---P--G--G--P--N--T--V--Y--L--Q--V--V--A--A--G--G-
                     |---------|---------|---------|---------|---------
                     201      211       221       231       241

Hs.HPC2.exon1        CCGGGACTCGGGCGCCGCGCTCTACGTCTTCTCCGAGTTCAACCGgtcag
Hs.HPC2.exon1.pep    -R--D--S--G--A--A--L--Y--V--F--S--E--F--N
Mm.HPC2.exon2        CCGGGACGCGGGGGCTGCTCTCTATGTCTTCTCGGAATACAACAGgtcag
Mm.HPC2.exon1.pep    -R--D--A--G--A--A--L--Y--V--F--S--E--Y--N
                     |---------|---------|---------|---------|---------
                     251      261       271       281       291

Hs.HPC2.exon1        tcaacgagccacgccccgtcccgctgggccctcagtgcggcgcagcctct
Hs.HPC2.exon1.pep
Mm.HPC2.exon2        agtgggccgacagccctgggggattggccccagcgccacgtgctcgggag
Mm.HPC2.exon1.pep
                     |---------|---------|---------|---------|---------
                     301      311       321       331       341
```

```
(HSA)ELAC2       674  VRMGK..DATLIHEATLEDGL...........................BEEAVEKTHSTTSQAISVGMRMNAEFTMLNHFSQRYAKVPLF....SPNFSEKVGVAFDHM
(MMU)Elac2       670  VQMGK..DATLIHEATLEDGL...........................BEEAVEKTHSTTSQAINVGMRMNAEPIMLNHFSQRYAKIIPLF....SPDFNEKVGIAFDHM
(CEL)CE16965     699  VEBGK..DADVLVHESTFEDGHEVDMTPKPPKKLAKISSLADAMRKRHSTMGQAVDVGKRMNAKHILTHFSARYPKVPVL...PEYLDKENIGVAMDML
(ATH)gi6850339   717  VEASR..DATLIHEATFEDAL...........................IBEALAKNHSTTKEAIDVGSAANVRIVLTHFSQRYPKIPVID....ESHMENTCIAFDLM
(SCE)YKR079C     708  SLEIGY.NSDLLIHEATLENQL..........................LEDAVKKKKHCTINEAIGVSNKMNARKLILTHFSQRYPKLPQLD.NNIDVMAREFCFAFDSM (HSA)ELAC1       261  GGVKLCFEADLLTHEATLDDAQ...........................MDKAKEHGHSTPQMAATFAKICPRAKRLVLTHFSQRYKPVALAREGOTDGIAELKKQAESVL
(Es_c)elaC       226  LDLAK..GVDVWHEATLDITM.............................EAKANSRGHSSTRQAATLAREAGVGKLIITTHVSSRYDDKGC...QHLLRECRSIFPATELA
(Syn_sp)gi2500943 219  IALAQ..EADLLVHEATFAHQD............................AQLAFDRLHSTSTMAAQVALLANVKQLIMTHFSPRYAPGNPLQLENLLAEAQAIFPNTRLA
(Me_t)gi2622965  215  IKLAE..GAELIHESTLEAGS.............................EDKAABSGHSTAREAAEVARSAGVKRLILTHLSTRYKRT....EVILEARQVFPVTDVA ▽R781
(HSA)ELAC1       751  KVCFGDFPTMPKLIPPLKALFAGDIEBMEERREKRELRQVRAALLSRELAGGLEDGEPQQKRAHTEEPQAKKVRAQ
(MMU)Elac2       747  KVCFGDFPTVPKLIPPLKALFAGDIEEMVERREKRELRIVRAALLTQQ.ADSPEDREPQQKRAHTDEPHSPQSKKESVANTLGARV
(CEL)CE16965     794  RVRFDHLPLVSKLLPIFREVFVAELFELTIKKEQRVLKDKELSEKRGQLKA
(ATH)gi6850339   794  SINMADLHVLPKVLPYFKTLFRDEMVEDEDADDVAMDLKEBAL
(SCE)YKR079C     789  IVDYEKIGEQQRIFPLLNKAFVEEKEBEDVDDVESVQDLEVKLKKHKKN (HSA)ELAC1       344  DLQEVTLAEDFMVISIPIKK
(Es_c)elaC       304  NDF..TVFNV
(Syn_sp)gi2500943 300  RDF.LTVEIPRRTADPAIAMSTPQASPA
(Me_t)gi2622965  291  DDL.MTVEVKAYDSSPDS
```

FIG. 6B-2

1920s - 1950s CASES VS. DIVERGENT CONTROLS

OBSERVED

| | CASES | CONTROLS | | |
|---|---|---|---|---|
| 00, 01, 02 | 372 | 139 | | |
| 11, 12, 22 | 57 (13.3%) | 9 (6.1%) | ODDS RATIO | 2.4 |
| | | | P-VALUE | 0.026 |
| 00, 01, 11 | 387 | 143 | | |
| 02, 12, 22 | 42 (9.8%) | 5 (3.4%) | ODDS RATIO | 3.1 |
| | | | P-VALUE | 0.022 |
| 00, 01 | 347 | 137 | | |
| 02, 11, 12, 22 | 82 (19.1%) | 11 (7.4%) | ODDS RATIO | 2.9 |
| | | | P-VALUE | 0.001 |

1920s - 1950s CASES VS. PEDIGREE UNAFFECTEDS

| | CASES | CONTROLS | | |
|---|---|---|---|---|
| 00, 01, 02 | 372 | 2151 | | |
| 11, 12, 22 | 57 (13.3%) | 220 (9.3%) | ODDS RATIO | 1.5 |
| | | | P-VALUE | 0.013 |
| 00, 01, 02 | 372 | 2151 | | |
| 11 | 40 (9.3%) | 170 (7.2%) | ODDS RATIO 11 | 1.4 |
| 12, 22 | 17 (4.0%) | 50 (2.1%) | ODDS RATIO 12,22 | 2.0 |
| | | | P-VALUE | 0.017 |
| | | | TREND STATISTIC | 8.09 |
| | | | P-VALUE | 0.004 |

|  | (HSA) ELAC2 | | | (MMU) Elac2 | | | (CEL) CE16965 | | | (ATH) gi6850339 | | | (SCE) YKR079C | | |
|---|---|---|---|---|---|---|---|---|---|---|---|---|---|---|---|
|  | %ID | %SIM | %GAP | %ID | %SIM | %GAP | %ID | %SIM | %GAP | %ID | %SIM | %GAP | %ID | %SIM | %GAP |
| (HSA) ELAC2 | 100.0 | 100.0 | 0.0 | – | – | – | – | – | – | – | – | – | – | – | – |
| (MMU) Elac2 | 81.6 | 88.0 | 1.8 | 100.0 | 100.0 | 0.0 | – | – | – | – | – | – | – | – | – |
| (CEL) CE16965 | 24.2 | 43.0 | 14.0 | 24.6 | 44.0 | 15.7 | 100.0 | 100.0 | 0.0 | – | – | – | – | – | – |
| (ATH) gi6850339 | 25.6 | 47.0 | 23.5 | 25.4 | 46.0 | 25.0 | 21.0 | 44.0 | 21.1 | 100.0 | 100.0 | 0.0 | – | – | – |
| (SCE) YKR079C | 21.8 | 41.0 | 20.8 | 21.7 | 43.0 | 21.4 | 18.2 | 43.0 | 21.4 | 21.8 | 41.0 | 16.3 | 100.0 | 100.0 | 0.0 |

CHROMOSOME 17P-LINKED PROSTATE CANCER SUSCEPTIBILITY GENE AND A PARALOG AND ORTHOLOGOUS GENES

CROSS REFERENCE TO RELATED APPLICATION

This application is a continuation-in-part of Ser. No. 09/434,382, filed Nov. 5, 1999 and is related to U.S. provisional patent application Ser. No. 60/107,468, filed Nov. 6, 1998, which are incorporated herein by reference.

This application was made with Government support under Grant Nos. CA62154 and CA64477 from the National Institutes of Health. The United States Government has certain rights in this invention.

BACKGROUND OF THE INVENTION

The publications and other materials used herein to illuminate the background of the invention, and in particular, cases to provide additional details respecting the practice, are incorporated herein by reference, and for convenience, are referenced by author and date in the following text and respectively grouped in the appended List of References.

The genetics of cancer is complicated, involving the function of three loosely defined classes of genes: (1) dominant, positive regulators of the transformed state (oncogenes); (2) recessive, negative regulators of the transformed state (tumor suppressor genes); and (3) genes that modify risk without playing a direct role in the biology of transformed cells (risk modifiers).

Specific germline alleles of certain oncogenes and tumor suppressor genes are causally associated with predisposition to cancer. This set of genes is referred to as tumor predisposition genes. Some of the tumor predisposition genes which have been cloned and characterized influence susceptibility to: 1) Retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); 8) Multiple endocrine neoplasia type 2A (MEN2A); 9) Melanoma (CDKN2 and CDK4); 10) Breast and ovarian cancer (BRCA1 and BRCA2); 11) Cowden disease (MMAC1); 12) Multiple endocrine neoplasia (MEN1); 13) Nevoid basal cell carcinoma syndrome (PTC); 14) Tuberous sclerosis 2 (TSC2); 15) Xeroderma pigtpentosum (genes involved in nucleotide excision repair); 16) Hereditary nonpolyposis colorectal cancer (genes involved in mismatch repair).

Specific germline alleles of certain risk modifier genes are also associated with predisposition to cancer, but the increased risk is sometimes only clearly expressed when it is combined with certain environmental, dietary, or other factors. Alcohol dehydrogenase CADH) oxidizes ethanol to acetaldehyde, a chemical which is both mutagenic and carcinogenic in lab animals. The enzyme encoded by the $ADH3^1$ allele oxidizes ethanol relatively quickly, whereas the enzyme encoded by the $ADH3^2$ allele oxidizes ethanol more slowly. $ADH3^1$ homozygotes presumably have a high capacity for synthesis of acetaldehyde; those who also drink heavily are at increased risk for oral cavity, esophageal, and (in women) breast cancer relative to $ADH3^2$ homozygotes who drink equally heavily (Harty et al., 1997; Hori et al., 1997; Shields, 1997). The acetyltransferases encoded by N-acetyltransferase 1 (NAT1) and N-acetyltransferase 2 (NAT2) catalyze the acetylation of numerous xenobiotics including the aromatic amine carcinogens derived from smoking tobacco products. Individuals who are homozygous for slow acetylating forms of NAT2 who are also heavy smokers are at greater risk for lung, bladder, and (in females) breast cancer than individuals who smoke equally heavily but are homozygous for fast acetylating forms of NAT2 (Shields, 1997; 13ouchardy et al., 1998).

The risk of hormone related cancers such as breast and prostate cancer may be modulated by allelic variants in enzymes that play a role in estrogen or androgen metabolism, or variants in proteins that mediate the biological effects of estrogens or androgens. A polymoiphic CAG repeat in the human androgen receptor gene encodes a polymorphic polyglutamine tract near the amino-terminus of the protein. The length of the polyglutamine tract is inversely correlated with the transcriptional activation activity of the androgen receptor and thus one aspect of the biological response to androgens. Men whose androgen receptor contains a relatively short polyglutamine tract are at higher risk for prostate cancer, especially high stage/high histologic grade prostate cancer, than men whose androgen receptor contains a relatively long polyglutamine tract (Giovannucci et al., 1997).

Prostate cancer is the most common cancer in men in many western countries, and the second leading cause of cancer deaths in men. It accounts for more than 40,000 deaths in the US annually. The number of deaths is likely to continue rising over the next 10 to 15 years. In the US, prostate cancer is estimated to cost $1.5 billion per year in direct medical expenses. In addition to the burden of suffering, it is a major public-health issue. Numerous studies have provided evidence for familial clustering of prostate cancer, indicating that family history is a major risk factor for this disease (Cannon et al., 1982; Steinberg et al., 1990; Carter et al, 1993).

Prostate cancer has long been recognized to be, in part, a familial disease with a genetic component (Woolf, 1960a; Cannon et al., 1982; Carter et al., 1992). Numerous investigators have examined the evidence for genetic inheritance and concluded that the data are most consistent with dominant inheritance for a major susceptibility locus or loci. Woolf (1960b), described a relative risk of 3.0 of developing prostate cancer among first-degree relatives of prostate cancer cases in Utah using death certificate data. Relative risks ranging from 3 to 11 for first-degree relatives of prostate cancer cases have been reported (Cannon et al., 1 982; Woolf, 1960b; Fincham et al., 1990; Meikle et al., 1985; Krain, 1974; Morganti et al., 1956; Goldgar et al., 1994). Carter et al. (1992) performed segregation analysis on families ascertained through a single prostate cancer proband. The analysis suggested Mendelian inheritance in a subset of families through autosomal dominant inheritance of a rare (q=0.003), high-risk allele with estimated cumulative risk of prostate cancer for carriers of 88% by age 85. Inherited prostate cancer susceptibility accounted for a significant proportion of early-onset disease, and overall was responsible for 9% of prostate occurrence by age 85. Recent results demonstrate that at least four loci exist which convey susceptibility to prostate cancer as well as other cancers. These loci are HPC1 on chromosome 1q24, (Smith et al., 1996), HPCX on chromosome Xq27–28 (Xu et al., 1998), PCAP at 1q42 (Berthon et al., 1998) and CAPB at 1p36 (Gibbs et al., 1999a). All four suggestions of linkage for prostate cancer predisposition were the result of hints arising from genome-wide searches. Although only the HPC1 linkage has so far been confirmed (Cooney et al., 1997; Neuhausen et al., 1999; Xu and ICPCG, 2000), it is becoming clear that a large number of genes contribute to familial prostate cancer. It also seems clear, both from published hereditary prostate cancer linkage studies and from genotyping of our family resource at the above mentioned loci, that no single predisposition locus mapped to date is by itself responsible for a large portion of familial prostate cancer (Neuhausen et al., 1999; Eeles et al., 1998; Gibbs et al., 1999b; Lange et al., 1999; Berry et al., 2000; Suarez et al., 2000: Goode et al., 2000).

A comparison to the cloning of, and risk profile attributed to, breast cancer susceptibility genes provides an instructive example. The profusion of proposed prostate loci, coupled with minimal confirmation or refined localization following initial publication of these linkages, contrasts sharply with studies of the breast and ovarian cancer susceptibility genes BRCA1 and BRCA2. Linkage to BRCA1 was first published in 1990 (Hall et al., 1990); groups competing to identify this gene moved swiftly from confirmatory studies through efforts to refine the localization to the gene identification in 1994 (Miki et al., 1994). With expanded genomics resources, the time from linkage (Wooster et al., 1994) to complete cloning (Wooster et al., 1995; Tavtigian et al., 1996) of BRCA2 was only slightly more than 1 year. Ongoing mutation screening and careful modeling of age specific and familial risks indicate that these two genes account for virtually all extended breast and ovarian cancer families (Antoniou et al., 2000) and the majority of breast cancer families with more than five cases, especially those that include an early-onset component (Ford et al., 1998).

Even so, a fraction of familial breast cancer risk is manifest in smaller family clusters with average age at diagnosis. While BRCA1 and BRCA2 only account for a portion of this component of breast cancer risk (Peto et al., 1999), there are no published and confirmed linkages based on these types of pedigrees to date. Standard genetic analysis appears to be limited by the problems of low penetrance and genetic complexity. It is possible that analysis of genetic predisposition in families with excess prostate cancer also reflects these issues. As absence of distinction by age at diagnosis/onset would also be consistent with the influence of multiple susceptibility genes harboring only moderate risk sequence variants, one might therefore ask what relative contribution low frequency high risk variants analogous to mutations in BRCA1/2, versus higher frequency, moderate risk sequence variants, make to the population risk of prostate cancer.

Indeed, evidence that moderate risk sequence variants in a number of specific genes contribute to prostate cancer susceptibility is beginning to accumulate. For example, a polymorphic CAG repeat within the androgen receptor open reading frame encoding a variable length polyglutamine tract shows an inverse relationship between repeat length and the transcriptional transactivation activity of the receptor (Chamberlain et al., 1994; Kazemi-Esfarjani et al., 1995). Accordingly, a series of studies show an association between shorter androgen receptor CAG repeat length and prostate cancer risk (Giovannucci et al., 1997; Stanford et al., 1997), although it is not entirely clear whether the association is with diagnosis of prostate cancer or severity of disease (Bratt et al., 1999). Second, a number of missense variants have been observed in the steroid 5α-reductase type II gene (SRD5A2), responsible for conversion of testosterone to the more active androgen dihydrotestosterone in the prostate (Makridakis et al., 1997). One of these variants, Ala 49 Thr, has been reported to increase the catalytic activity of the enzyme, and is associated with increased risk of advanced prostate cancer (Makridakis et al., 1999; Jaffe et al., 2000). Finally, several groups have reported an excess of prostate cancer in large BRCA2 pedigrees (Sigurdsson et al., 1997; Breast Cancer Linkage Consortium, 1999), though the relative risk that these mutations confer for prostate cancer is considerably lower than for breast cancer. Further, these effects may be variant specific as association has not been confirmed among men who carry the Ashkenazi BRCA2 founder mutation 6174delT (Wilkens et al., 1999; Nastiuk et al., 1999; Hubert et al., 1999). If these and similar sequence variants play a role in a significant fraction of prostate cancer, then models of the genetic component of familial prostate cancer may need to incorporate both linkage evidence for major susceptibility loci and association evidence for moderate risk sequence variants.

The Utah population provides a unique resource for examining the genetic basis of disease. Extended high risk pedigrees containing many cases can be ascertained as units instead of by expansion from individual probands. While these pedigrees are an extremely powerful resource for linkage studies, they also allow analysis of segregation of moderate risk sequence variants through multiple generations of both cases and their unaffected relatives.

Detection of genetic linkage for prostate cancer susceptibility to a defined segment of a chromosome requires that DNA sequence variants within that chromosomal segment confer the cancer susceptibility. This is usually taken to mean that the causal sequence variant(s) will either alter the expression of one or more linked genes or will alter the function of one of the linked genes. However, detection of the genetic linkage does not necessarily provide evidence for what class of gene (i.e. tumor suppressor, oncogene, or risk modifier) is affected by the causal sequence variant(s).

Most strategies for proceeding from genetic linkage of prostate cancer susceptibility to chromosome 17p to identification of the 17p-linked prostate cancer predisposing gene (HPC2) require precise genetic localization studies to define a discrete segment of the chromosome within which the causal sequence variant(s) must map. Gene identification projects based on precise genetic localization are called positional cloning projects. The general strategy in positional cloning is to find all of the genes located within the genetically defined interval, identify sequence variants in and around those genes, and then determine which of those sequence variants either alter the expression or the function of one (or more) of the associated genes. Segregation of such sequence variants with the disease in the linked kindreds must also be demonstrated. We have executed a positional cloning project in the HPC2 region of chromosome 17p and found a gene, herein named HPC2, germline mutations which predisposes individuals to prostate cancer.

SUMMARY OF THE INVENTION

The present invention relates generally to the field of human genetics. Specifically, the present invention relates to methods and materials used to isolate and detect a human prostate cancer predisposing gene (HPC2) some alleles of which cause susceptibility to cancer, in particular prostate cancer. More specifically, the present invention relates to germline mutations in the HPC2 gene and their use in the diagnosis of predisposition to prostate cancer. The invention also relates to presymptomatic therapy of individuals who carry deleterious alleles of the HPC2 gene. The invention further relates to somatic mutations in the HPC2 gene in human prostate cancer and their use in the diagnosis and prognosis of human prostate cancer. Additionally, the invention relates to somatic mutations in the HPC2 gene in other human cancers and their use in the diagnosis and prognosis of human cancers. The invention also relates to the therapy of human cancers which have a mutation in the HPC2 gene, including gene therapy protein replacement therapy, protein mimetics, and inhibitors. The invention further relates to the screening of drugs for cancer therapy. The invention also relates to the screening of the HPC2 gene for mutations, which are useful for diagnosing the predisposition to prostate cancer. The HPC2 gene is useful as a marker for the HPC2 locus and as a marker for prostate cancer. Finally, a paralog of HPC2 as well as orthologs of HPC2 in mouse, chimpanzee and gorilla have been isolated and characterized.

BRIEF DESCRIPTION OF THE DRAWINGS

FIG. 4 is an alignment of the sequence of exon 1 of the human HPC2 gene with exon 1 of the mouse HPC2 gene. The figure also shows an alignment of the peptide sequence encoded by exon 1 of the human HPC2 gene with the peptide sequence encoded by exon 1 of the mouse HPC2 gene. The human DNA sequence is SEQ ID NO:210; the human amino acid sequence is SEQ ID NO:211; the mouse DNA sequence is SEQ ID NO:212 and the mouse amino acid sequence is SEQ ID NO:213.

FIG. 5A shows kindred 4102. The dark bar denotes the 1641 insG bearing haplotype. Individuals 061 and 107 carry part of the frameshift haplotype, but neither carries the frameshift due to recombination events. There are no data to distinguish which of the founders, individuals 050 and 051, carried the frameshift. The second shared haplotype in kindred 4102 is denoted by a light gray bar. Again, there are no data to distinguish which of the founders, individuals 005 and 006, carried the haplotype. FIG. 5B shows kindred 4289. Individuals 064, 066, 067, 068 and 072 share a recombinant chromosome that carries the His 781 missense change.

FIGS. 6A–B are a multiple protein alignment of ELAC1/2 family members. ELAC2 family members were selected from human (HSA), mouse (MMU), C. elegans (CEL), A. tholiana (ATH) and S. cerevisiae (SCE). The A. thaliana genome encodes more than one family member; gi6850339 was selected because it aligned with fewer gaps. ELAC1 family members were selected from human, *E. coli* (Ec_c), the blue-green algae Synechocy stis (Syn) and the archaebacterium *Methanobacterium thermoautotrophicum* (Me_ t). Alignments were based on BLASTp searches and then optimized by inspection. The positions of Ser 217, Ala 541 and Arg 781 in human ELAC2 are marked by down arrows. The sequences shown in FIGS. 6A–B are: human ELAC2 is SEQ ID NO:2, mouse Elac2 is SEQ ID NO:222, C. elegans CE16965 is SEQ ID NO:227, *A. thaliana* gi 6850339 is SEQ ID NO:228, *S. cerevisiae* YKR079C is SEQ ID NO:229, human ELAC1 is SEQ ID NO:220, *E. coli* claC is SEQ ID NO:230, Synechocystis gi2500943 is SEQ ID NO:231, and *Methanobacterium thermoautotrophicum* gi2622965 is SEQ ID NO:232.

FIG. 8 shows the results of association tests.

FIG. 9 shows a multiple protein alignment demonstrating conservation of sequence elements between ELAC2, PSO2 and CPSF73 families. The alignments shown for segments of PSO2 and CPSF73 family members were taken from more extensive alignments that contain family members from a larger set of species, analogous to the ELAC1/2 alignments of FIGS. 6A–B. The seven 1 lis or Cys residues that are conserved across two or more of the gene families are marked by down arrows. The position of Ala 541 in human ELAC2 is also marked by a down arrow. The sequences shown in FIG. 9 are partial sequences of the following: human CPSF73 is SEQ ID NO:233, *A. thaliana* gi6751699 is SEQ ID NO:234, *S. cerevisiae* YSH1 is SEQ ID NO:235, Synechocystis gi2496795 is SEQ ID NO:236, *Methanobacterium thermoautotrophicum* gi2622312 is SEQ ID NO:237, human ha3611 is SEQ ID NO:238, *A. thaliana* gi2979557 is SEQ ID NO:239, *S. cerevisiae* PSO2 is SEQ ID NO:240, human ELAC2 is SEQ ID NO:2, *A. thaliana* gi6850339 is SEQ ID NO:228, and *S. cerevisiae* YKR079C is SEQ ID NO:229.

FIG. 10 shows a similarity comparison among the ELAC2 family members aligned in FIGS. 6A–B.

FIGS. 11A–B show Multiple Tissue Northern (MTN) filters (Clontech) probed with the human ELAC1 ORF. Note that a 3 kb ELAC1 transcript is detected in all tissues. FIGS. 11C–D show the same filters probed with human β-actin as a loading control.

Figure 12:
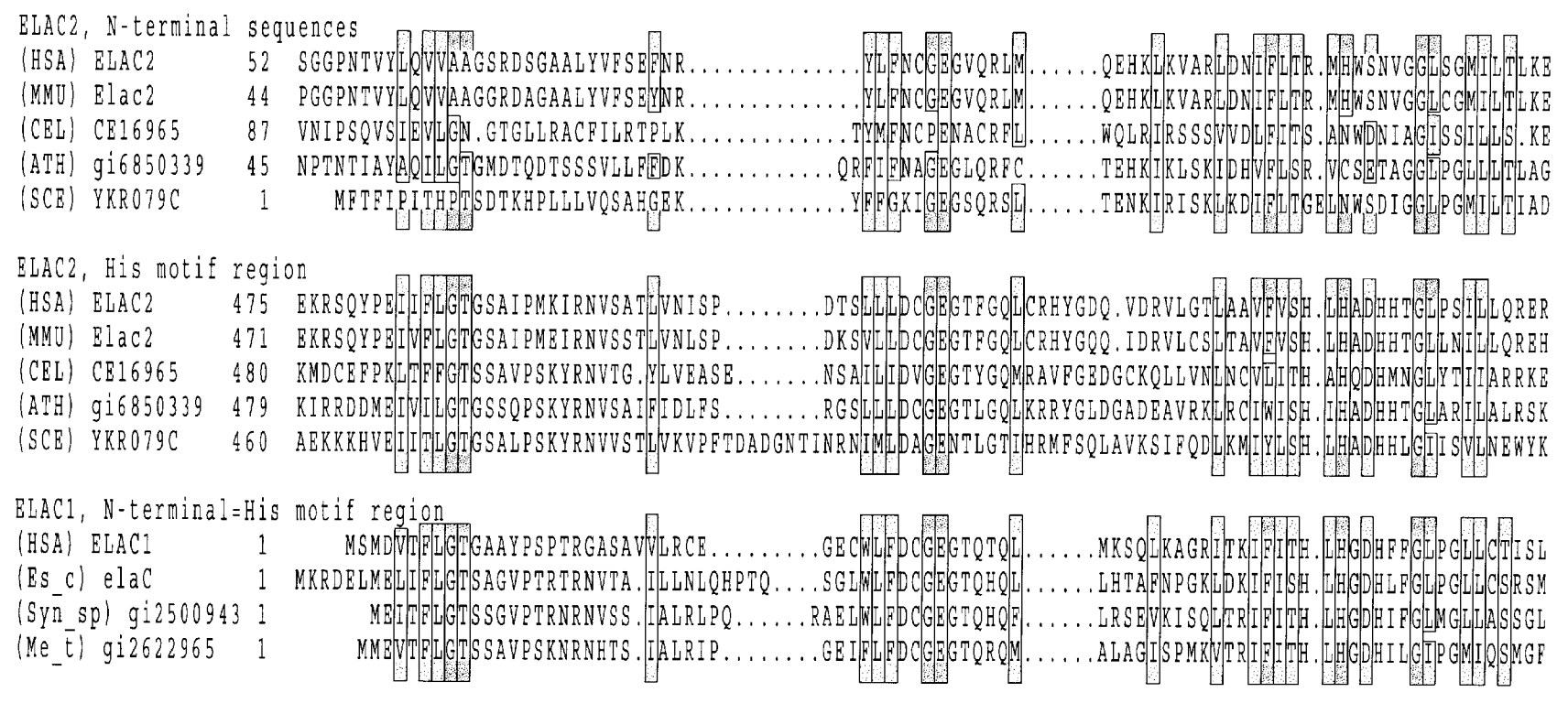

FIG. 12 shows a multiple protein alignment demonstrating similarity between an N-terminal segment of the ELAC2 family members and the sequence context of the histidine motif shared by ELAC1 and ELAC2 family members. Species abbreviations are as in FIGS. 6A–B. The sequences shown in FIG. 12 are partial sequences of the following: human ELAC2 is SEQ ID NO:2, mouse Elac2 is SEQ ID NO:222, C. elegans CE16965 is SEQ ID NO:227, *A. thaliana* gi6850339 is SEQ ID NO:228, *S. cerevisiae* YKR079C is SEQ ID NO:229, human ELAC1 is SEQ ID NO:220, *E. coli* elaC is SEQ ID NO:230, Synechocystis gi2500943 is SEQ ID NO:231, and *Methanobacterium thermoautotrophicum* gi2622965 is SEQ ID NO:232.

BRIEF DESCRIPTION OF THE TABLES

Figure 1:
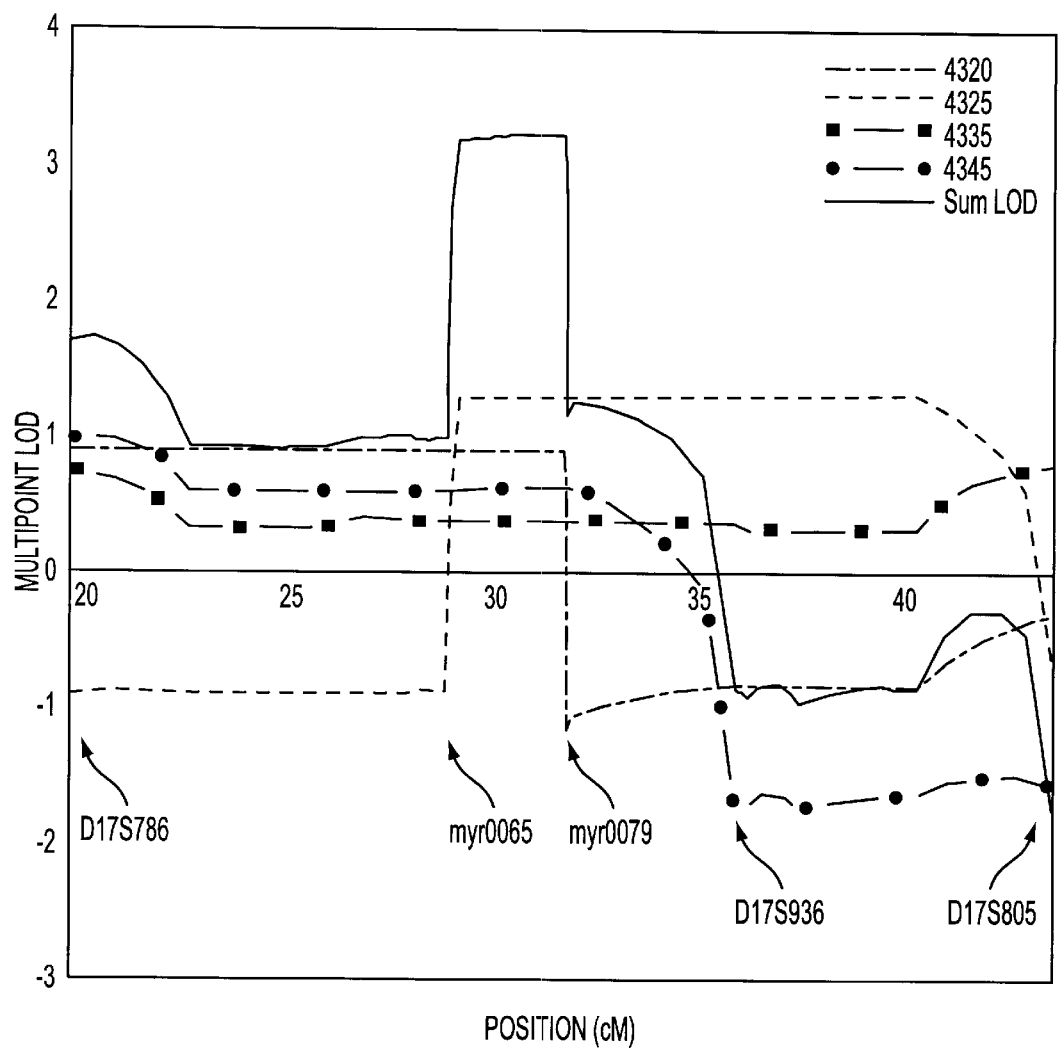
FIG. 1 is a multipoint linkage analysis of 4 kindreds that show suggestive evidence for linkage to the HPC2 prostate cancer susceptibility locus relative to chromosome 17p markers.

Table 1 is a compilation of 2-point LOD scores for markers in the HPC2 region.

Table 2A lists the family resource used to detect linkage of HPC2 to chromosome 17p.

Table 2B lists two-point LOD scores using the Utah age-specific model.

Table 3 is a summary of resource genotyped for the association tests.

Table 4 is a list of the accession numbers of human EST sequences used to assemble a tentative, partial cDNA sequence of the human HPC2 gene.

Table 5 is a list of the primers used for obtaining 5' RACE products that contained the start codon and part of the 5' UTR of the human HPC2 gene, primers used to prepare a full length human HPC2 expression construct, and primers used to check the sequence of that construct.

Table 6 is a list of the accession numbers of mouse EST sequences used to assemble a tentative, partial cDNA sequence of the mouse HPC2 gene.

Table 7 is a list of the primers used for obtaining 5' RACE products that contained the start codon and part of the 5' UTR of the mouse HPC2 gene, primers used to prepare a full length mouse HPC2 expression construct, and primers used to check the sequence of that construct.

Table 8 is a list of the primers used to mutation screen the human HPC2 gene from genomic DNA.

Table 9 is a summary of germline sequence variants of the human HPC2 gene.

Table 10 is a list of the allele frequencies of HPC2.

SUMMARY OF SEQUENCE LISTING

SEQ ID NO:1 is the nucleotide sequence for the human HPC2 cDNA from the start codon through the stop codon.

SEQ ID NO:2 is the amino acid sequence for the human HPC2 protein.

SEQ ID NO:3 is the nucleotide sequence for the human HPC2 cDNA from 50 base pairs before the start codon through the end of the 3' UTR.

SEQ ID NO:4 to SEQ ID NO:27 are the sequences of exon 1 to exon 24 of the human HPC2 gene.

SEQ ID NO:28 is the genomic sequence of the human HPC2 gene.

SEQ ID NOs:29–190 are nucleotide sequences of primers used to identify the human and/or mouse HPC2 genes or to screen for mutations.

SEQ ID NOs:191–209 are nucleotide sequences of the HPC2 around and including various sequence variants.

SEQ ID NO:210 is the nucleotide sequence of human HPC2 exon 1 and SEQ ID NO:211 is the corresponding amino acid sequence as shown in FIG. 4.

SEQ ID NO:212 is nucleotide sequence of mouse HPC2 exon 1 and SEQ ID NO:213 is the corresponding amino acid sequence as shown in FIG. 4.

SEQ ID NO:214 is a histidine containing motif found in HPC2/ELA2 and ELAC1.

SEQ ID NO:215 is exon 1 of ELAC1.

SEQ ID NO:216 is exon 2 of ELAC1 plus surrounding genomic sequence.

SEQ ID NO:217 is exon 3 of ELAC1 plus surrounding genomic sequence.

SEQ ID NO:218 is exon 4 of ELAC1 plus surrounding genomic sequence.

SEQ ID NO:219 is the cDNA for ELAC1 and SEQ ID NO:220 is the amino acid sequence for ELAC1.

SEQ ID NO:221 is the cDNA for mouse ELAC2 and SEQ ID NO:222 is the amino acid sequence for mouse ELAC2.

SEQ ID NO:223 is the cDNA for chimpanzee ELAC2 and SEQ ID NO:224 is the amino acid sequence for chimpanzee ELAC2.

SEQ ID NO:225 is the cDNA for gorilla ELAC2 and SEQ ID NO:226 is the amino acid sequence for gorilla ELAC2.

Figure 6A-1:
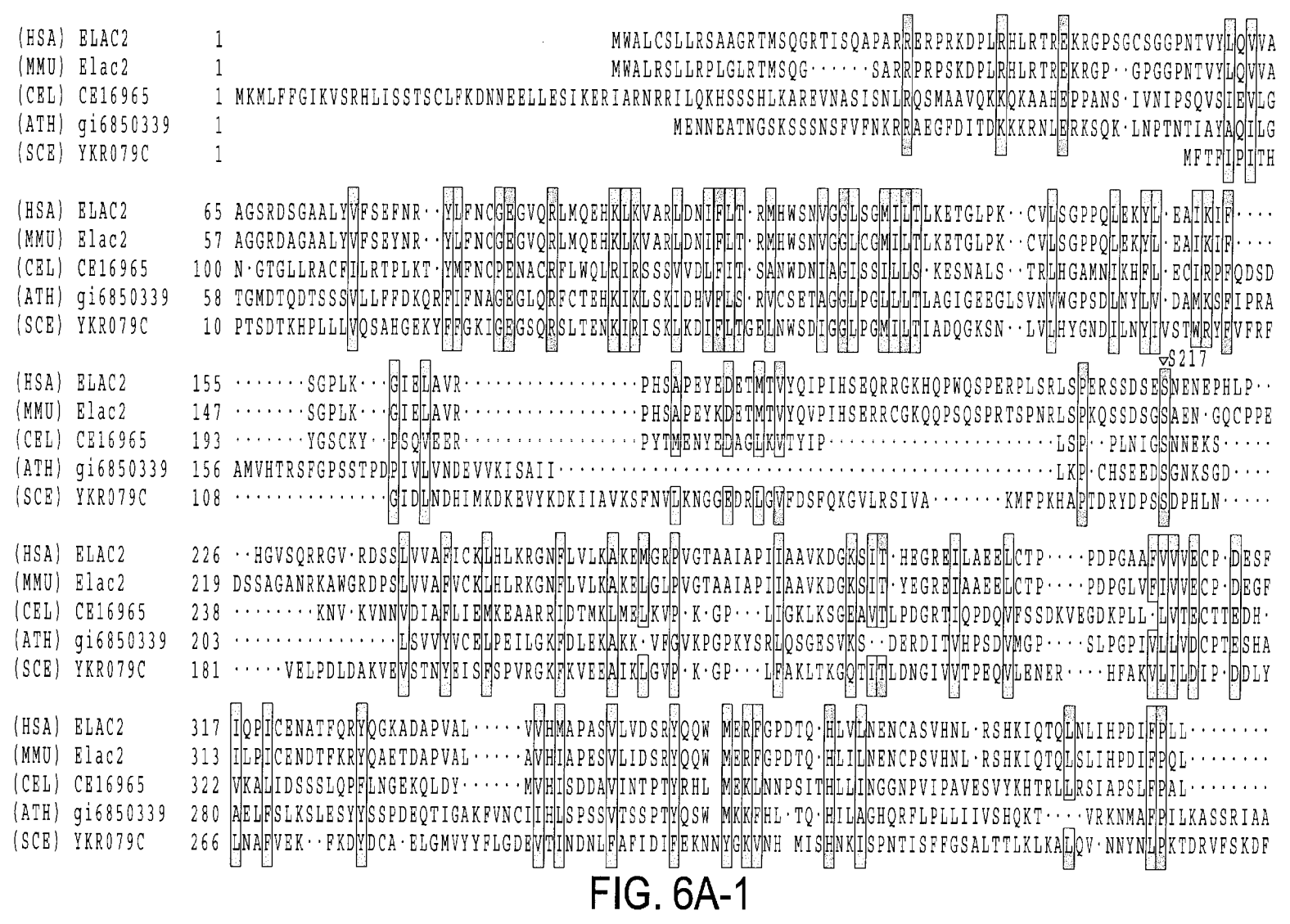
Figure 6A-2:
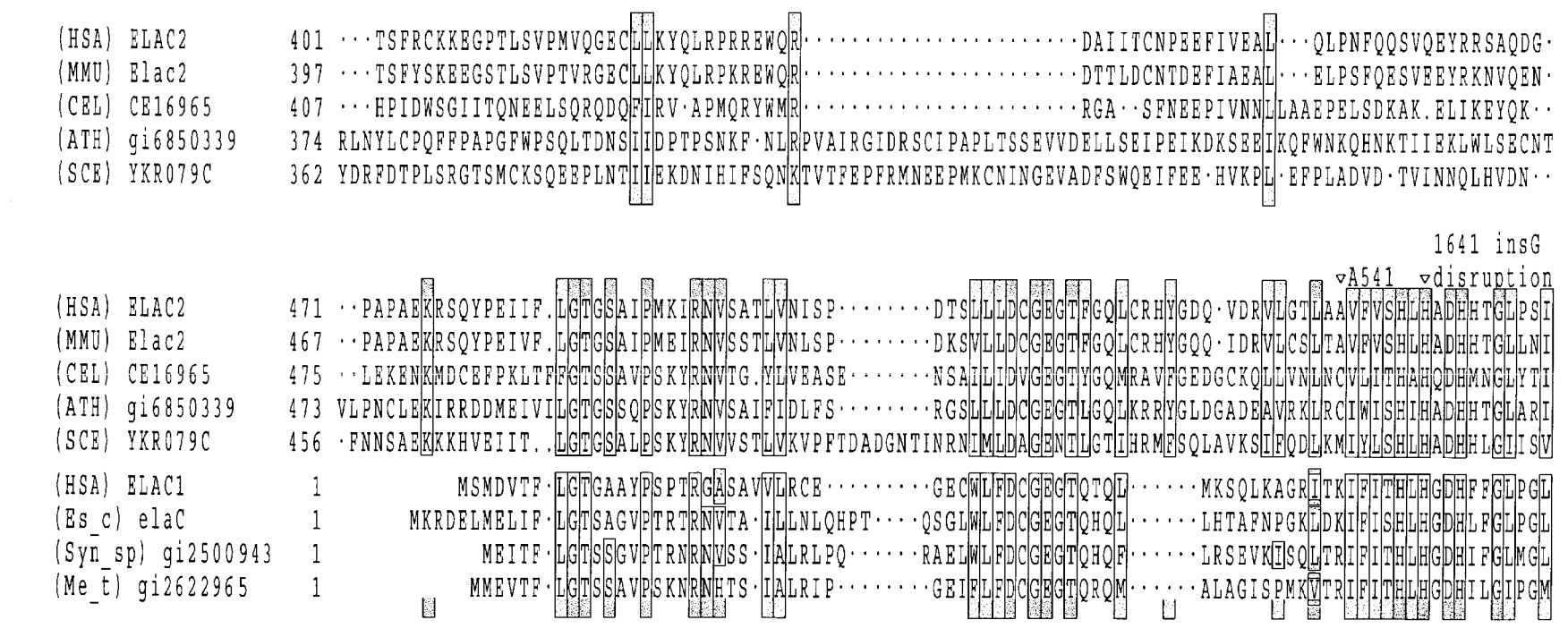

SEQ ID NOs:227–229 are the amino acid sequences for ELAC2 family member proteins from *C. elegans*, *A. thaliana* and *S. cerevisiae* as shown in FIG. 6A.

Figure 6B-1:
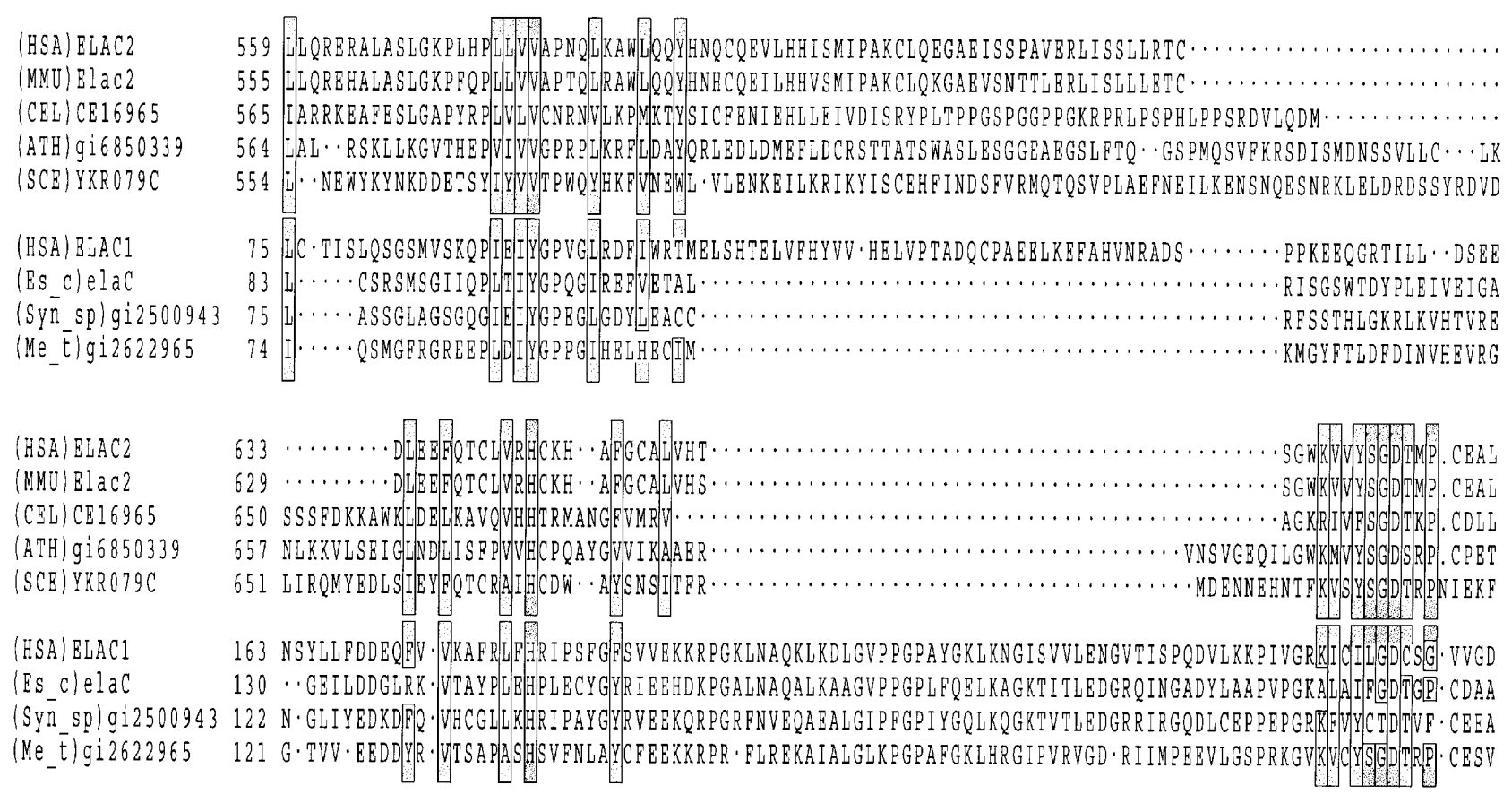

SEQ ID NOs:230–232 are the amino acid sequences for ELAC1 family member proteins from *E. coli*, Synechocystis and *Methanobacterium thermoautotrophicum* as shown in FIGS. 6A–B.

SEQ ID NOs:233–240 are amino acid sequences of proteins from CPSF73 and PSO2 families as shown in FIG. 9. These are, respectively, human CPSF73, *A. thaliana* gi6751699, *S. cerevisiae* YSH1, Synechocystis gi2496795. *Methanobacterium thermoautotrophicum* gi2622312, human ha3611, *A. thaliana* gi2979557 and *S. cerevisiae* PSO2. The sequences for the ELAC2 family of FIG. 9 are SEQ ID NO:2 for human, SEQ ID NO:228 for *A. thaliana* (as for FIGS. 6A–B) and SEQ ID NO:229 for *S. cerevisiae* (as for FIGS. 6A–B). The sequence listing shows the complete sequences of these proteins whereas FIG. 9 shows only portions of each sequence.

DETAILED DESCRIPTION OF THE INVENTION

The present invention provides an isolated polynucleotide comprising all, or a portion of the HPC2 locus or of a mutated HPC2 locus, preferably at least eight bases and not more than about 27 kb in length. Such polynuclcotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the HPC2 locus or its expression product in an analyte. Such methods may further comprise the step of amplifying the portion of the HPC2 locus, and may further include a step of providing a set of polynucleotides which are primers for amplification of said portion of the HPC2 locus. The method is useful for either diagnosis of the predisposition to cancer or the diagnosis or prognosis of cancer. The HPC2 gene is useful as a marker for the HPC2 locus and as a marker for prostate cancer.

The present invention also provides isolated antibodies, preferably monoclonal antibodies, which specifically bind to an isolated polypeptide comprised of at least five amino acid residues encoded by the HPC2 locus.

The present invention also provides kits for detecting in an analyte a polynucleotide comprising a portion of the HPC2 locus, the kits comprising a polynucleotide complementary to the portion of the HPC2 locus packaged in a suitable container, and instructions for its use.

The present invention further provides methods of preparing a polynucleotide comprising polymerizing nucleotides to yield a sequence comprised of at least eight consecutive nucleotides of the HPC2 locus; and methods of preparing a polypeptide comprising polymerizing amino acids to yield a sequence comprising at least five amino acids encoded within the HPC2 locus.

The present invention further provides methods of screening the HPC2 gene to identify mutations. Such methods may further comprise the step of amplifying a portion of the HPC2 locus, and may further include a step of providing a set of polynucleotides which are primers for amplification of said portion of the HPC2 locus. Such methods may also include a step of providing the complete set of short polynucleotides defined by the sequence of HPC2 or discrete subsets of that sequence, all single-base substitutions of that sequence or discrete subsets of that sequence, all 1-, 2-, 3-, or 4-base deletions of that sequence or discrete subsets of that sequence, and all 1-, 2-, 3-, or 4-base insertions in that sequence or discrete subsets of that sequence. The method is useful for identifying mutations for use in either diagnosis of the predisposition to cancer or the diagnosis or prognosis of cancer.

The present invention further provides methods of screening suspected HPC2 mutant alleles to identify mutations in the HPC2 gene.

In addition, the present invention provides methods to screen drugs for inhibition or restoration of HPC2 gene product function as an anticancer therapy.

The present invention also provides the means necessary for production of gene-based therapies directed at cancer cells. These therapeutic agents may take the form of polynucleotides comprising all or a portion of the HPC2 locus placed in appropriate vectors or delivered to target cells in more direct ways such that the function of the HPC2 protein is reconstituted. Therapeutic agents may also take the form of polypeptides based on either a portion of, or the entire protein sequence of HPC2. These may functionally replace the activity of HPC2 in vivo.

Finally, the present invention provides the sequence of a paralog of HPC2, herein called ELAC1, as well as the sequences of HPC2 orthologs from mouse, chimpanzee and gorilla. These orthologs are named ELAC2.

It is a discovery of the present invention that the HPC2 locus which predisposes individuals to prostate cancer, is a gene encoding an HPC2 protein, which has been found to be non-identical to publicly available protein or cDNA sequences. This gene is termed HPC2 herein. It is a discovery of the present invention that mutations in the HPC2 locus in the germline are indicative of a predisposition to prostate cancer. Finally, it is a discovery of the present invention that germline mutations in the HPC2 locus are also associated with prostate cancer and other types of cancer. The mutational events of the HPC2 locus can involve deletions, insertions and nucleotide substitutions within the coding sequence and the non-coding sequence.

Useful Diagnostic Techniques

According to the diagnostic and prognostic method of the present invention, alteration of the wild-type HPC2 locus is detected. In addition, the method can be performed by detecting the wild-type HPC2 locus and confirming the lack of a predisposition to cancer at the HPC2 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are somatically mutated, then a late neoplastic state is indicated. The finding of HPC2 mutations thus provides both diagnostic and prognostic information. An HPC2 allele which is not deleted (e.g., found on the sister chromosome to a chromosome carrying an HPC2 deletion) can be screened for other mutations, such as insertions, small deletions, and point mutations. It is believed that many mutations found in tumor tissues will be those leading to decreased expression of the HPC2 gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to reduction or loss of expression of the HPC2 gene product, expression of an altered HPC2 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

Predisposition to cancers, such as prostate cancer, and the other cancers identified herein, can be ascertained by testing any tissue of a human for mutations of the HPC2 gene. For example, a person who has inherited a germline HPC2 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the HPC2 gene. Alteration of a wild-type HPC2 allele, whether, for example, by point mutation or deletion, can be detected by any of the means discussed herein.

There are several methods that can be used to detect DNA sequence variation. Direct DNA sequencing, either manual sequencing(or automated fluorescent sequencing can detect sequence variation. For a gene as large as HPC2, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonuclcotide (ASO) hybridization can be utilized to rapidly screen large numbers of other samples for that same mutation. Such a technique can utilize probes which are labeled with gold nanoparticles to yield a visual color result (Elghanian et al., 1997).

In order to detect the alteration of the wild-type HPC2 gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

Detection of point mutations may be accomplished by molecular cloning of the HPC2 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular HPC2 mutation. If the particular HPC2 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the HPC2 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques arc less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type HPC2 gene coding sequence. The riboprobe and either mRNA or DNA isolated from the tumor tissue arc annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A. an RNA product will be seen which is smaller than the full length duplex RNA for the riboprobe and the mRNA or DNA. The riboprobe need not be the full length of the HPC2 mRNA or gene but can be a segment of either. If the riboprobe comprises only a segment of the HPC2 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the HPC2 gene can also be detected using Southern hybridization, especially if the changes are gross rearrangements. such as deletions and insertions.

DNA sequences of the HPC2 gene which have been amplified by use of PCR may also be screened using allele-specific probes. These probes are nucleic acid oligomers, each of which contains a region of the HPC2 gene sequence harboring a known mutation. For example, one oligomer may be about 30 nucleotides in length (although shorter and longer oligomers are also usable as well recognized by those of skill in the art), corresponding to a portion of the HPC2 gene sequence. By use of a battery of such allele-specific probes, PCR amplification products can be screened to identify the presence of a previously identified mutation in the HPC2 gene. Hybridization of allele-specific probes with amplified HPC2 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Bonnan, 1 996) and been the subject of an editorial (Nature Genetics, 1996). Also see Fodor (1997).

The most definitive test for mutations in a candidate locus is to directly compare genomic HPC2 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of HPC2 can be detected by examining the non-coding regions, such as introns and regulatory sequences near or within the HPC2 gene. An early indication that mutations in noncoding regions are important may come from Northern blot experiments that reveal messenger RNA molecules of abnormal size or abundance in cancer patients as compared to control individuals.

Alteration of HPC2 mRNA expression can be detected by any techniques known in the art. These include Northern blot analysis, PCR amplification and RNase protection. Diminished mRNA expression indicates an alteration of the wild-type HPC2 gene. Alteration of wild-type HPC2 genes can also be detected by screening for alteration of wild-type HPC2 protein. For example, monoclonal antibodies immunoreactive with HPC2 can be used to screen a tissue. Lack of cognate antigen would indicate an HPC2 mutation. Antibodies specific for products of mutant alleles could also be used to detect mutant HPC2 gene product. Such immunological assays can be done in any convenient formats known in the art. These include Western blots, immunohistochemical assays and ELISA assays. Any means for detecting an altered HPC2 protein can be used to detect alteration of wild-type HPC2 genes. Functional assays, such as protein binding determinations, can be used. In addition, assays can be used which detect HPC2 biochemical function. Finding a mutant HPC9 gene product indicates alteration of a wild-type HPC2 gene.

Mutant HPC2 genes or gene products can also be detected in other human body samples, such as serum, stool, urine and sputum. The same techniques discussed above for detection of mutant HPC2 genes or gene products in tissues can be applied to other body samples. Cancer cells are sloughed off from tumors and appear in such body samples. In addition the HPC2 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant HPC2 genes or gene products.

The methods of diagnosis of the present invention are applicable to any tumor in which HPC2 has a role in tumorigenesis. The diagnostic method of the present invention is useful for clinicians, so they can decide upon an appropriate course of treatment.

The primer pairs of the present invention are useful for determination of the nucleotide sequence of a particular HPC2 allele using PCR. The pairs of single-stranded DNA primers can be annealed to sequences within or surrounding the HPC2 gene on chromosome 17 in order to prime amplifying DNA synthesis of the HPC2 gene itself. A complete set of these primers allows synthesis of all of the nucleotides of the HPC2 gene coding sequences, i.e., the exons. The set of primers preferably allows synthesis of both intron and exon sequences. Allele-specific primers can also be used. Such primers anneal only to particular HPC2 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from HPC2 sequences or sequences adjacent to HPC2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the HPC2 open reading frame shown in SEQ ID NOs:1 and 3, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the HPC2 gene or mRNA using other techniques.

It has been discovered that individuals with the wild-type HPC2 gene do not have cancer which results from the HPC2 allele. However, mutations which interfere with the function of the HPC2 protein are involved in the pathogenesis of cancer. Thus, the presence of an altered (or a mutant) HPC2 gene which produces a protein having a loss of function, or altered function. directly correlates to an increased risk of cancer. In order to detect an HPC2 gene mutation, a biological sample is prepared and analyzed for a difference between the sequence of the HPC2 allele being analyzed and the sequence of the wild-type HPC2 allele. Mutant HPC2 alleles can be initially identified by any of the techniques described above. The mutant alleles are then sequenced to identify the specific mutation of the particular mutant allele. Alternatively, mutant HPC2 alleles can be initially identified by identifying mutant (altered) HPC2 proteins, using conventional techniques. The mutant alleles are then sequenced to identify the specific mutation for each allele. The mutations, especially those which lead to an altered function of the HPC2 protein, are then used for the diagnostic and prognostic methods of the present invention.

Definitions

The present invention employs the following definitions:

"Amplification of Polynuckeotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); and Wu and Wallace, 1989 (for LCR), U.S. Pat. Nos. 5,270,184 and 5,455,166 and Walker et al., 1992 (for SDA); Spargo et al., 1996 (for thermophilic SDA) and U.S. Pat. No. 5,409,818; Fahy et al., 1991 and Compton, 1991 for 3SR and NASBA. Reagents and hardware for conducting PCR are commercially available. Primers useful to amplify sequences from the HPC2 region or HPC2 paralogs or orthologs are preferably complementary to, and hybridize specifically to sequences in the HPC2 region or paralog or ortholog region or in regions that flank a target region therein. HPC2 sequences or paralog or ortholog sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the HPC2 polypeptides or to polypeptides encoded by paralogs or orthologs of HPC2 and fragments thereof or to polynucleotide sequences from the HPC2 region, or to polynucleotide sequences which arc paralogs or orthologs of HPC2, particularly from the HPC2 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactive to the HPC2 polypeptide or fragment or to polypeptides or fragments encoded by paralogs or orthologs of HPC2. Monoclonal antibodies may be made by injecting mice with the protein polypeptides, fusion proteins or fragments thereof. Monoclonal antibodies will be screened by ELISA and tested for specific immunoreactive with HPC2 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-1}$ $M^{-1}$ or preferably $10^{-9}$ to $10^{-1}$ $M^{-1}$ or stronger will typically be made by standard procedures as described, e.g., in liarlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"HPC2 Allele" refers to normal alleles of the HPC2 locus as well as alleles carrying variations that predispose individuals to develop prostate cancer. Such predisposing alleles are also called "HPC2 susceptibility alleles".

"HPC2 Locus", "HPC2 Gene", "HPC2 Nucleic Acids" or "HPC2 Polynucleotide" each refer to polynucleotides, all of which are in the HPC2 region, that are likely to be expressed in normal tissue, certain alleles of which predispose an individual to develop prostate cancers. Mutations at the HPC2 locus may be involved in the initiation and/or progression of other types of tumors. The locus is indicated in part by mutations that predispose individuals to develop cancer. These mutations fall within the HPC2 region described infra. The HPC2 locus is intended to include coding sequences, intervening sequences and regulatory elements controlling transcription and/or translation. The HPC2 locus is intended to include all allelic variations of the DNA sequence.

The term HPC2 is used interchangeably throughout this disclosure with the terms ELAC2 and HPC2/ELAC2. This holds true regardless of whether the term refers to a nucleic acid, allele, gene, locus, protein or peptide.

These terms, when applied to a nucleic acid, refer to a nucleic acid which encodes an HPC2 polypeptide, fragment, homolog or variant, including, e.g., protein fusions or deletions. The nucleic acids of the present invention will possess a sequence which is either derived from, or substantially similar to a natural HPC2-encoding gene or one having substantial homology with a natural HPC2-encoding gene or a portion thereof.

The HPC2 gene or nucleic acid includes normal alleles of the HPC2 gene, including silent alleles having no effect on the amino acid sequence of the HPC2 polypeptide as well as alleles leading to amino acid sequence variants of the HPC2 polypeptide that do not substantially affect its function. These terms also include alleles having one or more mutations which adversely affect the function of the HPC2 polypeptide. A mutation may be a change in the HPC2 nucleic acid sequence which produces a deleterious change in the amino acid sequence of the HPC2 polypeptide, resulting in partial or complete loss of HPC2 function, or may be a change in the nucleic acid sequence which results in the loss of effective HPC2 expression or the production of aberrant forms of the HPC2 polypeptide.

The HPC2 nucleic acid may be that shown in SEQ ID NOs:1, 3 or 28 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NOs:1, 3 or 28 yet encode a polypeptide with the same amino acid sequence as shown in SEQ ID NO:1. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The HPC2 gene also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to HPC2, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to HPC2. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the HPC2 region or the HPC2 paralog called ELAC1 or the mouse, chimpanzee or gorilla orthologs of HPC2, herein called mouse ELAC2, chimpanzee ELAC2 or gorilla ELAC2. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library arc spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an HPC2-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehlinger Mannheirn, Amersham, Promega Biotec, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"HPC2 Region" refers to a portion of human chromosome 17 bounded by the markers D17S947 and D17S799. This region contains the HPC2 locus, including the HPC2 gene.

As used herein, the terms "HPC2 locus", "HPC2 allele" and "HPC2 region" all refer to the double-stranded DNA comprising the locus, allele, or region, as well as either of the single-stranded DNAs comprising the locus, allele or region.

As used herein, a "portion" of the HPC2 locus or region or allele is defined as having a minimal size of at least about eight nucleotides, or preferably about 15 nucteotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from any of SEQ ID NOs:1 or 3–28, its complement or functionally equivalent nucleic acid sequences. The present invention does not include nucleic acids which exist in the prior art. That is, the present invention includes all nucleic acids having at least 8 nucleotides derived from any of SEQ ID NOs:1 or 3–28 with the proviso that it does not include nucleic acids existing in the prior art.

"HPC2 protein" or "HPC2 polypeptide" refers to a protein or polypeptide encoded by the HPC2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the alt, both naturally and non-naturally occurring. Ordinarily, such polypeptides will be at least about 50% homologous to the native 1HPC2 sequence, preferably in excess of about 90%, and more preferably at least about 95% homologous. Also included are proteins encoded by DNA which hybridize under high or low stringency conditions, to HPC2-encoding nucleic acids and closely related polypeptides or proteins retrieved by antisera to the HPC2 protein(s).

An HPC2 polypeptide may be that derived from any of the exons described herein which may be in isolated and/or purified form, flee or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of an HPC2 polypeptide. Such polypeptidcs may have an amino acid sequence which differs from that derived from any of the exons described herein by one or more of addition, substitution, deletion or insertion of one or more amino acids. Preferred such polypeptides have HPC2 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an HPC2 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of an HPC2, ELAC1 or ELAC2 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of a natural HPC2, ELAC1 or ELAC2 polypeptide.

"Probes". Polynucleotide polymorphisms associated with HPC2 alleles which predispose to certain cancers or are associated with most cancers are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an HPC2 susceptibility allele. An example of high stringency conditions is to hybridize to filter bound DNA in 0.5 M NaHPO$_4$, 7% sodium dodecyl sulfate (SDS), 1 mM EDTA at 65° C. and to wash in 0.1×SSC/0.1% SDS at 68° C. (Ausubel et al., 1992). Less stringent conditions, such as moderately stringent conditions, are defined as above but with the wash step being in 0.2×SSC/0. 1% SDS at 42° C.

Probes for HPC2 alleles may be derived from the sequences of the HPC2 region, its cDNA, functionally equivalent sequences, or the complements thereof. The probes may be of any suitable length, which span all or a portion of the HPC2 region, and which allow specific hybridization to the HPC2 region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel el al, 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding HPC2 are preferred as probes. This definition therefore includes probes of sizes 8 nucleotides through 9000 nucleotides. Thus, this definition includes probes of 8, 12, 15, 20, 25, 40, 60. 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding HPC2 is present in a cell or tissue. The present invention includes all novel probes having at least 8 nucleotides derived from any of SEQ ID NOs:1 or 3–28 its complement or functionally equivalent nucleic acid sequences. The present invention does not include probes which exist in the prior art. That is, the present invention includes all probes having at least 8 nucleotides derived from any of SEQ ID NOs:1 or 3–28 with the proviso that they do not include probes existing in the prior art.

Similar considerations and nucleotide lengths are also applicable to primers which may be used for the amplification of all or part of the HPC2 gene. Thus, a definition for primers includes primers of 8, 12, 15, 20, 25, 40, 60, 80, 100, 200, 300, 400, 500 nucleotides, or primers having, any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding HPC2 is present in a cell or tissue. The present invention includes all novel primers having at least 8 nucleotides derived from the HIC2 locus for amplifying the HPC2 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for HPC2, ELAC1 and ELAC2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of HPC2, ELAC1 or ELAC2 polypeptides. Immunological activities include both immunogenic function in a target immune system, as well as sharing of immunological epitopes for binding, serving as either a competitor or substitute antigen for an epitope of the HPC2, ELAC1 or ELAC2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for HPC2, ELAC1 or ELAC2 polypeptides or fragments thereof is described below.

The present invention also provides for fusion polypeptides, comprising HPC2, ELAC1 or ELAC2 polypeptides and fragments. Homologous polypeptides may be fusions between two or more HPC2, ELAC1 or ELAC2 polypeptide sequences or between the sequences of HPC2, ELAC1 or ELAC2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase. Type, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the HPC2, ELAC1 or ELAC2 polypeptides from other biological material, such as from cells transformed with recombinant nucleic acids encoding HPC2, ELAC1 or ELAC2 and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

An HPC2, ELAC1 or ELAC2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells arc inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer. Gribskov, M. and Devereux, J., eds., M Stockton Press, New York, 1991). Methods commonly employed to determine identity between two sequences include, but are not limited to those disclosed in *Guide to Hupe Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or similarity exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705, as well as the software described above with reference to nucleic acid homology. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type HPC2, ELAC1 or ELAC2 nucleic acid or wild-type HPC2, ELAC1 or ELAC2 polypeptide. The modified polypeptide will be substantially homologous to the wild-type HPC2, ELAC1 or ELAC2 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type HPC2, ELAC1 or ELAC2 polypeptide. Alternatively, the similarity of function (activity) of the modified polypeptide may be higher than the activity of the wild-type HPC2, ELAC1 or ELAC2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type HPC2, ELAC1 or ELAC2 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et at., 1982; Sambrook et al., 1989, Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically
Synthesized Nucleic Acids; Vectors,
Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence CARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HPC2 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with HPC2, ELAC1 or ELAC2 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735, 500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alaninc racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfcction employing calcium chloride, rubidium chloride calcium phosphate, DEAE-dextran, or other substances; microprojectile bombardment, lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the HPC2, ELAC1 or ELAC2 nucleic acids or portions thereof in vectors or other expression vehicles in compatible prokaryotic or eukaryotic host cells. The most commonly used prokaryotic hosts are strains of *Escheiichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts. the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be usefuil not only for the production of the nucleic acids and polypeptides of the present invention, but also, for example, in studying the characteristics of HPC2, ELAC1 or ELAC2 polypeptides.

The HPC2, ELAC1 or ELAC2 gene products can also be expressed in transgenic animals. Animals of any species, including, but not limited to, mice, rats, rabbits, guinea pigs, pigs, micro-pigs, goats and non-human primates, c.g., baboons, monkeys and chimpanzees, may be used to generate HPC2, ELAC1 or ELAC2 transgenic animals.

Any technique known in the art may be used to introduce the HPC2, ELAC1 or ELAC2 gene transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., 1985); gene targeting in embryonic stem cells (Thompson et al., 1989); electroporation of embryos (Lo, 1983); and sperm-mediated gene transfer (Lavitrano et al., 1989); etc. For a review of such techniques, see Gordon (1989), which is incorporated by reference herein in its entirety.

The present invention provides for transgenic animals that carry the HPC2, ELAC1 or ELAC2 transgene in all their cells, as well as animals which carry the transcene in some, but not all of their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (1992). The regulatory sequences required for such a cell-type specific activation will depend upon the particular cell type of interest, and will be apparent to those of skill in the art. When it is desired that the HPC2, ELAC1 or ELAC2 gene transgene be integrated into the chromosomal site of the endogenous HPC2, ELAC1 or ELAC2 gene, gene targeting is preferred. Briefly, when such a technique is to be utilized, vectors containing some nucleotide sequences homologous to the endogenous HPC2, ELAC1 or ELAC2 gene are designed for the purpose of integrating, via homologous recombination with chromosomal sequences, into and disrupting the function of the nucleotide sequence of the endogenous HPC2, ELAC1 or ELAC2 gene. The transgene may also be selectively introduced into a particular cell type, thus inactivating the endogenous HPC2, ELAC1 or ELAC2 gene in only that cell type, by following, for example, the teaching of Gu et al. (1994). The regulatory sequences required for such a cell-type specific inactivation will depend upon the particular cell type of interest, and will be apparent to those of skill in the art.

Once transgenic animals have been generated, the expression of the recombinant HPC2, ELAC1 or ELAC2 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in sill hybridization analysis, and RT-PCR. Samples of HPC2, ELAC1 or ELAC2 gene-expressing tissue, may also be evaluated immunocytochemically using antibodies specific for the HPC2, ELAC1 or ELAC2 transgene product.

Antisense polynucleotide sequences are useful in preventing or diminishing the expression of the HPC2, ELAC1 or ELAC2 locus, as will be appreciated by those skilled in the art. For example, polynucleotide vectors cont,ioring all or a portion of the HPC2 locus or other sequences from the HPC2 region (particularly those flanking the HPC2 locus) may be placed under the control of a promoter in an antisense orientation and introduced into a cell. Expression of such an antisense construct within a cell will interfere with HPC2 transcription and/or translation and/or replication.

The probes and primers based on the HPC2 gene sequences disclosed herein are used to identify homologous HPC2 gene sequences and proteins in other species. These HPC2 gene sequences and proteins are used in the diagnostic/prognostic, therapeutic and drug screening method s described herein for the species from which they have been isolated.

Methods of Use: Nucleic Acid Diapnosis and Diagnostic Kits

In order to detect the presence of an HPC2 allele predisposing an individual to cancer, a biological sample such as blood is prepared and analyzed for the presence or absence of susceptibility alleles of HPC2. In order to detect the presence of neoplasia, the progression toward malignancy of a precursor lesion, or as a prognostic indicator, a biological sample of the lesion is prepared and analyzed for the presence or absence of mutant alleles of HPC2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis .

Initially, the screening method involves amplification of the relevant HPC2 sequences. In another preferred embodiment of the invention, the screening method involves a non-PCR based strategy. Such screening methods include two-step label amplification methodologies that are well known in the art. Both PCR and non-PCR based screening strategies can detect targfet sequences with a high level of sensitivity.

The most popular method used today is target amplification. here. the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 17. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Ujnder certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding HPC2. Allele specific probes are also contemplated within the scope of this example and exemplary allele specific probes include probes encompassing the predisposing or potentially predisposing mutations summarized in Table 9 of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting HPC2. Thus, in one example to detect the presence of HPC2 in a cell sample, more than one probe complementary to HPC2 is employed and in particular the number of different probes is alternatively 2, 3, or 5 different nucleic acid probe sequences. In another example, to detect the presence of mutations in the HPC2 gene sequence in a patient, more than one probe complementary to HPC2 is employed where the cocktail includes probes capable of binding to the allele-specific mutations identified in populations of patients with alterations in HPC2. In this embodiment, any number of probes can be used, and will preferably include probes corresponding to the major gene mutations identified as predisposing an individual to prostate cancer.

Methods of Use: Peptide Diagnosis and Diagnostic Kits

The neoplastic condition of lesions can also be detected on the basis of the alteration of wild-type HPC2 polypeptide. Such alterations can be determined by sequence analysis in accordance with conventional techniques. More preferably, antibodies (polyclonal or monoclonal) are used to detect differences in, or the absence of, HPC2 peptides. The antibodies may be prepared as discussed above under the heading "Antibodies" and as further shown in Examples 16 and 17. Other techniques for raising and purifying antibodies are well known in the art and any such techniques may be chosen to achieve the preparations claimed in this invention. In a preferred embodiment of the invention, antibodies will immunoprecipitate HPC2 proteins from solution as well as react with HPC2 protein on Western or immunoblots of polyacrylamide gels. In another preferred embodiment, antibodies will detect HPC2 proteins in paraffin or frozen tissue sections, usinll immunocytochemical techniques.

Preferred embodiments relating to methods for detecting HPC2 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference, and exemplified in Example 19.

Methods of Use: Drug Screening

This invention is particularly useful for screening compounds by using the HPC2, ELAC1 or ELAC2 polypeptide or binding fragment thereof in any of a variety of drug screening techniques.

The HPC2, ELAC1 or ELAC2 polypeptide or fragment employed in such a test may either be free in solution affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an HPC2, ELAC1 or ELAC2 polypeptide or fragment and the agent being tested, or examine the degree to which the formation of a complex between an HPC2, ELAC1 or ELAC2 polypeptide or fragment and a known ligand is interfered with by the agent being tested.

Thus, the present invention provides methods of screening for drugs comprising contacting such an agent with an HPC2, ELAC1 or ELAC2 polypeptide or fragment thereof and assaying (i) for the presence of a complex between the agent and the HPC2, ELAC1 or ELAC2 polypeptide or fragment, or (ii) for the presence of a complex between the HPC2, ELAC1 or ELAC2 polypeptide or fragment and a ligand, by methods well known in the art. In such competitive binding assays the HPC2, ELAC1 or ELAC2 polypeptide or fragment is typically labeled. Free HPC2, ELAC1 or ELAC2 polypeptide or fragment is separated from that present in a protein:protein complex, and the amount of free (i.e., uncomplexed) label is a measure of the binding of the agent being tested to HPC2, ELAC1 or ELAC2 or its interference with HPC2:ligand, ELAC1:ligand or ELAC2:ligand binding, respectively. One may also measure the amount of bound, rather than free, HPC2, ELAC1 or ELAC2. It is also possible to label the ligand rather than the HPC2, ELAC1 or ELAC2 and to measure the amount of ligand binding to HPC2, ELAC1 or ELAC2 in the presence and in the absence of the drug being tested.

Another technique for drug screening provides high throughput screening for compounds having suitable binding affinity to the HPC2, ELAC1 or ELAC2 polypeptides and is described in detail in Geysen (published PCT WO 84/03564). Briefly stated, large numbers of different small peptide test compounds are synthesized on a solid substrate, such as plastic pins or some other surface. The peptide test compounds are reacted with HPC2, ELAC1 or ELAC2 polypeptide and washed. Bound HPC2, ELAC1 or ELLAC2 polypeptide is then detected by methods well known in the art.

Purified HPC2, ELAC1 or ELAC2 can be coated directly onto plates for use in the aforementioned drug screening techniques. However, non-neutralizing antibodies to the polypeptide can be used to capture antibodies to immobilize the HPC2, ELAC1 or ELAC2 polypeptide on the solid phase.

This invention also contemplates the use of competitive drug screening assays in which neutralizing antibodies capable of specifically binding the HPC2, ELAC1 or ELAC2 polypeptide compete with a test compound for binding to the HPC2, ELAC1 or ELAC2 polypeptide or fragments thereof. In this manner, the antibodies can be used to detect the presence of any peptide which shares one or more antigenic determinants of the HPC2, ELAC1 or ELAC2 polypeptide.

A further technique for drug screening involves the use of host eukaryotic cell lines or cells (such as described above) which have a nonfunctional HPC2, ELAC1 or ELAC2 gene. These host cell lines or cells are defective at the HPC2, ELAC1 or ELAC2 polypeptide level. The host cell lines or cells are grown in the presence of drug compound. The rate of growth of the host cells is measured to determine if the compound is capable of regulating the growth of HPC2, ELAC1 or ELAC2 defective cells.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an HPC2, ELAC1 or ELAC2 specific binding partner, or to find mimetics of an HPC2, ELAC1 or ELAC2 polypeptide.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., HPC2 polypeptide) or, for example, of the HPC2-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., HPC2 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved HPC2, ELAC1 or ELAC2 polypeptide activity or stability or which act as inhibitors, agonists, antagonists, etc. of HPC2, ELAC1 or ELAC2 polypeptide activity. By virtue of the availability of cloned HPC2, ELAC1 and ELAC2 sequences, sufficient amounts of the HPC2, ELAC1 or ELAC2 polypeptide may be made available to perform such analytical studies as x-ray crystallogaphy. In addition, the knowledge of the HPC2, ELAC1 and ELAC2 protein sequences provided herein will guide those employing computer modeling techniques in place of, or in addition to x-ray crystallography.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment of prostate cancer, use of such a substance in the manufacture of a composition for administration, e.g., for treatment of prostate cancer, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" arc often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Gene Therapy

According to the present invention, a method is also provided of supplying wild-type HPC2 function to a cell which carries mutant HPC2 alleles. Supplying such a function should suppress neoplastic growth of the recipient cells. The wild-type HPC2 gene or a part of the gene may be introduced into the cell in a vector such that the gene remains extrachromosomal. In such a situation, the gene will be expressed by the cell from the extrachromosomal location. If a gene fragment is introduced and expressed in a cell carrying, a mutant HPC2 allele, the gene fragment should encode a part of the HPC2 protein which is required for non-neoplastic growth of the cell. More preferred is the situation where the wild-type HPC2 gene or a part thereof is introduced into the mutant cell in such a way that it recombines with the endogenous mutant HPC2 gene present in the cell. Such recombination requires a double recombination event which results in the correction of the HPC2 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the practitioner. Cells transformed with the wild-type l-HPC2 gene can be used as model systems to study cancer remission and drug treatments which promote such remission.

As generally discussed above, the HPC2 gene or fragment, where applicable, may be employed in gene therapy methods in order to increase the amount of the expression products of such genes in cancer cells. Such gene therapy is particularly appropriate for use in both cancerous and pre-cancerous cells, in which the level of HPC2 polypeptide is absent or diminished compared to normal cells. It may also be useful to increase the level of expression of a given HPC2 gene even in those tumor cells in which the mutant gene is expressed at a "normal" level, but the gene product is not fully functional.

Gene therapy would be carried out according to generally accepted methods for example, as described by Friedman (1991) or Culver (1996). Cells from a patient's tumor would be first analyzed by the diagnostic methods described above, to ascertain the production of HPC2 polypeptide in the tumor cells. A virus or plasmid vector (see further details below), containing a copy of the HPC2 gene linked to expression control elements and capable of replicating inside the tumor cells, is prepared. Alternatively, the vector may be replication deficient and is replicated in helper cells for use in gene therapy. Suitable vectors are known, such as disclosed in U.S. Pat. No. 5,252.479 and PCT published application WO 93/07282 and U.S. Pat. Nos. 5,691,198; 5,747,469; 5,436,146 and 5,753,500. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992: Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpes viruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Fluang, 1989; Kaneda et al, 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1991; Curiel et al, 1992). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes HPC2, expression will produce HPC2. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to prostate tissues, e.g., epithelial cells of the prostate, are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps which can be performed singly or jointly. In the first step, prepubescent females who carry an HPC2 susceptibility allele are treated with a gene delivery vehicle such that some or all of their mammary ductal epithelial precursor cells receive at least one additional copy of a functional normal HPC2 allele. In this step, the treated individuals have reduced risk of prostate cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the prostate of a full term pregnancy.

Methods of Use: Peptide Therapy

Peptides which have HPC2, ELAC1 or ELAC2 activity can be supplied to cells which carry mutant or missing HPC2, ELAC1 or ELAC2 alleles. Protein can be produced by expression of the cDNA sequence in bacteria, for example, using known expression vectors. Alternatively, HPC2, ELAC1 or ELAC2 polypeptide can be extracted from HPC2-, ELAC1- or ELAC2-producing mammalian cells. In addition, the techniques of synthetic chemistry can be employed to synthesize HPC2, ELAC1 or ELAC2 protein. Any of such techniques can provide the preparation of the present invention which comprises the HPC2, ELAC1 or ELAC2 protein. Preparation is substantially free of other human proteins. This is most readily accomplished by synthesis in a microorganism or in vitro.

Active HPC2, ELAC1 or ELAC2 molecules can be introduced into cells by microinjection or by use of liposomes, for example. Alternatively, some active molecules may be taken up by cells, actively or by diffusion. Extracellular application of the HPC2, ELAC1 or ELAC2 gene product may be sufficient to affect tumor growth. Supply of molecules with HPC2 activity should lead to partial reversal of the neoplastic state. Other molecules with HPC2 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant HPC2, ELAC1 or ELAC2 allele can be used as model systems to study and test for substances which have potential as therapeutic agents. The cells are typically cultured epithelial cells. These may be isolated from individuals with HPC2, ELAC1 or ELAC2 mutations, either somatic or germline. Alternatively, the cell line can be engineered to carry the mutation in the HPC2, ELAC1 or ELAC2 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant HPC2, ELAC1 or ELAC2 alleles, usually from a second animal species, as well as insertion of disrupted homologous genes. Alternatively, the endogenous HPC2, ELAC1 or ELAC2 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) to produce knockout or transplacement animals. A transplacement is similar to a knockout because the endogenous gene is replaced, but in the case of a transplacement the replacement is by another version of the same gene. After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

In one embodiment of the invention, transgenic animals are produced which contain a functional transgene encoding a functional HPC2, ELAC1 or ELAC2 polypeptide or variants thereof. Transgenic animals expressing HPC2, ELAC1 or ELAC2 transgenes, recombinant cell lines derived from such animals and transgenic embryos may be useful in methods for screening for and identifying agents that induce or repress function of HPC2, ELAC1 or ELAC2. Transgenic animals of the present invention also can be used as models for studying indications such as disease.

In one embodiment of the invention, an HPC2, ELAC2 or ELAC2 ti-ansoene is introduced into a non-human host to produce a transgenic animal expressing a human or murine HPC2, ELAC1 or ELAC2 gene. The transgenic animal is produced by the integration of the transgene into the genome in a manner that permits the expression of the transgene. Methods for producing transgenic animals are generally described by Wagner and Hoppc (U.S. Pat. No. 4,873,191; which is incorporated herein by reference), Brinster et (H. 1985; which is incorporated herein by reference in its entirety) and in "Manipulating the Mouse Embryo; A Laboratory Manual" 2nd edition (eds., liogan, Beddington, Costantini and Long, Cold Spring Harbor Laboratory Press, 1994; which is incorporated herein by reference in its entirety).

It may be desirable to replace the endogenous HPC2, ELAC1 or ELAC2 by homologous recombination between the transgene and the endogenous gene; or the endogenous gene may be eliminated by deletion as in the preparation of "knock-out" animals. Typically, an HPC2, ELAC1 or ELAC2 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress HPC2 or express a mutant form of the polypeptide. Alternatively, the absence of an HPC2, ELAC1 or ELAC2 in "knock-out" mice permits the study of the effects that loss of HPC2, ELAC1 or ELAC2 protein has on a cell in vivo. Knock-out mice also provide a model for the development of HPC2-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant HPC2, ELAC1 or ELAC2 may be exposed to test substances. These test substances can be screened for the ability to reduce overexpression of wild-type HPC2, ELAC1 or ELAC2 or impair the expression or function of mutant HPC2, ELAC1 or ELAC2.

Pharmaceutical Compositions and Routes of Administration

The HPC2, ELAC1 or ELAC2 polypeptides, antibodies, peptides and nucleic acids of the present invention can be formulated in pharmaceutical compositions, which are prepared according to conventional pharmaceutical compounding techniques. See, for example, *Reminoton's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, of which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used to deliver the active agent more specifically to certain types of cell, by the use of targeting systems such as antibodies or cell pecific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550.050 and published PCT application Nos. WO 92/19195. WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

As disclosed in the following Examples, on the basis of segregating mutations of HPC2 in kindreds 4102 and 4289, plus association between carriage of the common missense changes Leu 217 and Thr 541 with a diagnosis of prostate cancer, we conclude that HPC2 is a prostate cancer susceptibility gene.

While a 1641 insG frameshift found in kindred 4102 will clearly disrupt protein function, this is not obviously the case for the His 781 imiisseiise change in kindred 4289. Interestingly, this missense change occurred on a chromosome that also carries lieu 217 and Thr 541. Thus one might entertain an additive hypothesis to explain the relative strength of the three missense bearing alleles that we have observed. Substitution of leu for Ser 217 may change the character of a normally hydrophilic segment of the protein; the phenotype conferred is sufliciently modest that it is only detected when the variant is homozygous. Ala 541 is immediately adjacent to the histidine motif. At the position corresponding to Ala 541 in the ELAC1/2, CPSF73 and PSO2 gene families, the most common residue is alanine; when not alanine, the residue is hydrophobic, amide, or basic (FIGS. 6A–B, 9 and 12). Although threonine is observed at this position in other histidine motif containing gene families, it is rare or absent in these three closely related gene families. Thus, from sequence conservation considerations, it is quite reasonable that the Leu 217+Thr 541 allele should be more deleterious than Leu 217 alone, apparently sufficiently deleterious to be detected in a co-dominant to dominant association test. The kindred 4289 allele carries all three missense changes, Lieu 217, Thr 541 and His 781. Examination of the pedigree suggests that the allelc is dominant and sufficiently deleterious to demonstrate visible segregation with prostate cancer in an extended pedigree. Interestingly, the youngest affected carrier of this variant, 4289.003, is homozygous for Leu 217 and Thr 541. Thus his mother, the second ovarian cancer case in the pedigree, is an obligate carrier of a Leu 217+ Thr 541 allele. The observation of two ovarian cancer cases in this pedigree, both of whom carry deleterious alleles of ELAC2, is consistent with the possibility that the phenotype conferred by deleterious variants in this gene is not restricted to prostate cancer susceptibility.

The potential contributions of the androgen receptor CAG repeat and SRD5A2 Ala 49 Thr missense change to prostate cancer risk were first detected in association studies using sporadic cases and unaffected controls. However, straightforward decluction from the considerable literature on sib pair analyses would predict that such sequence variants should be enriched among affected sibs versus isolated cases, and it follows that such sequence variants should contribute to a larger fraction of familial than truly sporadic prostate cancer cases. Thus one might expect genotypes at moderate risk susceptibility genes such as the androgen receptor, SRD5A2, and the common missense changes in HPC2/ELAC2, to confound linkage studies aimed at detecting and localizing lower prevalence, higher risk susceptibility genes. However, inclusion of genotype information from pedigree members at multiple moderate risk loci may allow refined definition of the liability classes used by multipoint linkage software, thereby increasing the power of the analysis. Stratification of cases by genotype would also facilitate positional cloning projects by providing another criterion by which to distinguish between true recombinant carriers and confounding sporadic cases.

The genetic data presented demonstrate that there are deleterious sequence variants in HPC2/ELAC2 that contribute to prostate cancer risk. Elucidating the functional alteration by which a moderate risk sequence variant such as Leu 217 contributes to a late onset pathology could prove difficult because its manifestation could be quite subtle. However, a mutation as dramatic as a frameshift leading to protein truncation within the likely active site of an enzyme should have a more easily detected effect on cell physiology. Conservation of the C-terminal domain of the gene through the eubacteria and archaebacteria, combined with the observation that the *S. cerevisiae* ortholog YRK079C is essential, emphasize that the function of the ELAC1/2 gene family is of fundamental biological interest.

The identification of the association between the HPC2 gene mutations and prostate cancer permits the early presymptomatic screening of individuals to identify those at risk for developing prostate cancer. TIo identify such individuals, HPC2 alleles are screened for mutations either directly or after cloning the alleles. TIhe alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide ASO), dot blot analysis and PCR-SSCP analysis. Also useful is the recently developed technique of DNA microchip technology. For example, either (1) the nucleotide sequence of both the cloned alleles and normal HPC2 gene or appropriate fragment (coding sequence or genomic sequence) are determined and then compared, or (2) the RNA transcripts of the HPC2 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the HPC2 oene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal HPC2 gene.

Alternatively, polymerase chain reactions (PCRs) are performed with primer pairs for the 5 region or the exons of the HPC2 gene. PCRs can also be performed with primer pairs based on any sequence of the normal HPC2 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common HPC2 gene variants by amplifying the individual s DNA using suitable primer pairs and analyzing the amplified product, e.g., by dot-blot hybridization using allele-specific oligonucleotide probes.

The second method employs RNase A to assist in the detection of differences between the normal HPC2 gene and defective genes. This comparison is performed in steps using small (~500 bp) restriction fragments of the HPC2 gene as the probe. First, the HPC2 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the HPC2 gene fragments are transcribed in vitro using the SP6 transcription system, well known in the art, in the presence of $[\alpha\text{-}^{32}P]GTP$, generating radiolabeled RNA transcripts of both strands of the gene.

Individually, these RNA transcripts are used to form heteroduplexes with the allelic DNA using conventional techniques. Mismatches that occui in the RNA:DNA heteroduplex, owing to sequence differences between the HPC2 fragment and the HPC2 allele subdlone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the HPC2. These variants can take a number of forms. The most severe forms would be frame shift mutations or large deletions which would cause the gene to code for an abnormal protein or one which would significantly alter protein expression. Lress severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk prostate cancer, at, or even before, birth. Presymptomatic diagnosis of these epilepsies will enable prevention of these disorders.

EXAMPLES

The present invention is further detailed in the following Examples, which are offered by way of illustration and are not intended to limit the invention in any manner. Standard techniques well known in the art or the techniques specifically described below are utilized.

Example 1

Linkage Analysis

All participants signed informed consent documents. This research project has the approval of the University of Utah School of Medicine Institutional Review Board. Ninety-seven percent of cancer cases have been confirmed through medical records (and/or through the Utah Cancer Registry for prostate cancer cases diagnosed in Utah). Two-point linkage analysis was performed with the package LINKAGE (Lathrop et al., 1984) using the FASTLINK implementation (Cottingham et al., 1993; Schaffer et al., 1994). The statistical analysis for the inheritance of susceptibility to prostate cancer used a model that assumes age-specific incidence rates from the Utah Cancer Registry, and a relative risk of 2.5 for first-degree relatives. Susceptibility to prostate cancer was assumed due to a dominant allele with a population frequency of 0.003. The details of the model are more thoroughly defined in Neulhausen et al. (1999). Marker allele frequencies were estimated from unrelated individuals present in the pedigrees. Linkage in the presence of heterogeneity was assessed by the admixture test (A-test) of Ott (1986), using HOMOG, which postulates two family types linked and unlinked. Three-point linkage analysis was performed using VITESSE (O'Connell and Weeks, 1995).

Example 2

Physical Mapping

BAC DNA was purified and directly sequenced as previously described (Couch et al., 1996). DNA sequences at the SP6 and T7 ends of isolated BAC clones were used to develop STSs that were used for mapping and contig extension. Greater than 95% sequence coverage of the FIG. 1 BAC tiling path was obtained by sequencing plasmid sub-libraries generated from these clones. The sequence data obtained were assembled into contigs using Acembly, version 4.3 (U. Sauvage, D. Thierry-Mieg and J. Thierry-Mieg; Centre National de la Recherche Scientifique, France). Subsequently, a complete sequence of this interval was released by the MIT genome center.

Example 3

Genetic Localization of HPC2

A. Early Studies

A set of high risk prostate cancer kindreds has been collected in Utah since 1990 for the purpose of localization of prostate cancer susceptibility loci. In February 1996, linkage analysis of data from a genome scan performed on a subset of the families noted evidence for linkage with markers on chromosome 17p. Subsequent analysis of more markers in this region of chromosome 17p in a larger set of families has led to strong linkage evidence for a susceptibility gene.

TABLE 1

Chromosome 17p Two-point Linkage Evidence

| Marker | 17p map position | Heterogeneity Lod Score |
|---|---|---|
| D17S786 | 20.0 | 4.21 |
| Myr 0022 | 25.5 | 3.99 |
| Myr 0088 | 27.0 | 3.46 |
| D17S947 | 31.6 | 2.32 |
| Myr 0084 | 31.9 | 3.02 |
| Myr 0079 | 32.0 | 0.99 |
| D17S805 | 43.6 | 2.25 |

The study of specific kindreds with strong evidence of linkage to chromosome 17p allows the definition of a most likely region for the susceptibility locus by identifying the smallest inherited piece of chromosome 17p shared by the prostate cancer cases in the kindred. The minimal genetically defined region is based on a telomeric recombinant in kindred 4325 and a centromeric recombinant in kindred 4320. Kindred 4325 was ascertained from a sibship of early onset prostate cancer cases. There are 6 affected brothers in this family, one of whom also has an affected son. Five of the 6 affected brothers, and the affected son, all share the same piece of chromosome 17p from somewhere below marker myr0065 down to and including marker D17S805. Kindred 4320 was also ascertained from a sibship of early onset prostate cancer cases. In this kindred 3 affected brothers and an affected nephew share a piece of chromosome 17p from D17S786 down to and including myr0084. Together, the kindred 4325 and kindred 4320 recombinants define a minimal region of about 1 megabase (FIG. 2A); this localization is well supported by a larger set of recombinants in both directions.

B. Recent Studies

We originally performed a orenome-wide search for prostate cancer predisposition loci using a small set of Utah high risk prostate cancer pedigrees and a set of 300 polymoiphic markers. The pedigrees were not selected for early age of cancer onset, but were a subset of families ascertained using the Utah Population Database. The first eight pedigrees analyzed gave suoaestive evidence of linkage on chromosome 17p near marker D17S520, although significance was not established. We increased the density of markers in the region and expanded the analysis to 33 pedigrees (Table 2A). Analysis of the additional data, using a dominant model integrated with Utah age-specific incidence, yielded the two-point linkage evidence shown in Table 2B. A maximum two-point LOD score of 4.5 was observed at marker D17S1289, theta=0.07, and a maximum three-point LOD score of 4.3 was observed using the markers D17S1289 and D17S921. Based on these data, we initiated a positional cloning project, focusing on the interval between D17S 1289 and D17S921.

TABLE 2A

Family Resource Used to Detect Linkage to 17p

| | |
|---|---|
| Number of pedigrees | 3.3 |
| Total number of cases | 338 |
| Totai number of typed cases | 188 |
| Mean number of cases/pedigree (range) | 10.2 (2–29) |
| Mean number of typed cases/pedigree (range) | 5.7 (1–16) |
| Mean age of typed cases at diagnosis (range) | 68.3(35≠88) |

TABLE 2B

Two-point LOD Scores Using Utah Age-specific Model

| Marker | distance (cM)† | Max LOD¥ (theta) | Hetero geneity LOD (alpha, theta) |
|---|---|---|---|
| D17S796 | — | 0.11 (.37) | 0.10 (1.00, 0.4) |
| D17S952 | 10.2 | 0.90 (.17) | 0.87 (1.00, 0.2) |
| D17S786 | 10.4 | 0.00 (.50) | 0.95 (0.20, 0.0) |
| D17S945 | 12.7 | 0.38 (.28) | 1.41 (0.25, 0.0) |
| D17S520 | 15.0 | 0.69 (.26) | 0.64 (1.00, 0.3) |
| D17S974 | 15.1 | 1.01 (.20) | 1.20 (0.40, 0.01) |
| D17S1289 | 15.2 | 4.53 (.07) | 4.43 (1.00, 0.1) |
| D17S1159 | 15.4 | 0.50 (.27) | 1.38 (0.25, 0.0) |
| GATA134G03 | 15.7 | 0.48 (.20) | 0.78 (0.75, 0.2) |
| D17S954 | 16.2 | 0.00 (.50) | 0.11 (0.40, 0.2) |
| D17S969 | 18.2 | 0.54 (.21) | 0.55 (0.85, 0.2) |
| D17S799 | 22.0 | 0.30 (.26) | 0.44 (0.70, 0.2) |
| D17S921 | 25.2 | 1.41 (.10) | 1.42 (0.95, 0.1) |
| D17S953 | 29.2 | 1.04 (.25) | 0.94 (1.00, 0.3) |
| D17S925 | 31.2 | 0.02 (.45) | 0.00 (1.00, 0.0) |
| D17S798 | 36.2 | 0.02 (.43) | 0.02 (1.00, 0.4) |

†Distances estimated from data using CRIMAP (Lander and Green, 1987).
¥Maximum LOD scores interpolated using the standard quadratic function.

In order to refine the localization of the implied susceptibility gene, we expanded to the set of 127 families (Table 3) which have now been typed at both this locus and the HPC1 locus. Although the overall data set neither provides significant LOD score evidence for linkage on chromosome 17 nor provides sufficient evidence for de novo identification of the HPC1 locus (Neuhausen et al., 1999), complete haplotyping of the pedigree resource revealed a similar number of prostate cancer-associated haplotypes at each locus.

TABLE 3

Summary of Resource Genotyped for the Association Tests

| | |
|---|---|
| Number of pedigrees | 127 |
| Total number of cases | 2,402 |
| Total number of typed cases | 700 |
| Total number of typed pedigree unaffecteds | 3,295 |
| Total number of typed divergent controls | 243 |
| Mean number of cases/pedigree (range) | 18.3 (3–74) |
| Mean number of typed cases/pedigree (range) | 5.5 (1–34) |
| Mean age of typed cases at diagnosis (range) | 66.5(39–88) |

Early in our analysis, we observed that at both 17p and HPC1 many of our pedigrees segregate haplotypes that are shared by four or more cases, but also contain enough noncarrying cases with respect to either locus to eliminate any linkage evidence within the pedigree, as estimated by LOD score. For instance, 12 affected individuals from kindred 4333 share an HPC1 haplotype and 9 affecteds in kindred 4344 share a 17p haplotype, but neither pedigree shows LOD score evidence for linkage at either locus. While we r ecognize that this phenomenon may be due simply to lack of linkage, we hypothesized that the underlying cause is actually genetic complexity that is greater than the linkage models can accommodate. We subsequently used multipoint haplotyping software (Thomas et al., 2000) to define segregating haplotypes, and then classified those haplotypes into three groups, depending on strength of evidence: group 1 haplotypes, used for both localization and mutation screening, were defined as haplotypes shared by 4 or more cases and giving a LOD score$\geq$1.0 in the pedigree where they were identified, or haplotypes shared by 6 or more cases irrespective of LOD score; group 2 haplotypes, used for mutation screening only, were defined as haplotypes shared by 4 cases with 0.5<LOD<1.0 in the pedigree where they were identified, or haplotypes shared by 5 cases with LOD<1.0; and finally, haplotypes that failed to meet either of the above criteria.

Figure 3:
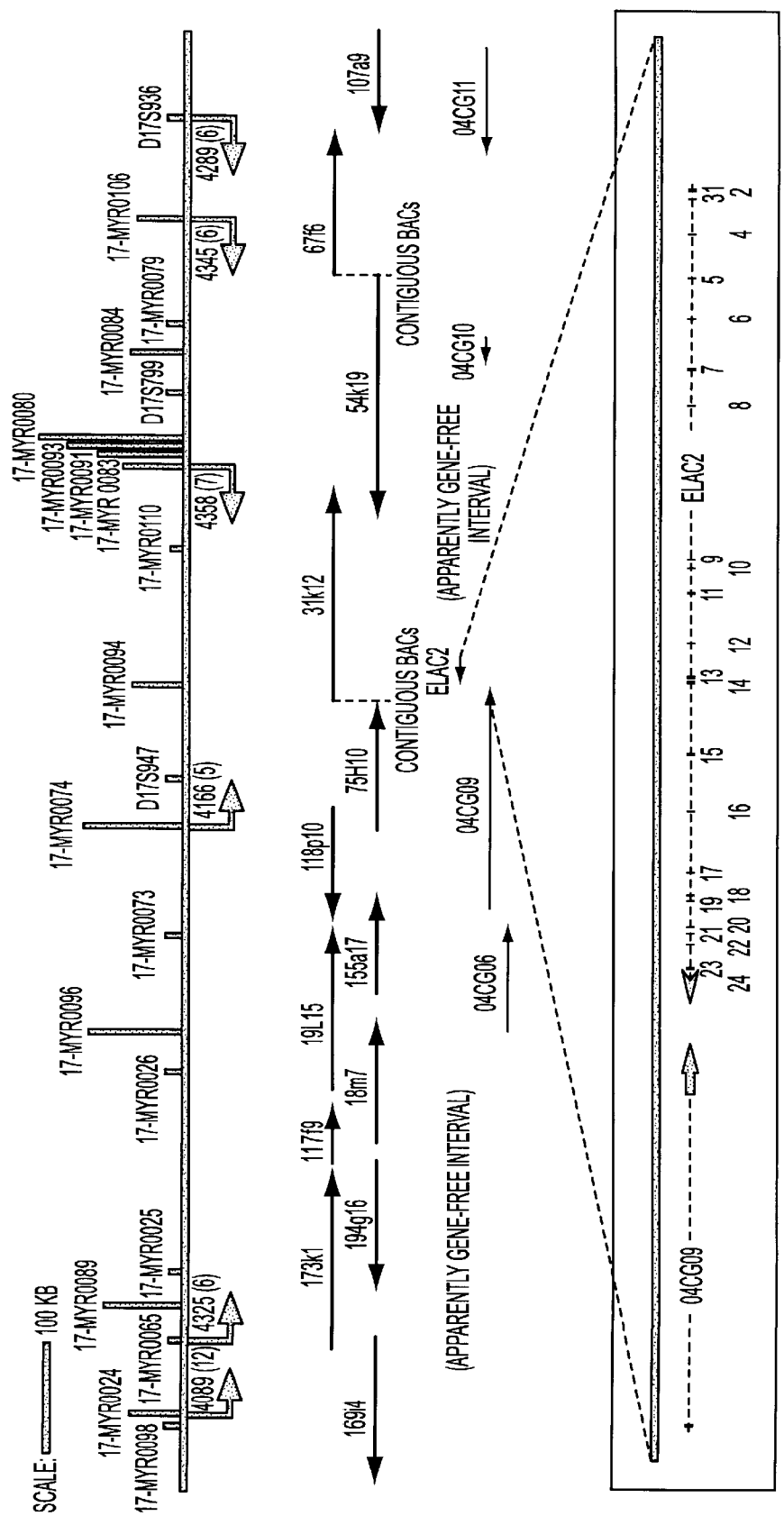
FIG. 3 shows recombinant, physical and transcript maps centered at the human ELAC2 locus on chromosome 17p. The top portion shows genetic markers and recombinants. Microsatellite markers developed at Myriad Genetics, Inc. are given as 17-MYR####. Nested within the arrows that represent meiotic recombinants are the pedigree in which the recombinant occurred and, in parentheses, the number of cases who carry the haplotype on which the recombinant occurred. The second portion of the figure shows a BAC contig tiling path across this interval. The T7 end of each BAC is denoted with an arrowhead. The third portion of the figure shows transcription units identified in the interval. The bottom portion of the figure is an expanded view of a 40 kb segment at the SP6 end of BAC 31k12 showing the relative positions of two exons of the gene 04CG09 and all of the coding exons of ELAC2.

Considering group 1 and 2 haplotypes together, evidence at HPC1 and 17p is quite similar: 43 haplotypes at HPC1 versus 42 at 17p and 258 affected haplotype carriers at HPC1 versus 232 at 17p. Focusing on the group 1 haplotypes, evidence at HPC1 is relatively stronger: 26 group 1 haplotypes at HPC1 versus 18 at 17p and an average of 7.2 affected carriers per group 1 haplotype at HPC1 versus 6.6 at 17p. However. there is one other critical difference between the linkage evidence for the two regions. At HPC1, meiotic recombinant mapping using the group 1 haplotypes has thus far failed to define a consistent region. This is also reflected in the ICPCG HPC1 study (Xu, 2000); in this work, most of the evidence for linkage comes from a combination of the Utah and Hopkins data sets, but the locations with the best evidence for linkage in each of the individual sets map approximately 15 cM apart. In contrast, recombinant mapping in affected carriers of 17p group 1 haplotypes defined a consistent region (FIG. 3). As a result, we were able to focus our contig assembly, transcript map development, and mutation screening efforts on an approximately 1 MB interval centered on D17S947 (FIG. 3).

One of the genes mapping near D17S947 shares amino acid sequence similarity with members of the NCBI Cluster of Orthologous Groups (Tatusov et al., 1997) COG1234, typified by the uncharacterized *E. coli* ORF elaC and the uncharacterized *S. cerevisiae* ORF YKR079C. On mutation screening this candidate gene from the genomic DNA of prostate cancer cases carrying 17p group 1 haplotypes, a germline frameshift mutation, 1641 insG, was found in a carrier from kindred 4102. Following detection of this frameshift, the gene, which we shall refer to as ELAC2 because it is the larger of two human genes that we have found that are homologs of *E. coli* elaC, was subjected to careful sequence and intense genetic analyses.

Example 4

Contig Assembly and Genomic Sequencing in the Minimal Genetically Defined HPC2 Region Contig assembly. Given a genetically defined interval flanked by meiotic recombinants, one needs to generate a contig of genomic clones that spans that interval. Publicly available resources, such as the Whitehead integrated maps of the human genome (e.g., the WICGR Chr 17 map) provide aligned chromosome maps of genetic markers, other sequence tagged sites (STSs), radiation hybrid map data, and CEPH yeast artificial chromosome (YAC) clones.

Figure 2A:
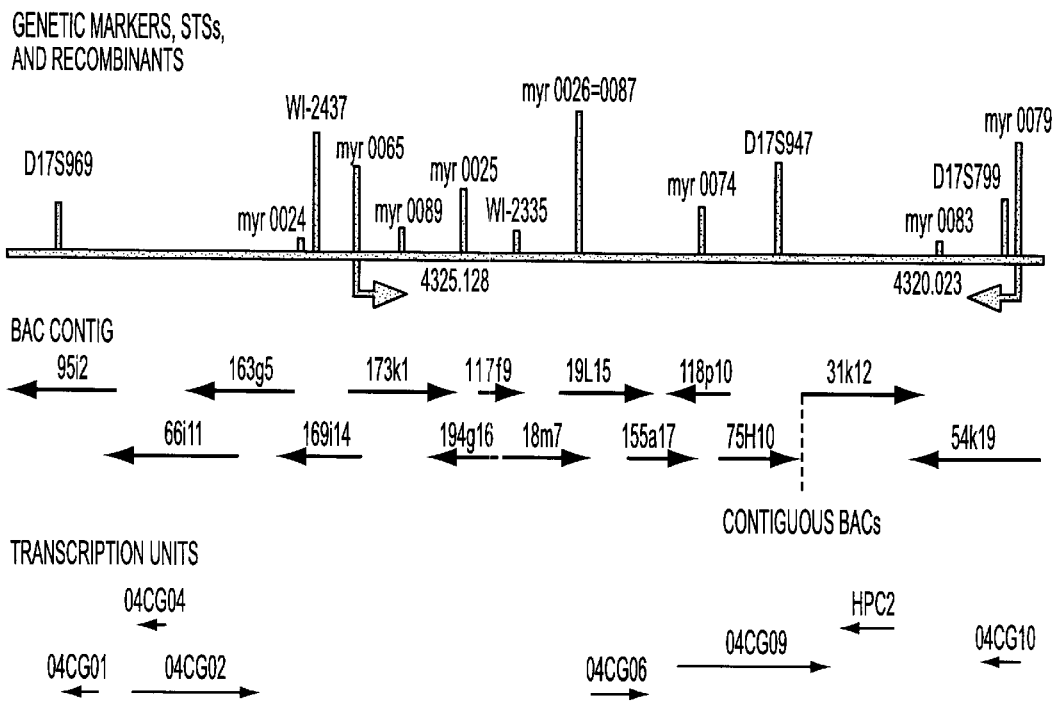
FIGS. 2A–B are diagrams showing the order of genetic markers and recombinant boundaries neighboring HPC2, a schematic map of BACs spanning the HPC2 region, a schematic map of transcription units within the HPC2 region, and two diagrams of the HPC2 transcription unit showing the locations of the exons of HPC2 relative to the BAC to which it maps and relative to each other. The individual exons are numbered.

Oligonucleotide primer pairs for the markers located in the interval were synthesized and used to screen libraries of bacterial artificial chromosomes (BACs) to identify BACs in the region. The initial set of markers used was D17S969. WI-2437, WI-2335, D17S947, and D17S799 (FIG. 2A). BACs identified with these markers were end-sequenced. PCR primers designed from those end sequences were used as markers to arrange the initial BACs into contigs. The outermost marker from each contig was used in successive rounds of BAC library screening, eventually enabling the completion of a BAC clone contig that spanned the genetically defined interval. A set of overlapping but non-redundant BAC clones that spanned this interval (FIG. 2A) was then selected for use in subsequent molecular cloning protocols such as genomic sequencing.

Genomic sequenicing. Given a tiling path of BAC clones across a defined interval, one useful gene finding strategy is to generate an almost complete genomic sequence of that interval. Two types of random genomic cloHe sublibraries were prepared from each BAC on the tiling path; these were Sau 3A partial digest libraries with inserts in the 5 to 8 kb size range, and random shear libraries with inserts in the 1.0 to 1.5 kb size range. Plasmid DNA from individual clones from the Sau 3A sublibraries sufficient in number to generate an, on average, 1× redundant sequence of each BAC was prepared using an Autogen robotic plasmid preparation machine (Integrated Separation Systems). Insert DNA from individual clones from the random shear sublibraries sufficient in number to generate an, on average, 5× redundant sequence of each BAC, was prepared by PCR with vector primers directly from aliquots of bacterial cultures of each individual clone. The resulting DNA templates were subjected to DNA sequencing from both ends with M13 forward or reverse fluorescent dye-labeled primers on ABI 377 sequencers.

These sequences were assembled into sequence contigs using the program Acem.bly (Thierry-Mieg et al., 1995; Durbin and Thierry-Mieg, 1991). The genomic sequence contigs were placed in a Genetic Data Environment (GDE) (Smith et al., 1994) local database for subsequent similarity searches. Similarities among genomic DNA sequences and GenBank entries—both DNA and protein—were identified using BLAST (Altschul et al., 1990). The DNA sequences were also characterized with respect to short period repeats, CpG content, and long open reading frames.

Example 5

Sequence Assembly of the Human HPC2 Gene

Figure 2B:
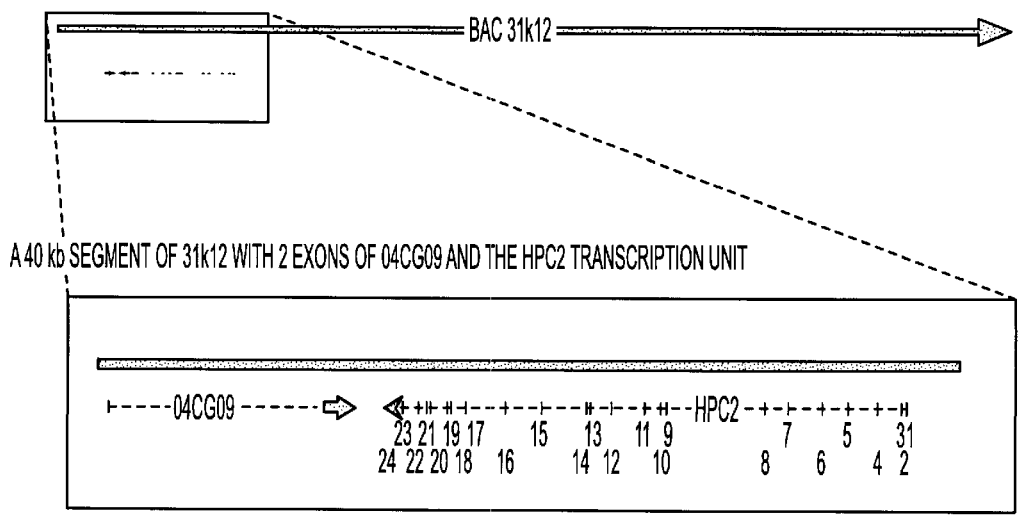

A BLASTn (Altschul et al., 1990) search of geniomic sequences from BAC 31k12 against dbEST identified two independent sets of human ESTs that, when parsed across the BAC 31k12 enomic sequences, revealed the presence of two independent multi-exon candidate genes, 04CG09 and the HPC2 gene (FIG. 2B). A subset of the EST sequences assigned to HPC2 (Table 4) was assembled to produce a tentative partial cDNA sequence for the gene.

TABLE 4

Human ESTs Used to Assemble a Tentative Partial Human HPC2 cDNA Sequence

| EST Accession # | Exon Span |
|---|---|
| AA679618 | 1→6 |
| Z17886 | 4→8 |
| W37591 | 7→12 |
| AA310236 | 12→16 |
| R55841 | 15→19 |
| T34216 | 18→21 |
| AA634909 | 20→24 |
| AA504412 | 23→24 |
| R42795 | 24→polyA |

The individual exons of the human HPC2 gene were identified by parsing that tentative cDNA sequence across the BAC 31k12 genomic sequence (see schematics in FIG. 2B). After we had identified the HPC2 gene, the MIT genome sequencing completely sequenced another BAC, 597m12, that also contains all of the exons of HPC2 (GenBank accession # AC005277) The sequence of the human HPC2 gene was corrected both by comparison of the sequences of the individual exons from the tentative cDNA assembly to the corresponding genomic sequences of BACs 31k12 and 597m 12, and by mutation screening, the gene from a set of human genomic DNAs (see Example 8).

The original tentative human HPC2 cDNA sequence contained neither the start codon nor any of the 5' UTR. These were obtained by biotin capture 5' RACE (Tavtigian et al., 1996). Briefly, a biotinylated reverse primer, CA4cg07.BR2, was designed from the sequence of the third exon of the human HPC2 gene and used, along with the anchor primer 5ampA, for a first round of PCR amplification from human fetal liver cDNA that had been prepared such that the 5' ends of cDNA molecules are anchored with the sequence 5tag1. The resulting PCR products were captured on streptavidin paramagnetic particles (Dynal), washed, and used as template in a second round PCR amplification. A phosphorylated reverse primer, CA4cg07.PR2, was designed from the sequence of the second exon of the human HPC2 sequence and used, along with the nested phospho-iylated anchor primer 5ampB, for the second round PCR amplification. The resulting 5' RACE products were gel purified and sequenced with the primer CA4cg07.PR2 using dye-terminator chemistry and ABI 377 sequencers. Analysis of the sequences of these 5' RACE products yielded both the start codon and part of the 5' UTR including an in-frame stop codon (FIG. 4). Sequences of the human primers used for 5' RACE are given in Table 5.

A full length human HPC2 cDNA was amplified from human head and neck cDNA using the primers CA4cg7.ATG and CA4cg7.TGA. The cDNA was ligated into the vector pGEM-T Easy (Promega) and transformed into *E. coli*. The sequence of the cDNA clone was confirmed by dye terminator sequencing on ABI 377 sequencers. Sequences of primers used to amplify the cDNA construct and confirm the sequence of the cDNA clone are also given in Table 5.

TABLE 5

Primers Used in 5'RACE,cDNA Cloning and Sequence Confirmation of a Full-length Human HPC2 cDNA Sequence (SEQ ID NO:)

5'RACE PRIMERS

```
5tag1        CAG GAA TTC AGC ACA TAC TCA TTG TTC Agn n (29)
5AmpA        CAG GAA TTC AGC ACA TAC TCA (30)
5AmpB        (P)TT CAG CAC ATA CTC ATT GTT CA (31)
CA4cgD7.BR2  (B)TG AAC GCC TTC TCC ACA GT (32)
CA4cgO7.PR2  (P)GT ACC CGC TGC CAC CAC (33)
```
EXPRESSION CONSTRUCT PRIMERS

```
CA4cg7.ATG   GCT AGG ATC CGC CAC CAT GTG GGC GCT TTG CTC (34)
CA4cg7.TGA   GCT ACT CGA GTC ACT GGG CTC TGA CCT TC (35)
```
SEQUENCING PRIMERS

```
M13F20       GTA AAA CGA CGG CCA GT (36)
M13R20       GGA AAC AGC TAT GAC CAT G (37)
CA4cg7F1     TGC GCA CGC GAG AGA AG (38)
CA4cg7R1     CGC TTC TCT CGC GTG CG (39)
CA4cg7F2     TCT AAT GTT GGG GGC TTA (40)
CA4cg7R2     TAA GCC CCC AAC ATT AGA (41)
CA4cg7F3     TGA AAA TGA GCC ACA CCT (42)
CA4Cg7R3     AGG TGT GGC TCA TTT TCA (43)
CA4Cg7F4     CAT TCA ACC CAT CTG TGA (44)
CA4Cg7R4     TCA CAG ATG GGT TGA ATG (45)
CA4cg7F5     TGA ATG CCT CCT CAA GTA (46)
CA4cg7R5     TAC TTG AGG AGG CAT TCA (47)
CA4cg7F6     GCT ACT GGA CTG TGG TGA (48)
```

TABLE 5-continued

Primers Used in 5'RACE,cDNA Cloning and Sequence Confirmation of a Full-length Human HPC2 cDNA

| | Sequence (SEQ ID NO:) |
|---|---|
| CA4cg7R6 | TCA CCA CAG TCC AGT AGC (49) |
| CA4cg7F7 | TGG AAG AGT TTC AGA CCT G (50) |
| CA4Cg7R7 | CAG GTC TGA AAC TCT TCC A (51) |
| CA4Cg7F8 | CGC AGG GAC GCA CCA TA (52) |
| CA4Cg7R8 | GGT TGA ACT CGG AGA AGA (53) |
| CA4Cg7F9 | CAA CTG GAA AAA TAC CTC G (54) |
| CA4cg7F10 | GCA GAG TCC AGA AAG GC (55) |
| CA4cg7F11 | AGA GGA AAC TTC TTG GTG C (56) |
| CA4cg7F12 | ACC AAG GAA AGG CAG ATG (57) |
| CA4cg7F13 | GTC AAC ATA AGC CCC GAC (58) |
| CA4cg7F14 | GGC TGC TGT GTT TGT GTC (59) |
| CA4cg7R14 | GAA GGC ATT TGG CAG GA (60) |
| CA4cg7F15 | TAT GAT TCC TGC CAA ATG (61) |
| CA4cg7R15 | TCC AGC CAG AGG TGT GC (62) |
| CA4cg7F16 | TGC GAG GCT CTG GTC CG (63) |
| CA4cg7R16 | GGG CAT TGT TGG AAA GTC (64) |
| CA4cg7F17 | TGT TTG CTG GCG ACA TC (65) | n n- the last 2 nucleotides of the anchor sequence 5tagl are specific for each cDNA prep.
(P)indicates phosphate at the 5' end of the oligo
(B)indicates biotin at the 5' end of the oligo

Example 6

Sequence Assembly of the Mouse HPC2 Gene

A BLAST search of the assembled HPC2 cDNA sequence against dbEST identified 5 mouse ESTs that derived from a very similar gene, the mouse ortholog of HPC2, Mm.HPC2; their accession numbers are listed in Table 6.

TABLE 6

Mouse ESTs Used to Assemble a Tentative Partial Mm.HPC2 cDNA Sequence

| EST Accession # | Exon Span |
|---|---|
| AA563096 | 1→5 |
| AA518169 | 8→14 |
| A1132016 | 16→17 |
| AA184645 | 19→24 |
| AA174437 | 24→24 |

The original partial Mm.HPC2 cDNA sequence contained the start codon but little of the 5' UTR. More extensive 5' UTR sequence was obtained by 5' RACE. Briefly, a biotinylated reverse primer, m04cg07BR1, was designed from the sequence of the fourth exon of the mouse HPC2 gene and used, along with the anchor primer 5ampA, for a first round of PCR amplification from mouse embryo cDNA that had been prepared such that the 5' ends of cDNA molecules are anchored with the sequence 5tag1. The resulting PCR products were captured on streptavidin paramagnetic particles (Dynal), washed, and used as template in a second round PCR amplification. A phosphorylated reverse primer, m04cg07PR1, was designed from the sequence of the third exon of the mouse HPC2 sequence and used, along with the nested phosphorylated anchor primer 5ampB, for the second round PCR amplification. The resulting 5' RACE products were gel purified and sequenced with the primers m04cg07PRI and m04cg07 exon2 rev using dye-terminator chemistry and ABI 377 sequencers. Analysis of the sequences of these 5' RACE products yielded both the start codon and part of the 5' UTR including an in-frame stop codon (FIG. 4). Sequences of the primers used for 5' RACE are given in Table 7.

More extensive 5' UTR sequence, sequence that may be from the promoter, and the sequences of intron 1 and intron 2 of the mouse HPC2 gene were obtained by genomic sequencing. BAC 428n12 was obtained from a mouse genomic library by screening the library by PCR with a pair of primers (04CG7.m11f1 and 04CG7.m11r1, Table 7) derived from exon 11 of the mouse HPC2 cDNA sequence. A primer pair derived from the SP6 end sequence of BAC 428n12 (428n12.S6.F1 and 428n12.S6.F1, Table 7) was used to screen the mouse BAC library by PCR; several overlapping BACs, including BAC 199n11, were identified. BACs 428n12 and 199n11 were sequenced with a series of 13 sequencing primers (mcg7f1 to mcg7r7, Table 7) derived from mouse HPC2 cDNA dye-terminator chemistry and ABI 377 sequencers. A subset of these sequences were assembled into a genomic sequence contig extending from 280 bp upstream of the ATG start codon of exon 1 into exon 3.

A full length mouse HPC2 cDNA is amplified from mouse embryo, placenta, or fetal brain cDNA using the primers msCA4cg7.f out and msCA4cg7.r out The cDNA is reamplified with the primers msCA4cg7.ATG and msCA4cg7.TFGA. The resulting PCR products are gel purified, ligated into the vector pGEM-T Easy (Promega), and transformed into E. coli. The sequence of the cDNA clone are confirmed dye terminator sequencing on ABI 377 sequencers. Sequences of primers in use to amplify the cDNA construct are also given in Table 7.

TABLE 7

Primers Used in 5' RACE and cDNA
Cloning of a Full-length Mouse HPC2 cDNA

Sequence (SEQ ID NO:)

5'RACE PRIMERS

| | |
|---|---|
| 5tag1 | CAG GAA TTC AGC ACA TAC TCA TTG TTC Agn n (66) |
| 5AmpA | CAG GAA TTC AGC ACA TAC TCA (67) |
| 5 Amp B | (P)TT CAG CAC ATA CTC ATT GTT CA (68) |
| mO4cgO7BR1 | (B)CA GAA CAC ATT TGG GAA GC (69) |
| mO4cgO7PR1 | (P)GA TGT TGT CCA AGC GAG C (70) |

BAC library screening primers

| | |
|---|---|
| 04CG7.ml 1fl | TGA CAC ACA GCA CCT GA (71) |
| 04CG7.ml 1rl | GAA GAT GTC AGG GTG GA (72) |
| 428n12.S6.F1 | CAG GCA TAC CAC TAC AGA (73) |
| 428n12.S6.R1 | TAT CAA CTT CTA GGC AAG TG (74) |

Genomic sequencing primers

| | |
|---|---|
| mcg7f1 | GCA CCA TGT CGC AGG GTT C (75) |
| mcg7r1 | GAA CCC TGC GAC ATG GTG C (76) |
| mcg7f2 | TCG CAG GGT TCG GCT CGT C (77) |
| mcg7r2 | AAC CCT GCG ACA TGG TGC G (78) |
| mcg7f3 | AAA GAC CCA CTG CGA CAC C (79) |
| mcg7r3 | GCA GGT GTC GCA GTG GGT C (80) |
| mcg7f4 | CCG AAC ACC GTG TAC CTG CA (81) |
| mcg7r4 | CAG GTA CAC GGT GTT CGG G (82) |
| mcg7f5 | GTC TTC TCG GAA TAC AAC AGG (83) |
| mcg7r5 | CTG TTG TAT TCC GAG AAG AC (84) |
| mcg7F6 | AAG GCG TCC AAC GAC TTA TG (85) |
| mcg7r6 | AGT CGT TGG ACG CCT TCT CC (86) |
| mcg7r7 | TCC GAG TCA GAA AGA TGT TG (87) |

EXPRESSION CONSTRUCT PRIMERS

PRIMARY PCR

| | |
|---|---|
| msCA4cg7.f out | GCC TTG TCA GCC TGG TG (88) |
| msCA4cg7.r out | AGG AAG TGA GCA GAG CG (89) |

SECCNDARY PCR

| | |
|---|---|
| msCA4cg7.ATG | GCT AAA GCT TGC CAC CAT GTG GGC GCT CCG CTC (90) |
| msCA4cg7.TGA | GCT ACT CGA GTC ACA CTC GCG CTC CTA (91) |

SEQUENCING PRIMERS

| | |
|---|---|
| mO4cgO7 exon2 rev | GCC TTC TCC GCA GTT A (92) | nn- the last 2 nucleotides of the anchor sequence 5tag1 are specific for each cDNA prep
(P)indicates phosphate at the 5' end of the oligo
(B)indicates biotin at the 5' end of the oligo

Example 7

Northern Blots

Prehybridization and hybridization were performed at 42° C. in 50% formamide, 5×SSPE, 1.0% SDS, 5×Denhardt's mixture, 0.2 mg/mL denatured salmon sperm DNA, and 2 μg/mL poly(A). Dextran sulfate (4% v/v) was included in the hybridization solution only. The membranes were washed twice in 2×SSC/0.1% SDS at 20° C. for 30 minutes. followed by a stringency wash in 0.1×SSC/0.1% SDS at 50° C. for 30 minutes.

Example 8

Mutation Screening of the Human HPC2 Gene

Using genomic DNAs from prostate kindred members, prostate cancer affecteds and tumor cell lines as templates, nested PCR amplifications were performed to generate PCR products to screen for mutations in the HPC2 gene. The primers listed in Table 8 were used to amplify segments of the HPC2 gene. Using the outer primer pair for each amplicon (1A–1P, i.e., forward A and reverse P of amplicon 1), 10–20 ng of genomic DNA were subjected to a 25 cycle primary amplification, after which the PCR products were diluted 45-fold and reamplified using nested M13-tailed primers (1B–1Q, 1C–1R i.e., nested forward B and nested reverse Q of amplicon 1 or nested forward C and nested reverse R of amplicon 1) for another 23 cycles. In general. samples were amplified with Taq Platinum (Life Technologies) DNA polymerase; cycling parameters included an initial denaturation step at 95° C. for 3 min, followed by cycles of denaturation at 96° C. (12 s), annealing at 55° C. (15 s) and extension at 72° C. (30–60 s). After the PCR reactions, excess primers and deoxynucleotide triphosphates were digested with exonuclease I (United States Biochemicals) and shrimp alkaline phosphatase (Amersham). PCR products were sequenced with M13 forward or reverse fluorescent (Big Dye. ABI) dye-labeled primers on ABI 377 sequencers. Chromatograms were analyzed for the presence of polymorphisms or sequence aberrations in either the Macintosh program Sequencher (Gene Codes) or the Java program Mutscreen. We obtained more than 95% double strand sequence coverage for the entire open reading frame of all samples screened.

TABLE 8

Primers Used to Mutation Screen the HPC2 Gene from Genomic DNA

| Exon/Primer name | Sequence (SEQ ID NO:) |
|---|---|
| HPC2 exon 1 | |
| ca4cg7.m1Anew | CCG CTT GAG ACG CTC TAG TAT (93) |
| ca4cg7.m1P | GCT CCG AAA GTG CTG ACA G (94) |
| ca4cg7.m1Bnew | GTT TTC CCA GTC ACG ACG TTT CTA TTG GAT GAG CAG CCT (95) |
| ca4cg7.m1Qnew | AGG AAA CAG CTA TGA CCA TGC CTG CGA TAT GGT GCG TC (96) |
| ca4cg7.m1C | GTT TTC CCA GTC ACG ACG CTC AGT TTT GGT GGA GAC G (97) |
| ca4cg7.m1Rnew | AGG AAA CAG CTA TGA CCA TGT GCC CCG ATG CTC AGA G (98) |
| HPC2 exons 2 & 3 | (primary) |
| ca4cg7.m2 & 23 A2 | AAT GGT GTC AGA GAG TTT ACA G (99) |
| ca4cg7.m2 & 23P | GCT ATT TGG GAG GCT GAG G (100) |
| HPC2 exon 2 | (nested) |
| ca4cg7.m2B | GTT TTC CCA GTC ACG ACG AAT GGT GTC AGA GAG TTT ACA G (101) |
| ca4cg7.m2Q | AGG AAA CAG CTA TGA CCA TGA ACA AGG ACC ACT TTT GCT AT (102) |
| HPC2 exon 3 | (nested) |
| ca4cg7.m23B | GTT TTC CCA GTC ACG ACG TTT ATA GCA AAA GTG GTC CTT G (103) |
| ca4cg7.m23Q | AGG AAA CAG CTA TGA CCA TGA GAC TTC CCA CCA GCC TC (104) |
| HPC2 exon 4 | |
| ca4.cg07.m24A | CCT TGC TGC TTC ACC CTA G (105) |
| ca4.cg07.m24P | TGC TTT ATA TGT GCT GCT ACG (106) |
| ca4cg7.m24B | GTT TTC CCA GTC ACG ACG CAT CTT CCC TGG TTG TAC TTC (107) |
| ca4.cg07.m24Q | AGG AAA CAG CTA TGA CCA TCT GCA GGG CAG AAG ACT GAT (108) |
| HPC2 exon 5 | |
| ca4cg7.m3A | CTA CAT TTG TTC AAC CAT AAC TG (109) |
| ca4cg7.m3P | GAT TTT GAG GTT TGA TGT TGA TG (110) |
| ca4cg7.m3B | GTT TTC CCA GTC ACG ACG CAT TTG TTC AAC CAT AAC TGC (111) |
| ca4cg7.m3Q | AGG AAA CAG CTA TGA CCA TAT TTG AGA GGT CAG GGC ATA (112) |
| HPC2 exon 6 | |
| ca4cg7.m4A | TCG TGT CAG ATT CCC ACC ATA (113) |
| ca4cg7.m4P | AGG CAT AAG TCA GAC ATC CGT (114) |
| ca4cg7.m4B | GTT TTC CCA GTC ACG ACG GTT ACT CTT CCC ACA CAT CTT C (115) |
| ca4cg7.m4Q | AGG AAA CAG CTA TGA CCA TCA CAG CAA GTG TTC AGT TTC TA (116) |
| HPC2 exon 7 | |
| ca4cg7.m5A | CAT TCC CAT GTA TGA ACG TCT (117) |
| ca4cg7.m5P | ATA GTA AGC CCA GGA AGA AGGA (118) |
| ca4cg7.m5B | GTT TTC CCA GTC ACG ACG CAT TCC CAT GTA TGA ACG TCT (119) |
| ca4cg7.m5Q | AGG AAA CAG CTA TGA CCA TCT ACA AGC ATT ACA AGG CAG AG (120) |
| HPC2 exon 8 | |
| ca4cg7.m6A | AGT GTC TTC AGC CTT TGT ATT G (121) |
| ca4cg7.m6P | ATC TGC TAT CTC TTC TTG TCT CA (122) |
| ca4cg7.m6B | GTT TTC CCA GTC ACG ACG ATC GGG TCA TAA TCA GTC TGT G (123) |
| ca4cg7.m6Q | AGG AAA CAG CTA TGA CCA TAT CTC TTC TTG TCT CAG GTA ACA (124) |
| HPC2 exons 9 & 10 | (primary) |
| ca4cg7.m7 & 8A | CTT CTG AAA GCA ATA AAC GCA T (125) |
| ca4cg7.m7 & 8P | GAT GTC AAA ACT GTT CCA CG (126) |
| HPC2 exon 9 | (nested) |
| ca4cg7.m7B | GTT TTC CCA GTC ACG ACG TAA AAC CAA CCT TCT TCA TTA G (127) |
| ca4cg7.m7Q | AGG AAA CAG CTA TGA CCA TAG CAA TGA TGG GAG CGA TG (128) |
| HPC2 exon 10 | (nested) |
| ca4cg7.m8B | GTT TTC CCA GTC ACG ACG GGC TTC TGG GGA CTC ACT G (129) |
| ca4cg7.m8Q | AGG AAA CAG CTA TGA CCA TCC TTC AAA AGT GGT GTC TGT AG (130) |
| HPC2 exon 11 | |
| ca4.cg07.m9A | GTA TCC ACA AAG AGA CCA GAA G (131) |
| ca4.cg07.m9P | CAC CAA CTA CCA ACA GTG ACT TA (132) |
| ca4.cg07.m9B | GTT TTC CCA GTC ACG ACG GCT CAC TGG ATA GGA TAT GTC AT (133) |
| ca4.cg07.m9Q | AGG AAA CAG CTA TGA CCA TCC AGA AAC ACA GCT CTT GCC (134) |
| HPC2 exon 12 | |
| ca4.cg07.m10A | GCT TGC CAG ATA CAG GAA TC (135) |
| ca4.cg07.m10P | ACA GAA AGT TTA GGC AGG TG (136) |
| ca4.cg07.m10B | GTT TTC CCA GTC ACG ACG ACG ATA CCC TCC CTG GCT (137) |
| ca4.cg07.m10Q | AGG AAA CAG CTA TGA CCA TAC AGA AAG TTT AGG CAG GTG (138) |
| HPC2 exons 13 & 14 | (primary) |
| ca4.cg07.m11 & 12A | CCT CTC ACT CTT CCC AGC AC (139) |
| ca4.cgG7.m11 & 12P | GGA GTA GGC TGC TTT TCT AAA T (140) |
| HPC2 exon 13 | (nested) |
| ca4.cg07.m11B | GTT TTC CCA GTC ACG ACG GAA CAC CTC ATC CTC ATT ACC A (141) |
| ca4.cg07.m11Q | AGG AAA CAG CTA TGA CCA TAA GAG ACA AAA CAC ATT CAT GG (142) |
| HPC2 exon 14 | (nested) |
| ca4.cg07.m12B | GTT TTC CCA GTC ACG ACG GTT TCC GCT GTA AGG TAG TGT (143) |
| ca4.cg07.m12Q | AGG AAA CAG CTA TGA CCA TCT GGA ACA TTT ACT ATG TGG CTA (144) |
| HCP2 exon 15 | |
| ca4.cg07.m13A | TGC TAG TGG GTA GAG GTC AG (145) |
| ca4.cg07.m13P | ACT GAA AGC CAG GTT AGA ATG (146) |
| ca4.cg07.m13B | GTT TTC CCA GTC ACG ACG ACC CTG TCC GTC ACC TGA G (147) |
| ca4.cg07.m13Q | AGG AAA CAG CTA TGA CCA TCC CAC CAG CAC TCC ACT TA (148) |
| HPC2 exon 16 | |

TABLE 8-continued

Primers Used to Mutation Screen the HPC2 Gene from Genomic DNA

| Exon/Primer name | Sequence (SEQ ID NO:) |
|---|---|
| ca4cgo7.m14A | TGT GAA GAC GGG ATA ACC TGA (149) |
| ca4cgo7.m14P | GAC AGG GCT TGA TAC CGCA (150) |
| ca4cgo7.m14B | GTT TTC CCA GTC ACG ACG ATG CTG GCT CAC TTT TGA CC (151) |
| ca4cgo7.m14Q | AGG AAA CAG CTA TGA CCA TGAC TGG TGA GTA CAG CAG GA (152) |
| HPC2 exon 17 | |
| ca4.cgo7.m15A | CCA GCC TTT GTG TAA GTC TAC (153) |
| ca4.cgo7.m15P | TCT GGG CAA GTT TGG AAG C (154) |
| ca4.cgo7.m15B | GTT TTC CCA GTC ACG ACG TCC AAA GCA GAC ATC AGC CTC (155) |
| ca4.cgo7.m15Q | AGG AAA CAG CTA TGA CCA TGG AGG AAA AGA CGC AGC CA (156) |
| HPC2 exon 18 | |
| ca4.cgo7.m16A | CGC TTT CTG CCT GTG ACA T (157) |
| ca4.cgo7.m16P | TTC TGT CCT TCA GCC AAT GC (158) |
| ca4.cgo7.m16B | GTT TTC CCA GTC ACG ACG TTA GAG GCT GGT GGG TGA C (159) |
| ca4.cgo7.m16Q | AGG AAA CAG CTA TGA CCA TCA TCT CAA TAA AAA CTG GAG TGC (160) |
| HPC2 exon 19 | |
| ca4.cgo7.m17A | CAC TTG ATG GGC GTT CTG AG (161) |
| ca4.cgo7.m17P | TTC TGT CCT TCA GCC AAT GC (162) |
| ca4.cgo7.m17B | GTT TTC CCA GTC ACG ACG TTC CAG CGG TTT ACA CAT CA (163) |
| ca4.cgo7.m17Q | AGG AAA CAG CTA TGA CCA TTA CCC CAG TGT CCA CCT TG (164) |
| HPC2 exons 20 & 21 | (primary) |
| CA4CG7.m18 & 22A | GGG TTC TCC AGC CAA AGA CT (165) |
| CA4CG7.m18 & 22P | CTG AGT CTC CTG CCT CTG C (166) |
| HPC2 exon 20 | (nested) |
| ca4.cgo7.m18B | GTT TTC CCA GTC ACG ACG GGG TTC TCC AGC CAA AGA CT (167) |
| ca4.cgo7.m18Q | AGG AAA CAG CTA TGA CCA TGT GGG GCT GGA AGG CTC TG (168) |
| HPC2 exon 21 | (nested) |
| ca4.cgo7.m22B | GTT TTC CCA GTC ACG ACG AAG AGG TAA GGG GCA CAG C (169) |
| ca4.cgo7.m22Q | AGG AAA CAG CTA TGA CCA TCT GAG TCT CCT GCC TCT GC (170) |
| HPC2 exon 22 | |
| ca4.cgo7.m19A | GCT GAG TGT TGA GAC CAG GA (171) |
| ca4.cgo7.m19P | AGA CAA ACG ACG GCT GCT C (172) |
| ca4.cgo7.m19B | GTT TTC CCA GTC ACG ACG TTG AGA CCA GGA AAC AGC AC (173) |
| ca4.cgo7.m19Q | AGG AAA CAG CTA TGA CCA TGA GAG GAT GTG GGC GAC AA (174) |
| HPC2 exon 23 | |
| ca4.cgo7.m20A | GGG AGA TGG TGC TGG CTA C (175) |
| ca4.cgo7.m20P | CCT GGT TAG TGA TGG GTA GAT (176) |
| ca4.cgo7.m20B | GTT TTC CCA GTC ACG ACG CAG GGT CTG TGC CAC TGT C (177) |
| ca4.cgo7.m20Q | AGG AAA CAG CTA TGA CCA TCT CAG TGT GTA GAG TCC TGT C (178) |
| HPC2 exon 24 | splice acceptor and open reading frame |
| ca4.cgo7.m21A | TTG ATT TTG AGA GCA TCT GGA C (179) |
| ca4.cgo7.m21P | CTC GGA CAC TTA GAC CCA CTG (180) |
| ca4.cgo7.m21B1 | GTT TTC CCA GTC ACG ACG TGC ATC CCT TCC AGC TCC T (181) |
| ca4.cgo7.m21Q | AGG AAA CAG CTA TGA CCA TGA CAC ACA GCC TTC TGA GTT CA (182) |
| ca4.cgo7.m21C | GTT TTC CCA GTC ACG ACG CCA CAC AGA GGA GCC ACA G (183) |
| ca4.cgo7.m21R | AGG AAA CAG CTA TGA CCA TAC CAG TCC TAA GAG GCA TCT ATA (184) |
| HPC2 exon 24 | 3'untranslated region |
| ca4.cg07.m21.3'UTR A | CCA CAC AGA GGA GCC ACA G (185) |
| ca4.cg07.m21.3'UTR P | CCA GAG GTG CTC ACT ACG AC (186) |
| ca4.cg07.m21.3'UTR B | GTT TTC CCA GTC ACG ACG AGG TCA GAG CCC AGT GAA GAT (187) |
| ca4.cg07.m21.3'UTR Q | AGG AAA CAG CTA TGA CCA TCA TCT GCT TGC TTC CGT GTG (188) |
| ca4.cg07.m21.3'UTR C | GTT TTC CCA GTC ACG ACG TCA GGA TAG GTG GTA TGG AGC (189) |
| ca4.cg07.m21.3'UTR R | AGG AAA CAG CTA TGA CCA TCG GAC ACT TAG ACC CAC TGA T (190) |

Table 9

Sequence Variants

| Variant name | Sequence (SEQ ID NO:) | Coding effect* |
|---|---|---|
| C650T | AGACTCCGAGTYGAATGAAAATG (191) | Ser217Leu |
| A1560G | GGTGAGGGCACRTTTGGGCAGCT (192) | Thr520Thr |
| G1621A | GCACCCTGGCTRCTGTGTTTGTG (193) | Ala541Thr |
| 1641 insG (normal) | GTGTCCCACCTG-CACGCAGATCA (194) | |
| (with insertion of G) | GTGTCCCACCTGGCACGCAGATCA (195) | frameshift |
| C1722T | AAGCCGCTTCAYCCTTTGCTGGT (196) | His574His |
| A1893G | GCTGTTGCGAACRTGTGATTTGGA (197) | Thr631Thr |
| C2632G | GAGGCTTGGGSTCCCACATAAG (198) | |
| C2687T | CCTGGCACAGCYGCGGGCCAGGA (199) | |
| G2801A | AATCCAGCAAARTGATTCCCTGC (200) | |
| IVS2 T-11C | Taaatgttttytcattcttag (201) | |
| IVS5 T-14C | Ttgctgttgtgyggttttcttgt (202) | |

Table 9-continued

Sequence Variants

| Variant name | Sequence (SEQ ID NO:) | Coding effect* |
|---|---|---|
| IVS10 23InsGAT (normal) | ggttttcttgat---tcagcagttaca (203) | |
| (with insertion of GAT) | Ggttttcttgatgattcagcagttaca (204) | |
| IVS13 C15T | Gtgtctcagacyggccccttgtc (205) | |
| IVS14 A17T | Tgccatcttgawctaatggaatc (206) | |
| IVS14 T-8C | Cttctctctctycctgcagggat (207) | |
| IVS16 C41T | Catcaagggcaygtttacttttt (208) | |
| IVS19 C26G | Cagccttgcccsctgggctgttg (209) | |

*based on conceptual translation of the HPC2 ORF for each allele of the sequence variant.

Figure 5A:
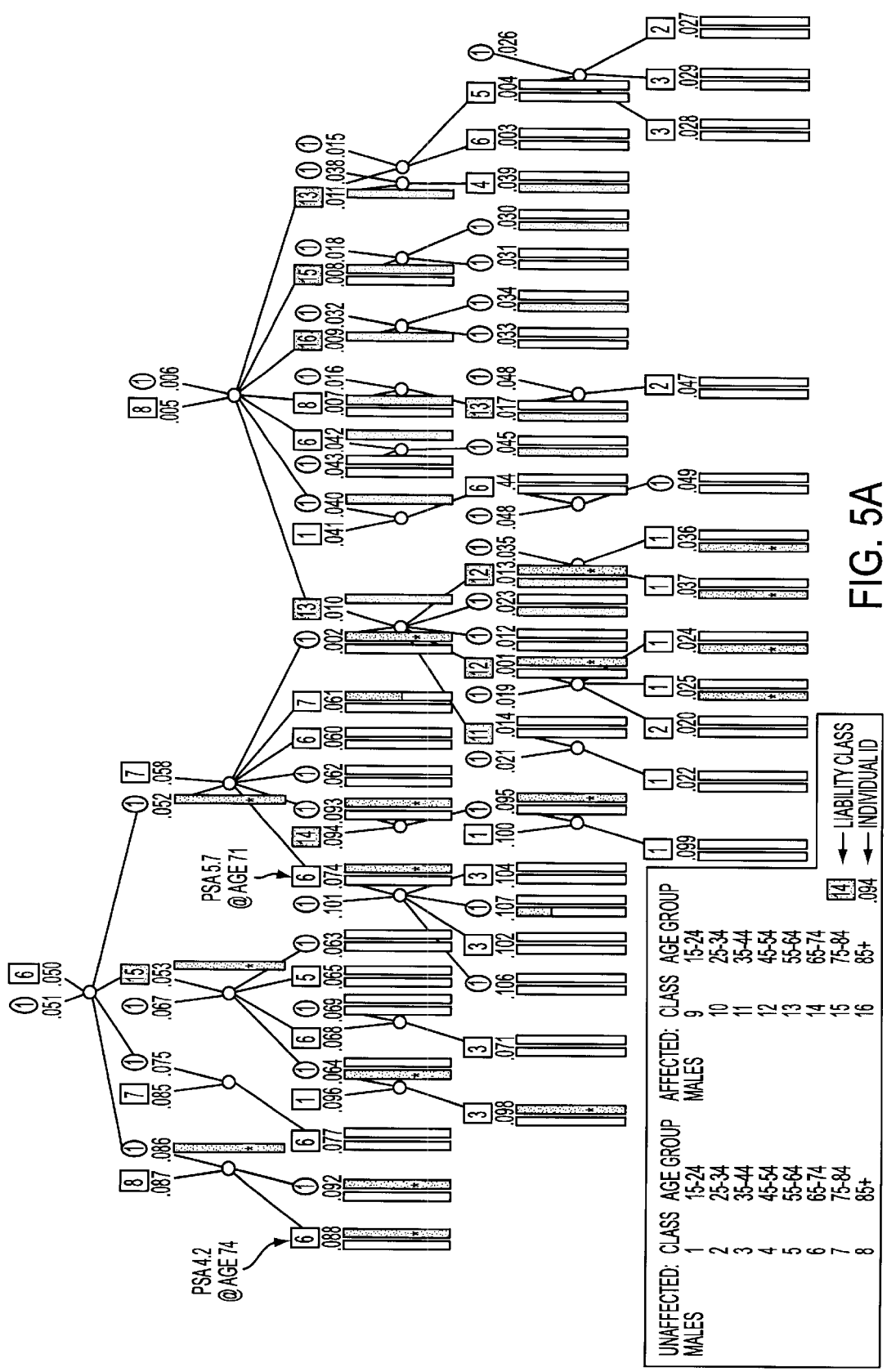
FIGS. 5A–B show kindreds 4102 and 4289. The pedigrees have been genotyped over a 20 cM interval extending from D17S786 to D17S805. Haplotypes are represented by the bars; the dark gray haplotype segregating in each pedigree is the mutation bearing chromosome. The relative position of ELAC2 is denoted by * (white on black or white on gray).

Kindred 4102 was ascertained as a higch risk cluster with eight prostate cancer cases in a three generation pedigree. Genotyping, revealed that six of the eig,ht cases shared a chromosome 17p haplotype. The youngest (age at diagnosis of 46) affected carrier of this shared haplotype, 4102.013 (i.e., kindred #4102, individual #013; FIG. 5A), was selected for mutation screening. On mutations screening lymphocyte DNA from 4102.013), we detected a frameshift, 1641 insG, in ELAC2. A test for segregation revealed that the framneshift was not on the father's chromosome, but rather was inherited through the carrier's mother, 4102.002. Her affected uncle 4102.053 was diagnosed with and died of prostate cancer at age 76 in the 1960s. Genotyping of his children demonstrated thathe was an obligate frameshift carrier. In all, there are five male frameshift carriers over age 45 in the pedigree. Of these, three have prostate cancer, the fourth has a PSA of 5.7 at age 71, and the fifth has a PSA of 4.2 at age 74 (FIG. 5A). The frameshift occurs at His 548, within the histidine motif (FIGS. 6A–B) and is predicted to be quite disruptive to the protein.

Figure 5B:
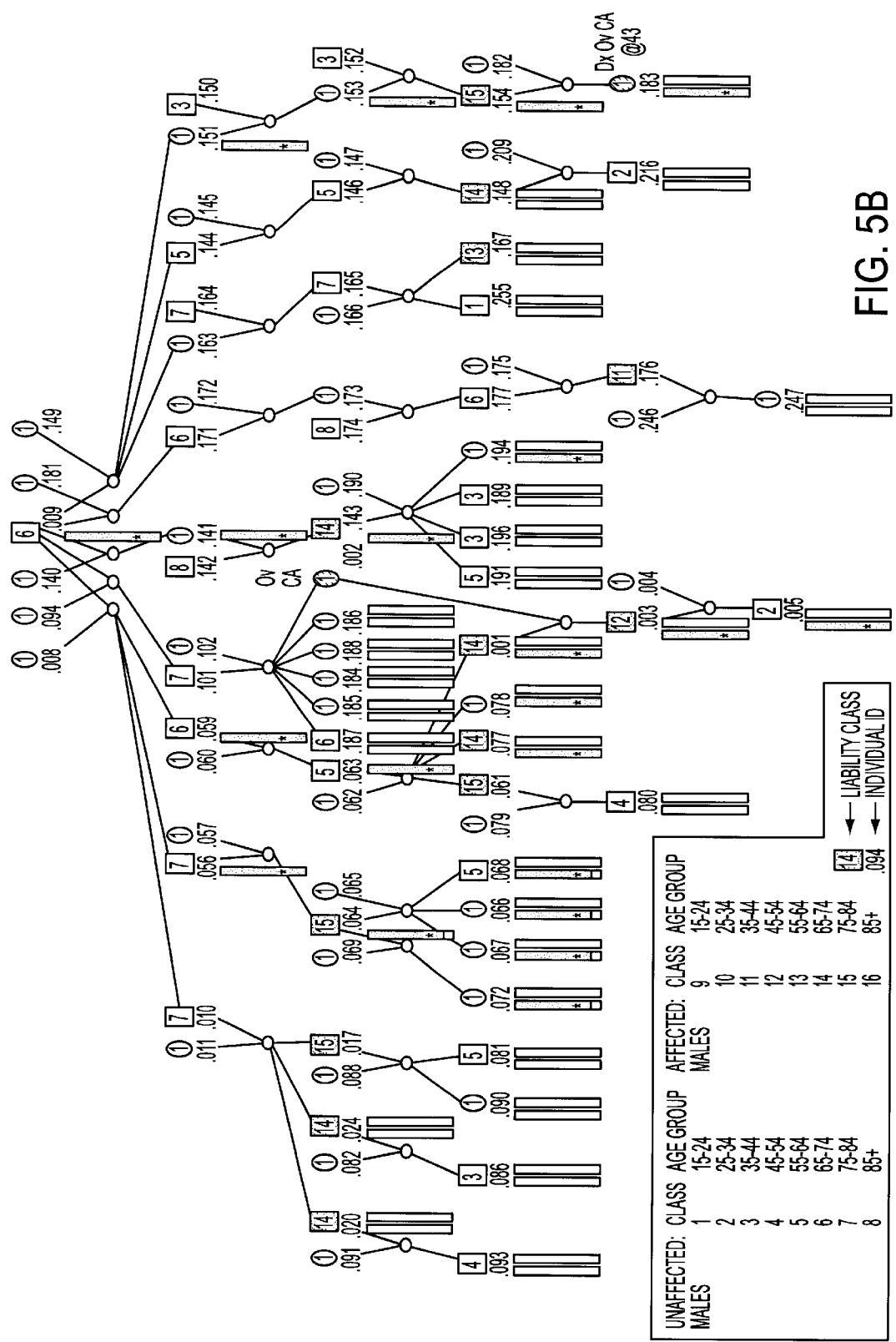

As the frameshift 1641 insG was found in an individual with early onset prostate cancer, we screened an additional 45 prostate cancer cases with early age at diagnosis (Dx<55 years), irrespective of evidence of linkage to any locus, for mutations in ELAC2. An alteration, Arg 781 His, was identified in individual 4289.003, diagnosed with prostate cancer at age 50. Upon expansion of his pedigree, the mutation was traced back four generations to 4289.006, who had affected descendants from five known wives. Prostate cancer cases who carry the missense change have been found among the descendants from three of these five marriages. Of thirteen prostate cancer cases in the pedigree, six carry the missense change, three are unknown, and four are non-carriers. In addition, a female carrier of this missense change, 4289.183, was diagnosed with ovarian cancer at age 43 (FIG. 5B). Within the generations with phenotype information, there are only two unaffected male mutation carriers over age 45; 4289.068 (PSA of 0.6 at age 60) and 4289.063, who died of a heart attack at age 62. We have no additional information on 4289.063; however, two of 4289.063's sons and a grandson are carriers who have been diagnosed with prostate cancer. The missense change occurs in a very highly charged stretch of amino acid residues near the C-terminus of the protein. Arg 781 is conserved in mouse (FIGS. 6A–B), and the charge character of the sequence segment is conserved in *C. elegans*. While one cannot definitively predict that this missense change will affect protein function, expansion from a single affected mutation carrier to a pedigree with a LOD score of 1.3 provides good evidence that the mutation is in fact deleterious.

The identification of two mutations provides strong evidence that ELAC2 is a prostate cancer susceptibility gene. However, after screening 42 haplotypes with evidence for linkage at 17p. we have found only these two high-rislk mutations. Thus it seems that only a small fraction of prostate cancer pedigrees segregate obvious mutations in the ELAC2 coding sequence. We do not yet know what fraction of the pedigrees harbor subtle gene rearrangements or regulatory mutations.

Taken together, the observation that the frameshift HPC2 1641insG segregates with prostate cancer across three generations of kindred 4102, and the inference from shared sequence similarity that the frameshift HPC2 1641insG must be deleterious to the function of the HPC2 protein, establish that deleterious germline mutations in the HPC2 gene confer susceptibility to prostate cancer.

Example 9

Common Missense Changes in HPC2

When our original set of linked pedigrees was screened for mutations in ELAC2, we observed several occurrences of the non-conservative missense change Ser 217 Leu. This missense change is embedded in an extremely hydrophilic segment of the protein sequence. Like the common human allele, the mouse and *C. elegans* residues at this position are also serine. Although the sequence of this segment is not well conserved, its hydrophilic character is (FIGS. 6A–B); thus substitution of a bulky hydrophobic residue for Ser 217 could result in structural consequences to the protein.

Figure 7:
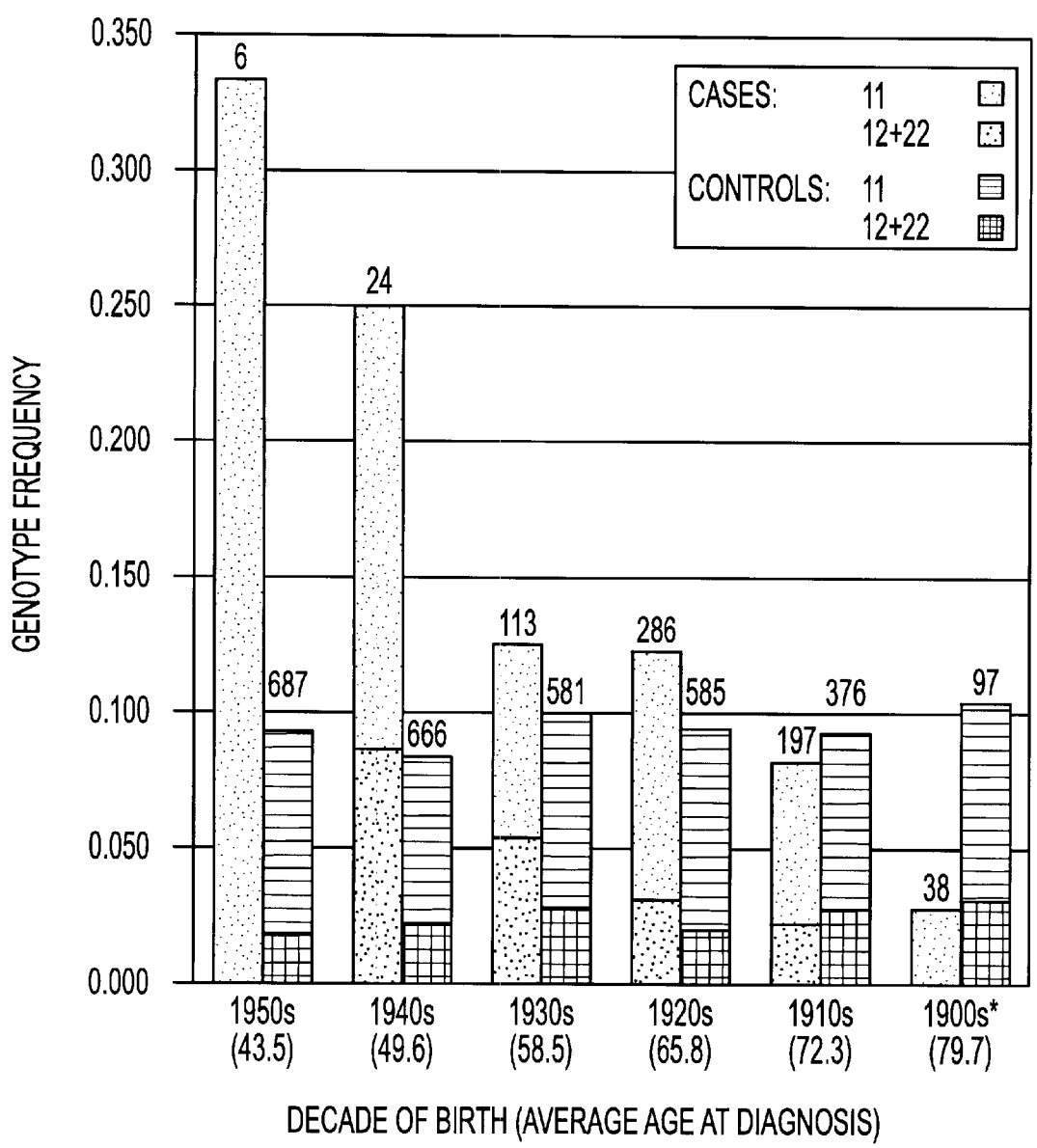
FIG. 7 shows recessive genotype frequencies by birth cohort.
Figure 11A:
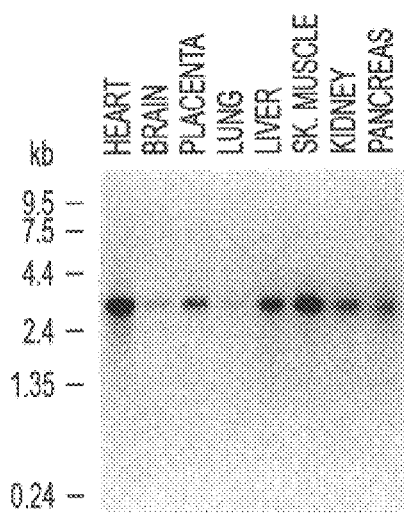
FIGS. 11A–D shows an analysis of ELAC1 expression in human tissues.
Figure 11B:
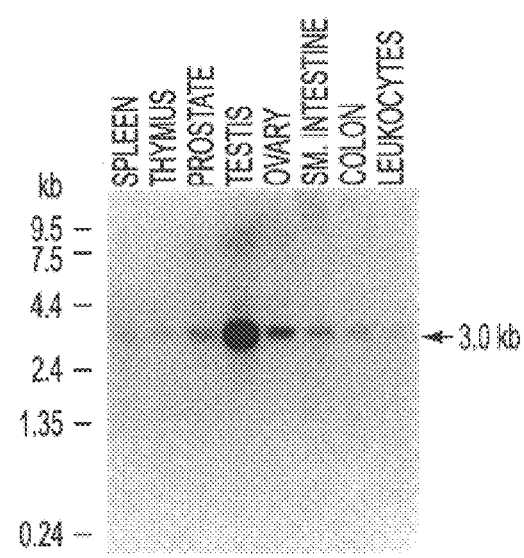
Figure 11C:
Figure 11D:

We analyzed this sequence variant in our pedigree cases, unaffected pedigree members, and an unrelated set of males who have no diagnosis of cancer (divergent controls). The total number of individuals typed exceeded 4,000 (Table 3), with an overall allele frequency of 30% for Leu 217. A logistic regression was performed for disease status to delineate effects of genotypes at Ser 217 Leu versus birth year (a demographic datum collected on all participants). We observed a significant interaction between genotype and birth year (p=0.027), indicating that association tests should be performed which appropriately considered birth cohort. FIG. 7 illustrates this birth effect, showing that genotype frequencies differ across birth cohorts for cases, but appear more uniform for the unaffected controls. We subsequently chose to analyze the effect of genotype in individuals born after 1919, since the data suggest that a different risk pattern may exist for individuals born before this date.

Association tests are consistent with the hypothesis that the Leu 217 variant is deleterious or in disequilibrium with another deleterious variant. Prostate cancer patients born between 1920 and 1959 have a significantly higher proportion of Leu 217 homozygotes than either the divergent controls (57/429 vs. 9/148, p-value=0.026) or the unaffected pedigree members (57/429 vs. 220/2371, p-value=0.013) (FIGS. 7 and 8). That Leu 217 is so common could be explained by the allele contributing to a common disease in a recessive manner.

Upon mutation screening ELAC2 in the set of early onset prostate cancer cases, we also observed several occurrences of a second non-conservative missense change, Ala 541 Thr. This missense change occurs at the border of the histidine motif (FIGS. 6A–B and 9) and thus may well affect the protein's function. This variant has been examined in the same set of cases and controls, where it has an overall allele frequency of 4%. Thr 541 is in strong disequilibrium with Leu 217; in fact, we have yet to observe a chromosome that carries Thr 541 that does not also carry Leu 217. Another logistic regression was performed to investigate effects of genotypes at Ala 541 Thr. Again, a significant interaction between genotype and birth year was found (p=0.003), along with evidence for an effect of genotype at Ala 541 Thr on disease status. Table 10 shows the allele frequencies.

TABLE 10

Allele Definitions

| Allele | Defining Sequence Variant(s) | Note |
|---|---|---|
| 0 | wt | Matches mouse at polymorphic positions |
| 1 | Leu 217 | Allele frequency = 26.0% |
| 2 | Leu 217 + Thr 541 | Allele frequency = 3.9% |

The carrier frequency of Thr 541 is significantly higher in prostate cancer cases than divergent controls such that the variant appears to be dominant and deleterious (carrier frequency of 42/429 vs. 5/148, p-value=0.022) (FIG. 8). In contrast, the Thr 541 carrier frequency is not significantly higher in the cases than the unaffected pedigree members. However, in the c omparison between cases and pedigree unaffecteds, when Leu 217 homozygotes are subdivided into Thr 541 carriers and non-carriers, the presence of Thr 541 is associated with a higher odds ratio (2.0 vs. 1.4) and the model remains statistically significant (p-value=0.017, trend test p-value 0.004) (FIG. 8). Thus both comparisons support the hypothesis that the allele bearing both Thr 541 and Leu 217 is more deleterious than the allele bearing just Leu 217.

Example 10

Identification of HPC2-interacting Proteins by Two-hybrid Analysis

DNA fragments encoding all or portions of HPC2 are nsated to a two-hybrid DNA-binding domain vector such as pGBT.C such that the coding sequence of HPC2 is in-frame with coding sequence for the Gal4p DNA-bindingy domain. A plasmid that encodes a DNA-binding domain fusion to a fragment of HPC2 is introduced into the yeast reporter strain (such as J692) along with a library of cDNAs fused to an activation domain. Transformants are spread onto 20–150 mm plates of selective media, such as yeast minimal media laclking leucine, tryptophan, and histidine, and containing 25 mM 3-amino-1,2,4-triazole. After one week incubation at 30° C., yeast colonies are assayed for expression of the lacZ reporter gene by β-galactosidase filter assay. Colonies that both grow in the absence of histidine and are positive for production of β-galactosidase arc chosen for further characterization.

The activation domain plasmid is purified from positive colonies by the smash-and-grab technique. These plasmids are intro duced into E. coli (e.g., DH10B (Gibco BRL) by electroporation and purified from E. coli by the alkaline lysis method. an test for the specificity of the interaction specific activation domain plasmids are cotransformed into strain J692 with plasmids encoding various DNA-bindings domain fusion proteins, including fisions to segments of HPC2 and human lamin C. Transformants from these experiments are assayed for expression of the HIS3 and lacZ reporter genes. Positives that express reporter genes with Hs.HPC2 constructs and not with lamin C constructs encode bona fide HPC2-interacting proteins. These proteins are identified and characterized by sequence analysis of the insert of the appropriate activation domain plasmid.

This procedure is repeated with mutant forms of the HPC2 gene, to identify proteins that interact with only the mutant protein or to determine whether a mutant form of the HPC2 protein can or cannot interact with a protein known to interact with wild-type HPC2.

Example 11

Identification and Sequencing of Orthologs and a Paralog of the Human HPC2 Gene

All species living on the Earth now are thought to have evolved from a single common ancestor that lived in the distant past, perhaps 3.5 to 4 billion years ago. This means that any pair of species must share a common ancestor species that lived at some time in the past. Admittedly, this view is a bit simplistic because, for instance, the nuclear genomes and mitoehondrial genomes of eukaryotes are thought to have independent prokaryotic ancestries. During the evolution of an ancestral species into two or more extant daughter species, the genes present in the genome of the ancestral species evolve into the genes present in the genomes of the daughter species. The evolutionary history of the genes present in the daughter species can be quite complex because the individual genes can evolve through a diverse set of processes including nucleotide substitution, insertion, deletion, gene duplication, gene conversion, lateral transfer, etc. Even so, the evolutionary history of related genes in related organisms can often be sorted out, especially if the pair/set of species share a relatively recent common ancestor or if the genes being analyzed evolved primarily through nucleotide substitutions and/or small insertions and/or small deletions, but not gene duplications or gene conversions. When, upon analysis, it appears that a single gene in one species and a single gene in another species have evolved from a single gene in a common ancestor species, those genes are termed orthologs.

Knowledge of the identity of genes orthologous to disease-related human genes can often be quite useful.

The human HPC2 cDNA sequence was assembled from a combination of ESTs, hybrid selected clones, and 5' RACE (Rapid Amplification of cDNA Ends) products; the orthologous mouse Elac2 cDNA sequence was assembled from ESTs and 5' RACE products. Conceptual translation of the human cDNA sequence yielded a protein of 826 amino acids; parsing the cDNA sequence across the corresponding genomic sequence revealed 24 coding exons (FIG. 3). Mouse Elac2 encodes a protein of 831 residues in 25 exons. BLAST (Altschul et al., 1990) searches of the ELAC2 sequence against GenBank readily revealed a single ortholog in S. cerevisiae (YKR079C) and a single ortholog in C. elegans (CE16965, CELE04A4.4), but two related sequences in S. pombe and A. thaliana. Alignment of representative family members revealed a block of good conservation near the N-termini and a series of blocks of high similarity across the C-terminal half of the proteins (FIGS. 6A–B and 10).

Hybridization of RNA blots to labeled fragments of human ELAC2 cDNA revealed a single transcript of approximately 3 kb (FIGS. 11A–D), in agreement with our full-length cDNA assembly of 2,970 bp. The transcript was detected in all tissues surveyed and, like BRCA1 and BRCA2, was most abundant in testis. The apparent size of the transcript agrees well with our full length cDNA assembly, 2970 bp. There was no evidence from RNA blots, EST sequences, or RT-PCR experiments of significant alternative splicing of the transcript.

In the course of surveying ESTs derived from this gene, we identified a small number of human and rabbit ESTs derived from a second, related gene. The human cDNA sequence of this related gene was assembled from a combination of ESTs and 5' RACE products. Conceptual translation revealed that the transcript encodes a protein of 363 residues. Radiation hybrid mapping placed the gene at approximately 365 cR on chromosome 18. When this sequence, along with representative sequences from a eubacterium (E. coli elaC), a cyanobacterium (Synechocystis sp. gi2500943/SLR0050) and an archaebacterium (M. thermooautotrophicum gi2622965) was added into the multiprotein alignment (FIGS. 6A–B), it became apparent that two distinct groups of proteins were represented; a group of larger proteins (800–900 aa) restricted to the eukaryotes, and a group of smaller proteins (300 to 400 aa) that align with the C-terminal half of the former group and includes sequences from the eukaryotes, eubacteria, and archaebacteria. As the 363 residue human protein falls into this second group and is more similar to E. coli elaC than is ELAC2, we will refer to it as ELAC1.

The alignment revealed a striking histidine containing motif, φφφ[S/T]HxHxDflxxG (SEQ ID NO:214), where φ can be any large hydrophobic residue, near the N-terminus of the ELAC1 group, and in the C-terminal portion of the ELAC2 group. This motif is reminiscent of the histidine motif found in the metallo-β-lactamases (Melino et al., 1998) and suggests, in accord with the annotation for COG1234 (www.ncbi.nlm.nih.gov/COG/index.html), that the proteins are metal-dependent hydrolases. While assembling the multiple alignment, we observed that the sequence within which the histidine motif is embedded also aligns with the ELAC2 N-terminal conserved block (FIG. 12), leading us to predict that some structural feature of the protein is repeated. Even so, the N-terminal copy of the repeated sequence would not necessarily retain metal-dependent hydrolase activity, as the histidine motif itself is not conserved.

Figure 13:
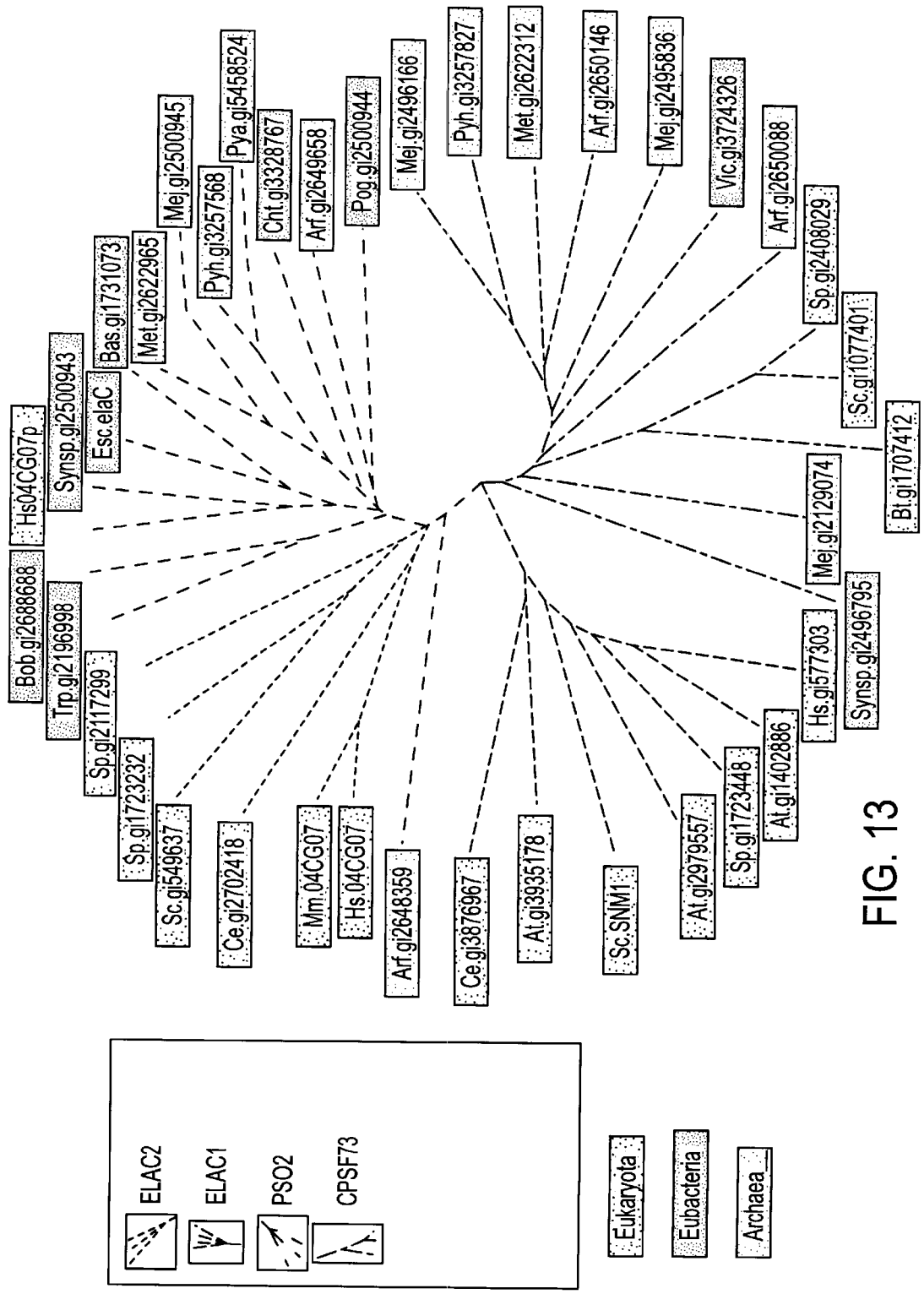
FIG. 13 shows the relationship between ELAC1/2, PSO2 and CPSF73 gene family members. The tree is a distance-based depiction of pairwise sequence similarities determined from a manual alignment of the ~67 amino acids immediately surrounding the histidine motif. ClustalX (Thompson et al., 1997) was used to calculate the percent divergence of each sequence on a pairwise basis and neighbor joining (Saitou and Nei, 1987) was applied to the resulting distance matrix. The treefile produced from ClustalX was visualized using TreeView (Page, 1996) and further edited in a graphics program for aesthetics. The scale bar indicates amino acid substitutions per residue.

Thorough BLAST searches of GenBank using sequences containing this histidine motif, combined with iterative motif searches (Nevill-Manning et al., 1998) using the eMOTIF SCAN website (http://dna.stanford.edu/scan), revealed two other families of proteins that share extended amino acid sequence similarity with members of COG1234. The similarity includes 4 to 6 shared motifs distributed across the ELAC1 domain (FIG. 9). One such family is the PSO2 (or SNM1) family of DNA inter-strand crosslink repair proteins (Haase et al., 1989; Meniel et al., 1995; Niegemann and Brendel, 1994), present only in eukaryotes. The second family encodes the 73 kDa subunit of the mRNA cleavage and polyadenylation specificity factor (CPSF73) (Chanfreau et al., 1996; Jenny et al., 1994; Jenny et al., 1996). Surprisingly, members of this latter gene family are present in both eukaryotes and archaebacteria, as well as a cyanobacterium. These three gene families, ELAC1/2, PSO2 and CPSF73, are equally similar to each other (FIGS. 9 and 13); indeed they were originally placed in a single COG (Tatusov et al., 1997). While PSO2 is required for repair of DNA inter-strand crosslinks following treatment of cells with, for instance, 8-methoxypsoralen plus UV-irradiation (Menial et al., 1995), the actual substrate for the protein's presumptive metal-dependent hydrolase activity has not been defined. Similarly, although CPSF73 is a component of the mRNA 3' end cleavage and polyadenylation specificity factor. it has neither the 3' end cleavage nor the polyadenylation activity, and the substrate for its presumptive metal-dependent hydrolase activity is unknown. While the S. cerevisiae CPSF73 ortholog YSH1 (BRR5) is an essential gene, PSO2 is not. Given the phylogenetic conservation of the ELAC1 domain and the observation that S. cerevisiae encodes only a single member of this gene family, YKR079C, we asked whether it is an essential gene. To answer this question, we performed one-step gene disruption of YKR079C using URA3 as a selectable marker in yeast diploid cells. Two heterozygote knockout strains were sporulated and tetrads were dissected. Each tetrad yielded 1 or 2 viable haploid colonies; these were all URA⁻ and YKR079C wt. Thus we concluded that, like YSH1, YKR079C is an essential gene.

In addition to the histidine motif and the local sequence context in which it is embedded, ELAC1/2, PSO2 and CPSF73 proteins share a series of sequence features, some shared pairwise between the gene families and others by all three. Strikingly, all three families have three or four conserved histidine or cysteine positions, past the histidine motif, that lie within these shared regions and can be aligned across the gene families (FIG. 9). The arrangement is reminiscent of the binuclear zinc binding active site of some metallo-β lactamases (Carfi et al., 1998; Fabiane et al., 1998) and the shared similarity between the metallo-β lactamases and glyoxalase H (Melino et al., 1998). This series of sequence similarities leads to three predictions. First, the extended similarity between the ELAC1/2, PSO2 and CPSF73 protein families suggests that they share a domain of approximately 300 residues and this domain constitutes a metal-dependent hydrolase that coordinates two-divalent cations in its active site. Second, the overall fold of this domain is likely to be similar to that of the metallo-β lactamases. Third, similarity between the region surrounding the ELAC1/2 histidine motif and the N-terminus of the ELAC2 proteins suggests that these proteins are comprised of two structurally similar domains and arose from a direct repeat/duplication of an ancestral ELAC1-type gene.

A number of members of the ELAC1/2 family are auotated in GenBank as sulfatases or sulfatase homologs. The annotation appears to be assigned through sequence similarity to the atsA gene of Alteromonas carrageenovora. The atsA protein contains a histidline motif and has been demonstrated to have aryl sulfatase activity in vitro (Barbeyron et al., 1995), though its sequence does not contain any of the typical sulfatase motifs listed by PROSITE. No other experimentally verified aryl sulfatase contains the histidine motif. As the E. coli protein most similar to A. carrageenovora atsA is elaC, atsA may well be a diverged member of the ELAC1 gene family (BLASTp and alignment not shown). Accordingly, ELAC1 family members should be tested for aryl sulfatase activity; however, it is not apparent whether ELAC1 and ELAC2 family members have the same substrate.

In addition to the paralog and the mouse ortholog mmELAC2 (for Mus musculus ELAC2), orthologs of HPC2 have been identified in chimpanzee and gorilla. These are ptELAC2 (*Pan troglodytes* ELAC2) and ggELAC2 (*Gorilla gorilla* ELAC2).

Example 12

Multiple Protein Sequence Alignments

For the alignment of FIGS. 6A–B, shading criteria were identity (white on black) or conservative substitution (white on gray) for all ELAC2 sequences with a residue at that position, with four of the five sequences actually having to have a residue at that position. Shaded positions in the ELAC2 sequences were propagated into the ELAC1 sequences. For the alignment of FIG. 12, two shading criteria were used: (1) Identity or conservative substitution across the ELAC2 N-terminal alignment and identity or conservative substitution across either the ELAC1 or ELAC2 His motif. (2) Identity or conservative substitution across both the ELAC1 and ELAC2 His motif, with some conservation across the ELAC2 N-terminal alignment. For the alignment of FIG. 9, shading criteria were identity or conservative substitution across two out of the three (CPSF73, PSO2, ELAC2) protein families represented.

Example 13

Analysis of the HPC2 Gene

The structure and function of HPC2 gene are determined according to the following methods.

Biological Studies. Mammalian expression vectors containing HPC2 cDNA are constructed and transfected into appropriate prostate carcinoma cells with lesions in the gene. Wild-type HPC2 cDNA as well as altered HPC2 cDNA are utilized. The altered HPC2 cDNA can be obtained from altered HPC2 alleles or produced as described below. Phenotypic reversion in cultures (e.g., cell morphology, doubling time, anchorage-independent growth) and in animals (e.g., tumorigenicity) is examined. The studies will employ both wild-type and mutant forms of the gene.

Molecular Genetics Studies. In vitro mutagenesis is performed to construct deletion mutants and missense mutants (by single base-pair substitutions in individual codons and alanine scanning mutagenesis). The mutants are used in biological. biochemical and biophysical studies.

Mechanism Studies. The ability of HPC2 protein to bind to known and unknown DNA sequences is examined. Its ability to transactivate promoters is analyzed by transient reporter expression systems in mammalian cells. Conventional procedures such as particle-capture and yeast two-hybrid system are used to discover and identify any functional partners. The nature and functions of the partners are characterized. These partners in turn are targets for drc u discovery.

Structural Studies. Recombinant proteins are produced in *E. coli*, yeast, insect and/or mammalian cells and are used in crystallographic and NMR studies. Molecular modeling of the proteins is also employed. These studies facilitate structure-driven drug design.

Example 14

*S. cerevisiae* Gene Knockout

The URA3 Allene was PCR amplified with tailed primers resulting in a product flanked by 42 bp of YKR079C codins sequences (amino acids at 3–16 and 818–831). The resulting PCR product was transformed into yeast dipoid strain YPH501 (Stratagene); URA$^+$ clones were screened for disruption by the presence of a shorter PCR product at the YKR079C locus. The knock-out clones were further confirmed by sequencing the shorter PCR product for the presence of URA3 sequences. two heterozygote knockout strains were sporulated and tetrads dissected. Each tetrad yielded 1 or 2 viable colonies. These were oenotyped at YKR079C and tested for Growth on URA plates.

Example 15

Association Tests

STSs for Ser 217 Leu and Ala 541 Thr were amplified by allele specific PCR using, fluorescently labeled oligos. Allele calls were imade with our automated gyenotyping system. Genotype calls required good allele calls at both markers. Logistic regression analyses were performed uisingo the SPSS statistical software paelkage. The chi-squared statistics for the 2×2 contingency tables were calculated with the Yate s correction. The trend statistic for the 3×2 contingency table was calculated with the Cochraln-Aroeitagre trend test (Cochran, p1954; Amaitage, 1955) using a simple linear trend (0,1,2) for the row scores.

Example 16

Generation of Polyclonal Antibody Against HPC2

Segments of HPC2 coding sequence are expressed as fusion protein in *E. coli*. The overexpressed proteins are purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of HPC2 coding sequence was cloned as a fusion protein in plasmid PET5A (Novagen, Inc., Madison, Wis. The HPC2 incorporated sequences might include SEQ ID NOs:1, 3 or 28 or portions thereof. After induction with IPTG, the overexpression of a fusion protein with the expected molecular weight is verified by SDS/PAGE. Fusion proteins are purified from the gel by clectroelution. The identification of the protein as the HPC2 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure can be repeated to generate antibodies against mutant forms of the HPC2 protein. These antibodies, in conjunction with antibodies to wild type HPC2, are used to detect the presence and the relative level of the mutant forms in various tissues and biological fluids.

Example 17

Generation of Monoclonal Antibodies Specific for HPC2

Monoclonal antibodies are generated according to the following protocol. Mice are immunized with immunogen comprisingo intact HPC2 or HPC2 peptidcs (wild type or mutant) conjugated to keyhole limpet hemocyanin using glutaraldelhydc or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using, polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of HPC2 specific antibodies by ELISA or RIA using wild type or mutant HPC2 target protein. Cells in positive wells are expanded and subsloned to establish and confirm monoclonality.

Clones with the desired specificities are expanded and grown as ascites in mice or in a hollow fiber system to produce sufficient quantities of antibody for characterization and assay development.

Example 18

Isolation of HPC2 Bindinob Peptides

Peptides that bind to the HPC2 gene product are isolated from both chemical and phage-displayed random peptide libraries a s follows.

Fraguments of the HPC2 gene product are expressed as GST and His-tag fusion proteins in both *E. coli* and SF9 cells. The fusion protein is isolated using either a glutathione matrix (for GST fusions proteins) or nickel chelation matrix (for His-tag fusion proteins). This taret fusion protein preparation is either screened directly as described below, or hluted with slutathione or imidizole. The target protein is ixmobilized to either a surface such as polystyrene; or a resin such as agarose; or solid supports using either direct absorption, covalent linkage reagents such as plutaraldehyde, or linedage agents such as biotip-avidin.

Two types of random peptide libraries of varyinm lengths are generated: synthetic peptide libraries that may contain derivatized residues, for example by phosphorylationi or myristylation, and phage-displayed peptide libraries which may be phosphorylated. These libraries are incubated with immobilized HPC1 gene product in a variety of physiological buffers. Next, unbound peptides are removed by repeated was hes, and bound peptides recovered by a variety of elution reagents such as low or high pH, strong denaturants, glutathione, or imidizole. Recovered synthetic peptide mixtures are sent to commercial services for peptide microsequencing to identify enriched residues. Recovered phane are amplified rescreened, plaque purified, and then sequenced to determined the identity of the displayed peptides.

Use of HPC1 binding peptides. Peptides identified from the above screens are syn thesized in larger quantities as biotin conjaugosates by coimercial services. These peptides are used in both solid and solution phase competition assays with HPC1 and its interacting partners identified in yeast 2-hybrid screens. Versions of these peptides that are fused to membrane-permeable motifs (Lin et al., 1995; Rojas et al., 1996) will be chemically synthesized, added to cultured cells and the effects on growth, apoptosis, differentiation, cofactor response, and internal changes will be assayed.

Example 19

Sandwich Assay for HPC2

Monoclonal antibody is attached to a solid surface such as a plate, tube. bead, or particle. Preferably, the antibody is attached to the well surface of a 96-well ELISA plate. 100 $\mu$l sample (e.g., serum, urine, tissue cytosol) containing the HPC2 peptide/protein (wild-type or mutant) is added to the solid phase antibody. The sample is incubated for 2 hrs at room temperature. Next the sample fluid is decanted, and the solid phase is washed with buffer to remove unbound material. 100 $\mu$L of a second monoclonal antibody (to a different determinant on the HPC2 peptide/protein) is added to the solid phase. This antibody is labeled with a detector molecule (e.g., 125-I, enzyme, fluorophore, or a chroiiioplhore) and the solid phase with the second antibody is incubated for two hrs at room temperature. The second antibody is decanted and the solid phase is washed with buffer to remove unbound material.

The amount of bound label, which is proportional to the amount of HPC2 peptide/protein present in the sample, is quantified. Separate assays are performed using monoclonal antibodies which are specific for the wild-type HPC2 as well as monoclonal antibodies specific for each of the mutations identified in HPC2.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1990). *J. Mol. Biol.* 215: 403–410.
Altschul S F, et al. (1997). *Nucl. Acids Res.* 25:3389–3402.
Anand R (1992). *Techniques for the Analysis of Complex Genomes*, (Academic Press).
Anderson W F, et al. (1980). *Proc. Natl. Acad. Sci. USA* 77:5399–5403.
Antoniou A C, et al. (2000). *Genet. Epidemiol.* 18:173–190.
Armitage P (1955). *Biometrics* 11:375–386.
Ausubel F M, et al. (1992). *Current Protocols in Molecular Biology*, (J. Wiley and Sons, NY).
Bandyopadhyay P K and Temin HM (1984). *Mol. Cell. Biol.* 4:749–754.
Barbeyron T, et al. (1 995). *MicrolbioloAy* 141:2897–2904.
Bartel P L, et al. (1993). "Using the 2-hybrid system to detect protein-protein interactions." In: *Cellular Interactions in Development: A Practical Approach*, Oxford University Press, pp. 153–179.
Beaucage S L and Caruthers MH (1981). *Tetra. Letts.* 22:1859–1862.
Berglund P, et al. (1993). *Biotechnology* 11:916–920.
Berkner K L (1992). *Curr. Top. Microbiol. Immunol.* 158:39–66.
Berkner K L, et al. (1988). *BioTechniques* 6:616–629.
Berry R, et al. (2000). *Am. J. Hum. Genet.* 66:539–546.
Berthon P, et al. (1998). *Am. J. Hum. Genet.* 62:1416–1424.
Borman S (1996). *Chemical & Engineering News*, Decemnber 9 issue pp. 42–43.
Bouchardy C, et al. (1998). *Pharmacogenetics* 8:291–298.
Bratt O, et al. (1999). *Br. J. Cancer* 81:672–676.
Breakefield X O and Geller A I (1 987). *Mol. Neurobiol.* 1:337–371.
Breast Cancer Linkage Consortium (1999). *J. Natl. Cancer Inst.* 91:1310–1316.
Brinster R L, et al. (1981). *Cell* 27:223–231.
Buchschacher G L and Panganiban AT (1992). *J. Virol.* 66:2731–2739.
Cannon L, et al. (1982). *Cancer Surveys* 1:47–69.
Capecchi M R (1989). *Science* 244:1288–1292.

Carfi A, et al. (1998). *Acta Crysatcllagr. D Biol. Cryallogr.* 54:45–57.
Cariello N F (1988). *Am. J Hitman Genetics* 42:726–734.
Carter B S, et al. (1992). *Proc. Natl. Acad. Si. USA* 89:3367–3371.
Carter B S, et al. (1993). *J Urol.* 150:797–802.
Chamberlain N L, et al. (1994). *Nucl. Acidys Res.* 22:3181–3186.
Chanfreau G, et al. (1996). *Science* 274:1511–1514.
Chee M, et al. (1996). *Science* 274:610–614.
Chevray P M and Nathans DN (1992). *Proc. Nail. Acad. Sci. USA* 89:5789–5793.
Cochran W G (1954). *Biometrics* 10:417–451.
Compton J (1991). *Nature* 350:91–92.
Conner B J et al. (1983). *Proc. Natl. Acad. Sci. USA* 80:278–282.
Cooney K A, et al. (1997). *J. Natl. Cancer Inst.* 89:955–959.
Costantini F and Lacy E (1981). *Nature* 294:92–94.
Cotten M, et al. (1990). *Proc. Natl. Acad. Sci. USA* 87:4033–4037.
Cottingham R W, et al. (1993). *Am. J. Hum. Genet.* 53:252–263.
Cotton R G, et al. (1988). *Proc. Natl. Acad. Sci. USA* 85:4397–4401.
Couch F J, et al. (1996). *Genomics* 36:86–99.
Culver K W, et al. (1992). *Science* 256:1550–1552.
Curiel D T, et al. (1991). *Proc. Natl. Acad. Sci. USA* 88:8850–8854.
Curiel D T, et al. (1992). *Hum. Gene Ther.* 3:147–154.
DeRisi J, et al. (1996). *Nature Genetics* 14:457–460.
Deutscher, M (1990). *Meth. Enzymology* 182:83–89 (Academic Press, San Diego, Calif.).
Donehower L A, et al. (1992). *Nature* 356:215–221.
Durbin R and Thierry-Mieg J (1991). A *C. elegans* Database. Documentation, code and data available from anonymous FTP servers at lirmm.lirmm.fr, cele.mrc-lmb.cam.ac.uk and ncbi.nlm.nih.gov.
Editorial (1996). *Nature Genetics* 14:367–370.
Eeles R A, et al. (1998). *Am. J. Hum. Genet.* 62:653–658.
Elghanian R, et al. (1997). *Science* 277:1078–1081.
*Enhancers and Eukaryotic Gene Expression*, Cold Spring Harbor Press, Cold Spring Harbor, N.Y.(1983).
Erickson J, et al. (1990). *Science* 249:527–533.
Fabiane S M, et al. (1998). *Biochemistry* 37:12404–12411.
Fahy E, et al. (1991). *PCR Methods Appl.* 1:25–33.
Feil R, et al., (1996). *Proc. Natl. Acad. Sci. USA* 93:10887–10890.
Felgner P L, et al. (1987). *Proc. Naitl. Acad. Sci. USA* 84:7413–7417.
Fields S and Song O-K (1989). *Nature* 340:245–246.
Fiers W, et al. (1978). *Nature* 273:113–120.
Fincham S M, et al. (1990). *The Prostate* 17:189–206.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Ford D, et cil. (1998). *Am. J. Hum. Genet.* 62:676–689.
Freese A, et al. (1990). *Biochem. Phaimncol.* 40:2189–2199.
Friedman T (1991). In: *Therapy for Genetic Diseases*, T. Friedman, ed., Oxford University Press, pp. 105–121.
Gagneten S, et al. (1997). *Nucl. Acids Res.* 25:3326–3331.
Gibbs M, et caL (1999a). *Am. J. Hum. Genet.* 64:776–787.
Gibbs M, et al. (1999b). *Am. J. Humn. Genet.* 64:1087–1095.
Giovannucci E, et al. (1997). *Proc. Natl. Acad. Sci. USA* 94:3320–3323.
Glover D (1985). *DNA Cloning*, I and II (Oxford Press).
Goding (1986). *Monoclonal Antibodies: Principles and Practice*, 2d ed. (Academic Press, NY).
Godowski P J, et al. (1988). *Science* 241:812–816.
Goldgar D E, et al. (1994). *J. Natl. Can. Inst.* 86:3:200–209.
Goode E L, et al. (2000). *Genet. Epidemiol.* 18:251–275.
Gordon J W, et al. (1980). *Proc. Nail. Acad. Sci. USA* 77:7380–7384.
Gordon J W (1989). *Intl. Rev. Cytol.* 115:171–229.
Gorziglia M and Kapikian AZ (1992). *J. Virol.* 66:4407–4412.
Graham F L and van der Eb AJ (1973). *Virology* 52:456–467.
Grompe M (1993). *Nature Genetics* 5:111–117.
Grompe M, et al. (1989). *Proc. Natl. Acad. Sci. USA* 86:5855–5892.
Gu H, et al. (1994). *Science* 265:103–106.
Guthrie G and Fink GR (1991). *Guide to Yeast Genetics and Molecular Biology* (Academic Press).
Haase E, et al. (1989). *Mol. Gen. Genet.* 218:64–71.
Hacia J G, et al. (1996). *Nature Genetics* 14:441–447.
Hall J M, et al. (1990). *Science* 250:1684–1689.
Harlow E and Inane D (1988). *Antibodies: A Laboratory Manual* (Cold Spring Harbor Laboratory, Cold Spring Harbor, N.Y.).
Harty L C, et al. (1997). *J. Natl. Cacncer Inst.* 89:1698–1705.
Hasty P, et al. (1991). *Nature* 350:243–246.
Helseth E, et al. (1990). *J. Virol.* 64:2416–2420.
Hodgson J (1991). *Bio/Technology* 9:19–21.
Hori H, et al. (1997). *J. Clin. Gastroenterol.* 25:568–575.
Hubert A, et al. (1999). *Am. J. Hum. Genet.* 65:921–924.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al. (1986). *Nucl. Acicls Res.* 14:6115–6128.
Jaffe J M, et al. (2000). *Cancer Res.* 60:1626–1630.
Jakoby W B and Pastan IH (eds.) (1979). Cell Culture. *Methods in Enzymology*, Vol. 58 (Academic Press, Inc., liarconit Brace Jovanovich (NY)).
Jenny A, et al. (1994). *Mol. Cell. Biol.* 14:8183–8190.
Jenny A, et al. (1996). *Science* 274:1514–1517.
Johnson P A, et al. (1992). *J. Virol.* 66:2952–2965.
Johnson, et al. (1993). "Peptide Turn Mimetics" In: *Biotechnolooy and Pharmacy*, Pezzuto et al., eds., Chapman and Hall, NY.
Kaneda Y, et al. (1989). *J. Biol. Chem.* 264:12126–12129.
Kanehisa M (1984). *Nucl. Acids Res.* 12:203–213.
Kazemi-Esfarjani P, et al. (1995). *Hum. Mol. Genet.* 4:523–527.
Kinszler K W, et al. (1991). *Science* 251:1366–1370.
Kohler G and Milstein C (1975). *Nature* 256:495–497.
Krain L S (1974). *Preventive Medicine* 3:154–159.
Kubo T. et al. (1988). *FEBS Lett.* 241:119–125.
Kyte J and Doolittle R F (1982). *J. Mol. Biol.* 157:105–132.
Landegrcn U, et al. (1988). *Science* 242:229–237.
Lander E S and Green P (1987). *Proc. Natl. Acad. Sci. USA* 84:2363–2367.
Lange E M, et al. (1999). *Clin. Cancer Res.* 5:4013–4020.
Lasko M, et al. (1992). *Proc. Natl. Acad. Sci. USA* 89:6232–6236.
Lathrop G M (1984). *Proc. Nail. Acaci. Sci. USA* 81:3443–3446.
Lavitrano M, et al. (1989). *Cell* 57:717–723.
Lee J E, et al. (1995). *Science* 268:836–844.
Lim C S, et al. (1991). *Circulation* 83:2007–2011.
Lin Y Z, et al. (1995). *J. Biol. Chem.* 270:14255–14258.
Lipshutz R J, et al. (1995). *BioTechniques* 19:442–447.

Lo C W (1983). *Mol. Cell. Biol.* 3:1803–1814.
Lobe C G and Nagy A (1998). *Bioessays* 20:200–208.
Lockhart D J, et al. (1996). *Nature Biotechnology* 14:1675–1680.
Madzak C, et al. (1992). *J. Gen. Virol.* 73:1533–1536.
Makridakis N, et al. (1997). *Cancer Res.* 57:1020–1022.
Makridakis N M, et al. (1999). *Lancet* 354:975–978.
Maniatis T, et al. (1982). *Molecular Cloning: A Laboratory Manual* (Cold Spring Harbor Laboratory, Cold Springy Harbor. N.Y.).
Mann R and Baltimore D (1985). *J. Virol.* 54:401–407.
Margolskee R F (1992). *Curr. Top. Microbiol. Inmmunol.* 158:67–95.
Martin R, et al. (1990). *BioTechniques* 9:762–768.
Matteucci M D and Caruthers Mll (1 981). *J Am. Chem. Soc.* 103:3185.
Matthews J A and Kricka LJ (1988). *Anal. Biochem.* 169:1.
Meikle A W, et al. (1985). *Prostate* 6:121–128.
Melino S, et al. (1998). *TIBS* 23:381–382.
Meniel V, et al. (1995). *Mutagenesis* 10:543–548.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miki Y, et al. (1994). *Science* 266:66–71.
Miller A D (1992). *Curr. Top. Microbiol. Immunol.* 158:1–24.
Miller A D, et al. (1985). *Mol. Cell. Biol.* 5:43 1–437.
Miller A D, et al. (1988). *J Virol.* 62:4337–4345.
Modrich P (1991). *Ann. Rev. Genet.* 25:229–253.
Mombaerts P, et al. (1992). *Cell* 68:869–877.
Morganti G. et al. (1956). *Acta Geneticae Medicae et Gemellogogiae* 6:304–305.
Moss B (1992). *Curr. Top. Microbiol. Inmmunol.* 158:25–38.
Moss B (1996). *Proc. Natl. Acad Sci. USA* 93:11341–11348.
Muzyczka N (1992). *Curr. Top. Microbiol. Immunol.* 158:97–129.
Nabel (1992). *Hum. Gene Ther.* 3:399–410.
Nabel E G, et al. (1990). *Science* 249:1285–1288.
Naldini L, et al. (1996). *Science* 272:263–267.
Nastiuk K L, et al. (1999). *Prostate* 40:172–177.
Nevill-Manning C G, et al. (1998). *Proc. Natl. Accid. Sci. USA* 95:5865–5871.
Neuhausen S L, et al. (1999). *Hum. Mol. Genet.* 8:2437–2442.
Newton C R, et al. (1989). *Nucl. Acids Res.* 17:2503–2516.
Nguyen Q, et al. (1992). *BioTechniques* 13:116–123.
Niegemann E and Brendel M (1994). *Mutal. Res.* 315:275–279.
Novack D F, et al. (1986). *Proc. Natl. Acaci. Sci. USA* 83:586–590.
O'Connell J R and Weeks DE (1995). *Nat. Genet.* 11:402–408.
Ohi S, et al. (1990). *Gene* 89:279–282.
Orita M, et al. (1989). *Proc. Natl. Acad. Sci. USA* 86:2776–2770.
Osterrieder N and Wolf E (1998). *Rev. Sci. Tech.* 17:351–364.
Ott J (1986). *Genet. Epidemiol. Suppl.* 1:251–257.
Page K A, et a. (1990). *J. Virol.* 64:5270–5276.
Page R D M (1996). *Computer Applications in the Biosciences* 12:357–358.
Pellicer A, et al. (1980). *Science* 209:1414–1422.
Peto J, et al. (1999). *J. Natl. Cancer Inst.* 91:943–949.
Petropoulos C J, et al. (1992). *J. Virol.* 66:3391–3397.
Philpott K L, et al. (1992). *Science* 256:1448–1452.
Quantin B, et al. (1992). *Proc. Natl. Acad. Sci. USA* 89:2581–2584.
*Remington's Pharmaceutical Sciences*, 18th Ed. (1990, Mack Publishing Co., Easton, Pa.).
Rigby P W J, et al. (1977). *J. Mol. Biol.* 113:237–251.
Rojas M, et al. (1996). *J. Biol. Chem.* 271:27456–27461.
Rosenfeld M A, et al. (1992). *Cell* 68:143–155.
Ruano G and Kidd K K (1989). *Nucl. Acids Res.* 17:8392.
Russell D and Hirata R (1998). *Nature Genetics* 18:323–328.
Saitou N and Nei M (1987). *Mol. Biol. Evol.* 4:406–425.
Sambrook J, et al. (1989). *Molecular Cloning: A Laboratorv Manual*, 2nd Ed. (Cold Spring Harbor Laboratory, Cold Spring larbor, N.Y.).
Schaffer A A, et al. (1994). *Hum. Hered.* 44:225–237.
Scharf S J (1986). *Science* 233:1076–1078.
Schneider G, et al. (1998). *Nature Genetics* 18:180–183.
Scopes R (1982). *Protein Purification: Principles and Practice*, (Springer-Verlag, NY).
Shastry B S (1995). *Experientia* 51:1028–1039.
Shastry B S (1998). *Mol. Cell. Biochem.* 181:163–179.
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1975). *Proc. Natl. Acad. Sci. USA* 72:989–993.
Shields P B (1997). *Proc. Dept. Defense BCRP Era of Hope meeting*, Vol. 1 ("Frontiers in Prevention and Detection"), pp.9–10.
Shimada T, et al. (1991). *J. Clin. Invest.* 88:1043–1047.
Shinkai Y, et al. (1992). *Cell* 68:855–867.
Shoemaker D D, et al. (1996). *Nature Genetics* 14:450–456.
Sigurdsson S, et al. (1997). *J. Mol. Med.* 75:758–761.
Smith J R, et al. (1996). *Science* 274:1371–1374.
Smith S W, et al. (1 994). *CABIOS* 10:671–675.
Snouwaert J N, et al. (1992). *Science* 257:1083–1088.
Sorge J, et al. (1984). *Mol. Cell. Biol.* 4:1730–1737.
Spargo C A, et al. (1996). *Mol. Cell. Probes* 10:247–256.
Stanford J L, et al. (1997). *Cancer Res.* 57:1194–1198.
Steinberg G D, et al. (1990). *Prostate* 17:337–347.
Stewart M J, et al. (1992). *Hum Gene Thei.* 3:267–275.
Stratford-Perricaudet L D, et al. (1990). *Hum. Gene Ther*, 1:241–256.
Suarez B K, et al. (2000). *Am. J. Hum. Genet.* 66:933–944.
Tatusov R L, et al. (1997). *Science* 278:631–637.
Tavtigian S V, et al. (1996). *Nat. Genet.* 12:333–337.
Thierry-Mieg D, et al. (1995). Ace.mbly. A graphic interactive program to support shotgun and directed sequencing projects.
Thomas A, et al. (2000). *Statistics cacn Computing* In press.
Thompson J D, et al. (1997). *Nucl. Acids Res.* 25:4876–4882.
Thompson S, et al. (1989). *Cell* 56:313–321.
Valancius V and Smithies 0 (1991). *Mol. Cell Biol.* 11: 1402–1408.
Van der Putten H, et al. (1985). *Proc. Natl. Acadc. Sci. USA* 82:6148–6152.
Wagner E, et al. (1990). *Proc. Natl. Acad. Sci. USA* 87:3410–3414.
Wagner E, et al. (1991). *Proc. Natl. Acad. Sci. USA* 88:4255–4259.
Walker G T et al. (1992). *Nucl. Acids Res.* 20:1691–1696.
Wang C Y and lluang L (1989). *Biochemistry* 28:9508–9514.
Wartell R M, et al. (1990). *Nucl. Acids Res.* 18:2699–2705.
Wells J A (1991). *Methods in Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.

Wilkens E P, et al. (1 999). *Prostate* 39:280–284.
Wilkinson G W and Akrigg A (1992). *Nucleic Acids Res.* 20:2233–2239.
Wolff J A, et al. (1990). *Science* 247:1465–1468.
Wolff J A, et al. (1991). *BioTechniques* 11:474–485.
Woolf C M (1960a). *Cancer* 13:361–364.
Woolf C M (1960b). *Cancer* 13: 739–744.
Wooster R, et al. (1994). *Science* 265:2088–2090.
Wooster R, et al. (1995). *Nature* 378:789–792.
Wu DY and Wallace RB (1989). *Genoimics* 4:560–569.
Wu CH, et al. (1989). *J. Biol. Chem.* 264:16985–16987.
Wu GY, et al. (1991). *J. Biol. Chem.* 266:14338–14342.
Xu J, et al. (1998). *Nat. Genet.* 20:175–179.
Xu J (2000). *Am. J. Hum. Genet.* 66:945–957.
Zenke M, et al. (1990). *Proc. Natl. Acad. Sci. USA* 87:3655–3659.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 4,873,191
U.S. Pat. No. 5,252,479
U.S. Pat. No. 5,270,184
U.S. Pat. No. 5,409,818
U.S. Pat. No. 5,436,146
U.S. Pat. No. 5,455,166
U.S. Pat. No. 5,550,050
U.S. Pat. No. 5,691,198
U.S. Pat. No. 5,735,500
U.S. Pat. No. 5,747,469
Hitzeman et al., EP 73,675A
EPO Publication No. 225,807
EP 425,731 A
European Patent Application Publication No. 0332435
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/12635

What is claimed is:

1. An isolated nucleic acid wherein said nucleic acid is selected from the group consisting of i) a nucleic acid which would encode the polypeptide of SEQ ID NO:2 but for the presence of a base insertion between what would be codons 547 and 548 of a nucleic acid encoding the polypeptide of SEQ ID NO:2, ii) a nucleic acid encoding the polypeptide of SBQ ID NO:2 wherein amino acid 781 is histidine rather than arginine, iii) a nucleic acid encoding the polypeptide of SEQ ID NO:2 wherein amino acid 217 is leucine rather than serine iv) a nucleic acid encoding the polypeptide of SEQ ID NO:2 wherein amino acid 541 is threonine rather than alanine, and v) a nucleic acid encoding the polypeptide of SEQ ID NO:2 wherein amino acid 217 is leucine rather than serine and wherein amino acid 541 is threonine rather than alanine.

* * * * *

SEQUENCE LISTING

<160> NUMBER OF SEQ ID NOS: 240

<210> SEQ ID NO 1
<211> LENGTH: 2481
<212> TYPE: DNA
<213> ORGANISM: Homo sapiens
<220> FEATURE:
<221> NAME/KEY: CDS
<222> LOCATION: (1)..(2478)

<400> SEQUENCE: 1

```
atg tgg gcg ctt tgc tcg ctg ctg cgg tcc gcg gcc gga cgc acc atg        48
Met Trp Ala Leu Cys Ser Leu Leu Arg Ser Ala Ala Gly Arg Thr Met
 1               5                   10                  15 tcg cag gga cgc acc ata tcg cag gca ccc gcc cgc cgc gag cgg ccg        96
Ser Gln Gly Arg Thr Ile Ser Gln Ala Pro Ala Arg Arg Glu Arg Pro
             20                  25                  30 cgc aag gac ccg ctg cgg cac ctg cgc acg cga gag aag cgc gga ccg       144
Arg Lys Asp Pro Leu Arg His Leu Arg Thr Arg Glu Lys Arg Gly Pro
         35                  40                  45 tcg ggg tgc tcc ggc ggc cca aac acc gtg tac ctg cag gtg gtg gca       192
Ser Gly Cys Ser Gly Gly Pro Asn Thr Val Tyr Leu Gln Val Val Ala
     50                  55                  60 gcg ggt agc cgg gac tcg ggc gcc gcg ctc tac gtc ttc tcc gag ttc       240
Ala Gly Ser Arg Asp Ser Gly Ala Ala Leu Tyr Val Phe Ser Glu Phe
 65                  70                  75                  80 aac cgg tat ctc ttc aac tgt gga gaa ggc gtt cag aga ctc atg cag       288
Asn Arg Tyr Leu Phe Asn Cys Gly Glu Gly Val Gln Arg Leu Met Gln
                 85                  90                  95 gag cac aag tta aag gtt gct cgc ctg gac aac ata ttc ctg aca cga       336
Glu His Lys Leu Lys Val Ala Arg Leu Asp Asn Ile Phe Leu Thr Arg
            100                 105                 110
```

```
atg cac tgg tct aat gtt ggg ggc tta agt gga atg att ctt act tta      384
Met His Trp Ser Asn Val Gly Gly Leu Ser Gly Met Ile Leu Thr Leu
        115                 120                 125 aag gaa acc ggg ctt cca aag tgt gta ctt tct gga cct cca caa ctg      432
Lys Glu Thr Gly Leu Pro Lys Cys Val Leu Ser Gly Pro Pro Gln Leu
130                 135                 140 gaa aaa tac ctc gaa gca atc aaa ata ttt tct ggt cca ttg aaa gga      480
Glu Lys Tyr Leu Glu Ala Ile Lys Ile Phe Ser Gly Pro Leu Lys Gly
145                 150                 155                 160 ata gaa ctg gct gtg cgg ccc cac tct gcc cca gaa tac gag gat gaa      528
Ile Glu Leu Ala Val Arg Pro His Ser Ala Pro Glu Tyr Glu Asp Glu
                165                 170                 175 acc atg aca gtt tac cag atc ccc ata cac agt gaa cag agg agg gga      576
Thr Met Thr Val Tyr Gln Ile Pro Ile His Ser Glu Gln Arg Arg Gly
            180                 185                 190 aag cac caa cca tgg cag agt cca gaa agg cct ctc agc agg ctc agt      624
Lys His Gln Pro Trp Gln Ser Pro Glu Arg Pro Leu Ser Arg Leu Ser
        195                 200                 205 cca gag cga tct tca gac tcc gag tcg aat gaa aat gag cca cac ctt      672
Pro Glu Arg Ser Ser Asp Ser Glu Ser Asn Glu Asn Glu Pro His Leu
    210                 215                 220 cca cat ggt gtt agc cag aga aga ggg gtc agg gac tct tcc ctg gtc      720
Pro His Gly Val Ser Gln Arg Arg Gly Val Arg Asp Ser Ser Leu Val
225                 230                 235                 240 gta gct ttc atc tgt aag ctt cac tta aag aga gga aac ttc ttg gtg      768
Val Ala Phe Ile Cys Lys Leu His Leu Lys Arg Gly Asn Phe Leu Val
                245                 250                 255 ctc aaa gca aag gag atg ggc ctc cca gtt ggg aca gct gcc atc gct      816
Leu Lys Ala Lys Glu Met Gly Leu Pro Val Gly Thr Ala Ala Ile Ala
            260                 265                 270 ccc atc att gct gct gtc aag gac ggg aaa agc atc act cat gaa gga      864
Pro Ile Ile Ala Ala Val Lys Asp Gly Lys Ser Ile Thr His Glu Gly
        275                 280                 285 aga gag att ttg gct gaa gag ctg tgt act cct cca gat cct ggt gct      912
Arg Glu Ile Leu Ala Glu Glu Leu Cys Thr Pro Pro Asp Pro Gly Ala
    290                 295                 300 gct ttt gtg gtg gta gaa tgt cca gat gaa agc ttc att caa ccc atc      960
Ala Phe Val Val Val Glu Cys Pro Asp Glu Ser Phe Ile Gln Pro Ile
305                 310                 315                 320 tgt gag aat gcc acc ttt cag agg tac caa gga aag gca gat gcc ccc     1008
Cys Glu Asn Ala Thr Phe Gln Arg Tyr Gln Gly Lys Ala Asp Ala Pro
                325                 330                 335 gtg gcc ttg gtg gtt cac atg gcc cca gca tct gtg ctt gtg gac agc     1056
Val Ala Leu Val Val His Met Ala Pro Ala Ser Val Leu Val Asp Ser
            340                 345                 350 agg tac cag cag tgg atg gag agg ttt ggg cct gac acc cag cac ttg     1104
Arg Tyr Gln Gln Trp Met Glu Arg Phe Gly Pro Asp Thr Gln His Leu
        355                 360                 365 gtc ctg aat gag aac tgt gcc tca gtt cac aac ctt cgc agc cac aag     1152
Val Leu Asn Glu Asn Cys Ala Ser Val His Asn Leu Arg Ser His Lys
    370                 375                 380 att caa acc cag ctc aac ctc atc cac ccg gac atc ttc ccc ctg ctc     1200
Ile Gln Thr Gln Leu Asn Leu Ile His Pro Asp Ile Phe Pro Leu Leu
385                 390                 395                 400 acc agt ttc cgc tgt aag aag gag ggc ccc acc ctc agt gtg ccc atg     1248
Thr Ser Phe Arg Cys Lys Lys Glu Gly Pro Thr Leu Ser Val Pro Met
                405                 410                 415 gtt cag ggt gaa tgc ctc ctc aag tac cag ctc cgt ccc agg agg gag     1296
Val Gln Gly Glu Cys Leu Leu Lys Tyr Gln Leu Arg Pro Arg Arg Glu
```

```
                    420                 425                 430
tgg cag agg gat gcc att att act tgc aat cct gag gaa ttc ata gtt    1344
Trp Gln Arg Asp Ala Ile Ile Thr Cys Asn Pro Glu Glu Phe Ile Val
        435                 440                 445 gag gcg ctg cag ctt ccc aac ttc cag cag agc gtg cag gag tac agg    1392
Glu Ala Leu Gln Leu Pro Asn Phe Gln Gln Ser Val Gln Glu Tyr Arg
    450                 455                 460 agg agt gcg cag gac ggc cca gcc cca gca gag aaa aga agt cag tac    1440
Arg Ser Ala Gln Asp Gly Pro Ala Pro Ala Glu Lys Arg Ser Gln Tyr
465                 470                 475                 480 cca gaa atc atc ttc ctt gga aca ggg tct gcc atc ccg atg aag att    1488
Pro Glu Ile Ile Phe Leu Gly Thr Gly Ser Ala Ile Pro Met Lys Ile
                485                 490                 495 cga aat gtc agt gcc aca ctt gtc aac ata agc ccc gac acg tct ctg    1536
Arg Asn Val Ser Ala Thr Leu Val Asn Ile Ser Pro Asp Thr Ser Leu
            500                 505                 510 cta ctg gac tgt ggt gag ggc aca ttt ggg cag ctg tgc cgt cat tac    1584
Leu Leu Asp Cys Gly Glu Gly Thr Phe Gly Gln Leu Cys Arg His Tyr
        515                 520                 525 gga gac cag gtg gac agg gtc ctg ggc acc ctg gct gct gtg ttt gtg    1632
Gly Asp Gln Val Asp Arg Val Leu Gly Thr Leu Ala Ala Val Phe Val
    530                 535                 540 tcc cac ctg cac gca gat cac cac acg ggc ttg cca agt atc ttg ctg    1680
Ser His Leu His Ala Asp His His Thr Gly Leu Pro Ser Ile Leu Leu
545                 550                 555                 560 cag aga gaa cgc gcc ttg gca tct ttg gga aag ccg ctt cac cct ttg    1728
Gln Arg Glu Arg Ala Leu Ala Ser Leu Gly Lys Pro Leu His Pro Leu
                565                 570                 575 ctg gtg gtt gcc ccc aac cag ctc aaa gcc tgg ctc cag cag tac cac    1776
Leu Val Val Ala Pro Asn Gln Leu Lys Ala Trp Leu Gln Gln Tyr His
            580                 585                 590 aac cag tgc cag gag gtc ctg cac cac atc agt atg att cct gcc aaa    1824
Asn Gln Cys Gln Glu Val Leu His His Ile Ser Met Ile Pro Ala Lys
        595                 600                 605 tgc ctt cag gaa ggg gct gag atc tcc agt cct gca gtg gaa aga ttg    1872
Cys Leu Gln Glu Gly Ala Glu Ile Ser Ser Pro Ala Val Glu Arg Leu
    610                 615                 620 atc agt tcg ctg ttg cga aca tgt gat ttg gaa gag ttt cag acc tgt    1920
Ile Ser Ser Leu Leu Arg Thr Cys Asp Leu Glu Glu Phe Gln Thr Cys
625                 630                 635                 640 ctg gtg cgg cac tgc aag cat gcg ttt ggc tgt gcg ctg gtg cac acc    1968
Leu Val Arg His Cys Lys His Ala Phe Gly Cys Ala Leu Val His Thr
                645                 650                 655 tct ggc tgg aaa gtg gtc tat tcc ggg gac acc atg ccc tgc gag gct    2016
Ser Gly Trp Lys Val Val Tyr Ser Gly Asp Thr Met Pro Cys Glu Ala
            660                 665                 670 ctg gtc cgg atg ggg aaa gat gcc acc ctc ctg ata cat gaa gcc acc    2064
Leu Val Arg Met Gly Lys Asp Ala Thr Leu Leu Ile His Glu Ala Thr
        675                 680                 685 ctg gaa gat ggt ttg gaa gag gaa gca gtg gaa aag aca cac agc aca    2112
Leu Glu Asp Gly Leu Glu Glu Glu Ala Val Glu Lys Thr His Ser Thr
    690                 695                 700 acg tcc caa gcc atc agc gtg ggg atg cgg atg aac gcg gag ttc att    2160
Thr Ser Gln Ala Ile Ser Val Gly Met Arg Met Asn Ala Glu Phe Ile
705                 710                 715                 720 atg ctg aac cac ttc agc cag cgc tat gcc aag gtc ccc ctc ttc agc    2208
Met Leu Asn His Phe Ser Gln Arg Tyr Ala Lys Val Pro Leu Phe Ser
                725                 730                 735 ccc aac ttc agc gag aaa gtg gga gtt gcc ttt gac cac atg aag gtc    2256
```

```
                Pro Asn Phe Ser Glu Lys Val Gly Val Ala Phe Asp His Met Lys Val
                                740                 745                 750 tgc ttt gga gac ttt cca aca atg ccc aag ctg att ccc cca ctg aaa           2304
Cys Phe Gly Asp Phe Pro Thr Met Pro Lys Leu Ile Pro Pro Leu Lys
        755                 760                 765 gcc ctg ttt gct ggc gac atc gag gag atg gag gag cgc agg gag aag           2352
Ala Leu Phe Ala Gly Asp Ile Glu Glu Met Glu Glu Arg Arg Glu Lys
    770                 775                 780 cgg gag ctg cgg cag gtg cgg gcg gcc ctc ctg tcc agg gag ctg gca           2400
Arg Glu Leu Arg Gln Val Arg Ala Ala Leu Leu Ser Arg Glu Leu Ala
785                 790                 795                 800 ggc ggc ctg gag gat ggg gag cct cag cag aag cgg gcc cac aca gag           2448
Gly Gly Leu Glu Asp Gly Glu Pro Gln Gln Lys Arg Ala His Thr Glu
                805                 810                 815 gag cca cag gcc aag aag gtc aga gcc cag tga                               2481
Glu Pro Gln Ala Lys Lys Val Arg Ala Gln
            820                 825
```

<210> SEQ ID NO 2
<211> LENGTH: 826
<212> TYPE: PRT
<213> ORGANISM: Homo sapiens

<400> SEQUENCE: 2

```
Met Trp Ala Leu Cys Ser Leu Leu Arg Ser Ala Ala Gly Arg Thr Met
  1               5                  10                  15

Ser Gln Gly Arg Thr Ile Ser Gln Ala Pro Ala Arg Arg Glu Arg Pro
                 20                  25                  30

Arg Lys Asp Pro Leu Arg His Leu Arg Thr Arg Glu Lys Arg Gly Pro
             35                  40                  45

Ser Gly Cys Ser Gly Gly Pro Asn Thr Val Tyr Leu Gln Val Val Ala
         50                  55                  60

Ala Gly Ser Arg Asp Ser Gly Ala Ala Leu Tyr Val Phe Ser Glu Phe
 65                  70                  75                  80

Asn Arg Tyr Leu Phe Asn Cys Gly Glu Gly Val Gln Arg Leu Met Gln
                 85                  90                  95

Glu His Lys Leu Lys Val Ala Arg Leu Asp Asn Ile Phe Leu Thr Arg
                100                 105                 110

Met His Trp Ser Asn Val Gly Gly Leu Ser Gly Met Ile Leu Thr Leu
            115                 120                 125

Lys Glu Thr Gly Leu Pro Lys Cys Val Leu Ser Gly Pro Pro Gln Leu
130                 135                 140

Glu Lys Tyr Leu Glu Ala Ile Lys Ile Phe Ser Gly Pro Leu Lys Gly
145                 150                 155                 160

Ile Glu Leu Ala Val Arg Pro His Ser Ala Pro Glu Tyr Glu Asp Glu
                165                 170                 175

Thr Met Thr Val Tyr Gln Ile Pro Ile His Ser Glu Gln Arg Arg Gly
                180                 185                 190

Lys His Gln Pro Trp Gln Ser Pro Glu Arg Pro Leu Ser Arg Leu Ser
            195                 200                 205

Pro Glu Arg Ser Ser Asp Ser Glu Ser Asn Glu Asn Glu Pro His Leu
        210                 215                 220

Pro His Gly Val Ser Gln Arg Arg Gly Val Arg Asp Ser Ser Leu Val
225                 230                 235                 240

Val Ala Phe Ile Cys Lys Leu His Leu Lys Arg Gly Asn Phe Leu Val
                245                 250                 255
```

-continued

Leu Lys Ala Lys Glu Met Gly Leu Pro Val Gly Thr Ala Ala Ile Ala
            260                 265                 270

Pro Ile Ile Ala Ala Val Lys Asp Gly Lys Ser Ile Thr His Glu Gly
            275                 280                 285

Arg Glu Ile Leu Ala Glu Leu Cys Thr Pro Pro Asp Pro Gly Ala
            290                 295                 300

Ala Phe Val Val Val Glu Cys Pro Asp Glu Ser Phe Ile Gln Pro Ile
305                 310                 315                 320

Cys Glu Asn Ala Thr Phe Gln Arg Tyr Gln Gly Lys Ala Asp Ala Pro
                    325                 330                 335

Val Ala Leu Val Val His Met Ala Pro Ala Ser Val Leu Val Asp Ser
                    340                 345                 350

Arg Tyr Gln Gln Trp Met Glu Arg Phe Gly Pro Asp Thr Gln His Leu
                    355                 360                 365

Val Leu Asn Glu Asn Cys Ala Ser Val His Asn Leu Arg Ser His Lys
                    370                 375                 380

Ile Gln Thr Gln Leu Asn Leu Ile His Pro Asp Ile Phe Pro Leu Leu
385                 390                 395                 400

Thr Ser Phe Arg Cys Lys Lys Glu Gly Pro Thr Leu Ser Val Pro Met
                    405                 410                 415

Val Gln Gly Glu Cys Leu Leu Lys Tyr Gln Leu Arg Pro Arg Arg Glu
                    420                 425                 430

Trp Gln Arg Asp Ala Ile Ile Thr Cys Asn Pro Glu Glu Phe Ile Val
                    435                 440                 445

Glu Ala Leu Gln Leu Pro Asn Phe Gln Gln Ser Val Gln Glu Tyr Arg
450                 455                 460

Arg Ser Ala Gln Asp Gly Pro Ala Pro Ala Glu Lys Arg Ser Gln Tyr
465                 470                 475                 480

Pro Glu Ile Ile Phe Leu Gly Thr Gly Ser Ala Ile Pro Met Lys Ile
                    485                 490                 495

Arg Asn Val Ser Ala Thr Leu Val Asn Ile Ser Pro Asp Thr Ser Leu
                    500                 505                 510

Leu Leu Asp Cys Gly Glu Gly Thr Phe Gly Gln Leu Cys Arg His Tyr
                    515                 520                 525

Gly Asp Gln Val Asp Arg Val Leu Gly Thr Leu Ala Ala Val Phe Val
                    530                 535                 540

Ser His Leu His Ala Asp His His Thr Gly Leu Pro Ser Ile Leu Leu
545                 550                 555                 560

Gln Arg Glu Arg Ala Leu Ala Ser Leu Gly Lys Pro Leu His Pro Leu
                    565                 570                 575

Leu Val Val Ala Pro Asn Gln Leu Lys Ala Trp Leu Gln Gln Tyr His
                    580                 585                 590

Asn Gln Cys Gln Glu Val Leu His His Ile Ser Met Ile Pro Ala Lys
                    595                 600                 605

Cys Leu Gln Glu Gly Ala Glu Ile Ser Ser Pro Ala Val Glu Arg Leu
                    610                 615                 620

Ile Ser Ser Leu Leu Arg Thr Cys Asp Leu Glu Glu Phe Gln Thr Cys
625                 630                 635                 640

Leu Val Arg His Cys Lys His Ala Phe Gly Cys Ala Leu Val His Thr
                    645                 650                 655

Ser Gly Trp Lys Val Val Tyr Ser Gly Asp Thr Met Pro Cys Glu Ala
                    660                 665                 670

Leu Val Arg Met Gly Lys Asp Ala Thr Leu Leu Ile His Glu Ala Thr

```
            675                 680                 685
Leu Glu Asp Gly Leu Glu Glu Ala Val Glu Lys Thr His Ser Thr
        690                 695                 700
Thr Ser Gln Ala Ile Ser Val Gly Met Arg Met Asn Ala Glu Phe Ile
705                 710                 715                 720
Met Leu Asn His Phe Ser Gln Arg Tyr Ala Lys Val Pro Leu Phe Ser
                725                 730                 735
Pro Asn Phe Ser Glu Lys Val Gly Val Ala Phe Asp His Met Lys Val
            740                 745                 750
Cys Phe Gly Asp Phe Pro Thr Met Pro Lys Leu Ile Pro Pro Leu Lys
        755                 760                 765
Ala Leu Phe Ala Gly Asp Ile Glu Glu Met Glu Glu Arg Arg Glu Lys
770                 775                 780
Arg Glu Leu Arg Gln Val Arg Ala Ala Leu Leu Ser Arg Glu Leu Ala
785                 790                 795                 800
Gly Gly Leu Glu Asp Gly Glu Pro Gln Gln Lys Arg Ala His Thr Glu
                805                 810                 815
Glu Pro Gln Ala Lys Lys Val Arg Ala Gln
            820                 825

<210> SEQ ID NO 3
<211> LENGTH: 2958
<212> TYPE: DNA
<213> ORGANISM: Homo sapiens
<220> FEATURE:
<221> NAME/KEY: misc_feature
<222> LOCATION: (51)..(2531)
<223> OTHER INFORMATION: coding sequence as in SEQ ID NO:1

<400> SEQUENCE: 3
cgcgggcgta ggtgaccggc ggctttctca gttttggtgg agacgggcgc atgtgggcgc      60
tttgctcgct gctgcggtcc gcggccggac gcaccatgtc gcaggacgcg accatatcgc     120
aggcacccgc ccgccgcgag cggccgcgca aggacccgct gcggcacctg cgcacgcgag     180
agaagcgcgg accgtcgggg tgctccggcg gcccaaacac cgtgtacctg caggtggtgg     240
cagcgggtag ccgggactcg ggcgccgcgc tctacgtctt ctccgagttc aaccggtatc     300
tcttcaactg tggagaaggc gttcagagac tcatgcagga gcacaagtta aggttgctc     360
gcctggacaa catattcctg acacgaatgc actggtctaa tgttggggc ttaagtggaa     420
tgattcttac tttaaaggaa accgggcttc caaagtgtgt actttctgga cctccacaac     480
tggaaaaata cctcgaagca atcaaaatat tttctggtcc attgaaagga atagaactgg     540
ctgtgcggcc ccactctgcc ccagaatacg aggatgaaac catgacagtt taccagatcc     600
ccatacacag tgaacagagg aggggaaagc accaaccatg gcagagtcca gaaaggcctc     660
tcagcaggct cagtccagag cgatcttcag actccgagtc gaatgaaaat gagccacacc     720
ttccacatgg tgttagccag agaagagggg tcagggactc ttccctggtc gtagctttca     780
tctgtaagct tcacttaaag agaggaaact tcttggtgct caaagcaaag gagatgggcc     840
tcccagttgg gacagctgcc atcgctccca tcattgctgc tgtcaaggac gggaaaagca     900
tcactcatga aggaagagag atttttggctg aagagctgtg tactcctcca gatcctggtg     960
ctgctttttgt ggtggtagaa tgtccagatg aaagcttcat tcaacccatc tgtgagaatg    1020
ccacctttca gaggtaccaa ggaaaggcag atgcccccgt ggccttggtg gttcacatgg    1080
ccccagcatc tgtgccttgtg gacagcaggt accagcagtg gatggagagg tttgggcctg    1140
```

-continued

```
acacccagca cttggtcctg aatgagaact gtgcctcagt tcacaacctt cgcagccaca      1200
agattcaaac ccagctcaac ctcatccacc cggacatctt cccctgctc accagtttcc       1260 gctgtaagaa ggagggcccc accctcagtg tgcccatggt tcagggtgaa tgcctcctca      1320
agtaccagct ccgtcccagg agggagtggc agagggatgc cattattact tgcaatcctg      1380
aggaattcat agttgaggcg ctgcagcttc ccaacttcca gcagagcgtg caggagtaca      1440
ggaggagtgc gcaggacggc ccagcccag cagagaaaag aagtcagtac ccagaaatca       1500
tcttccttgg aacagggtct gccatcccga tgaagattcg aaatgtcagt gccacacttg      1560
tcaacataag ccccgacacg tctctgctac tggactgtgg tgagggcaca tttgggcagc      1620
tgtgccgtca ttacggagac caggtggaca gggtcctggg cacccggct gctgtgtttg       1680 tgtcccacct gcacgcagat caccacacgg gcttgccaag tatcttgctg cagagagaac      1740
gcgccttggc atctttggga aagccgcttc accctttgct ggtggttgcc cccaaccagc      1800
tcaaagcctg gctccagcag taccacaacc agtgccagga ggtcctgcac cacatcagta      1860
tgattcctgc caaatgcctt caggaagggg ctgagatctc cagtcctgca gtggaaagat      1920
tgatcagttc gctgttgcga acatgtgatt tggaagagtt tcagacctgt ctggtgcggc      1980
actgcaagca tgcgtttggc tgtgcgctgg tgcacacctc tggctggaaa gtggtctatt      2040
ccggggacac catgccctgc gaggctctgg tccggatggg gaaagatgcc accctcctga      2100
tacatgaagc caccctggaa gatggttttg gaagaggaagc agtggaaaag acacacagca      2160
caacgtccca agccatcagc gtggggatgc ggatgaacgc ggagttcatt atgctgaacc      2220
acttcagcca gcgctatgcc aaggtccccc tcttcagccc caacttcagc gagaaagtgg      2280
gagttgcctt tgaccacatg aaggtctgct ttggagactt tccaacaatg cccaagctga      2340 ttccccccact gaaagccctg tttgctggcg acatcgagga gatggaggag cgcagggaga      2400
agcgggagct gcggcaggtg cgggcggccc tcctgtccag ggagctggca ggcggcctgg      2460
aggatgggga gcctcagcag aagcgggccc acacagagga gccacaggcc aagaaggtca      2520
gagcccagtg aagatctggg agaccctgaa ctcagaaggc tgtgtgtctt ctgccccacg      2580
cacgcacccg tatctgccct ccttgctggt agaagctgaa gagcacggtc ccccaggagg      2640
cagctcagga taggtggtat ggagctgtgc cgaggcttgg gctcccacat aagcactagt      2700
ctatagatgc ctcttaggac tggtgcctgg cacagccgcg ggccaggagg ctgccacacg      2760
gaagcaagca gatgaactaa tttcatttca aggcagtttt taaagaagtc ttggaaacag      2820
acggcggcac cttcctctca atccagcaaa gtgattccct gcacaccaga gacaagcaga      2880
gtaacaggat cagtgggtct aagtgtccga gacttaacga aaatagtatt tcagctgcaa      2940
taaagattga gtttgcaa                                                   2958
```

<210> SEQ ID NO 4
<211> LENGTH: 295
<212> TYPE: DNA
<213> ORGANISM: Homo sapiens
<220> FEATURE:
<221> NAME/KEY: misc_feature
<222> LOCATION: (51)..(295)
<223> OTHER INFORMATION: exon 1

<400> SEQUENCE: 4

```
cgcgggcgta ggtgaccggc ggctttctca gttttggtgg agacgggcgc atgtgggcgc        60
tttgctcgct gctgcggtcc gcggccggac gcaccatgtc gcaggacgc accatatcgc       120 aggcacccgc ccgccgcgag cggccgcgca aggacccgct gcggcacctg cgcacgcgag      180
```

```
agaagcgcgg accgtcgggg tgctccggcg gcccaaacac cgtgtacctg caggtggtgg      240
cagcgggtag ccgggactcg ggcgccgcgc tctacgtctt ctccgagttc aaccg          295

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: exon 2

<400> SEQUENCE: 5
gtatctcttc aactgtggag aaggcgttca gagactcatg caggagcaca a              51

<210> SEQ ID NO 6
<211> LENGTH: 71
<212> TYPE: DNA
<213> ORGANISM: Homo sapiens
<220> FEATURE:
<221> NAME/KEY: misc_feature
<222> LOCATION: (1)..(71)
<223> OTHER INFORMATION: exon 3

<400> SEQUENCE: 6
gttaaaggtt gctcgcctgg acaacatatt cctgacacga atgcactggt ctaatgttgg     60
gggcttaagt g                                                          71

<210> SEQ ID NO 7
<211> LENGTH: 65
<212> TYPE: DNA
<213> ORGANISM: Homo sapiens
<220> FEATURE:
<221> NAME/KEY: misc_feature
<222> LOCATION: (1)..(65)
<223> OTHER INFORMATION: exon 4

<400> SEQUENCE: 7
gaatgattct tactttaaag gaaaccgggc ttccaaagtg tgtactttct ggacctccac     60
aactg                                                                 65

<210> SEQ ID NO 8
<211> LENGTH: 58
<212> TYPE: DNA
<213> ORGANISM: Homo sapiens
<220> FEATURE:
<221> NAME/KEY: misc_feature
<222> LOCATION: (1)..(58)
<223> OTHER INFORMATION: exon 5

<400> SEQUENCE: 8
gaaaaatacc tcgaagcaat caaaatattt tctggtccat tgaaaggaat agaactgg       58

<210> SEQ ID NO 9
<211> LENGTH: 69
<212> TYPE: DNA
<213> ORGANISM: Homo sapiens
<220> FEATURE:
<221> NAME/KEY: misc_feature
<222> LOCATION: (1)..(69)
<223> OTHER INFORMATION: exon 6

<400> SEQUENCE: 9
ctgtgcggcc ccactctgcc ccagaatacg aggatgaaac catgacagtt taccagatcc    60
```

```
ccatacaca                                                             69

<210> SEQ ID NO 10
<211> LENGTH: 120
<212> TYPE: DNA
<213> ORGANISM: Homo sapiens
<220> FEATURE:
<221> NAME/KEY: misc_feature
<222> LOCATION: (1)..(120)
<223> OTHER INFORMATION: exon 7

<400> SEQUENCE: 10
gtgaacagag gagggggaaag caccaaccat ggcagagtcc agaaaggcct ctcagcaggc    60
tcagtccaga gcgatcttca gactccgagt cgaatgaaaa tgagccacac cttccacatg   120

<210> SEQ ID NO 11
<211> LENGTH: 59
<212> TYPE: DNA
<213> ORGANISM: Homo sapiens
<220> FEATURE:
<221> NAME/KEY: misc_feature
<222> LOCATION: (1)..(59)
<223> OTHER INFORMATION: exon 8

<400> SEQUENCE: 11
gtgttagcca gagaagaggg gtcagggact cttccctggt cgtagctttc atctgtaag     59

<210> SEQ ID NO 12
<211> LENGTH: 59
<212> TYPE: DNA
<213> ORGANISM: Homo sapiens
<220> FEATURE:
<221> NAME/KEY: misc_feature
<222> LOCATION: (1)..(59)
<223> OTHER INFORMATION: exon 9

<400> SEQUENCE: 12
cttcacttaa agagaggaaa cttcttggtg ctcaaagcaa aggagatggg cctcccagt     59

<210> SEQ ID NO 13
<211> LENGTH: 73
<212> TYPE: DNA
<213> ORGANISM: Homo sapiens
<220> FEATURE:
<221> NAME/KEY: misc_feature
<222> LOCATION: (1)..(73)
<223> OTHER INFORMATION: exon 10

<400> SEQUENCE: 13
tgggacagct gccatcgctc ccatcattgc tgctgtcaag acgggaaaa gcatcactca     60 tgaaggaaga gag                                                       73

<210> SEQ ID NO 14
<211> LENGTH: 113
<212> TYPE: DNA
<213> ORGANISM: Homo sapiens
<220> FEATURE:
<221> NAME/KEY: misc_feature
<222> LOCATION: (1)..(113)
<223> OTHER INFORMATION: exon 11

<400> SEQUENCE: 14
attttggctg aagagctgtg tactcctcca gatcctggtg ctgcttttgt ggtggtagaa    60
tgtccagatg aaagcttcat tcaacccatc tgtgagaatg ccacctttca gag          113
```

<210> SEQ ID NO 15
<211> LENGTH: 96
<212> TYPE: DNA
<213> ORGANISM: Homo sapiens
<220> FEATURE:
<221> NAME/KEY: misc_feature
<222> LOCATION: (1)..(96)
<223> OTHER INFORMATION: exon 12

<400> SEQUENCE: 15
gtaccaagga aaggcagatg cccccgtggc cttggtggtt cacatggccc cagcatctgt      60
gcttgtggac agcaggtacc agcagtggat ggagag                                96

<210> SEQ ID NO 16
<211> LENGTH: 139
<212> TYPE: DNA
<213> ORGANISM: Homo sapiens
<220> FEATURE:
<221> NAME/KEY: misc_feature
<222> LOCATION: (1)..(139)
<223> OTHER INFORMATION: exon 13

<400> SEQUENCE: 16
gtttgggcct gacacccagc acttggtcct gaatgagaac tgtgcctcag ttcacaacct      60
tcgcagccac aagattcaaa cccagctcaa cctcatccac ccggacatct tccccctgct     120
caccagtttc cgctgtaag                                                  139

<210> SEQ ID NO 17
<211> LENGTH: 86
<212> TYPE: DNA
<213> ORGANISM: Homo sapiens
<220> FEATURE:
<221> NAME/KEY: misc_feature
<222> LOCATION: (1)..(86)
<223> OTHER INFORMATION: exon 14

<400> SEQUENCE: 17
aaggagggcc ccaccctcag tgtgcccatg gttcagggtg aatgcctcct caagtaccag      60
ctccgtccca ggagggagtg gcagag                                           86

<210> SEQ ID NO 18
<211> LENGTH: 119
<212> TYPE: DNA
<213> ORGANISM: Homo sapiens
<220> FEATURE:
<221> NAME/KEY: misc_feature
<222> LOCATION: (1)..(119)
<223> OTHER INFORMATION: exon 15

<400> SEQUENCE: 18
ggatgccatt attacttgca atcctgagga attcatagtt gaggcgctgc agcttcccaa      60
cttccagcag agcgtgcagg agtacaggag gagtgcgcag gacggcccag ccccagcag      119

<210> SEQ ID NO 19
<211> LENGTH: 97
<212> TYPE: DNA
<213> ORGANISM: Homo sapiens
<220> FEATURE:
<221> NAME/KEY: misc_feature
<222> LOCATION: (1)..(97)
<223> OTHER INFORMATION: exon 16

<400> SEQUENCE: 19
agaaaagaag tcagtaccca gaaatcatct tccttggaac agggtctgcc atcccgatga      60
agattcgaaa tgtcagtgcc acacttgtca acataag                                97

<210> SEQ ID NO 20
<211> LENGTH: 139
<212> TYPE: DNA
<213> ORGANISM: Homo sapiens
<220> FEATURE:
<221> NAME/KEY: misc_feature
<222> LOCATION: (1)..(139)
<223> OTHER INFORMATION: exon 17

<400> SEQUENCE: 20
ccccgacacg tctctgctac tggactgtgg tgagggcaca tttgggcagc tgtgccgtca      60
ttacggagac caggtggaca gggtcctggg caccctggct gctgtgtttg tgtcccacct     120
gcacgcagat caccacacg                                                  139

<210> SEQ ID NO 21
<211> LENGTH: 39
<212> TYPE: DNA
<213> ORGANISM: Homo sapiens
<220> FEATURE:
<221> NAME/KEY: misc_feature
<222> LOCATION: (1)..(39)
<223> OTHER INFORMATION: exon 18

<400> SEQUENCE: 21
ggcttgccaa gtatcttgct gcagagagaa cgcgccttg                             39

<210> SEQ ID NO 22
<211> LENGTH: 110
<212> TYPE: DNA
<213> ORGANISM: Homo sapiens
<220> FEATURE:
<221> NAME/KEY: misc_feature
<222> LOCATION: (1)..(110)
<223> OTHER INFORMATION: exon 19

<400> SEQUENCE: 22
gcatctttgg gaaagccgct tcacccttttg ctggtggttg cccccaacca gctcaaagcc     60
tggctccagc agtaccacaa ccagtgccag gaggtcctgc accacatcag                110

<210> SEQ ID NO 23
<211> LENGTH: 100
<212> TYPE: DNA
<213> ORGANISM: Homo sapiens
<220> FEATURE:
<221> NAME/KEY: misc_feature
<222> LOCATION: (1)..(100)
<223> OTHER INFORMATION: exon 20

<400> SEQUENCE: 23
tatgattcct gccaaatgcc ttcaggaagg ggctgagatc tccagtcctg cagtggaaag      60
attgatcagt tcgctgttgc gaacatgtga tttggaagag                           100

<210> SEQ ID NO 24
<211> LENGTH: 121
<212> TYPE: DNA
<213> ORGANISM: Homo sapiens
<220> FEATURE:
<221> NAME/KEY: misc_feature
<222> LOCATION: (1)..(121)
<223> OTHER INFORMATION: exon 21

<400> SEQUENCE: 24
tttcagacct gtctggtgcg gcactgcaag catgcgtttg ctgtgcgct ggtgcacacc       60

```
tctggctgga aagtggtcta ttccggggac accatgccct gcgaggctct ggtccggatg      120
g                                                                      121

<210> SEQ ID NO 25
<211> LENGTH: 79
<212> TYPE: DNA
<213> ORGANISM: Homo sapiens
<220> FEATURE:
<221> NAME/KEY: misc_feature
<222> LOCATION: (1)..(79)
<223> OTHER INFORMATION: exon 22

<400> SEQUENCE: 25
ggaaagatgc caccctcctg atacatgaag ccaccctgga agatggtttg aagaggaag       60 cagtggaaaa gacacacag                                                   79

<210> SEQ ID NO 26
<211> LENGTH: 145
<212> TYPE: DNA
<213> ORGANISM: Homo sapiens
<220> FEATURE:
<221> NAME/KEY: misc_feature
<222> LOCATION: (1)..(145)
<223> OTHER INFORMATION: exon 23

<400> SEQUENCE: 26
cacaacgtcc caagccatca gcgtggggat gcggatgaac gcggagttca ttatgctgaa      60
ccacttcagc cagcgctatg ccaaggtccc cctcttcagc cccaacttca gcgagaaagt      120
gggagttgcc tttgaccaca tgaag                                            145

<210> SEQ ID NO 27
<211> LENGTH: 655
<212> TYPE: DNA
<213> ORGANISM: Homo sapiens
<220> FEATURE:
<221> NAME/KEY: misc_feature
<222> LOCATION: (1)..(228)
<223> OTHER INFORMATION: exon 24
<221> NAME/KEY: polyA_signal
<222> LOCATION: (636)..(641)

<400> SEQUENCE: 27
gtctgctttg gagactttcc aacaatgccc aagctgattc ccccactgaa agccctgttt      60
gctggcgaca tcgaggagat ggaggagcgc agggagaagc gggagctgcg gcaggtgcgg      120
gcggccctcc tgtccaggga gctggcaggc ggcctggagg atgggagcc tcagcagaag      180 cgggcccaca cagaggagcc acaggccaag aaggtcagag cccagtgaag atctgggaga      240
ccctgaactc agaaggctgt gtgtcttctg ccccacgcac gcaccgtat ctgccctcct      300 tgctggtaga agctgaagag cacggtcccc caggaggcag ctcaggatag gtggtatgga      360
gctgtgccga ggcttgggct cccacataag cactagtcta tagatgcctc ttaggactgg      420
tgcctggcac agccgcgggc caggaggctg ccacacggaa gcaagcagat gaactaattt      480
catttcaagg cagttttta agaagtcttg gaaacagacg gcggcacctt tcctctaatc      540
cagcaaagtg attccctgca caccagagac aagcagagta acaggatcag tgggtctaag      600
tgtccgagac ttaacgaaaa tagtatttca gctgcaataa agattgagtt tgcaa          655

<210> SEQ ID NO 28
<211> LENGTH: 26664
<212> TYPE: DNA
```

```
<213> ORGANISM: Homo sapiens
<220> FEATURE:
<221> NAME/KEY: misc_feature
<222> LOCATION: (910)..(13104)
<223> OTHER INFORMATION: exon 1: 910-1154; exon 2: 1736-1786; exon 3:
      1925-1995; exon 4: 3025-3089; exon 5: 4361-4418;
      exon 6: 5582-5650; exon 7: 7075-7194; exon 8:
      8186-8244; exon 9: 12878-12936; exon 10:
<221> NAME/KEY: misc_feature
<222> LOCATION: (13756)..(22917)
<223> OTHER INFORMATION: exon 11: 13756-13868; exon 12: 15283-15378;
      exon 13: 16278-16416; exon 14: 16498-16583; exon 15:
      18583-18701; exon 16: 20349-20445; exon 17:
      22172-22310; exon 18: 22879-22917
<221> NAME/KEY: misc_feature
<222> LOCATION: (23045)..(26452)
<223> OTHER INFORMATION: exon 19: 23045-23154; exon 20: 23795-23895;
      exon 21: 23973-24093; exon 22: 24354-24432; exon 23:
      25026-25170; exon 24: 25812-26036; polyadenylation
      signal: 26447-26452
<221> NAME/KEY: variation
<222> LOCATION: (826)..(23879)
<223> OTHER INFORMATION: s at positions 826 and 23180 is G or C; y at
      positions 1914, 5568, 7165, 16431, 1857 and 20486
      is C or T; n at position 13128 is t or tgat; r at
      positions 22211 and 23879 is A or G.

<400> SEQUENCE: 28
tatcaggtga ctgaattcta tattctgaag taggagatac tgttattgct gttattacat      60
tttacacata agaaagctga ggctctgaga ggtcaagatc acgcagctaa caaatgagcc     120
aagactcttg ctttagagct tgtcctctat tcttgctttt ctttccaaaa aacactacaa     180
tttttgtttt gttttgtttt gttttgagac agggtctcga ggtgtcaccc aggctggagt     240
gcagtggcgc gatttcgact caccgcaacc tccgcctccg cgcttaagcg attctcctgc     300
ctcagcctcc caagtagctg ggactacaag ctcgggacac cacgtaaaaa tgatcaagtt     360
ctaacatgta tgcatacgaa ttacaatgga aataaaatta gcaaagcgct tatgctaatg     420
ctcaatacaa ttgatttcct cacatttaat cctcacaacc actacaacca cctctaactc     480
aagctctgag ggactgacgt gcccggagga cacagtctt atctggtgag aacaggagcg      540
ttttagcgaa actccaaact cctaggtccc gccttcccca ggaaggcttt tcctggcact     600
gtgcttccgg aagtcccgcc ccaggagaaa aacagcttcc ggaaaaaatt gcggccggca     660
aaccggaaca gaactagggg cggggccgct tgagacgctc tagtattcct ctactctatg     720
gccactgtca attgacaagt cccgagcggt aaagctcctt tctattggat gagcagcctc     780
gcgtaggcgg gaagctcggt gcacggcgcg ctgattggct ggatcsgcca tgcggagcgg     840
ctaggtggtg cacgggaaac gcgggcgtag gtgaccggcg gctttctcag ttttggtgga     900
gacgggcgca tgtgggcgct ttgctcgctg ctgcggtccg cggccggacg caccatgtcg     960
cagggacgca ccatatcgca ggcacccgcc cgccgcgagc ggccgcgcaa ggacccgctg    1020
cggcacctgc gcacgcgaga gaagcgcgga ccgtcgggcg ctccggcgg cccaaacacc     1080 gtgtacctgc aggtggtggc agcgggtagc cgggactcgg gcgccgcgct ctacgtcttc    1140
tccgagttca accggtcagt caacgagcca cgccccgtcc cgctgggccc tcagtgcggc    1200
gcagcctctg agcatcgggg cacctcccag ggcttcggct tccctgcttc acacatgtgg    1260
ttcactgttg cggggttcg tggagttatg gtgggtggga aatccgagat tctttgcatc     1320
catgtgattt ctgcggatct gtgaagaact tcaggcctgg gtctgagcgt ccttttccca    1380
acccttgggc cccggcctgg ctgtcagcac tttcggagct ccaccctctt ccgtgcaccc    1440
caaggccagt gtgtcgttgt tagcgtgtgg ggtggacaga tctggtgtgt agccggtggt    1500
```

-continued

```
ggagaaagga ctcattttgt cctagcaccc acacacacag gcccccactc ctctccacct    1560
ctgctaagga gggctcaaaa cccaccagca taaatgtggc tcggtagtcc aacgtggact    1620 tttaatttt ttttctttt ttttttcca gagtctacaa taaaacatct aattggtgtc      1680
agagagttta cagaataaaa ccttctgaat gtcttgtgta atgtttgtct tgtaggtatc    1740
tcttcaactg tggagaaggc gttcagagac tcatgcagga gcacaagtga gtcagtctct    1800
tgctttcgga gggggagttg attacggggc ttgaaagccg aaatgagagg ccagttgttt    1860
tttatagcaa aagtggtcct tgttctgttc atgttatcct gtttaaatgt tttytcattc    1920
ttaggttaaa ggttgctcgc ctggacaaca tattcctgac acgaatgcac tggtctaatg    1980
ttgggggctt aagtggtgag tatattcttt gcagtgtcag aggctggtgg gaagtctctg    2040
ggattttaac cggctttacc attttccaa gtctggggtg ggcagctact tttttttttt    2100 ttttttttt tgtcagtggc gtgatcttgg ctcactgcaa cctttgcctt ctgggctcag    2160
gtgatcccct cacctcagcc tcccaaatag ctgggaccac acgtgtgccc catcacacct    2220
ggctaatttt ttttgtatgt tttgtagcga cggggttttg ctatgttgcc caggctggtc    2280
tcaaacttct gcgatcctcc tgtctcggcc tcccagagtg ctgggattac aggcatgagc    2340
caccgcacct ggcctggaat tcttttata ccagcccagt cagcagcagc acagagcatt     2400
aaaagctgtg actcaggaga acagatttta atatggatac cacctcttaa gtgttaccat    2460
ccacttagtt tcttgcgttg cggggacaga gatttgtggc agtaaactgg agagtctagc    2520
agtggtgatt acagttaata tgtttaccgc agacgccatt ggcacattgg cagccacaca    2580
catacccact gtccagatta ccctgtcatt tatgtctatc aaccggaagg tcaggattgt    2640
gttgcagcca aattgtgtgg gcttggtggc atggaccgga aggagtgaag tgttagacca    2700
gtctcccttc tcagggctga gactagggtg aggcacttag ggtgccagcc cttcacttgc    2760
atgattcctt acattttgca cactgggtgc cttgctgctt caccctagtg acagctcagc    2820
ccattctaga ggcatttaaa gaatatttgg tgtctgttac acctctagct ggcatcactt    2880
ctgctctgta catcttccct ggttgtactt ccaaagctgg aaggtggaga gtagataaa     2940 tagttggatt agtacggggt gctcctcctg ttagtgacga caggtcaaat tgatgagaga    3000
tctgatttta tgcatccttt ttaggaatga ttcttacttt aaaggaaacc gggcttccaa    3060
agtgtgtact ttctggacct ccacaactgg tgagtctttc ctgacacatc tttcaaaagc    3120
aatctttcct tttgtaatat cagtaacaag aattttcctt tttgcaaatc agtcttctgc    3180
cctccagaga tacctggtcg ttgaaacgct tccccttca agttaaaaag acttgagttc     3240
tgattaacta tgtgaccttg atcaagttac tttacctttc tgagctttag tttattcatc    3300
tataagatga ctatcacgtt tcatagagtt gttaaagatt aaatgacgta gcagcacata    3360
taaagcacta atcactttta ttagatatat gtttggcacc aagtaggcac acaagaaagg    3420
gcagcttttg tttttattca ataaatttct gacatcttct tacctttcag tccagcttat    3480
tacactcttg agaaggcgtg tgtgtgttgt tgaatataac agttcatttt ccagtcctta    3540
agaagaaagt caccaagacc tgttaagtct ttccccaaaa taacgtttga aatccatcca    3600
tttgtctctt attgaggcct tccttatttc tgttttctat gcctgtaaac tacaatagcc    3660
tcccatattc attctcgcct tcctgtaatc catctgccac acagcagcca gagaggtcac    3720
ttcaagacag aaaagtagtg tgtcacttgc caccctaaag cccttcatgg gctccccatt    3780
gcaatacaat caaaacacct tgatatgcc tacaagtcct gtaggccccg gccgctaccc     3840
acacttccat ctgtacccat cgctgaactg cagctgcatg ggctgactct tatgtccctc    3900
```

-continued

```
taactccctg gccacttcag gactttcgcc cttccgcggg ttccctctgc ctcttctaat    3960
tgctgcctat attgttactg aaccttcagg gctcagctag agggtcattt actccagaac    4020
tgcctcttct tctctagaca agttggatcc cagccttctg tattttttcat tttccttgca   4080 gagcacttag cataatgcca ctaagctgtt tctgttatcg tgtttccttt tgtctcctcc    4140
actggcctga ttagagcaag gcctccatct cttttttcctg ctatatcctt ggcatctgat   4200
ataatggata ctcagtaaat atttgtaata aatgatgttc aaaatattta ctaagctttg    4260
ttttatgttg ataccctattg gtaacctttt aaatacttga atagttgctg tgttctacat   4320
ttgttcaacc ataactgctc atttctttgt ttttcattag gaaaaatacc tcgaagcaat    4380
caaaatattt tctggtccat tgaaaggaat agaactgggt acgtctttgt ctgtgactca    4440
tcctctgcta tttctaactt atatatgccc tgacctctca aattagaatc cattaaaaac    4500
atcaacatca aacctcaaaa tcaaatgctt catcaccacg agatttttttt tttttttttt   4560 tttttttggat agagtcttgc tttcttacca ggctggagtg cagtggcatg atctcggctc   4620
actgcaacct ccacctcctg ggttcaagcc attctcccac ctcagcctcc tgagtagcta    4680
ggactacagg cgcatgccat cacgctcagc taattttttg tattttttagt agagacgggg   4740 tttcaccatg ttggccagga tagtctcgat ctcttgacct tgtgatctgc ccgcctcagc    4800
ctcccaaaat gagctaccat gtggctggag atgggatttc taaatagtga catttctgt     4860 gttcccacct catgctgtaa aaatagggc caggtcggca ggagtgattg aacagctgat     4920
gcctgcctgt gtacatgctg tgtggcattc tccatccaga cggcagggct cctgcctcag    4980
ttccagaggt gcttctcgtc gttgagttgc tttgagttgg gggcgggggt gacaagggtt    5040
ccctagaggt tttgtggcca acttttgtaca ttgaaacgca gctccagctg cgcagggggg    5100
cttacagcct cttgatggga agaggcctca ctgaggatgc tagtagggct cttgtcctgg    5160
cactggtgtg tatctgtggc ttgttaatac tcctctttta tagaaacact aatactttgt    5220
ttcaaaatat acatcagctc ttctggtttg cgatgatagg ttccctggct tcactattct    5280
gtttgttaac ttgggtctct gaaagttgag tactagtttc ttgttttttca attttttaacg  5340 gatagtcacc aaagattata atgtcttttc atctggctgt agtaaatata aatggctgac    5400
caaaatacac ttttatttat ttcctaaaaa tggtaatctc cttagaaagt ctggttttcg    5460
tgtcagattc ccaccataat tctgaggcaa ttcagttgct cgtggttggt gatcctgaag    5520
ttactcttcc cacacatctt cactaatgca atcactttgc tgttgtgygg ttttcttgta    5580
gctgtgcggc cccactctgc cccagaatac gaggatgaaa ccatgacagt ttaccagatc    5640
cccatacaca gtgagtatga aagccaggtt tcccaggagg agggtgtacg tcctgagtaa    5700
agaaaacatg gatgaaaata gaaactgaac acttgctgtg ggcaccctgt tttgtgttct    5760
gagcatgatt agaaaattta gttgaggaat gaagatatgg ctcctgccct ggcttataaa    5820
cttacggatg tctgacttat gcctaatgat agtgattatg ctttggaata ttagataatc    5880
aagcactgtt ggtaaataga ttgcattcaa gtttgcacat tcattgcttg gaggttttttt  5940 cccacaggcg taatacccctc ttttgatcag acgatcatga agaggtttgc acagatagat   6000
ttttttaaat aaataatgat tacagcaacc taaaagaagt gttgttgggg gttagaagct    6060
cctgcaaatt ccgaagtatc agggccagat gatgtggtct tagcttagga aaagagttag    6120
tcttgtcctt gaacttggct aaagacattc atgtctggtt ttacttacat gtgaagagag    6180
taccaagcag taggggtatt tccttgttag tactaactaa tgtgatgctt actaagtagt    6240
```

-continued

```
gctgatgggt gacagaccag agcacccagc aaaggccaga gaagtccaga acctggcgag    6300
gagatgaggc ttacactgac tgaaggcaga aggcagcagg gaggagagga atgtgccgga    6360
gcaatggcac aagtgctcct aggccagtgc tgtgatgagc tgatcagcac tcccattgcc    6420
tggcttgctc ctcctgctca gatgccttct ctcacctgac ccctgctgta gccaccccca    6480
gcctgagttg catccacctg tttgttgtcc atttccagca ccctgttctt cgctccatgg    6540
catgtgacag ttaactttca tatgtgattt gcgtgatcga tgttaacatg ctcagttttg    6600
ccgatcactg ttttttcagt gtccagcggc cctcagtgag tgaacttacg ttcattctcg    6660
ttgcagctgt gctttagctt cttagagcag cgaattttt tcccttgatc ttgagcctta    6720
actaaatgta aaatgaggct ccttcttgag ataggtaccc tttgggtcta tgtgttttag    6780
cgggagtgat gataataaat aagcatgtct acaacccaca tgctgtttag ataacacgtt    6840
gttgagttgg tactgtggcc gaggctgtga gctaagcaga aacataaaca ttaataggac    6900
ataggtgcag cccagaaacc aggtaggaag ttaactaact agttatttcc tactgtatag    6960
taaaaggtgt gctgatttaa ttggcgttct ggcattccca tgtatgaacg tctgggcctt    7020
ggctgtcagc tcaccttgtg cagtgtgtaa tttggtggta tctgtactga ccaggtgaac    7080
agaggagggg aaagcaccaa ccatggcaga gtccagaaag gcctctcagc aggctcagtc    7140
cagagcgatc ttcagactcc gagtygaatg aaaatgagcc acaccttcca catggtaata    7200
gtataaacaa aacagagcag cagaaaggct tgcgttttct taattctctg ccttgtaatg    7260
cttgtagaga gtcattattg taagaaagcc aggtgtgtaa acagatcctt cttcctgggc    7320
ttactataac ttggcccgtt gggggaatga gaagggttgt tgtaaaggtg gcagcctgca    7380
actttaataa tgaccagtcc acagttttgg ccacccaggg tctgggtagg cccaaaactg    7440
tgttctgttt tcccagagga gaacagggcc tgacaaacgg attcattttg tattttcat    7500 taatgtaaca tttatgcaaa ttttccatta atgtggaaac tataactgct aagccaatga    7560
gacagtcaaa tcagtgagag gctctgcacg tcttccagaa tgacagccca ctgggaaacg    7620
gagttaaaag tccaagatga gatgtagctc aggagtcagg ccgcttcggg agtttgttgt    7680
ccttaacaga aggtcagcgt tggcaaagct cggcagctcc tctttctgtc ctgaggtctt    7740
gtctagtgac tgagaacagg ctgacccta tgtgctgtcc ttgtttggat ggcaccgggt    7800
aaagactgac accagcattt tctctgcagg cctttgaact tttgtgttat ttcatatatt    7860
atatgtgtta taaagcacat tacaatatat ttttctctgt cttctccagt cctaggtgaa    7920
atgtgtcatt taaaaaaaat ttcacttgcc attctaaagt ttttctggtg agagttttgt    7980 gttttttcatt tacgcaaaca catctccaca taagtaggga aaaaaagtct tcttgagtat    8040
attagtgtct tcagcctttg tattgggaca gtagcgtcca ttaatttta tgtgaagtga    8100 aattaggtat cgggtcataa tcagtctgtg atgtcttcac agctttcaca tttaccttgt    8160
gataatcaag tgtgttttc ctcaggtgtt agccagagaa gagggtcag ggactcttcc    8220 ctggtcgtag ctttcatctg taaggtaagg aagactttcc ggaggctgt acatgactgg    8280 ggtcttggtc agcgacctct ggtttgcact ttttcattaa tttgagggta ggcactcctg    8340
ttacctgaga caagaagaga tagcagatct tcagaaaagc tgatggaagg ccgggtgcag    8400
tggctcacgc ctgtaatccc agcactttgg gagtccaagg caggtggatc acgaggtcag    8460
gagtttgaga acagcctgac caacgtggtg aaaccctgtc tgtactaaaa atacaaaaat    8520
tagctgggtg tggtggcgca tgcctgtaat cccagctact gagaggcca aggcaagaga    8580 atcgcttgaa cacaggaggc ggaggttgca gtgagttgag attgcaccat tgcactccag    8640
```

-continued

```
cctgggtgac agagcaagac tctctcaaag aaaaaaaaaa ttcgatagaa atgacactgg    8700
caatgagcct gcaacaagta ttactactga cctttcataa ttgtcatcac ttgtaggttt    8760
cagagtttag atgctctgtt tctcaaaata accccatact tttatttcct tttaaatttt    8820
tttccagtgc cctgtcagcc tccgtacatt tttttttttt tttttgaga ccatgtctgt     8880 ctccatcgcc taggctggag tgtgcagtgg cacaatctcg gctcactgca gcctccacct    8940
cccaggttca gtgattctc ctgcctcagc ctcccaagta gctaggatta taggtgcgcg     9000
ccaccacacc cagttaattt ttgtattttt agtagagatg gggtttcacc atgttggcca    9060
ggctggtttc actcctgacc tcaggtgatc cacccacctt ggcctcccaa aatgctggga    9120
ttacaggcgt gaagcactgt gcctggtcca tattctttta tatttgccaa tgattggtcc    9180
ttttagaatt cagaaattat tgaaggcagc tgtgtttgtt ttccttcaac tccatcaggc    9240
ctttattcaa agtcttttaa ctctgtttta ctttatttca ttcccctgca atagctaagg    9300
tctaacacca gattaattgg aatattagct agcattcaca aaggcctaga tctgtaactc    9360
tgaaattggt caaattccat taaaaatttt tgttacaata agctgtttgt aagatctgac    9420
tagtggctta ttttttaatag aattttgcat taaaatttta tcaatacaat ttgcaacaaa    9480
tttgtctaaa tatgtgaaaa gatttcattg ccttttttgtg ggcttagatt atttttttaat    9540 gttgattttg aaatatattt ggaattgtta tctaaattct aaaagctaca agtgaaaata    9600
ataatgaaag taagtagtta atattagtgg caagatcatt gccagtatca tttctatcga    9660
tttatttgaa taatgtgatt ttcataaaag ttaagtacta ctgttaacag gcttattact    9720
tgtatgtttc tgagttttag atagcaaaat cattttttaa agttttaaaa atattttatt    9780
tttgataatc tatatttata ttgtctgatt tttaaactgt tttctatggt aatctttaaa    9840
tcgtattcct gctttccgga ataggtaaca gtgagcatga tgaaaagtga caagctcact    9900
tttacacact cgggcagttg ccctattatc aggcagccgt tcctgggggc tgccagctgc    9960
ctgccctggc ttttccatct ccttccttgc tgtcttctgc ggctccttct gagggctgct   10020
gtcactggat tagcctataa cgcctttccc ctcttctaat taatttgctg ctctcaggtg   10080
aggttttgga aagcaataaa gctgagctag gtcaagttcc aggagtctct tggcatgagg   10140
acctgaaaaa ctcatctgtt ggaagacctc ggctttgggc agctggtgca ctgttgggc    10200 gttattggct gcgttctggc tctcatcagt cttccagata ctctgcattc ctcagagagg   10260
aacatatctc catgggttga gttcagctcc cagggagatg ggtttccctg ccttaagtcg   10320
gcaagtacct tttttttttct tttttgaga cagagtctcg ctctgtcacc aggctggagt   10380
gcagtggtgc gatcttggct cactgcaacc tctgcctccc aggtcaagc agttctcctg    10440 cctcagcctc ccgagtagct gggactacag gagcgcacca ccatgcccag ctaattttg    10500 tatttttta gtagagacgg ggtttcacca tgttggccag gatggtctgg atctcttgat    10560
ttcctgatcc gcctgccttg gcctcccaaa gtgctgggat tacaggcgtg agccatcatg   10620
accagccttt atgtttcttt gtttgttttg ttttctgag atggagtctc gctctgttgc    10680
ccaggctgga gtgcagtgtt gccatctcga cttactgcaa cctctgcctt ccaggttcaa    10740
gtgattcctt gcctcagcct cccgtgtagc tgggatcaca ggtgcctgcc accatgcccg   10800
gctaattttt gtattgttag tagacacagg gtttcgccat gttggccagg ctagtctcga   10860
actcctgacc tcaagtgatc tgccttcctc agctcctaa agtgctgggg ttacaggagt    10920
gaaccaccat gcccagcctt caattacctt ttatttattt tatttattta tttatttttg   10980
```

-continued

```
agacggagtc tttctgtgtt gcccaggctg gagtgcggtg cgcaatctt agctcactgc   11040
aacctcctcc tcccaggctc aagtgattct catgcatcag cttcccgagt agctgggact   11100
tcaggtgccc gccaccacac ttggctaatt tttgtgtttt tagtagagac ggggtttcac   11160
catgttggcc aggctggtct tgaatttctg acctcaaatg atcctcctgc ttcagcctcc   11220
caaagtgctg ggattacagg cgtgagccac tgcccccaac agcaagtacc ttttaaacat   11280
tagagacatt tagttgccat cctcaaaccc gtttgggtgt gtggagagaa tgttgggtcg   11340
tgacatggtt gttagttatc taaagatgtc agccatcaat catcactgtg tgatgtgcac   11400
actgaagctg taatccttca tctaggatga tatttttaa gatggaaaat tctacaaccc   11460
tgagaataag gatttcagat ccaaatttga gactcagccc tacgagtaac tctttaactt   11520
cagagagtta aagaagatg cacagttgat gaagatttaa aggagaaaat ggaaatcaaa   11580
tgtcatttag cactcaaagg cctacatgtc atttctgaca ttttttctgtt tgtgtgaaat   11640
tttttttttc ctataaaatg attgtgaagt tttctggtag aattattgtt tgcctttcta   11700
atgtaatagc atattagggt tttttttttt ttcttttttct tttttgaga cagagtctca   11760
ctctgtcgcc caggctggag tgcagtggca cgatctcggg tcactgcaat cttccgcctc   11820
ctgggttcct gcctcagcct cccgagtagc tgggactaca ggcgcacgtc accacacccg   11880
gctaattttt tgtattttta gtagtgacag ggattcaccg tcttagccag gtggtcttg    11940
atctcctgac ctcatgatct acccgcctcg gcttcccaaa gtgctgggat tacaggcatg   12000
agccgctgtg cctggctatt agagattttt tattataatt tatctccaag ataaaagcag   12060
tgacattata ttgccacata attgaaaaat acaagagaaa taaaaatcat ccatgctttt   12120
gttagcctat cactgtcatt gaatattat gttacatggc agtttgcttg ctggttgctc    12180
tgttaggcaa cgctctggtg acattccttt agctattaat tgaggaatgt agaatgacag   12240
aacagtgttt ctcctcaatg atacttgaag gatatttatt aactttcata ttgaattaca   12300
ttttattaaa tttataatga gttaatgctg ggaaataaaa cactgattta agtcattttg   12360
gcttttagta ctaaagcatt tgacaataaa tgacttcttc agaatatggt ataccttctg   12420
aaagcaataa acgcattta atgaattgta aggaaacaac atcatttat tttttatttt     12480
tttttttgag acagactttc gcttttgttg cctaggctgg agtgcaatgg cgcgatctcg   12540
gctcactgca acatccgcct ctgggttcaa gcgattctcc tgcctcagct tcctgagttg   12600
ctgggattac aggcacgtgc caccacgcct ggccaatttt gtattttag tagagacggg     12660
gtttctccac gttggtcagg ctggtctcaa actcctgacc tcaggtgatc tgcccgcctc   12720
agcctccgaa agtactggaa ttacaggcgt gagccaccgt gcctggccaa cattattatt   12780
tttttttaat ctagaaaaat acacttctaa gaaaattgat taaaaccaac cttcttcatt   12840
agccctaag atcacatcta tgttctcttt gttgcagctt cacttaaaga gaggaaactt    12900
cttggtgctc aaagcaaagg agatgggcct cccagtgtga gtgtgggggg taaggcttct   12960
ggggactcac tggtacacc tgtccactta aggaaatcac atttcacaga ggccttgcct    13020
cttcatttca gtgggacagc tgccatcgct cccatcattg ctgctgtcaa ggacgggaaa   13080
agcatcactc atgaaggaag agaggtgaga tgcctggttt tcttgatnca gcagttacag   13140
gtagggtctg aaatgctggg cagagtctgt cttcttcagg ccctacagac accacttttg   13200
aaggacgtgg aacagtttgg acatcactca gctaagtgat aaaatggcct cttttatctg   13260
tgtttgtccc gcatgtcaac acggctgcat tcgagcattt ttgtagattg tccatttagg   13320
atctagtcac cgtcctcctt aaagggtgca tgctttcctt ggtacttgag ctcaggacag   13380
```

-continued

```
tgtctaacaa cagaccccat atggatgggc ctggggttta tggtccagag gaatgccaca   13440
gtattctatg tcaagatatt tcctctgact tctgaggaca ttaggaccag tggccacaga   13500
ctgaagaaaa ccttaatgcc aagcctcctt tcctggccag tgtaggcctg aagtgcctca   13560
acctgacagt tacctgttta ggtatccaca aagagaccag aagggtgttg atggtgatgt   13620
gtaaagttgg ttttgtgctt tgtttacctc tcagctcact ggataggata tgtcatgtta   13680
gcagttgcct tgaaggcagt tcagtttggt ggctgagctg tgaccccag tgggcgggct   13740 tatttggttt tgcagatttt ggctgaagag ctgtgtactc ctccagatcc tggtgctgct   13800
tttgtggtgg tagaatgtcc agatgaaagc ttcattcaac ccatctgtga gaatgccacc   13860
tttcagaggt aatgagggt ctctagggtg ggagaagtga gagctgaaac ccagcccagc   13920
atcgacatgg gcatcttgtg gcaagagctg tgtttctggg aagaccacta tctgggttta   13980
cagttcgagg gccggcactc ctgccttaag tcactgttgg tagttggtgg gctccggtgt   14040
acacagcctc aaagtgaaat tagaaaagat tgaaaactag aaacaactga ggactagaaa   14100
ttcaactaga actcttacag ctcttatacc agaagaaatt ctagaactt tttgaattct   14160 aactaatgcc ccagattatc atttggatta ttttgaactg aattaatttt cttccattac   14220
ctgcattgaa acaaatgagg tgggtcagag tgtgtgagac tgtcgtggtc aagagtccgt   14280
gttatgggat ggactcacag ctggggaatg tcttttgggc taactgccac tctgttgttg   14340
tcctctatcg aagttaacca gttttgcggt tcagctttca ttccagatgg aatcatcttt   14400
gacccaccta tctgagtttg aatcttttcc cccactctta atggtttacc tgtattttc   14460 ctgttcctag tttgtatcta tctgtatttt ttcacttgtt tttttctact taccacaaca   14520
aatccttttg ggctgctgta cccctttccga gtcagagcgt taggagttgt ttcatggtct   14580
gctttattct ctgtgggtga atttggatgc gctggtagcc ccggctttgt attttaatcc   14640
agttttgggc agcaaaacct cttcaatgaa tcaggtgtca tttgagagcc atgtgtggat   14700
gtgtgatgat gctgggatag ataaaaatag ctactgtgta tatttctttt taaagggaac   14760
tggagggaaa cacatcagca tgttagtaag tggtctgttg tccaggtggt gaaatttcag   14820
atgattttca tttctcgtgc ctgtgtctca ggtcctctgg aaggcagaca ccagggtggc   14880
attggaggtg caggaggttt attcgaggaa atttgactgt gagagaggaa ggagagaggg   14940
agcaggagga ggcagggaga gcctgggtct ggctttgcag gttggacccg tatgagtgga   15000
gagggtagga aggaagtgca gtgctgagaa aggatcagcc aggcctactg gaaagcccag   15060
agcagagctt gccagataca ggaatcccac gtccattgga aatggcccag caccggggtc   15120
tgccgtgagc agcctgctgt gagagcatgg cctgggcgtg gaggctgtca gctcactgca   15180
gtgctgcaga gggccgcacg ataccctcc ctggctgcgt ggtccctgtc ttggtgtgtc   15240
ctgagtctgc atcactttgt aaagcccac tcttctgccc aggtaccaag gaaaggcaga   15300 tgccccgtg gccttggtgg ttcacatggc cccagcatct gtgcttgtgg acagcaggta   15360
ccagcagtga atggagaggt atggagccca gcccagcggc acttgggta actcttctgg   15420 gcagtggtgg attcccctt cctcccctcg tgctctttcc agcgctacct accttctgc   15480 acctgcctaa actttctgtg ggattcctgc cttcccagaa ttctaggctt cccagatctg   15540
tgctacactc gtgaagaaaa tgcaccgcta ggtggcgcag tgtccacacg attccattta   15600
ttttacaccc tccacactct tcagggtgtc tgaacaaata ctgccgtttg gttgaggatt   15660
ccataagtga attccaaaga agagattgca gctataaaat gatagcttcc atttactgaa   15720
```

```
tgcccacttt gtgggaggca gtgtgtgaaa tacccttcat ttcacttcat ttcctctagg    15780
gtcgtcgcca gcagccctgg gaggtagatg tttagtcact ggaaggcatc ttttcctcg     15840 gggcatcgct ggccagggcc agtggagga gtatgagttg agctcgggtg cggggtgacc     15900
ttgggctgct ttttggcccc tgcccgtatc tccccacatg gcccgtttac ctgcccctca    15960
ctccatggcc tgctctcctg ctgtctcttt cattcctcag ggtttgggtc ccctatttgt    16020
atgccctgga catcttcttt ttcttgtttt tcctctcact cttcccagca cacctgaaag    16080
gcagctgagc tagggaacac cgggctttga gacagcagga gtgggaccat gtttggccat    16140
gtagtaacac tgcttgggggc aagtcactga actgtttgaa cacctcatcc tcattaccac    16200
tcctgagctc agcaccactc ctcaggggga gctgcctcct aacagacgct gcaaatgccg    16260
ggtctgtttc ttcacaggtt tgggcctgac acccagcact tggtcctgaa tgagaactgt    16320
gcctcagttc acaaccttcg cagccacaag attcaaaccc agctcaacct catccacccg    16380
gacatcttcc ccctgctcac cagtttccgc tgtaaggtag tgtctcagac yggccccttg    16440
tcggcccagc tctcgtcccc tctctttctc tccatgaatg tgttttgtct ctttcagaag    16500
gagggcccca ccctcagtgt gcccatggtt cagggtgaat gcctcctcaa gtaccagctc    16560
cgtcccagga gggagtggca gaggtctgtg ccatcttgaa ctaatggaat cgtctcagtc    16620
gagttgggaa acatttctgt aaatagccac atagtaaatg ttccaggagg ctctccagac    16680
catatggtct ctgttgtaac tattcaactc cgctttgagc acaaaagaaa cacgacaat     16740 aagctaatga atgggcttgg ctgtgtgcca gcgtgaattt atttagaaaa gcagcctact    16800
ccaggctggg ttgaggtggg cggattgggg ccagtagttc tccttttcca aaattgcctt    16860
gcatgggaat agcagtgata gagctcgtgt gtttcacagt atagaaaata ggaaatgtgt    16920
gatgaacaaa gtcacccata atcctgttgc ccagagataa tgattgataa cattttgtgt    16980
ttcttgattt gtgtatgtgg gtttatattg tcagtctttt cctgtatcac taaacagtct    17040
taagtaacaa gatttttatt ggtattccaa atagggatgt ttactcattt gggatgtttc    17100 caatttttg ttgtttttaa tgaatgaaac aataaatgtc ttatatataa atctttgatg    17160
ggaactctgt tcccttcaag tcattcctaa atgtgggatt actggcccag agtgtgagac    17220
ttgttaaggt acttgataaa tgtaagatgc catcttgaaa gcctcttcca gtacaatcca    17280
accaggaaag tgaacagcct tactgcccca catctttatt ttaattaatt aatttattta    17340
ttttatttat ttatttatttt tttgagacg gagtttcact cttgttgccc aggctggagt    17400
gcaatggcgt gatctcagct cactgcaacc tccgcctccc gggttcaagc atttctcctg    17460
ccccagcctc ccgaatagct ggaattacag gcgcctgcta ccacgcccgg ctaatttttt    17520 gtaatttag cagagacggg tttcaccatg ttggcaggct ggtctcgaac tcctgacctc    17580
aggtgatcca cccacctcag cctcccaaag tgttgggatt acaggcgtga gccgtgcccg    17640
gcctgtttta atttttaagg atctgaacct tgatttaag tttcctgccc actccacagt    17700
atttgtatta gaatagagca tgtgctggat tatgactgga tgctgtgtgc tgttgaggtt    17760
gggtagttgg ggccctttaa gagactatac tagcaagact cgggcccaca ggcaacatca    17820
cggggttgaa gaacctggtg tccctttgtt ggcatctgcg caggctctta acacacagca    17880
gcgatacaca gccctagccg acattcagat ttaccttgtg cttgtgaaaa atattgcaca    17940
gggcctgccc tagacctagt gaattagaat cttgagagtt aggcttggga ctcacaagct    18000
cccagatgat tttaatgctc agcgaggttg aagagccgcc tgtccaagga gttgccactc    18060
cgtgtgatct ggggcttgct aggaaagtgg gatctcaggc ctcactgcag agctgccgaa    18120
```

```
ctggcttctg cgttttgcca aggttcctgg gtgtgaacat gagtttcaga gtcactcctc   18180
tagggcccct gcttctcagc tcggaccatt gaccccctcag aggacatttg gcaacatctg   18240
gaaacgttct tggttgtcac agcctaggag gtgggtagtg gtgctgctag tgggtagagg   18300 tcagggtac tgcaccagga cagcagcact ggccacagaa aaaaactgtc ttgccctgag    18360
catcagtagt tccccgttga ctggccctga ggcagagcga tgcagcatcc aaaaggcggt   18420
ggagcagacc tgccccagat cctagtcact taaccttcag tgttgatctg aaggaacttc   18480
ctgcagattg tcccctgaa tttattctgg acatccccaa tggggtctgc tgaggccata    18540
taccctgtcc gtcacctgag atgcttctct ctctycctgc agggatgcca ttattacttg   18600
caatcctgag gaattcatag ttgaggcgct gcagcttccc aacttccagc agagcgtgca   18660
ggagtacagg aggagtgcgc aggacggccc agccccagca ggtgagtggg agcccacaga   18720
gcagcctttc tttcctgggc tctgcccctg ctgctgtttt cctagcatta agtggagtgc   18780
tggtggggcg cattctaacc tggcttttca gtctaatcca gggcttctct actcagctct   18840
acattagaat tatagtcatt ggaggagggg gctttgggga gtttaagaat cccaattcct   18900
ggctgggcgc ggtggctcac acctgtaatc ccagcacttc gggaggccga ggcaggtgga   18960
tcgcgaggtc gggagatcga gaccatcctg gctaacatga tgaaacccg tctctactaa    19020 aaatacaaaa attgctgggg cgtggcggcg gcgcctgta gtcccagcta ctcgggagac    19080
tgaggcagga gaatggcgag aacccgggag gcggagcttg cagtgagcca aggtcgtgcc   19140
actgcgctcc agcctggacg acagagtgag actccgtctc aaaaaaaaaa atcccaattc   19200
ctgtgcccca tcccacccaa tcagagcatt tggcgatggc acccaggcat tcttggcaag   19260
gcacgcactg agtgaaacgt tttagtgaac acctgtggaa agagctctga gcagggactt   19320
ggctggcaga gatctagtcc tggcttttgcg gatgcaaatc catggaggat cttgccacg    19380 tcactcaact gaggctgagg gccgggcaca ggctttggaa ccatcgggtc tccctggatt   19440
tgaatcctga ccctgcctct taccatcttc actggagacc tgggcgtctg agcctgtttc   19500 cccccttggga agcagagcat ttcctacctg gtagggctgg gaggatgcga ccgaagtgca   19560
tggtcttgca gtgagagctg gatgcaaggc acacactgtt ctcttgaaat aaatgacagt   19620
tcccagcata aagaaatgtc atttttaaa tgtaaaagaa ttacagcaat tcttttgaag   19680
aaaggactgg agaatttatt tgttcttctt agccttttgg tgacagatag cctgtgggtc   19740
ccacactggt gcgaagtcct tgtttcaga gcggttgcca ggggcctgcc agtcccctc    19800 ctgggaagct ggatagaact atgttgctta cccatctgtc ttagtctgtg ttttgttatt   19860
ataaaagaat atgtgagact gggtaattta tcaagaaag aggtgtattt agttcacggt   19920
tctgcgggct gagaattgaa ggtcacggcc ctagcttcca gtgaaggctt ccatgctgca   19980
tcataacgtg gcagaggagc gcaagtagga agtggacgct tgtgaagacg ggataacctg   20040
agctgcactc tggctttata acaaccccc tcctctgggga acaaatccat tcccttgaga   20100
agtaatgcag tctcctgaga gccagtactt actactgcag ctccaagcca ctcaggaggg   20160
tccgtccctg tagcccaaac gccttccact aggcccgcc tcccaaaacc gccatactag    20220
ggagcacgtt tccacatgag gtctggggac aaaccaatga cactcaaacc attgcacctt   20280
ctcatggctg catgctggct cacttttgac ccaaaggaat ggattgtttc acatggattt   20340
tttcacagag aaaagaagtc agtacccaga aatcatcttc cttggaacag ggtctgccat   20400
cccgatgaag attcgaaatg tcagtgccac acttgtcaac ataaggtatg ctgctttccc   20460
```

-continued

```
aggaagcatc cttccatcaa gggcaygttt acttttaaa caaaagtcct gctgtactca  20520
ccagtcgatt tgaaatgcgg tatcaagccc tgtcacttgt catgtcgact ggagtgtcca  20580
ggagaggagc gtggccttac tgcattttat agcctcagta gcaaacttta ccctgggaat  20640
caccaaaatt catcccatga tgtcttttaa taaacagctg attttactgt gggcagtaca  20700
cctagctaag aaattagctc ctttaatttt tacattaatc ctatgaagtg gtgaataact  20760
acccattttg ttgatgagtg acctgatatt cagagaggtg acttgctatg gttcctacag  20820
ctggtaagtg gggcatctga agtttgagcg gggacttggg gtcttgattg ctacatggta  20880
ttgtccccca gccatttgtt ggtagtatgt taaaaagctt tagggttttg cacatttgtg  20940
ttcagaacct ttattggatt ccccttgaca tgttttttag ttgattctct tgggtttgcc  21000
tggggtcatc agcagagaga ttagtcaaat gcgttgtgac atgtacacgt tatctctaca  21060
gatagtatgt gaagaaaata agattgtgaa ttaccaggtt tgttttaaat tttgctctgc  21120
catcttacat gctagtggtg gatgataaac aaccaaatag tgcattaaat atatacagca  21180
gtgacgagat gtgccctgac atcagaaata tacaatctgg ggtgtgtttc tctgtggatg  21240
aggacatgca ataaagcagc ttggagtgag ccggcctctc ccgggggctg agatcctggg  21300
ggaagaaggg cttttttgagt ttgacctgac accctgcgag cagcttttga accagctgaa  21360
gctaatggga aggtgctatt gccaccttgc ctccgcctcc cgactccttt ttcccccaga  21420
aggtaatgtc ttagcaccgg ggcttctctc tgcaaaatgg gtgcagccct ctcagtgttc  21480
gtggctcctc ccagagaatg aaggaggcca gagcgggtca gcactctctc tgccttggag  21540
cagagcttct gaaatggact gcacagcaga atagcccaag aagtttgtca gaatccagac  21600
ttccagagcc ctgcctaaaa ccaagtcaga aaccccgagt gacacctggg agtctgcgtt  21660
aactggctcc ctgaatgaag cacctgcagc ccgccctgca ccaggtgtct ttgaggacat  21720
gagctgagga aaccccgacc acttgcaaag ggggaaaagt ccgatggcag ctggacctag  21780
aaagagtctc atatggccca gtgcctgtcc tggtattttc aacagaggct gtggccacag  21840
tcaatctgca tggtcagatt cattgttagg actaaatgct ttaagcctcc tataaacttt  21900
ttttttttt ttttgatgcc cagcctttgt gtaagtctac ttgaaagggt ttcagggttc  21960
catggatact tctttgctat aaagaggatg acacatgtaa aatcacctt atggttaaat  22020
taattggctt ttatattagc tcctcaaagc aaagcaggag agacagaaat ttctgcagtt  22080
gcttcttggt cctgtccaaa gcagacatca gcctctgaac catcagcagt cttcctagtg  22140
gcagtgactc tcttcctctt ctcttctgca gccccgacac gtctctgcta ctggactgtg  22200
gtgagggcac rtttgggcag ctgtgccgtc attacgagga ccaggtggac agggtcctgg  22260
gcaccctggc tgctgtgttt gtgtcccacc tgcacgcaga tcaccacacg gtgagtgttg  22320
ggctggacca caaagctgga gcctggagga ggcactgcca cgttgagttg gcccctttggc  22380
tgcgtctttt cctccgcttc caaacttgcc cagagctttt gttactcatc tctggctagg  22440
aaatggtttt ttgcaaaact caacatagtc cttctgcgcc acaagaatgt cttctcttcc  22500
tgttcagttc ctttcctgca gcaggacagg tttgagttta cccagccttc cttgagtctt  22560
gaatctcaca cggcctgctc agcggaagct ttgaccggat gcaggaggtg tggctatgag  22620
accctcacct tggtctcctg gggtgccggg ccctgggccg ttgccctctt cccagcacgg  22680
gtcgtgtcgc tttctgcctg tgacatttca gggccatggc gcaggggct cggcctgtgc  22740
cacccccact gcgctgtgt tagaggctgg tgggtgacgt cgggctggca actcctgcaa  22800
gagagagggc tgcagaccct aacccggagg ggatggccct ggggcctggc tgacgcatgt  22860
```

```
ctcctgtttc cttgccaggg cttgccaagt atcttgctgc agagagaacg cgccttggta    22920
agtgtggcac ttgatgggcg ttctgagttt cagcggttta cacatcatcc gccatgcctc    22980
ttggcactcc agtttttatt gagatgttct gtcgtcgagt cggcacttgc attttttgtt    23040
ccaggcatct ttgggaaagc cgcttcaccc tttgctggtg gttgccccca accagctcaa    23100
agcctggctc cagcagtacc acaaccagtg ccaggaggtc ctgcaccaca tcaggtgagc    23160
atccagggca gcctggcccg stgggctgtt gcttgctgcc gtctccttca gaagctcaag    23220
gtggacactg gggtagttac caatatcccc cagcagcctt gcccttgaca tggtcccaga    23280
tggcagaagc aggggagaag tgcattggct gaaggacaga aaccattaga tagttcccat    23340
gtaatgctta ttttcttaga agcatttctt cccagtcctc atttgagttc tgagctgctt    23400
tctaaacttc gagcagcttt tcttgatgag acagttccag agccaagcac ccaaatagtg    23460
gctagcacag agaatgtcca tagcaggtgt gtggctagct ggcaggtggc accatcctca    23520
ccccaagggg aaggagtccc ctctgctgga gccatccgtg gcccgtgctg cctgagccgg    23580
aggcagcatt cacctgctgg gtttctccca gtggcctaga ggctttggtt tggctctttta  23640 tatttgactg ctgtttcctc atcatagtga ctatgattta actcatgttt tctcctaaga    23700
atgattttgg ggttctccag ccaaagactt aaactttggt tccagatgtc caagaaacgt    23760
ttattatcat tttaaatgtt ttgtcttttt acagtatgat tcctgccaaa tgccttcagg    23820 aagggggctga gatctccagt cctgcagtgg aaagattgat cagttcgctg ttgcgaacrt    23880
gtgatttgga agaggtaagg ggcacagccg caggcatcat gggggcgagg tggggagcag    23940
agctgcagag ccctccagcc ccacccttttc agtttcagac ctgtctggtg cggcactgca    24000
agcatgcgtt tggctgtgcg ctggtgcaca cctctggctg gaaagtggtc tattccgggg    24060
acaccatgcc ctgcgaggct ctggtccgga tgggtgagta gaggaagaag caagccaccc    24120
tgaggttgct ctggggtttg tgtagctgga ggtgaatgca ggtgggcttg cagggaaacg    24180
tcagcagagg caggagactc aggtccccac cctcagagtc tctggttgtc atcctagtag    24240
gcagacccag ggccagggga gctgagtgtt gagaccagga aacagcacgt gactgaggcc    24300
tgtgtgccgc tctcgcagag aactctgccc tgatccttgt gctgcttctc cagggaagga    24360
tgccaccctc ctgatacatg aagccaccct ggaagatggt ttggaagagg aagcagtgga    24420
aaagacacac aggtagcaaa ggccggtcag tccttgtcgc ccacatcctc tccctccccc    24480
actacgtgac actgagcagc cgtcgtttgt ctccactgat gtggggctgc cctgcttcct    24540
atcaagggct atgggggctt ccttgacctg tggcagtgct cacaggctct tggccttttat  24600 ttttgcagaa ttttctaagc aagattctag agtgaggcac agttttttga aagcatctag    24660
aaatcggctg aataaactat aagccatgtc agggaattgc caggggaagg cgggggctgg    24720
gggactgaat ttttggctgc taatttcaac gaaagagtgc attccccag gtgggccctg     24780 tggtttctct tgggtgccct catggacaga tttggcagcc agcacagagg gtgggcttca    24840 tccagggggtg tgtgcgaagg ctctggccct caggggagat tgtgctggct acggaggtgc   24900
ccgttaagaa aacccaccag cttccccggg tgccctggca gttgatggcc agggtctgtg    24960
ccactgtctg ctttgcagtc ttgcagttga gttcagcttc agtctgctct gtccttcacc    25020
tgcagcacaa cgtcccaagc catcagcgtg gggatgcgga tgaacgcgga gttcattatg    25080
ctgaaccact tcagccagcg ctatgccaag gtcccctct tcagcccaa cttcagcgag      25140 aaagtgggag ttgcctttga ccacatgaag gtctgtatgt cacacggaca gcacagggcg    25200
```

```
gggacggggc agggagacag gactctacac actgagtagg acggtcagct ggagtttgct    25260
ttcttatttg gggccaccgt gggaaaaggt tatctaccca tcactaacca ggtcgaacca    25320
ccctgggttt gctggtgaga cccacctcct gcaggggcca actagtcttc agtctcagtt    25380
cactggaaat ttctgagaat ccttttaggc ctggactgct cacacagtca tggcatttga    25440
gcctcagcac agacctgtga acaggtggt tgcctcttgt gagtgggaaa gccaggcctg    25500
acccttggcc ttccggaatg aagggcaga gccgagcca ggcctcgttt ttcaggagct    25560
tgattttgag agcatctgga ctgctctccc ttccctctcc ggaggccctt agccaggcct    25620
ggggagcctc tgccccttta gagggttccc tccatgccat tcttttttcc atttcagctg    25680
tggcctgttg gcttgtgcca aggaaggggc gttggcgctg ctgtgtgagc acatgactgc    25740
atcccttcca gctcctgtcc cccaccctg cccctctgag acatgtcctt gtcttctatt    25800
gtgtcttcta ggtctgcttt ggagactttc caacaatgcc caagctgatt cccccactga    25860
aagccctgtt tgctggcgac atcgaggaga tggaggagcg caggagaag cgggagctgc    25920 ggcaggtgcg ggcggccctc ctgtccaggg agctggcagg cggcctggag gatggggagc    25980
ctcagcagaa gcgggcccac acagaggagc acaggccaa gaaggtcaga gcccagtgaa    26040
gatctgggag accctgaact cagaaggctg tgtgtcttct gccccacgca cgcacccgta    26100
tctgccctcc ttgctggtag aagctgaaga gcacggtccc ccaggaggca gctcaggata    26160
ggtggtatgg agctgtgccg aggcttgggc tcccacataa gcactagtct atagatgcct    26220
cttaggactg gtgcctggca cagccgcggg ccaggaggct gccacacgga agcaagcaga    26280
tgaactaatt tcatttcaag gcagttttta aagaagtctt ggaaacagac ggcggcacct    26340
ttcctctaat ccagcaaagt gattccctgc acaccagaga caagcagagt aacaggatca    26400
gtgggtctaa gtgtccgaga cttaacgaaa atagtatttc agctgcaata aagattgagt    26460
ttgcaattgt gagttctttt gcttcctcct gctgctgcta cagagcaggg tctgctgtgc    26520
accaccttgg agaaggctct ctgtgctgta gtgtggcagc tgcctggtac ccgggtggct    26580
tggaagaagt cagctcccgt cgtagtgagc acctctggaa cctgtcctca gagagccacc    26640
cttattcgcc aagtcttttt gaca                                           26664
```

```
<210> SEQ ID NO 29
<211> LENGTH: 31
<212> TYPE: DNA
<213> ORGANISM: Homo sapiens

<400> SEQUENCE: 29
caggaattca gcacatactc attgttcagn n                                    31

<210> SEQ ID NO 30
<211> LENGTH: 21
<212> TYPE: DNA
<213> ORGANISM: Homo sapiens

<400> SEQUENCE: 30
caggaattca gcacatactc a                                               21

<210> SEQ ID NO 31
<211> LENGTH: 22
<212> TYPE: DNA
<213> ORGANISM: Homo sapiens

<400> SEQUENCE: 31
ttcagcacat actcattgtt ca                                              22
```

<210> SEQ ID NO 32
<211> LENGTH: 19
<212> TYPE: DNA
<213> ORGANISM: Homo sapiens

<400> SEQUENCE: 32
tgaacgcctt ctccacagt                                              19

<210> SEQ ID NO 33
<211> LENGTH: 17
<212> TYPE: DNA
<213> ORGANISM: Homo sapiens

<400> SEQUENCE: 33
gtacccgctg ccaccac                                                17

<210> SEQ ID NO 34
<211> LENGTH: 33
<212> TYPE: DNA
<213> ORGANISM: Homo sapiens

<400> SEQUENCE: 34
gctaggatcc gccaccatgt gggcgctttg ctc                              33

<210> SEQ ID NO 35
<211> LENGTH: 29
<212> TYPE: DNA
<213> ORGANISM: Homo sapiens

<400> SEQUENCE: 35
gctactcgag tcactgggct ctgaccttc                                   29

<210> SEQ ID NO 36
<211> LENGTH: 17
<212> TYPE: DNA
<213> ORGANISM: Homo sapiens

<400> SEQUENCE: 36
gtaaaacgac ggccagt                                                17

<210> SEQ ID NO 37
<211> LENGTH: 19
<212> TYPE: DNA
<213> ORGANISM: Homo sapiens

<400> SEQUENCE: 37
ggaaacagct atgaccatg                                              19

<210> SEQ ID NO 38
<211> LENGTH: 17
<212> TYPE: DNA
<213> ORGANISM: Homo sapiens

<400> SEQUENCE: 38
tgcgcacgcg agagaag                                                17

<210> SEQ ID NO 39
<211> LENGTH: 17
<212> TYPE: DNA

<400> SEQUENCE: 39

-continued cgcttctctc gcgtgcg 17

<210> SEQ ID NO 40
<211> LENGTH: 18
<212> TYPE: DNA
<213> ORGANISM: Homo sapiens

<400> SEQUENCE: 40
tctaatgttg ggggctta 18

<210> SEQ ID NO 41
<211> LENGTH: 18
<212> TYPE: DNA
<213> ORGANISM: Homo sapiens

<400> SEQUENCE: 41
taagccccca acattaga 18

<210> SEQ ID NO 42
<211> LENGTH: 18
<212> TYPE: DNA
<213> ORGANISM: Homo sapiens

<400> SEQUENCE: 42
tgaaaatgag ccacacct 18

<210> SEQ ID NO 43
<211> LENGTH: 18
<212> TYPE: DNA
<213> ORGANISM: Homo sapiens

<400> SEQUENCE: 43
aggtgtggct cattttca 18

<210> SEQ ID NO 44
<211> LENGTH: 18
<212> TYPE: DNA
<213> ORGANISM: Homo sapiens

<400> SEQUENCE: 44
cattcaaccc atctgtga 18

<210> SEQ ID NO 45
<211> LENGTH: 18
<212> TYPE: DNA
<213> ORGANISM: Homo sapiens

<400> SEQUENCE: 45
tcacagatgg gttgaatg 18

<210> SEQ ID NO 46
<211> LENGTH: 18
<212> TYPE: DNA
<213> ORGANISM: Homo sapiens

<400> SEQUENCE: 46
tgaatgcctc ctcaagta 18

<210> SEQ ID NO 47
<211> LENGTH: 18
<212> TYPE: DNA
<213> ORGANISM: Homo sapiens

<400> SEQUENCE: 47

```
tacttgagga ggcattca                                               18

<210> SEQ ID NO 48
<211> LENGTH: 18
<212> TYPE: DNA
<213> ORGANISM: Homo sapiens

<400> SEQUENCE: 48
gctactggac tgtggtga                                               18

<210> SEQ ID NO 49
<211> LENGTH: 18
<212> TYPE: DNA
<213> ORGANISM: Homo sapiens

<400> SEQUENCE: 49
tcaccacagt ccagtagc                                               18

<210> SEQ ID NO 50
<211> LENGTH: 19
<212> TYPE: DNA
<213> ORGANISM: Homo sapiens

<400> SEQUENCE: 50
tggaagagtt tcagacctg                                              19

<210> SEQ ID NO 51
<211> LENGTH: 19
<212> TYPE: DNA
<213> ORGANISM: Homo sapiens

<400> SEQUENCE: 51
caggtctgaa actcttcca                                              19

<210> SEQ ID NO 52
<211> LENGTH: 17
<212> TYPE: DNA
<213> ORGANISM: Homo sapiens

<400> SEQUENCE: 52
cgcagggacg caccata                                                17

<210> SEQ ID NO 53
<211> LENGTH: 18
<212> TYPE: DNA
<213> ORGANISM: Homo sapiens

<400> SEQUENCE: 53
ggttgaactc ggagaaga                                               18

<210> SEQ ID NO 54
<211> LENGTH: 19
<212> TYPE: DNA
<213> ORGANISM: Homo sapiens

<400> SEQUENCE: 54
caactggaaa aatacctcg                                              19

<210> SEQ ID NO 55
<211> LENGTH: 17
<212> TYPE: DNA
<213> ORGANISM: Homo sapiens
```

-continued

```
<400> SEQUENCE: 55
gcagagtcca gaaaggc                                                        17

<210> SEQ ID NO 56
<211> LENGTH: 19
<212> TYPE: DNA
<213> ORGANISM: Homo sapiens

<400> SEQUENCE: 56
agaggaaact tcttggtgc                                                      19

<210> SEQ ID NO 57
<211> LENGTH: 18
<212> TYPE: DNA
<213> ORGANISM: Homo sapiens

<400> SEQUENCE: 57
accaaggaaa ggcagatg                                                       18

<210> SEQ ID NO 58
<211> LENGTH: 18
<212> TYPE: DNA
<213> ORGANISM: Homo sapiens

<400> SEQUENCE: 58
gtcaacataa gccccgac                                                       18

<210> SEQ ID NO 59
<211> LENGTH: 18
<212> TYPE: DNA
<213> ORGANISM: Homo sapiens

<400> SEQUENCE: 59
ggctgctgtg tttgtgtc                                                       18

<210> SEQ ID NO 60
<211> LENGTH: 17
<212> TYPE: DNA
<213> ORGANISM: Homo sapiens

<400> SEQUENCE: 60
gaaggcattt ggcagga                                                        17

<210> SEQ ID NO 61
<211> LENGTH: 18
<212> TYPE: DNA
<213> ORGANISM: Homo sapiens

<400> SEQUENCE: 61
tatgattcct gccaaatg                                                       18

<210> SEQ ID NO 62
<211> LENGTH: 17
<212> TYPE: DNA
<213> ORGANISM: Homo sapiens

<400> SEQUENCE: 62
tccagccaga ggtgtgc                                                        17

<210> SEQ ID NO 63
<211> LENGTH: 17
<212> TYPE: DNA
<213> ORGANISM: Homo sapiens
```

<400> SEQUENCE: 63
tgcgaggctc tggtccg                                              17

<210> SEQ ID NO 64
<211> LENGTH: 18
<212> TYPE: DNA
<213> ORGANISM: Homo sapiens

<400> SEQUENCE: 64
gggcattgtt ggaaagtc                                             18

<210> SEQ ID NO 65
<211> LENGTH: 17
<212> TYPE: DNA
<213> ORGANISM: Homo sapiens

<400> SEQUENCE: 65
tgtttgctgg cgacatc                                              17

<210> SEQ ID NO 66
<211> LENGTH: 31
<212> TYPE: DNA
<213> ORGANISM: Homo sapiens

<400> SEQUENCE: 66
caggaattca gcacatactc attgttcagn n                              31

<210> SEQ ID NO 67
<211> LENGTH: 21
<212> TYPE: DNA
<213> ORGANISM: Homo sapiens

<400> SEQUENCE: 67
caggaattca gcacatactc a                                         21

<210> SEQ ID NO 68
<211> LENGTH: 22
<212> TYPE: DNA
<213> ORGANISM: Homo sapiens

<400> SEQUENCE: 68
ttcagcacat actcattgtt ca                                        22

<210> SEQ ID NO 69
<211> LENGTH: 19
<212> TYPE: DNA
<213> ORGANISM: Homo sapiens

<400> SEQUENCE: 69
cagaacacat ttgggaagc                                            19

<210> SEQ ID NO 70
<211> LENGTH: 18
<212> TYPE: DNA
<213> ORGANISM: Homo sapiens

<400> SEQUENCE: 70
gatgttgtcc aagcgagc                                             18

<210> SEQ ID NO 71
<211> LENGTH: 17
<212> TYPE: DNA

-continued

```
<213> ORGANISM: Homo sapiens

<400> SEQUENCE: 71
tgacacacag cacctga                                                    17

<210> SEQ ID NO 72
<211> LENGTH: 17
<212> TYPE: DNA
<213> ORGANISM: Homo sapiens

<400> SEQUENCE: 72
gaagatgtca gggtgga                                                    17

<210> SEQ ID NO 73
<211> LENGTH: 18
<212> TYPE: DNA
<213> ORGANISM: Homo sapiens

<400> SEQUENCE: 73
caggcatacc actacaga                                                   18

<210> SEQ ID NO 74
<211> LENGTH: 20
<212> TYPE: DNA
<213> ORGANISM: Homo sapiens

<400> SEQUENCE: 74
tatcaacttc taggcaagtg                                                 20

<210> SEQ ID NO 75
<211> LENGTH: 19
<212> TYPE: DNA
<213> ORGANISM: Homo sapiens

<400> SEQUENCE: 75
gcaccatgtc gcagggttc                                                  19

<210> SEQ ID NO 76
<211> LENGTH: 19
<212> TYPE: DNA
<213> ORGANISM: Homo sapiens

<400> SEQUENCE: 76
gaaccctgcg acatggtgc                                                  19

<210> SEQ ID NO 77
<211> LENGTH: 19
<212> TYPE: DNA
<213> ORGANISM: Homo sapiens

<400> SEQUENCE: 77
tcgcagggtt cggctcgtc                                                  19

<210> SEQ ID NO 78
<211> LENGTH: 19
<212> TYPE: DNA
<213> ORGANISM: Homo sapiens

<400> SEQUENCE: 78
aaccctgcga catggtgcg                                                  19

<210> SEQ ID NO 79
<211> LENGTH: 19
```

-continued

```
<212> TYPE: DNA
<213> ORGANISM: Homo sapiens

<400> SEQUENCE: 79
aaagacccac tgcgacacc                                                  19

<210> SEQ ID NO 80
<211> LENGTH: 19
<212> TYPE: DNA
<213> ORGANISM: Homo sapiens

<400> SEQUENCE: 80
gcaggtgtcg cagtgggtc                                                  19

<210> SEQ ID NO 81
<211> LENGTH: 20
<212> TYPE: DNA
<213> ORGANISM: Homo sapiens

<400> SEQUENCE: 81
ccgaacaccg tgtacctgca                                                 20

<210> SEQ ID NO 82
<211> LENGTH: 19
<212> TYPE: DNA
<213> ORGANISM: Homo sapiens

<400> SEQUENCE: 82
caggtacacg gtgttcggg                                                  19

<210> SEQ ID NO 83
<211> LENGTH: 21
<212> TYPE: DNA
<213> ORGANISM: Homo sapiens

<400> SEQUENCE: 83
gtcttctcgg aatacaacag g                                               21

<210> SEQ ID NO 84
<211> LENGTH: 20
<212> TYPE: DNA
<213> ORGANISM: Homo sapiens

<400> SEQUENCE: 84
ctgttgtatt ccgagaagac                                                 20

<210> SEQ ID NO 85
<211> LENGTH: 20
<212> TYPE: DNA
<213> ORGANISM: Homo sapiens

<400> SEQUENCE: 85
aaggcgtcca acgacttatg                                                 20

<210> SEQ ID NO 86
<211> LENGTH: 20
<212> TYPE: DNA
<213> ORGANISM: Homo sapiens

<400> SEQUENCE: 86
agtcgttgga cgccttctcc                                                 20

<210> SEQ ID NO 87
```

-continued

```
<211> LENGTH: 20
<212> TYPE: DNA
<213> ORGANISM: Homo sapiens

<400> SEQUENCE: 87
tccgagtcag aaagatgttg                                              20

<210> SEQ ID NO 88
<211> LENGTH: 17
<212> TYPE: DNA
<213> ORGANISM: Homo sapiens

<400> SEQUENCE: 88
gccttgtcag cctggtg                                                 17

<210> SEQ ID NO 89
<211> LENGTH: 17
<212> TYPE: DNA
<213> ORGANISM: Homo sapiens

<400> SEQUENCE: 89
aggaagtgag cagagcg                                                 17

<210> SEQ ID NO 90
<211> LENGTH: 33
<212> TYPE: DNA
<213> ORGANISM: Homo sapiens

<400> SEQUENCE: 90
gctaaagctt gccaccatgt gggcgctccg ctc                               33

<210> SEQ ID NO 91
<211> LENGTH: 27
<212> TYPE: DNA
<213> ORGANISM: Homo sapiens

<400> SEQUENCE: 91
gctactcgag tcacactcgc gctccta                                      27

<210> SEQ ID NO 92
<211> LENGTH: 16
<212> TYPE: DNA
<213> ORGANISM: Homo sapiens

<400> SEQUENCE: 92
gccttctccg cagtta                                                  16

<210> SEQ ID NO 93
<211> LENGTH: 21
<212> TYPE: DNA
<213> ORGANISM: Homo sapiens

<400> SEQUENCE: 93
ccgcctgaga cgctctagta t                                            21

<210> SEQ ID NO 94
<211> LENGTH: 19
<212> TYPE: DNA
<213> ORGANISM: Homo sapiens

<400> SEQUENCE: 94
gctccgaaag tgctgacag                                               19
```

-continued

<210> SEQ ID NO 95
<211> LENGTH: 39
<212> TYPE: DNA
<213> ORGANISM: Homo sapiens

<400> SEQUENCE: 95
gttttcccag tcacgacgtt tctattggat gagcagcct                    39

<210> SEQ ID NO 96
<211> LENGTH: 38
<212> TYPE: DNA
<213> ORGANISM: Homo sapiens

<400> SEQUENCE: 96
aggaaacagc tatgaccatg cctgcgatat ggtgcgtc                     38

<210> SEQ ID NO 97
<211> LENGTH: 37
<212> TYPE: DNA
<213> ORGANISM: Homo sapiens

<400> SEQUENCE: 97
gttttcccag tcacgacgct cagttttggt ggagacg                      37

<210> SEQ ID NO 98
<211> LENGTH: 37
<212> TYPE: DNA
<213> ORGANISM: Homo sapiens

<400> SEQUENCE: 98
aggaaacagc tatgaccatg tgccccgatg ctcagag                      37

<210> SEQ ID NO 99
<211> LENGTH: 22
<212> TYPE: DNA
<213> ORGANISM: Homo sapiens

<400> SEQUENCE: 99
aatggtgtca gagagtttac ag                                      22

<210> SEQ ID NO 100
<211> LENGTH: 19
<212> TYPE: DNA
<213> ORGANISM: Homo sapiens

<400> SEQUENCE: 100
gctatttggg aggctgagg                                          19

<210> SEQ ID NO 101
<211> LENGTH: 40
<212> TYPE: DNA
<213> ORGANISM: Homo sapiens

<400> SEQUENCE: 101
gttttcccag tcacgacgaa tggtgtcaga gagtttacag                   40

<210> SEQ ID NO 102
<211> LENGTH: 41
<212> TYPE: DNA
<213> ORGANISM: Homo sapiens

<400> SEQUENCE: 102
aggaaacagc tatgaccatg aacaaggacc acttttgcta t                 41

<210> SEQ ID NO 103
<211> LENGTH: 40
<212> TYPE: DNA
<213> ORGANISM: Homo sapiens

<400> SEQUENCE: 103
gttttcccag tcacgacgtt tatagcaaaa gtggtccttg                    40

<210> SEQ ID NO 104
<211> LENGTH: 38
<212> TYPE: DNA
<213> ORGANISM: Homo sapiens

<400> SEQUENCE: 104
aggaaacagc tatgaccatg agacttccca ccagcctc                      38

<210> SEQ ID NO 105
<211> LENGTH: 19
<212> TYPE: DNA
<213> ORGANISM: Homo sapiens

<400> SEQUENCE: 105
ccttgctgct tcaccctag                                           19

<210> SEQ ID NO 106
<211> LENGTH: 21
<212> TYPE: DNA
<213> ORGANISM: Homo sapiens

<400> SEQUENCE: 106
tgctttatat gtgctgctac g                                        21

<210> SEQ ID NO 107
<211> LENGTH: 39
<212> TYPE: DNA
<213> ORGANISM: Homo sapiens

<400> SEQUENCE: 107
gttttcccag tcacgacgca tcttccctgg ttgtacttc                     39

<210> SEQ ID NO 108
<211> LENGTH: 39
<212> TYPE: DNA
<213> ORGANISM: Homo sapiens

<400> SEQUENCE: 108
aggaaacagc tatgaccatc tggagggcag aagactgat                     39

<210> SEQ ID NO 109
<211> LENGTH: 23
<212> TYPE: DNA
<213> ORGANISM: Homo sapiens

<400> SEQUENCE: 109
ctacatttgt tcaaccataa ctg                                      23

<210> SEQ ID NO 110
<211> LENGTH: 23
<212> TYPE: DNA
<213> ORGANISM: Homo sapiens

<400> SEQUENCE: 110
gattttgagg tttgatgttg atg                                      23

<210> SEQ ID NO 111
<211> LENGTH: 39
<212> TYPE: DNA
<213> ORGANISM: Homo sapiens

<400> SEQUENCE: 111
gttttcccag tcacgacgca tttgttcaac cataactgc                    39

<210> SEQ ID NO 112
<211> LENGTH: 39
<212> TYPE: DNA
<213> ORGANISM: Homo sapiens

<400> SEQUENCE: 112
aggaaacagc tatgaccata tttgagaggt cagggcata                    39

<210> SEQ ID NO 113
<211> LENGTH: 21
<212> TYPE: DNA
<213> ORGANISM: Homo sapiens

<400> SEQUENCE: 113
tcgtgtcaga ttcccaccat a                                       21

<210> SEQ ID NO 114
<211> LENGTH: 21
<212> TYPE: DNA
<213> ORGANISM: Homo sapiens

<400> SEQUENCE: 114
aggcataagt cagacatccg t                                       21

<210> SEQ ID NO 115
<211> LENGTH: 40
<212> TYPE: DNA
<213> ORGANISM: Homo sapiens

<400> SEQUENCE: 115
gttttcccag tcacgacggt tactcttccc acacatcttc                   40

<210> SEQ ID NO 116
<211> LENGTH: 41
<212> TYPE: DNA
<213> ORGANISM: Homo sapiens

<400> SEQUENCE: 116
aggaaacagc tatgaccatc acagcaagtg ttcagtttct a                 41

<210> SEQ ID NO 117
<211> LENGTH: 21
<212> TYPE: DNA
<213> ORGANISM: Homo sapiens

<400> SEQUENCE: 117
cattcccatg tatgaacgtc t                                       21

<210> SEQ ID NO 118
<211> LENGTH: 22
<212> TYPE: DNA
<213> ORGANISM: Homo sapiens

<400> SEQUENCE: 118

-continued atagtaagcc caggaagaag ga                                    22

<210> SEQ ID NO 119
<211> LENGTH: 39
<212> TYPE: DNA
<213> ORGANISM: Homo sapiens

<400> SEQUENCE: 119
gttttcccag tcacgacgca ttcccatgta tgaacgtct                  39

<210> SEQ ID NO 120
<211> LENGTH: 41
<212> TYPE: DNA
<213> ORGANISM: Homo sapiens

<400> SEQUENCE: 120
aggaaacagc tatgaccatc tacaagcatt acaaggcaga g               41

<210> SEQ ID NO 121
<211> LENGTH: 22
<212> TYPE: DNA
<213> ORGANISM: Homo sapiens

<400> SEQUENCE: 121
agtgtcttca gcctttgtat tg                                    22

<210> SEQ ID NO 122
<211> LENGTH: 23
<212> TYPE: DNA
<213> ORGANISM: Homo sapiens

<400> SEQUENCE: 122
atctgctatc tcttcttgtc tca                                   23

<210> SEQ ID NO 123
<211> LENGTH: 40
<212> TYPE: DNA
<213> ORGANISM: Homo sapiens

<400> SEQUENCE: 123
gttttcccag tcacgacgat cgggtcataa tcagtctgtg                 40

<210> SEQ ID NO 124
<211> LENGTH: 42
<212> TYPE: DNA
<213> ORGANISM: Homo sapiens

<400> SEQUENCE: 124
aggaaacagc tatgaccata tctcttcttg tctcaggtaa ca              42

<210> SEQ ID NO 125
<211> LENGTH: 22
<212> TYPE: DNA
<213> ORGANISM: Homo sapiens

<400> SEQUENCE: 125
cttctgaaag caataaacgc at                                    22

<210> SEQ ID NO 126
<211> LENGTH: 20
<212> TYPE: DNA
<213> ORGANISM: Homo sapiens

<400> SEQUENCE: 126

```
gatgtccaaa ctgttccacg                                              20

<210> SEQ ID NO 127
<211> LENGTH: 40
<212> TYPE: DNA
<213> ORGANISM: Homo sapiens

<400> SEQUENCE: 127
gttttcccag tcacgacgta aaaccaacct tcttcattag                        40

<210> SEQ ID NO 128
<211> LENGTH: 38
<212> TYPE: DNA
<213> ORGANISM: Homo sapiens

<400> SEQUENCE: 128
aggaaacagc tatgaccata gcaatgatgg gagcgatg                          38

<210> SEQ ID NO 129
<211> LENGTH: 37
<212> TYPE: DNA
<213> ORGANISM: Homo sapiens

<400> SEQUENCE: 129
gttttcccag tcacgacggg cttctgggga ctcactg                           37

<210> SEQ ID NO 130
<211> LENGTH: 41
<212> TYPE: DNA
<213> ORGANISM: Homo sapiens

<400> SEQUENCE: 130
aggaaacagc tatgaccatc cttcaaaagt ggtgtctgta g                      41

<210> SEQ ID NO 131
<211> LENGTH: 22
<212> TYPE: DNA
<213> ORGANISM: Homo sapiens

<400> SEQUENCE: 131
gtatccacaa agagaccaga ag                                           22

<210> SEQ ID NO 132
<211> LENGTH: 23
<212> TYPE: DNA
<213> ORGANISM: Homo sapiens

<400> SEQUENCE: 132
caccaactac caacagtgac tta                                          23

<210> SEQ ID NO 133
<211> LENGTH: 41
<212> TYPE: DNA
<213> ORGANISM: Homo sapiens

<400> SEQUENCE: 133
gttttcccag tcacgacggc tcactggata ggatatgtca t                      41

<210> SEQ ID NO 134
<211> LENGTH: 39
<212> TYPE: DNA
<213> ORGANISM: Homo sapiens
```

```
<400> SEQUENCE: 134
aggaaacagc tatgaccatc cagaaacaca gctcttgcc                              39

<210> SEQ ID NO 135
<211> LENGTH: 20
<212> TYPE: DNA
<213> ORGANISM: Homo sapiens

<400> SEQUENCE: 135
gcttgccaga tacaggaatc                                                   20

<210> SEQ ID NO 136
<211> LENGTH: 20
<212> TYPE: DNA
<213> ORGANISM: Homo sapiens

<400> SEQUENCE: 136
acagaaagtt taggcaggtg                                                   20

<210> SEQ ID NO 137
<211> LENGTH: 37
<212> TYPE: DNA
<213> ORGANISM: Homo sapiens

<400> SEQUENCE: 137
gttttcccag tcacgacgac gatacccctc cctggct                                37

<210> SEQ ID NO 138
<211> LENGTH: 39
<212> TYPE: DNA
<213> ORGANISM: Homo sapiens

<400> SEQUENCE: 138
aggaaacagc tatgaccata cagaaagttt aggcaggtg                              39

<210> SEQ ID NO 139
<211> LENGTH: 20
<212> TYPE: DNA
<213> ORGANISM: Homo sapiens

<400> SEQUENCE: 139
cctctcactc ttcccagcac                                                   20

<210> SEQ ID NO 140
<211> LENGTH: 22
<212> TYPE: DNA
<213> ORGANISM: Homo sapiens

<400> SEQUENCE: 140
ggagtaggct gcttttctaa at                                                22

<210> SEQ ID NO 141
<211> LENGTH: 40
<212> TYPE: DNA
<213> ORGANISM: Homo sapiens

<400> SEQUENCE: 141
gttttcccag tcacgacgga acacctcatc ctcattacca                             40

<210> SEQ ID NO 142
<211> LENGTH: 41
<212> TYPE: DNA
<213> ORGANISM: Homo sapiens
```

<400> SEQUENCE: 142
aggaaacagc tatgaccata agagacaaaa cacattcatg g 41

<210> SEQ ID NO 143
<211> LENGTH: 39
<212> TYPE: DNA
<213> ORGANISM: Homo sapiens

<400> SEQUENCE: 143
gttttcccag tcacgacggt ttccgctgta aggtagtgt 39

<210> SEQ ID NO 144
<211> LENGTH: 42
<212> TYPE: DNA
<213> ORGANISM: Homo sapiens

<400> SEQUENCE: 144
aggaaacagc tatgaccatc tggaacattt actatgtggc ta 42

<210> SEQ ID NO 145
<211> LENGTH: 20
<212> TYPE: DNA
<213> ORGANISM: Homo sapiens

<400> SEQUENCE: 145
tgctagtggg tagaggtcag 20

<210> SEQ ID NO 146
<211> LENGTH: 21
<212> TYPE: DNA
<213> ORGANISM: Homo sapiens

<400> SEQUENCE: 146
actgaaagcc aggttagaat g 21

<210> SEQ ID NO 147
<211> LENGTH: 37
<212> TYPE: DNA
<213> ORGANISM: Homo sapiens

<400> SEQUENCE: 147
gttttcccag tcacgacgac cctgtccgtc acctgag 37

<210> SEQ ID NO 148
<211> LENGTH: 38
<212> TYPE: DNA
<213> ORGANISM: Homo sapiens

<400> SEQUENCE: 148
aggaaacagc tatgaccatc ccaccagcac tccactta 38

<210> SEQ ID NO 149
<211> LENGTH: 21
<212> TYPE: DNA
<213> ORGANISM: Homo sapiens

<400> SEQUENCE: 149
tgtgaagacg ggataacctg a 21

<210> SEQ ID NO 150
<211> LENGTH: 19
<212> TYPE: DNA

<213> ORGANISM: Homo sapiens

<400> SEQUENCE: 150
gacagggctt gataccgca                                                  19

<210> SEQ ID NO 151
<211> LENGTH: 38
<212> TYPE: DNA
<213> ORGANISM: Homo sapiens

<400> SEQUENCE: 151
gttttcccag tcacgacgat gctggctcac ttttgacc                             38

<210> SEQ ID NO 152
<211> LENGTH: 39
<212> TYPE: DNA
<213> ORGANISM: Homo sapiens

<400> SEQUENCE: 152
aggaaacagc tatgaccatg actggtgagt acagcagga                            39

<210> SEQ ID NO 153
<211> LENGTH: 21
<212> TYPE: DNA
<213> ORGANISM: Homo sapiens

<400> SEQUENCE: 153
ccagcctttg tgtaagtcta c                                               21

<210> SEQ ID NO 154
<211> LENGTH: 19
<212> TYPE: DNA
<213> ORGANISM: Homo sapiens

<400> SEQUENCE: 154
tctgggcaag tttggaagc                                                  19

<210> SEQ ID NO 155
<211> LENGTH: 39
<212> TYPE: DNA
<213> ORGANISM: Homo sapiens

<400> SEQUENCE: 155
gttttcccag tcacgacgtc caaagcagac atcagcctc                            39

<210> SEQ ID NO 156
<211> LENGTH: 38
<212> TYPE: DNA
<213> ORGANISM: Homo sapiens

<400> SEQUENCE: 156
aggaaacagc tatgaccatg gaggaaaaga cgcagcca                             38

<210> SEQ ID NO 157
<211> LENGTH: 19
<212> TYPE: DNA
<213> ORGANISM: Homo sapiens

<400> SEQUENCE: 157
cgctttctgc ctgtgacat                                                  19

<210> SEQ ID NO 158
<211> LENGTH: 20

-continued

```
<212> TYPE: DNA
<213> ORGANISM: Homo sapiens

<400> SEQUENCE: 158
ttctgtcctt cagccaatgc                                                20

<210> SEQ ID NO 159
<211> LENGTH: 37
<212> TYPE: DNA
<213> ORGANISM: Homo sapiens

<400> SEQUENCE: 159
gttttcccag tcacgacgtt agaggctggt gggtgac                              37

<210> SEQ ID NO 160
<211> LENGTH: 42
<212> TYPE: DNA
<213> ORGANISM: Homo sapiens

<400> SEQUENCE: 160
aggaaacagc tatgaccatc atctcaataa aaactggagt gc                       42

<210> SEQ ID NO 161
<211> LENGTH: 20
<212> TYPE: DNA
<213> ORGANISM: Homo sapiens

<400> SEQUENCE: 161
cacttgatgg gcgttctgag                                                20

<210> SEQ ID NO 162
<211> LENGTH: 20
<212> TYPE: DNA
<213> ORGANISM: Homo sapiens

<400> SEQUENCE: 162
ttctgtcctt cagccaatgc                                                20

<210> SEQ ID NO 163
<211> LENGTH: 38
<212> TYPE: DNA
<213> ORGANISM: Homo sapiens

<400> SEQUENCE: 163
gttttcccag tcacgacgtt ccagcggttt acacatca                            38

<210> SEQ ID NO 164
<211> LENGTH: 38
<212> TYPE: DNA
<213> ORGANISM: Homo sapiens

<400> SEQUENCE: 164
aggaaacagc tatgaccatt accccagtgt ccaccttg                             38

<210> SEQ ID NO 165
<211> LENGTH: 20
<212> TYPE: DNA
<213> ORGANISM: Homo sapiens

<400> SEQUENCE: 165
gggttctcca gccaaagact                                                20

<210> SEQ ID NO 166
```

-continued

<211> LENGTH: 19
<212> TYPE: DNA
<213> ORGANISM: Homo sapiens

<400> SEQUENCE: 166
ctgagtctcc tgcctctgc                                        19

<210> SEQ ID NO 167
<211> LENGTH: 38
<212> TYPE: DNA
<213> ORGANISM: Homo sapiens

<400> SEQUENCE: 167
gttttcccag tcacgacggg gttctccagc caaagact                   38

<210> SEQ ID NO 168
<211> LENGTH: 38
<212> TYPE: DNA
<213> ORGANISM: Homo sapiens

<400> SEQUENCE: 168
aggaaacagc tatgaccatg tgggctgga aggctctg                    38

<210> SEQ ID NO 169
<211> LENGTH: 37
<212> TYPE: DNA
<213> ORGANISM: Homo sapiens

<400> SEQUENCE: 169
gttttcccag tcacgacgaa gaggtaaggg gcacagc                    37

<210> SEQ ID NO 170
<211> LENGTH: 38
<212> TYPE: DNA
<213> ORGANISM: Homo sapiens

<400> SEQUENCE: 170
aggaaacagc tatgaccatc tgagtctcct gcctctgc                   38

<210> SEQ ID NO 171
<211> LENGTH: 20
<212> TYPE: DNA
<213> ORGANISM: Homo sapiens

<400> SEQUENCE: 171
gctgagtgtt gagaccagga                                       20

<210> SEQ ID NO 172
<211> LENGTH: 19
<212> TYPE: DNA
<213> ORGANISM: Homo sapiens

<400> SEQUENCE: 172
agacaaacga cggctgctc                                        19

<210> SEQ ID NO 173
<211> LENGTH: 38
<212> TYPE: DNA
<213> ORGANISM: Homo sapiens

<400> SEQUENCE: 173
gttttcccag tcacgacgtt gagaccagga aacagcac                   38

-continued

<210> SEQ ID NO 174
<211> LENGTH: 38
<212> TYPE: DNA
<213> ORGANISM: Homo sapiens

<400> SEQUENCE: 174
aggaaacagc tatgaccatg agaggatgtg ggcgacaa                      38

<210> SEQ ID NO 175
<211> LENGTH: 19
<212> TYPE: DNA
<213> ORGANISM: Homo sapiens

<400> SEQUENCE: 175
gggagatggt gctggctac                                           19

<210> SEQ ID NO 176
<211> LENGTH: 21
<212> TYPE: DNA
<213> ORGANISM: Homo sapiens

<400> SEQUENCE: 176
cctggttagt gatgggtaga t                                        21

<210> SEQ ID NO 177
<211> LENGTH: 37
<212> TYPE: DNA
<213> ORGANISM: Homo sapiens

<400> SEQUENCE: 177
gttttcccag tcacgacgca gggtctgtgc cactgtc                       37

<210> SEQ ID NO 178
<211> LENGTH: 40
<212> TYPE: DNA
<213> ORGANISM: Homo sapiens

<400> SEQUENCE: 178
aggaaacagc tatgaccatc tcagtgtgta gagtcctctc                    40

<210> SEQ ID NO 179
<211> LENGTH: 22
<212> TYPE: DNA
<213> ORGANISM: Homo sapiens

<400> SEQUENCE: 179
ttgattttga gagcatctgg ac                                       22

<210> SEQ ID NO 180
<211> LENGTH: 21
<212> TYPE: DNA
<213> ORGANISM: Homo sapiens

<400> SEQUENCE: 180
ctcggacact tagacccact g                                        21

<210> SEQ ID NO 181
<211> LENGTH: 37
<212> TYPE: DNA
<213> ORGANISM: Homo sapiens

<400> SEQUENCE: 181
gttttcccag tcacgacgtg catcccttcc agctcct                       37

<210> SEQ ID NO 182
<211> LENGTH: 41
<212> TYPE: DNA
<213> ORGANISM: Homo sapiens

<400> SEQUENCE: 182
aggaaacagc tatgaccatg acacacagcc ttctgagttc a                    41

<210> SEQ ID NO 183
<211> LENGTH: 37
<212> TYPE: DNA
<213> ORGANISM: Homo sapiens

<400> SEQUENCE: 183
gttttcccag tcacgacgcc acacagagga gccacag                         37

<210> SEQ ID NO 184
<211> LENGTH: 42
<212> TYPE: DNA
<213> ORGANISM: Homo sapiens

<400> SEQUENCE: 184
aggaaacagc tatgaccata ccagtcctaa gaggcatcta ta                   42

<210> SEQ ID NO 185
<211> LENGTH: 19
<212> TYPE: DNA
<213> ORGANISM: Homo sapiens

<400> SEQUENCE: 185
ccacacagag gagccacag                                             19

<210> SEQ ID NO 186
<211> LENGTH: 20
<212> TYPE: DNA
<213> ORGANISM: Homo sapiens

<400> SEQUENCE: 186
ccagaggtgc tcactacgac                                            20

<210> SEQ ID NO 187
<211> LENGTH: 39
<212> TYPE: DNA
<213> ORGANISM: Homo sapiens

<400> SEQUENCE: 187
gttttcccag tcacgacgag gtcagagccc agtgaagat                       39

<210> SEQ ID NO 188
<211> LENGTH: 39
<212> TYPE: DNA
<213> ORGANISM: Homo sapiens

<400> SEQUENCE: 188
aggaaacagc tatgaccatc atctgcttgc ttccgtgtg                       39

<210> SEQ ID NO 189
<211> LENGTH: 39
<212> TYPE: DNA
<213> ORGANISM: Homo sapiens

<400> SEQUENCE: 189
gttttcccag tcacgacgtc aggataggtg gtatggagc                       39

<210> SEQ ID NO 190
<211> LENGTH: 40
<212> TYPE: DNA
<213> ORGANISM: Homo sapiens

<400> SEQUENCE: 190
aggaaacagc tatgaccatc ggacacttag acccactgat            40

<210> SEQ ID NO 191
<211> LENGTH: 23
<212> TYPE: DNA
<213> ORGANISM: Homo sapiens

<400> SEQUENCE: 191
agactccgag tygaatgaaa atg                              23

<210> SEQ ID NO 192
<211> LENGTH: 23
<212> TYPE: DNA
<213> ORGANISM: Homo sapiens

<400> SEQUENCE: 192
ggtgagggca crtttgggca gct                              23

<210> SEQ ID NO 193
<211> LENGTH: 23
<212> TYPE: DNA
<213> ORGANISM: Homo sapiens

<400> SEQUENCE: 193
gcaccctggc trctgtgttt gtg                              23

<210> SEQ ID NO 194
<211> LENGTH: 23
<212> TYPE: DNA
<213> ORGANISM: Homo sapiens

<400> SEQUENCE: 194
gtgtcccacc tgcacgcaga tca                              23

<210> SEQ ID NO 195
<211> LENGTH: 24
<212> TYPE: DNA
<213> ORGANISM: Homo sapiens

<400> SEQUENCE: 195
gtgtcccacc tggcacgcag atca                             24

<210> SEQ ID NO 196
<211> LENGTH: 23
<212> TYPE: DNA
<213> ORGANISM: Homo sapiens

<400> SEQUENCE: 196
aagccgcttc ayccttgct ggt                               23

<210> SEQ ID NO 197
<211> LENGTH: 24
<212> TYPE: DNA
<213> ORGANISM: Homo sapiens

<400> SEQUENCE: 197

-continued gctgttgcga acrtgtgatt tgga                                              24

<210> SEQ ID NO 198
<211> LENGTH: 22
<212> TYPE: DNA
<213> ORGANISM: Homo sapiens

<400> SEQUENCE: 198
gaggcttggg stcccacata ag                                                22

<210> SEQ ID NO 199
<211> LENGTH: 23
<212> TYPE: DNA
<213> ORGANISM: Homo sapiens

<400> SEQUENCE: 199
cctggcacag cygcgggcca gga                                               23

<210> SEQ ID NO 200
<211> LENGTH: 23
<212> TYPE: DNA
<213> ORGANISM: Homo sapiens

<400> SEQUENCE: 200
aatccagcaa artgattccc tgc                                               23

<210> SEQ ID NO 201
<211> LENGTH: 21
<212> TYPE: DNA
<213> ORGANISM: Homo sapiens

<400> SEQUENCE: 201
taaatgtttt ytcattctta g                                                 21

<210> SEQ ID NO 202
<211> LENGTH: 23
<212> TYPE: DNA
<213> ORGANISM: Homo sapiens

<400> SEQUENCE: 202
ttgctgttgt gyggttttct tgt                                               23

<210> SEQ ID NO 203
<211> LENGTH: 24
<212> TYPE: DNA
<213> ORGANISM: Homo sapiens

<400> SEQUENCE: 203
ggttttcttg attcagcagt taca                                              24

<210> SEQ ID NO 204
<211> LENGTH: 27
<212> TYPE: DNA
<213> ORGANISM: Homo sapiens

<400> SEQUENCE: 204
ggttttcttg atgattcagc agttaca                                           27

<210> SEQ ID NO 205
<211> LENGTH: 23
<212> TYPE: DNA
<213> ORGANISM: Homo sapiens

<400> SEQUENCE: 205

```
gtgtctcaga cyggcccctt gtc                                              23

<210> SEQ ID NO 206
<211> LENGTH: 23
<212> TYPE: DNA
<213> ORGANISM: Homo sapiens

<400> SEQUENCE: 206
tgccatcttg awctaatgga atc                                              23

<210> SEQ ID NO 207
<211> LENGTH: 23
<212> TYPE: DNA
<213> ORGANISM: Homo sapiens

<400> SEQUENCE: 207
cttctctctc tycctgcagg gat                                              23

<210> SEQ ID NO 208
<211> LENGTH: 23
<212> TYPE: DNA
<213> ORGANISM: Homo sapiens

<400> SEQUENCE: 208
catcaagggc aygtttactt ttt                                              23

<210> SEQ ID NO 209
<211> LENGTH: 23
<212> TYPE: DNA
<213> ORGANISM: Homo sapiens

<400> SEQUENCE: 209
cagccttgcc csctgggctg ttg                                              23

<210> SEQ ID NO 210
<211> LENGTH: 350
<212> TYPE: DNA
<213> ORGANISM: Homo sapiens
<220> FEATURE:
<221> NAME/KEY: CDS
<222> LOCATION: (51)..(293)

<400> SEQUENCE: 210
cgcgggcgta ggtgaccggc ggctttctca gttttggtgg agacgggcgc atg tgg         56
                                                       Met Trp
                                                         1 gcg ctt tgc tcg ctg ctg cgg tcc gcg gcc gga cgc acc atg tcg cag       104
Ala Leu Cys Ser Leu Leu Arg Ser Ala Ala Gly Arg Thr Met Ser Gln
      5                   10                  15 gga cgc acc ata tcg cag gca ccc gcc cgc cgc gag cgg ccg cgc aag       152
Gly Arg Thr Ile Ser Gln Ala Pro Ala Arg Arg Glu Arg Pro Arg Lys
 20                  25                  30 gac ccg ctg cgg cac ctg cgc acg cga gag aag cgc gga ccg tcg ggg       200
Asp Pro Leu Arg His Leu Arg Thr Arg Glu Lys Arg Gly Pro Ser Gly
 35                  40                  45                  50 tgc tcc ggc ggc cca aac acc gtg tac ctg cag gtg gtg gca gcg ggt       248
Cys Ser Gly Gly Pro Asn Thr Val Tyr Leu Gln Val Val Ala Ala Gly
             55                  60                  65 agc cgg gac tcg ggc gcc gcg ctc tac gtc ttc tcc gag ttc aac           293
Ser Arg Asp Ser Gly Ala Ala Leu Tyr Val Phe Ser Glu Phe Asn
         70                  75                  80 cggtcagtca acgagccacg ccccgtcccg ctgggccctc agtgcggcgc agcctct        350
```

-continued

<210> SEQ ID NO 211
<211> LENGTH: 81
<212> TYPE: PRT
<213> ORGANISM: Homo sapiens

<400> SEQUENCE: 211

```
Met Trp Ala Leu Cys Ser Leu Leu Arg Ser Ala Ala Gly Arg Thr Met
 1               5                  10                  15

Ser Gln Gly Arg Thr Ile Ser Gln Ala Pro Ala Arg Arg Glu Arg Pro
            20                  25                  30

Arg Lys Asp Pro Leu Arg His Leu Arg Thr Arg Glu Lys Arg Gly Pro
        35                  40                  45

Ser Gly Cys Ser Gly Gly Pro Asn Thr Val Tyr Leu Gln Val Val Ala
    50                  55                  60

Ala Gly Ser Arg Asp Ser Gly Ala Ala Leu Tyr Val Phe Ser Glu Phe
65                  70                  75                  80

Asn
```

<210> SEQ ID NO 212
<211> LENGTH: 326
<212> TYPE: DNA
<213> ORGANISM: Mus musculus
<220> FEATURE:
<221> NAME/KEY: CDS
<222> LOCATION: (51)..(269)

<400> SEQUENCE: 212

```
tggcggcgtg agggtctgg ctgccttgtc agcctggtgt ggtcgggtgc atg tgg            56
                                                      Met Trp
                                                       1 gcg ctc cgc tca ctg ttg cgt ccc ctt ggc ctg cgc acc atg tcg cag         104
Ala Leu Arg Ser Leu Leu Arg Pro Leu Gly Leu Arg Thr Met Ser Gln
        5                  10                  15 ggt tcg gct cgt cgg ccg cgg cca ccc aag gac cca ctg cga cac ctg         152
Gly Ser Ala Arg Arg Pro Arg Pro Pro Lys Asp Pro Leu Arg His Leu
    20                  25                  30 cgt acg cgg gag aag cgc ggc ccg ggt ccc ggg ggc ccg aac acc gtg         200
Arg Thr Arg Glu Lys Arg Gly Pro Gly Pro Gly Gly Pro Asn Thr Val
35                  40                  45                  50 tac ctg cag gtg gtg gcg gcg ggc ggc cgg gac gcg ggg gct gct ctc         248
Tyr Leu Gln Val Val Ala Ala Gly Gly Arg Asp Ala Gly Ala Ala Leu
                55                  60                  65 tat gtc ttc tcg gaa tac aac aggtcagagt gggccgacag ccctggggga            299
Tyr Val Phe Ser Glu Tyr Asn
                70 ttggccccag cgccacgtgc tcgggag                                           326
```

<210> SEQ ID NO 213
<211> LENGTH: 73
<212> TYPE: PRT
<213> ORGANISM: Mus musculus

<400> SEQUENCE: 213

```
Met Trp Ala Leu Arg Ser Leu Leu Arg Pro Leu Gly Leu Arg Thr Met
 1               5                  10                  15

Ser Gln Gly Ser Ala Arg Arg Pro Arg Pro Pro Lys Asp Pro Leu Arg
            20                  25                  30

His Leu Arg Thr Arg Glu Lys Arg Gly Pro Gly Pro Gly Gly Pro Asn
        35                  40                  45
```

```
Thr Val Tyr Leu Gln Val Val Ala Ala Gly Gly Arg Asp Ala Gly Ala
        50                  55                  60
Ala Leu Tyr Val Phe Ser Glu Tyr Asn
 65                  70

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence:Histidine
      containing motif.
<221> NAME/KEY: SITE
<222> LOCATION: (1)..(3)
<223> OTHER INFORMATION: These amino acids can each be any large
      hydrophobic residue.
<221> NAME/KEY: SITE
<222> LOCATION: (4)
<223> OTHER INFORMATION: This is serine or threonine.
<221> NAME/KEY: SITE
<222> LOCATION: (6)
<223> OTHER INFORMATION: This can be any amino acid residue.
<221> NAME/KEY: SITE
<222> LOCATION: (8)
<223> OTHER INFORMATION: This can be any amino acid residue.
<221> NAME/KEY: SITE
<222> LOCATION: (11)..(12)
<223> OTHER INFORMATION: These can be any amino acid residues.

<400> SEQUENCE: 214

Xaa Xaa Xaa Xaa His Xaa His Xaa Asp His Xaa Xaa Gly
 1               5                   10

<210> SEQ ID NO 215
<211> LENGTH: 127
<212> TYPE: DNA
<213> ORGANISM: Homo sapiens
<220> FEATURE:
<221> NAME/KEY: misc_feature
<222> LOCATION: (1)..(127)
<223> OTHER INFORMATION: Exon 1.

<400> SEQUENCE: 215
tttaatacga ctcactatag ggaatttggc cctcgagnng aattcggcac gagggtagcc    60
ccgcgacagc tgggccgagg gtgcgggcct gcgctccctc ggctcctggc gcgggctcgg   120
ggagagg                                                            127

<210> SEQ ID NO 216
<211> LENGTH: 983
<212> TYPE: DNA
<213> ORGANISM: Homo sapiens
<220> FEATURE:
<221> NAME/KEY: intron
<222> LOCATION: (1)..(300)
<223> OTHER INFORMATION: Upstream intron of exon 2.
<221> NAME/KEY: misc_structure
<222> LOCATION: (301)..(465)
<223> OTHER INFORMATION: Exon 2.
<221> NAME/KEY: intron
<222> LOCATION: (466)..(983)
<223> OTHER INFORMATION: Intron downstream of exon 2.

<400> SEQUENCE: 216
gtctccatag ttttgccttt ttgagaacat catatagtta gaattcagct atagttttta    60
attgcctggg tttggttatt tttgtttgtt tgggtgtgtg aacaattata caagatttgt   120
taacttgtag ttttagccaa gttattaaaa ccttactgtg gatatgtgtg gaatactatg   180
```

-continued

| | |
|---|---|
| agagaccaag aatccagact gttctaaata accaaaaagt aataatagag ataaatatta | 240 |
| caggaatatg tttttggtcc agtgatatga aataatcccc agatgatctt tctgttgcag | 300 |
| ggtggaagat gtctatggat gtgacattcc tggggacggg tgcagcatac ccatctccaa | 360 |
| cccggggtgc ctctgctgtg gtccttcggt gtgaaggcga gtgctggctc tttgactgtg | 420 |
| gggagggaac acagacacag cttatgaaaa gccaacttaa agcaggttag tgtgccttca | 480 |
| gctatctcat taagaatttt ttgttgttct gcttcatttt cttggctctc cttggacatt | 540 |
| ttgtttagaa acagccctga tggttgcatc ccacttcagt gctacaccct ggtgagactt | 600 |
| ggaaggcctg caggcatctg gccacgtcca ctgaacttca tttacttatt tacttgcttt | 660 |
| tcatttatcc tgtagatgct gaaagcaagg attcatgtag gcttgggggtt tgggaaatgt | 720 |
| cgtgggatac accaggcata ttagatgaac actgccttag caaggaagca gtgtacatac | 780 |
| ttacctccac caggagatag ttttcatgag aggatgcaaa gggtaggaaa tgtttggagg | 840 |
| aggagatgtt gttttcctct tggggttatc aggtaaactt ctcagagaag ttgacctgtg | 900 |
| gattgtcaaa gagagagatt tcaggctgag agaagaaggc atttcatcag gggatggagt | 960 |
| gagcagagcc acacctggga gat | 983 |

<210> SEQ ID NO 217
<211> LENGTH: 1287
<212> TYPE: DNA
<213> ORGANISM: Homo sapiens
<220> FEATURE:
<221> NAME/KEY: intron
<222> LOCATION: (1)..(300)
<223> OTHER INFORMATION: Intron upstream of exon 3.
<221> NAME/KEY: misc_feature
<222> LOCATION: (301)..(768)
<223> OTHER INFORMATION: Exon 3.
<221> NAME/KEY: intron
<222> LOCATION: (769)..(1287)
<223> OTHER INFORMATION: Intron downstream of exon 3.

<400> SEQUENCE: 217

| | |
|---|---|
| gtgagctatg atcacaccac tgcactccag cctggatgac agagcaagac ctgtctcttt | 60 |
| aaaaaaaaaa aaactattaa aaacaaacaa acaaaaaacc acctggtgaa ataaagcctg | 120 |
| tcttcttgtt tttggaatca tgtagcaaaa tgtaaatgaa taagtttatg atgataagta | 180 |
| gaacttttaa attcaattta ctattttttaa tgtaaattgt taggcttgtt tcaaatagct | 240 |
| ttgtatgggt ttttagttaa tgaaaaattt ccaaacgtat ttctctatct caatcaaaag | 300 |
| ggagaattac caagatcttc atcacacacc ttcatggaga ccatttcttt ggccttcctg | 360 |
| ggctcctctg cacaatcagc ctgcagagtg gctccatggt gtccaaacag cctattgaaa | 420 |
| tctatggccc tgtagggctt cgggacttta tctggcgaac catggaactc tctcacacgg | 480 |
| agctggtctt ccattatgtg gttcatgaac tggttcctac agcagatcaa tgtcctgcag | 540 |
| aagaactaaa agaatttgcg catgtgaata gagcagacag tcctcccaaa gaggaacaag | 600 |
| gaagaactat cctgttagac tcagaagaaa actcatacct tctgtttgat gatgaacaat | 660 |
| ttgttgtaaa agcatttcgc ctcttttcaca gaattccctc atttgggttt tcagtcgtgg | 720 |
| aaaagaaacg cccaggtaaa ctcaatgcac agaaacttaa agaccttggt aagtgttttt | 780 |
| ttgtttttttg tttttttcccg ccttctcatc aatagggctc ctgttgactg aagctataag | 840 |
| aaatgtcata gtaaggccag gagttgtggc tcacgcctgt aatcctagca ctttgggagg | 900 |
| ccgaggtggg aggatcactt gagttcggga gttcaagacc agcctgggca acatggcgaa | 960 |
| accccatctc tactaaaaat acaaaaagta actgggtgtg gtgtcatgtg cctgtagtcc | 1020 |

-continued

```
cagctacttg gggggctgag gcaggaggat cacttgaacc tgggaggtca aggctgcagt      1080
aagccaagat agtgttacta tactccagct tgggtgacaa agcgaaactc tgtctcaaaa      1140
aaaaaaaagt gtcatagtaa gcttccactc ctctatccca ggcctgaaac tgacaatttc      1200
tcacttagtc ctttgtccaa agttgcttat taagaaatcc atgggccaa  aaaaatgcta      1260 tttagagcaa acccagtata catttga                                          1287
```

<210> SEQ ID NO 218
<211> LENGTH: 1378
<212> TYPE: DNA
<213> ORGANISM: Homo sapiens
<220> FEATURE:
<221> NAME/KEY: intron
<222> LOCATION: (1)..(300)
<223> OTHER INFORMATION: Intron upstream of exon 4.
<221> NAME/KEY: misc_feature
<222> LOCATION: (301)..(966)
<223> OTHER INFORMATION: Exon 4 with CDS ending at 764.
<221> NAME/KEY: intron
<222> LOCATION: (967)..(1378)
<223> OTHER INFORMATION: Intron downstream of exon 4.

<400> SEQUENCE: 218

```
tgtgcacagc agagaatcaa gaatgttaca gtgactacaa taaggtccta gtgatactta       60
ggagactaaa acttgtctga catgtatgca tgggaaatgt ttcaagtact aaggcattgc      120
taatatcaat caacactgaa attttaaaaa tgtataaatc cagttttcca caagtagtaa      180
aacatttata acaattatgg atgccttttc cattagctat ttgcaatgct gttaaaatag      240
actcttgaaa agtcataaat tccattccta tgatgtaatg ttatctgcct tcatcattag      300
gtgttccacc aggtcctgcc tatgggaagc tgaaaaatgg aatttctgtt gttctggaaa      360
atggggttac aatttctccc caagatgtct taaaaaagcc tattgttgga agaaaaatct      420
gcatattggg tgactgctct ggggttgtgg gtgatggagg agtaaaactg tgctttgaag      480
cagacctgtt gatccacgaa gcaaccctgg atgatgccca gatggacaaa gcaaaggagc      540
atggccacag cacaccacag atggcagcaa catttgcaaa gttgtgccgt gcaaagaggc      600
tggttctgac tcacttcagt cagaggtaca aaccagttgc cttggccaga gaaggagaaa      660
cagatggcat tgcagaacta aaaaagcaag ctgaatcagt gttagatctc caagaagtga      720
ctctagcaga agatttttatg gtgataagca ttccaatcaa gaaatgaaac cagtgttcct      780
gagtgcacac tgacatgtct gtgaatatgt tactgaacct atagtccagt ttttttattt      840
cttgttttag tctgaaatta tttgggccct aataatccta aaaagaatgg agctgcattg      900
atgaattggc tcagtattta aagggagcaa acttttttgat aataaatctt tttaagagaa      960
aaaaaaccca gcatcctttt tgaagtccag atttgtcaaa atgatagact attcagttat     1020
acatcttatt ttgtgctact accacagata gccaatattc catgcagtcc tgggcttagc     1080
ttctgcccag ctttattgct gctattggca aagagcacag gactcagccc tcgtggctaa     1140
aaatggtatt ttggcagttt gtattgaatc tgtttgtgtt attaacagaa gagggagaaa     1200
tgtcatgaga cgttggacag gcaggattga tgatagcatg accatagctt tgctggaata     1260
ctgaatgcag ggtttggcta ggtgtttatt ttaacatttt attaaacttt ctatttgggt     1320
cttaacccat ggttctcaac tggggtgaca ctgctcctct agaacaggtt gaaatatg      1378
```

<210> SEQ ID NO 219
<211> LENGTH: 1462
<212> TYPE: DNA

-continued

```
<213> ORGANISM: Homo sapiens
<220> FEATURE:
<221> NAME/KEY: CDS
<222> LOCATION: (136)..(1224)

<400> SEQUENCE: 219
```

| | |
|---|---:|
| tttaatacga ctcactatag ggaatttggc cctcgagnng aattcggcac gagggtagcc | 60 |
| ccgcgacagc tgggccgagg gtgcgggcct gcgctccctc ggctcctggc gcgggctcgg | 120 |
| ggagaggggt ggaag atg tct atg gat gtg aca ttc ctg ggg acg ggt gca<br>                  Met Ser Met Asp Val Thr Phe Leu Gly Thr Gly Ala<br>                   1             5              10 | 171 |
| gca tac cca tct cca acc cgg ggt gcc tct gct gtg gtc ctt cgg tgt<br>Ala Tyr Pro Ser Pro Thr Arg Gly Ala Ser Ala Val Val Leu Arg Cys<br>        15                  20                  25 | 219 |
| gaa ggc gag tgc tgg ctc ttt gac tgt ggg gag gga aca cag aca cag<br>Glu Gly Glu Cys Trp Leu Phe Asp Cys Gly Glu Gly Thr Gln Thr Gln<br> 30                 35                  40 | 267 |
| ctt atg aaa agc caa ctt aaa gca ggg aga att acc aag atc ttc atc<br>Leu Met Lys Ser Gln Leu Lys Ala Gly Arg Ile Thr Lys Ile Phe Ile<br> 45                 50              55              60 | 315 |
| aca cac ctt cat gga gac cat ttc ttt ggc ctt cct ggg ctc ctc tgc<br>Thr His Leu His Gly Asp His Phe Phe Gly Leu Pro Gly Leu Leu Cys<br>                  65                  70              75 | 363 |
| aca atc agc ctg cag agt ggc tcc atg gtg tcc aaa cag cct att gaa<br>Thr Ile Ser Leu Gln Ser Gly Ser Met Val Ser Lys Gln Pro Ile Glu<br>              80                  85              90 | 411 |
| atc tat ggc cct gta ggg ctt cgg gac ttt atc tgg cga acc atg gaa<br>Ile Tyr Gly Pro Val Gly Leu Arg Asp Phe Ile Trp Arg Thr Met Glu<br>         95                 100              105 | 459 |
| ctc tct cac acg gag ctg gtc ttc cat tat gtg gtt cat gaa ctg gtt<br>Leu Ser His Thr Glu Leu Val Phe His Tyr Val Val His Glu Leu Val<br> 110                 115              120 | 507 |
| cct aca gca gat caa tgt cct gca gaa gaa cta aaa gaa ttt gcg cat<br>Pro Thr Ala Asp Gln Cys Pro Ala Glu Glu Leu Lys Glu Phe Ala His<br>125                 130              135              140 | 555 |
| gtg aat aga gca gac agt cct ccc aaa gag gaa caa gga aga act atc<br>Val Asn Arg Ala Asp Ser Pro Pro Lys Glu Glu Gln Gly Arg Thr Ile<br>                 145              150              155 | 603 |
| ctg tta gac tca gaa gaa aac tca tac ctt ctg ttt gat gat gaa caa<br>Leu Leu Asp Ser Glu Glu Asn Ser Tyr Leu Leu Phe Asp Asp Glu Gln<br>            160              165              170 | 651 |
| ttt gtt gta aaa gca ttt cgc ctc ttt cac aga att ccc tca ttt ggg<br>Phe Val Val Lys Ala Phe Arg Leu Phe His Arg Ile Pro Ser Phe Gly<br>         175                 180              185 | 699 |
| ttt tca gtc gtg gaa aag aaa cgc cca ggt aaa ctc aat gca cag aaa<br>Phe Ser Val Val Glu Lys Lys Arg Pro Gly Lys Leu Asn Ala Gln Lys<br>190                 195              200 | 747 |
| ctt aaa gac ctt ggt gtt cca cca ggt cct gcc tat ggg aag ctg aaa<br>Leu Lys Asp Leu Gly Val Pro Pro Gly Pro Ala Tyr Gly Lys Leu Lys<br>205                 210              215              220 | 795 |
| aat gga att tct gtt gtt ctg gaa aat ggg gtt aca att tct ccc caa<br>Asn Gly Ile Ser Val Val Leu Glu Asn Gly Val Thr Ile Ser Pro Gln<br>                 225              230              235 | 843 |
| gat gtc tta aaa aag cct att gtt gga aga aaa atc tgc ata ttg ggt<br>Asp Val Leu Lys Lys Pro Ile Val Gly Arg Lys Ile Cys Ile Leu Gly<br>         240                 245              250 | 891 |
| gac tgc tct ggg gtt gtg ggt gat gga gga gta aaa ctg tgc ttt gaa<br>Asp Cys Ser Gly Val Val Gly Asp Gly Gly Val Lys Leu Cys Phe Glu<br>                 255              260              265 | 939 |

```
gca gac ctg ttg atc cac gaa gca acc ctg gat gat gcc cag atg gac      987
Ala Asp Leu Leu Ile His Glu Ala Thr Leu Asp Asp Ala Gln Met Asp
270                 275                 280 aaa gca aag gag cat ggc cac agc aca cca cag atg gca gca aca ttt     1035
Lys Ala Lys Glu His Gly His Ser Thr Pro Gln Met Ala Ala Thr Phe
285                 290                 295                 300 gca aag ttg tgc cgt gca aag agg ctg gtt ctg act cac ttc agt cag     1083
Ala Lys Leu Cys Arg Ala Lys Arg Leu Val Leu Thr His Phe Ser Gln
            305                 310                 315 agg tac aaa cca gtt gcc ttg gcc aga gaa gga gaa aca gat ggc att     1131
Arg Tyr Lys Pro Val Ala Leu Ala Arg Glu Gly Glu Thr Asp Gly Ile
        320                 325                 330 gca gaa cta aaa aag caa gct gaa tca gtg tta gat ctc caa gaa gtg     1179
Ala Glu Leu Lys Lys Gln Ala Glu Ser Val Leu Asp Leu Gln Glu Val
    335                 340                 345 act cta gca gaa gat ttt atg gtg ata agc att cca atc aag aaa         1224
Thr Leu Ala Glu Asp Phe Met Val Ile Ser Ile Pro Ile Lys Lys
350                 355                 360 tgaaaccagt gttcctgagt gcacactgac atgtctgtga atatgttact gaacctatag   1284
tccagttttt ttatttcttg ttttagtctg aaattatttg ggccctaata atcctaaaaa   1344
gaatggagct gcattgatga attggctcag tatttaaagg gagcaaactt tttgataata   1404
aatcttttta agagaaaaaa aaaaaaaaga aaaaagatct ataattaagc agggcat      1462

<210> SEQ ID NO 220
<211> LENGTH: 363
<212> TYPE: PRT
<213> ORGANISM: Homo sapiens

<400> SEQUENCE: 220

Met Ser Met Asp Val Thr Phe Leu Gly Thr Gly Ala Ala Tyr Pro Ser
1               5                   10                  15

Pro Thr Arg Gly Ala Ser Ala Val Val Leu Arg Cys Glu Gly Glu Cys
            20                  25                  30

Trp Leu Phe Asp Cys Gly Glu Gly Thr Gln Thr Gln Leu Met Lys Ser
        35                  40                  45

Gln Leu Lys Ala Gly Arg Ile Thr Lys Ile Phe Ile Thr His Leu His
    50                  55                  60

Gly Asp His Phe Phe Gly Leu Pro Gly Leu Leu Cys Thr Ile Ser Leu
65                  70                  75                  80

Gln Ser Gly Ser Met Val Ser Lys Gln Pro Ile Glu Ile Tyr Gly Pro
                85                  90                  95

Val Gly Leu Arg Asp Phe Ile Trp Arg Thr Met Glu Leu Ser His Thr
            100                 105                 110

Glu Leu Val Phe His Tyr Val His Glu Leu Val Pro Thr Ala Asp
        115                 120                 125

Gln Cys Pro Ala Glu Glu Leu Lys Glu Phe Ala His Val Asn Arg Ala
    130                 135                 140

Asp Ser Pro Pro Lys Glu Glu Gln Gly Arg Thr Ile Leu Leu Asp Ser
145                 150                 155                 160

Glu Glu Asn Ser Tyr Leu Leu Phe Asp Asp Glu Gln Phe Val Val Lys
                165                 170                 175

Ala Phe Arg Leu Phe His Arg Ile Pro Ser Phe Gly Phe Ser Val Val
            180                 185                 190

Glu Lys Lys Arg Pro Gly Lys Leu Asn Ala Gln Lys Leu Lys Asp Leu
        195                 200                 205
```

```
Gly Val Pro Pro Gly Pro Ala Tyr Gly Lys Leu Lys Asn Gly Ile Ser
    210                 215                 220

Val Val Leu Glu Asn Gly Val Thr Ile Ser Pro Gln Asp Val Leu Lys
225                 230                 235                 240

Lys Pro Ile Val Gly Arg Lys Ile Cys Ile Leu Gly Asp Cys Ser Gly
                245                 250                 255

Val Val Gly Asp Gly Gly Val Lys Leu Cys Phe Glu Ala Asp Leu Leu
            260                 265                 270

Ile His Glu Ala Thr Leu Asp Asp Ala Gln Met Asp Lys Ala Lys Glu
        275                 280                 285

His Gly His Ser Thr Pro Gln Met Ala Ala Thr Phe Ala Lys Leu Cys
    290                 295                 300

Arg Ala Lys Arg Leu Val Leu Thr His Phe Ser Gln Arg Tyr Lys Pro
305                 310                 315                 320

Val Ala Leu Ala Arg Glu Gly Glu Thr Asp Gly Ile Ala Glu Leu Lys
                325                 330                 335

Lys Gln Ala Glu Ser Val Leu Asp Leu Gln Glu Val Thr Leu Ala Glu
            340                 345                 350

Asp Phe Met Val Ile Ser Ile Pro Ile Lys Lys
            355                 360

<210> SEQ ID NO 221
<211> LENGTH: 2470
<212> TYPE: DNA
<213> ORGANISM: Mus musculus
<220> FEATURE:
<221> NAME/KEY: CDS
<222> LOCATION: (1)..(2466)

<400> SEQUENCE: 221 atg tgg gcg ctc cgc tca ctg ttg cgt ccc ctt ggc ctg cgc acc atg     48
Met Trp Ala Leu Arg Ser Leu Leu Arg Pro Leu Gly Leu Arg Thr Met
  1               5                  10                  15 tcg cag ggt tcg gct cgt cgg ccg cgg cca ccc aaa gac cca ctg cga     96
Ser Gln Gly Ser Ala Arg Arg Pro Arg Pro Pro Lys Asp Pro Leu Arg
             20                  25                  30 cac ctg cgt acg cgg gag aag cgc ggc ccg ggt ccc ggg ggc ccg aac    144
His Leu Arg Thr Arg Glu Lys Arg Gly Pro Gly Pro Gly Gly Pro Asn
         35                  40                  45 acc gtg tac ctg cag gtg gtg gcg gcg ggc ggc cgg gac gcg ggg gct    192
Thr Val Tyr Leu Gln Val Val Ala Ala Gly Gly Arg Asp Ala Gly Ala
     50                  55                  60 gct ctc tat gtc ttc tcg gaa tac aac agg tac ctt ttt aac tgc gga    240
Ala Leu Tyr Val Phe Ser Glu Tyr Asn Arg Tyr Leu Phe Asn Cys Gly
 65                  70                  75                  80 gaa ggc gtc caa cga ctt atg cag gaa cac aag act gaa agt cgc tcg    288
Glu Gly Val Gln Arg Leu Met Gln Glu His Lys Thr Glu Ser Arg Ser
                 85                  90                  95 ctt gac aac atc ttt ctg act cgg atg cat tgg tca aat gtt ggg ggg    336
Leu Asp Asn Ile Phe Leu Thr Arg Met His Trp Ser Asn Val Gly Gly
            100                 105                 110 ttg tgt gga atg att tta act tta aag gaa acc ggg ctt ccc aaa tgt    384
Leu Cys Gly Met Ile Leu Thr Leu Lys Glu Thr Gly Leu Pro Lys Cys
        115                 120                 125 gtt ctg tct gga cca cca cag ctg gag aaa tat cta gaa gca atc aaa    432
Val Leu Ser Gly Pro Pro Gln Leu Glu Lys Tyr Leu Glu Ala Ile Lys
    130                 135                 140 ata ttt tct ggt cca ttg aaa gga ata gaa ctg gcc gtg cgg cct cac    480
Ile Phe Ser Gly Pro Leu Lys Gly Ile Glu Leu Ala Val Arg Pro His
145                 150                 155                 160
```

```
                -continued
 145            150            155            160 tct gca cca gaa tac aag gat gag acc atg act gtt tac cag gtc cct    528
Ser Ala Pro Glu Tyr Lys Asp Glu Thr Met Thr Val Tyr Gln Val Pro
                165            170            175 atc cac agt gaa cgg agg tgt gga aag caa cag cca tcc cag agc ccc    576
Ile His Ser Glu Arg Arg Cys Gly Lys Gln Gln Pro Ser Gln Ser Pro
            180            185            190 aga aca tct ccc aac agg ctc agt ccc aaa cag tca tcg gac tct gga    624
Arg Thr Ser Pro Asn Arg Leu Ser Pro Lys Gln Ser Ser Asp Ser Gly
        195            200            205 tca gct gaa aat ggg cag tgc caa cag gaa agc atg ggg cag gga ccc    672
Ser Ala Glu Asn Gly Gln Cys Gln Gln Glu Ser Met Gly Gln Gly Pro
    210            215            220 tcc tta gtg gta gct ttt gtc tgc aag ctt cac ttg agg aaa gga aac    720
Ser Leu Val Val Ala Phe Val Cys Lys Leu His Leu Arg Lys Gly Asn
225            230            235            240 ttc ttg gtg ctt aaa gca aag gag ctg ggc ctt cct gtt ggg acg gcc    768
Phe Leu Val Leu Lys Ala Lys Glu Leu Gly Leu Pro Val Gly Thr Ala
                245            250            255 gcc att gca ccc atc att gct gct gtc aag gac ggg aag agt atc act    816
Ala Ile Ala Pro Ile Ile Ala Ala Val Lys Asp Gly Lys Ser Ile Thr
            260            265            270 tac gaa gga aga gag att gct gct gaa gag ctt tgt aca ccc cca gat    864
Tyr Glu Gly Arg Glu Ile Ala Ala Glu Glu Leu Cys Thr Pro Pro Asp
        275            280            285 cct ggt ctt gta ttc atc gtg gta gag tgt cct gat gaa gga ttc atc    912
Pro Gly Leu Val Phe Ile Val Val Glu Cys Pro Asp Glu Gly Phe Ile
    290            295            300 ctg ccc atc tgt gag aac gac acc ttt aaa agg tac cag gca gag gct    960
Leu Pro Ile Cys Glu Asn Asp Thr Phe Lys Arg Tyr Gln Ala Glu Ala
305            310            315            320 gat gca cct gtg gcg ctg gtg gtc cac ata gcc cca gaa tct gta ctc    1008
Asp Ala Pro Val Ala Leu Val Val His Ile Ala Pro Glu Ser Val Leu
                325            330            335 atc gac agc aga tac cag cag tgg atg gag agg ttc ggg cct gac aca    1056
Ile Asp Ser Arg Tyr Gln Gln Trp Met Glu Arg Phe Gly Pro Asp Thr
            340            345            350 cag cac ctg att ctg aat gag aat tgc ccc tcg gtc cac aac ctg cgc    1104
Gln His Leu Ile Leu Asn Glu Asn Cys Pro Ser Val His Asn Leu Arg
        355            360            365 agc cac aag att cag acc cag ctc agc ctc atc cac cct gac atc ttc    1152
Ser His Lys Ile Gln Thr Gln Leu Ser Leu Ile His Pro Asp Ile Phe
    370            375            380 ccc cag ctt acc agc ttc tat agt aag gag gaa ggg tcc acc ctc agc    1200
Pro Gln Leu Thr Ser Phe Tyr Ser Lys Glu Glu Gly Ser Thr Leu Ser
385            390            395            400 gtg cca aca gtt cgg ggt gaa tgc ctc ctc aag tat tca gtc cgc ccc    1248
Val Pro Thr Val Arg Gly Glu Cys Leu Leu Lys Tyr Ser Val Arg Pro
                405            410            415 aag aga gag tgg cag agg gat acc aca ctc gac tgc aat act gat gaa    1296
Lys Arg Glu Trp Gln Arg Asp Thr Thr Leu Asp Cys Asn Thr Asp Glu
            420            425            430 ttc ata gct gag gcc ttg gag ctc ccc agt ttc cag gag agt gtg gag    1344
Phe Ile Ala Glu Ala Leu Glu Leu Pro Ser Phe Gln Glu Ser Val Glu
        435            440            445 gag tat cgg aag aac gtg cag gaa aac cca gcc cca gca gag aaa aga    1392
Glu Tyr Arg Lys Asn Val Gln Glu Asn Pro Ala Pro Ala Glu Lys Arg
    450            455            460 agc cag tat cct gaa att gtc ttc ctg ggt acg ggg tct gcc atc cca    1440
```

```
Ser Gln Tyr Pro Glu Ile Val Phe Leu Gly Thr Gly Ser Ala Ile Pro
465                 470                 475                 480 atg gag atc cga aat gtc agt tcc aca ctc gtc aac cta agc cct gac       1488
Met Glu Ile Arg Asn Val Ser Ser Thr Leu Val Asn Leu Ser Pro Asp
                485                 490                 495 aag tca gtg ctc ctg gat tgt gga gaa ggc act ttt ggg cag ttg tgc       1536
Lys Ser Val Leu Leu Asp Cys Gly Glu Gly Thr Phe Gly Gln Leu Cys
            500                 505                 510 cgt cat tac gga cag caa ata gac cga gtc tta tgc agc ctc acg gct       1584
Arg His Tyr Gly Gln Gln Ile Asp Arg Val Leu Cys Ser Leu Thr Ala
        515                 520                 525 gtg ttt gtg tcc cac ctg cac gcc gac cac cac acg ggc ttg ctg aat       1632
Val Phe Val Ser His Leu His Ala Asp His His Thr Gly Leu Leu Asn
    530                 535                 540 atc ttg ctg cag aga gag cat gcg ttg gca tct ctg ggg aaa ccc ttc       1680
Ile Leu Leu Gln Arg Glu His Ala Leu Ala Ser Leu Gly Lys Pro Phe
545                 550                 555                 560 cag ccc ttg ctt gtg gtg gct cct acc cag ctc agg gcc tgg ctg cag       1728
Gln Pro Leu Leu Val Val Ala Pro Thr Gln Leu Arg Ala Trp Leu Gln
                565                 570                 575 cag tat cac aac cac tgc cag gag att ctg cac cac gtc agt atg att       1776
Gln Tyr His Asn His Cys Gln Glu Ile Leu His His Val Ser Met Ile
            580                 585                 590 cct gcc aaa tgc ctt cag aaa ggg gca gag gtc tcc aat act aca ttg       1824
Pro Ala Lys Cys Leu Gln Lys Gly Ala Glu Val Ser Asn Thr Thr Leu
        595                 600                 605 gaa agg ctg ata agc ttg ctg ttg gaa aca tgt gac tta gaa gaa ttt       1872
Glu Arg Leu Ile Ser Leu Leu Leu Glu Thr Cys Asp Leu Glu Glu Phe
    610                 615                 620 cag acc tgc ctg gta cgg cac tgc aag cat gct ttt ggc tgt gca ctg       1920
Gln Thr Cys Leu Val Arg His Cys Lys His Ala Phe Gly Cys Ala Leu
625                 630                 635                 640 gta cat tca tct ggc tgg aaa gtc gtc tac tcg ggg gat acc atg ccc       1968
Val His Ser Ser Gly Trp Lys Val Val Tyr Ser Gly Asp Thr Met Pro
                645                 650                 655 tgt gag gct ctg gtc cag atg ggg aaa gat gcc acc ctc ctg ata cat       2016
Cys Glu Ala Leu Val Gln Met Gly Lys Asp Ala Thr Leu Leu Ile His
            660                 665                 670 gaa gcc act ctg gag gat cnc ttg gaa gag gaa gca gta gag agg aca       2064
Glu Ala Thr Leu Glu Asp Xaa Leu Glu Glu Glu Ala Val Glu Arg Thr
        675                 680                 685 cac agc acc acc tcc cag gct att aat gtg ggg atg cgg atg aat gcg       2112
His Ser Thr Thr Ser Gln Ala Ile Asn Val Gly Met Arg Met Asn Ala
    690                 695                 700 gag ttc atc atg ctg aac cac ttc agt cag cgg tac gcn aag atc ccc       2160
Glu Phe Ile Met Leu Asn His Phe Ser Gln Arg Tyr Xaa Lys Ile Pro
705                 710                 715                 720 ctt ttc agc cct gac ttc aac gag aaa gtt ggc atc gcc ttt gac cac       2208
Leu Phe Ser Pro Asp Phe Asn Glu Lys Val Gly Ile Ala Phe Asp His
                725                 730                 735 atg aag gtc tgn ttt gga gac ttc ccg aca gtg ccc aag ctg att ccc       2256
Met Lys Val Xaa Phe Gly Asp Phe Pro Thr Val Pro Lys Leu Ile Pro
            740                 745                 750 cca ctg aag gcc ctg ttt gca ggt gac att gaa gag atg gtg gaa cgc       2304
Pro Leu Lys Ala Leu Phe Ala Gly Asp Ile Glu Glu Met Val Glu Arg
        755                 760                 765 agg gag aag agg gag cta cgg ctg gtg cga gca gcc ctc ctg acc cag       2352
Arg Glu Lys Arg Glu Leu Arg Leu Val Arg Ala Ala Leu Leu Thr Gln
    770                 775                 780
```

```
cag gca gac agc cca gag gac aga gaa ccc caa cag aag cgg gcc cac      2400
Gln Ala Asp Ser Pro Glu Asp Arg Glu Pro Gln Gln Lys Arg Ala His
785             790                 795                 800 aca gat gaa cca cac agc cca cag agc aag aag gag agc gtg gca aac      2448
Thr Asp Glu Pro His Ser Pro Gln Ser Lys Lys Glu Ser Val Ala Asn
            805                 810                 815 act tta gga gcg cga gtg tgag                                         2470
Thr Leu Gly Ala Arg Val
            820
```

<210> SEQ ID NO 222
<211> LENGTH: 822
<212> TYPE: PRT
<213> ORGANISM: Mus musculus

<400> SEQUENCE: 222

```
Met Trp Ala Leu Arg Ser Leu Leu Arg Pro Leu Gly Leu Arg Thr Met
 1               5                  10                  15

Ser Gln Gly Ser Ala Arg Arg Pro Arg Pro Lys Asp Pro Leu Arg
                20                  25                  30

His Leu Arg Thr Arg Glu Lys Arg Gly Pro Gly Pro Gly Pro Asn
            35                  40                  45

Thr Val Tyr Leu Gln Val Val Ala Ala Gly Arg Asp Ala Gly Ala
     50                  55                  60

Ala Leu Tyr Val Phe Ser Glu Tyr Asn Arg Tyr Leu Phe Asn Cys Gly
 65                  70                  75                  80

Glu Gly Val Gln Arg Leu Met Gln Glu His Lys Thr Glu Ser Arg Ser
                85                  90                  95

Leu Asp Asn Ile Phe Leu Thr Arg Met His Trp Ser Asn Val Gly Gly
            100                 105                 110

Leu Cys Gly Met Ile Leu Thr Leu Lys Glu Thr Gly Leu Pro Lys Cys
        115                 120                 125

Val Leu Ser Gly Pro Pro Gln Leu Glu Lys Tyr Leu Glu Ala Ile Lys
130                 135                 140

Ile Phe Ser Gly Pro Leu Lys Gly Ile Glu Leu Ala Val Arg Pro His
145                 150                 155                 160

Ser Ala Pro Glu Tyr Lys Asp Glu Thr Met Thr Val Tyr Gln Val Pro
                165                 170                 175

Ile His Ser Glu Arg Arg Cys Gly Lys Gln Gln Pro Ser Gln Ser Pro
            180                 185                 190

Arg Thr Ser Pro Asn Arg Leu Ser Pro Lys Gln Ser Ser Asp Ser Gly
        195                 200                 205

Ser Ala Glu Asn Gly Gln Cys Gln Gln Glu Ser Met Gly Gln Gly Pro
    210                 215                 220

Ser Leu Val Val Ala Phe Val Cys Lys Leu His Leu Arg Lys Gly Asn
225                 230                 235                 240

Phe Leu Val Leu Lys Ala Lys Glu Leu Gly Leu Pro Val Gly Thr Ala
                245                 250                 255

Ala Ile Ala Pro Ile Ile Ala Ala Val Lys Asp Gly Lys Ser Ile Thr
            260                 265                 270

Tyr Glu Gly Arg Glu Ile Ala Ala Glu Glu Leu Cys Thr Pro Pro Asp
        275                 280                 285

Pro Gly Leu Val Phe Ile Val Val Glu Cys Pro Asp Glu Gly Phe Ile
    290                 295                 300

Leu Pro Ile Cys Glu Asn Asp Thr Phe Lys Arg Tyr Gln Ala Glu Ala
305                 310                 315                 320
```

-continued

```
Asp Ala Pro Val Ala Leu Val His Ile Ala Pro Glu Ser Val Leu
            325                 330                 335

Ile Asp Ser Arg Tyr Gln Gln Trp Met Glu Arg Phe Gly Pro Asp Thr
            340                 345                 350

Gln His Leu Ile Leu Asn Glu Asn Cys Pro Ser Val His Asn Leu Arg
            355                 360                 365

Ser His Lys Ile Gln Thr Gln Leu Ser Leu Ile His Pro Asp Ile Phe
        370                 375                 380

Pro Gln Leu Thr Ser Phe Tyr Ser Lys Glu Glu Gly Ser Thr Leu Ser
385                 390                 395                 400

Val Pro Thr Val Arg Gly Glu Cys Leu Leu Lys Tyr Ser Val Arg Pro
            405                 410                 415

Lys Arg Glu Trp Gln Arg Asp Thr Thr Leu Asp Cys Asn Thr Asp Glu
            420                 425                 430

Phe Ile Ala Glu Ala Leu Glu Leu Pro Ser Phe Gln Glu Ser Val Glu
            435                 440                 445

Glu Tyr Arg Lys Asn Val Gln Glu Asn Pro Ala Pro Ala Glu Lys Arg
        450                 455                 460

Ser Gln Tyr Pro Glu Ile Val Phe Leu Gly Thr Gly Ser Ala Ile Pro
465                 470                 475                 480

Met Glu Ile Arg Asn Val Ser Ser Thr Leu Val Asn Leu Ser Pro Asp
            485                 490                 495

Lys Ser Val Leu Leu Asp Cys Gly Glu Gly Thr Phe Gly Gln Leu Cys
            500                 505                 510

Arg His Tyr Gly Gln Gln Ile Asp Arg Val Leu Cys Ser Leu Thr Ala
            515                 520                 525

Val Phe Val Ser His Leu His Ala Asp His His Thr Gly Leu Leu Asn
            530                 535                 540

Ile Leu Leu Gln Arg Glu His Ala Leu Ala Ser Leu Gly Lys Pro Phe
545                 550                 555                 560

Gln Pro Leu Leu Val Val Ala Pro Thr Gln Leu Arg Ala Trp Leu Gln
            565                 570                 575

Gln Tyr His Asn His Cys Gln Glu Ile Leu His His Val Ser Met Ile
            580                 585                 590

Pro Ala Lys Cys Leu Gln Lys Gly Ala Glu Val Ser Asn Thr Thr Leu
            595                 600                 605

Glu Arg Leu Ile Ser Leu Leu Glu Thr Cys Asp Leu Glu Glu Phe
            610                 615                 620

Gln Thr Cys Leu Val Arg His Cys Lys His Ala Phe Gly Cys Ala Leu
625                 630                 635                 640

Val His Ser Ser Gly Trp Lys Val Val Tyr Ser Gly Asp Thr Met Pro
            645                 650                 655

Cys Glu Ala Leu Val Gln Met Gly Lys Asp Ala Thr Leu Leu Ile His
            660                 665                 670

Glu Ala Thr Leu Glu Asp Xaa Leu Glu Glu Ala Val Glu Arg Thr
            675                 680                 685

His Ser Thr Thr Ser Gln Ala Ile Asn Val Gly Met Arg Met Asn Ala
        690                 695                 700

Glu Phe Ile Met Leu Asn His Phe Ser Gln Arg Tyr Xaa Lys Ile Pro
705                 710                 715                 720

Leu Phe Ser Pro Asp Phe Asn Glu Lys Val Gly Ile Ala Phe Asp His
            725                 730                 735
```

```
Met Lys Val Xaa Phe Gly Asp Phe Pro Thr Val Pro Lys Leu Ile Pro
            740                 745                 750

Pro Leu Lys Ala Leu Phe Ala Gly Asp Ile Glu Glu Met Val Glu Arg
            755                 760                 765

Arg Glu Lys Arg Glu Leu Arg Leu Val Arg Ala Ala Leu Leu Thr Gln
            770                 775                 780

Gln Ala Asp Ser Pro Glu Asp Arg Glu Pro Gln Gln Lys Arg Ala His
785                 790                 795                 800

Thr Asp Glu Pro His Ser Pro Gln Ser Lys Lys Glu Ser Val Ala Asn
                805                 810                 815

Thr Leu Gly Ala Arg Val
            820

<210> SEQ ID NO 223
<211> LENGTH: 2908
<212> TYPE: DNA
<213> ORGANISM: Pan troglodytes
<220> FEATURE:
<221> NAME/KEY: CDS
<222> LOCATION: (1)..(2478)

<400> SEQUENCE: 223 atg tgg gcg ctt tgc tcg ctg ctg cgg tcc gcg gcc gga cgc acc atg      48
Met Trp Ala Leu Cys Ser Leu Leu Arg Ser Ala Ala Gly Arg Thr Met
 1               5                  10                  15 tcg cag gga cgc acc ata tcg cag gca ccc gcc cgc cgc gag cgg ccg      96
Ser Gln Gly Arg Thr Ile Ser Gln Ala Pro Ala Arg Arg Glu Arg Pro
                20                  25                  30 cgc aag gac ccg ctg cgg cac ctg cgc acg cga gag aag cgc gga ccg     144
Arg Lys Asp Pro Leu Arg His Leu Arg Thr Arg Glu Lys Arg Gly Pro
            35                  40                  45 tcg ggg tgc tcc ggc ggc cca aac acc gtg tac ctg cag gtg gtg gca     192
Ser Gly Cys Ser Gly Gly Pro Asn Thr Val Tyr Leu Gln Val Val Ala
        50                  55                  60 gcg ggt agc cgg gac tcg ggc gcc gcg ctc tac gtc ttc tcc gag ttc     240
Ala Gly Ser Arg Asp Ser Gly Ala Ala Leu Tyr Val Phe Ser Glu Phe
 65                  70                  75                  80 aac cgg tat ctc ttc aac tgt gga gaa ggc att cag aga ctc atg cag     288
Asn Arg Tyr Leu Phe Asn Cys Gly Glu Gly Ile Gln Arg Leu Met Gln
                 85                  90                  95 gag cac aag tta aag gtt gct cgc ctg gac aac ata ttc ctg aca cga     336
Glu His Lys Leu Lys Val Ala Arg Leu Asp Asn Ile Phe Leu Thr Arg
                100                 105                 110 atg cac tgg tct aat gtt ggg ggc tta agt gga atg att ctt act tta     384
Met His Trp Ser Asn Val Gly Gly Leu Ser Gly Met Ile Leu Thr Leu
            115                 120                 125 aag gaa acc ggg ctt cca aag tgt gta ctt tct gga cct cca caa ctg     432
Lys Glu Thr Gly Leu Pro Lys Cys Val Leu Ser Gly Pro Pro Gln Leu
        130                 135                 140 gaa aaa tac ctc gaa gca atc aaa ata ttt tct ggt cca ttg aaa gga     480
Glu Lys Tyr Leu Glu Ala Ile Lys Ile Phe Ser Gly Pro Leu Lys Gly
145                 150                 155                 160 ata gaa ctg gct gtg cgg ccc cac tct gcc cca gaa tac gag gat gaa     528
Ile Glu Leu Ala Val Arg Pro His Ser Ala Pro Glu Tyr Glu Asp Glu
                165                 170                 175 acc atg aca gtt tac cag atc ccc ata cac agt gaa cag agg agg gga     576
Thr Met Thr Val Tyr Gln Ile Pro Ile His Ser Glu Gln Arg Arg Gly
                180                 185                 190 aag cac caa cca tgg cag agt cca gaa agg cct ctc agc agg ctc agt     624
Lys His Gln Pro Trp Gln Ser Pro Glu Arg Pro Leu Ser Arg Leu Ser
```

-continued

|  | 195 |  |  |  | 200 |  |  |  | 205 |  |  |  |  |
|---|---|---|---|---|---|---|---|---|---|---|---|---|---|
| cca | gag | cga | tct | tca | gac | tcc | gag | tca | aat | gaa | aat | gag | cca cac ctt | 672 |
| Pro | Glu | Arg | Ser | Ser | Asp | Ser | Glu | Ser | Asn | Glu | Asn | Glu | Pro His Leu |
|  | 210 |  |  |  | 215 |  |  |  | 220 |  |  |  |  |

| cca | cat | ggt | gtt | agc | cag | aga | aga | ggg | gtc | agg | gac | tct | tcc ctg gtc | 720 |
| Pro | His | Gly | Val | Ser | Gln | Arg | Arg | Gly | Val | Arg | Asp | Ser | Ser Leu Val |
| 225 |  |  |  |  | 230 |  |  |  |  | 235 |  |  | 240 |

| gta | gct | ttc | atc | tgt | aag | ctt | cac | tta | aag | aga | gga | aac | ttc ttg gtg | 768 |
| Val | Ala | Phe | Ile | Cys | Lys | Leu | His | Leu | Lys | Arg | Gly | Asn | Phe Leu Val |
|  |  |  |  | 245 |  |  |  |  | 250 |  |  |  | 255 |

| ctc | aaa | gca | aag | gag | atg | ggc | ctc | cca | gtt | ggg | aca | gct | gcc atc gct | 816 |
| Leu | Lys | Ala | Lys | Glu | Met | Gly | Leu | Pro | Val | Gly | Thr | Ala | Ala Ile Ala |
|  |  |  | 260 |  |  |  |  | 265 |  |  |  |  | 270 |

| ccc | atc | att | gct | gct | gtc | aag | gac | ggg | aaa | agc | atc | act | cat gaa gga | 864 |
| Pro | Ile | Ile | Ala | Ala | Val | Lys | Asp | Gly | Lys | Ser | Ile | Thr | His Glu Gly |
|  |  | 275 |  |  |  |  | 280 |  |  |  |  | 285 |  |

| aga | gag | att | ttg | gct | gaa | gag | ctg | tgt | act | cct | cca | gat | cct ggt gct | 912 |
| Arg | Glu | Ile | Leu | Ala | Glu | Glu | Leu | Cys | Thr | Pro | Pro | Asp | Pro Gly Ala |
| 290 |  |  |  |  | 295 |  |  |  |  | 300 |  |  |  |

| gct | ttt | gtg | gtg | gta | gaa | tgt | cca | gat | gaa | agc | ttc | att | caa ccc atc | 960 |
| Ala | Phe | Val | Val | Val | Glu | Cys | Pro | Asp | Glu | Ser | Phe | Ile | Gln Pro Ile |
| 305 |  |  |  |  | 310 |  |  |  |  | 315 |  |  | 320 |

| tgt | gag | aat | gcc | acc | ttt | cag | agg | tac | caa | gga | aag | gca | gat gcc ccc | 1008 |
| Cys | Glu | Asn | Ala | Thr | Phe | Gln | Arg | Tyr | Gln | Gly | Lys | Ala | Asp Ala Pro |
|  |  |  |  | 325 |  |  |  |  | 330 |  |  |  | 335 |

| gtg | gcc | ttg | gtg | gtt | cac | atg | gcc | cca | gaa | tct | gtg | ctt | gtg gac agc | 1056 |
| Val | Ala | Leu | Val | Val | His | Met | Ala | Pro | Glu | Ser | Val | Leu | Val Asp Ser |
|  |  |  |  | 340 |  |  |  |  | 345 |  |  |  | 350 |

| agg | tac | cag | cag | tgg | atg | gag | agg | ttt | ggg | cct | gac | acc | cag cac ttg | 1104 |
| Arg | Tyr | Gln | Gln | Trp | Met | Glu | Arg | Phe | Gly | Pro | Asp | Thr | Gln His Leu |
|  |  | 355 |  |  |  |  | 360 |  |  |  |  | 365 |  |

| gtc | ctg | aat | gag | aac | tgt | gcc | tca | gtt | cac | aac | ctt | cgc | agc cac aag | 1152 |
| Val | Leu | Asn | Glu | Asn | Cys | Ala | Ser | Val | His | Asn | Leu | Arg | Ser His Lys |
|  | 370 |  |  |  |  | 375 |  |  |  |  | 380 |  |  |

| att | caa | acc | cag | ctc | aac | ctc | atc | cac | ccg | gac | atc | ttc | ccc ctg ctc | 1200 |
| Ile | Gln | Thr | Gln | Leu | Asn | Leu | Ile | His | Pro | Asp | Ile | Phe | Pro Leu Leu |
| 385 |  |  |  |  | 390 |  |  |  |  | 395 |  |  | 400 |

| acc | agt | ttc | ccc | tgt | aag | aag | gag | ggc | ccc | acc | ctc | agt | gtg ccc atg | 1248 |
| Thr | Ser | Phe | Pro | Cys | Lys | Lys | Glu | Gly | Pro | Thr | Leu | Ser | Val Pro Met |
|  |  |  | 405 |  |  |  |  | 410 |  |  |  |  | 415 |

| gtt | cag | ggt | gaa | tgc | ctc | ctc | aag | tac | cag | ctc | cgt | ccc | agg agg gag | 1296 |
| Val | Gln | Gly | Glu | Cys | Leu | Leu | Lys | Tyr | Gln | Leu | Arg | Pro | Arg Arg Glu |
|  |  |  | 420 |  |  |  |  | 425 |  |  |  |  | 430 |

| tgg | cag | agg | gat | gcc | att | att | act | tgc | aat | cct | gag | gaa | ttc ata att | 1344 |
| Trp | Gln | Arg | Asp | Ala | Ile | Ile | Thr | Cys | Asn | Pro | Glu | Glu | Phe Ile Ile |
|  |  |  | 435 |  |  |  |  | 440 |  |  |  |  | 445 |

| gag | gcg | ctg | cag | ctt | ccc | aac | ttc | cag | cag | agt | gtg | cag | gag tac agg | 1392 |
| Glu | Ala | Leu | Gln | Leu | Pro | Asn | Phe | Gln | Gln | Ser | Val | Gln | Glu Tyr Arg |
|  | 450 |  |  |  |  | 455 |  |  |  |  | 460 |  |  |

| agg | agt | gcg | cag | gac | ggc | cca | gcc | cca | gca | gag | aaa | aga | agt cag tac | 1440 |
| Arg | Ser | Ala | Gln | Asp | Gly | Pro | Ala | Pro | Ala | Glu | Lys | Arg | Ser Gln Tyr |
| 465 |  |  |  | 470 |  |  |  |  | 475 |  |  |  | 480 |

| cca | gaa | atc | atc | ttc | ctt | gga | aca | ggg | tct | gcc | atc | ccg | atg aag att | 1488 |
| Pro | Glu | Ile | Ile | Phe | Leu | Gly | Thr | Gly | Ser | Ala | Ile | Pro | Met Lys Ile |
|  |  |  |  | 485 |  |  |  |  | 490 |  |  |  | 495 |

| cga | aat | gtc | agt | gcc | aca | ctt | gtc | aac | ata | agc | ccc | gac | acg tct ctg | 1536 |
| Arg | Asn | Val | Ser | Ala | Thr | Leu | Val | Asn | Ile | Ser | Pro | Asp | Thr Ser Leu |
|  |  |  | 500 |  |  |  |  | 505 |  |  |  |  | 510 |

| cta | ctg | gac | tgt | ggt | gag | ggc | acg | ttt | ggg | cag | ctg | tgc | cgt cat tac | 1584 |

```
Leu Leu Asp Cys Gly Glu Gly Thr Phe Gly Gln Leu Cys Arg His Tyr
        515                 520                 525 gga gac cag gtg gac agg gtc ctg ggc acc ctg gct gct gtg ttt gtg      1632
Gly Asp Gln Val Asp Arg Val Leu Gly Thr Leu Ala Ala Val Phe Val
530                 535                 540 tcc cac ctg cac gca gat cac cac acg ggc ttg cta aat atc ttg ctg      1680
Ser His Leu His Ala Asp His His Thr Gly Leu Leu Asn Ile Leu Leu
545                 550                 555                 560 cag aga gaa cga gcc ttg gca tct ttg gga aag ccc ttt cac cct ttg      1728
Gln Arg Glu Arg Ala Leu Ala Ser Leu Gly Lys Pro Phe His Pro Leu
            565                 570                 575 ctg gtg gtt gcc ccc aac cag ctc aaa gcc tgg ctc cag cag tac cac      1776
Leu Val Val Ala Pro Asn Gln Leu Lys Ala Trp Leu Gln Gln Tyr His
        580                 585                 590 aac cag tgc cag gag gtc ctg cac cac atc agt atg att cct gcc aaa      1824
Asn Gln Cys Gln Glu Val Leu His His Ile Ser Met Ile Pro Ala Lys
    595                 600                 605 tgc ctt cag gaa ggg gct gag atc tcc agt cct gca gtg gaa aga ttg      1872
Cys Leu Gln Glu Gly Ala Glu Ile Ser Ser Pro Ala Val Glu Arg Leu
610                 615                 620 atc agt tcg ctg ttg cga aca tgt gat ttg gaa gag ttt cag acc tgt      1920
Ile Ser Ser Leu Leu Arg Thr Cys Asp Leu Glu Glu Phe Gln Thr Cys
625                 630                 635                 640 ctg gtg cgg cac tgc aag cat gcg ttt ggc tgt gcg ctg gtg cac acc      1968
Leu Val Arg His Cys Lys His Ala Phe Gly Cys Ala Leu Val His Thr
                645                 650                 655 tct ggc tgg aaa gtg gtc tat tcc ggg gac acc atg ccc tgc gag gct      2016
Ser Gly Trp Lys Val Val Tyr Ser Gly Asp Thr Met Pro Cys Glu Ala
            660                 665                 670 ctg gtc cgg atg ggg aaa gat gcc acc ctc ctg ata cat gaa gcc acc      2064
Leu Val Arg Met Gly Lys Asp Ala Thr Leu Leu Ile His Glu Ala Thr
        675                 680                 685 ctg gaa gac ggt ttg gaa gag gaa gca gtg gaa aag aca cac agc aca      2112
Leu Glu Asp Gly Leu Glu Glu Glu Ala Val Glu Lys Thr His Ser Thr
    690                 695                 700 acg tcc caa gcc atc agc gtg ggg atg cgg atg aac gcg gag ttc att      2160
Thr Ser Gln Ala Ile Ser Val Gly Met Arg Met Asn Ala Glu Phe Ile
705                 710                 715                 720 atg ctg aac cac ttc agc cag cgc tat gcc aag gtc ccc ctc ttc agc      2208
Met Leu Asn His Phe Ser Gln Arg Tyr Ala Lys Val Pro Leu Phe Ser
                725                 730                 735 ccc aac ttc aac gag aaa gtg gga gtt gcc ttt gac cac atg aag gtc      2256
Pro Asn Phe Asn Glu Lys Val Gly Val Ala Phe Asp His Met Lys Val
            740                 745                 750 tgc ttt gga gac ttt gca aca atg ccc aag ctg att ccc cca ctg aaa      2304
Cys Phe Gly Asp Phe Ala Thr Met Pro Lys Leu Ile Pro Pro Leu Lys
        755                 760                 765 gcc ctg ttt gct ggc gac atc gag gag atg gag gag cgc agg gag aag      2352
Ala Leu Phe Ala Gly Asp Ile Glu Glu Met Glu Glu Arg Arg Glu Lys
    770                 775                 780 cgg gag ctg cgg cag gtg cgg gcg gcc ctc ctg tcc agg gag ctg gca      2400
Arg Glu Leu Arg Gln Val Arg Ala Ala Leu Leu Ser Arg Glu Leu Ala
785                 790                 795                 800 ggc ggc ctg gag gat ggg gag cct cag cag aaa cgg gcc cac aca gag      2448
Gly Gly Leu Glu Asp Gly Glu Pro Gln Gln Lys Arg Ala His Thr Glu
                805                 810                 815 gag cca cag gcc aag aag gtc aga gcc cag tgaagatctg ggagaccctg       2498
Glu Pro Gln Ala Lys Lys Val Arg Ala Gln
            820                 825
```

```
aattcagaag gctgtgtgtc ttctgcccca cgcacgcacc cgtatctgcc ctccttgctg    2558
gtagaagctg aagagcacgg tcccccagga ggcagctcag gataggtggt atggagctgt    2618
gccaaggctt gggctcccac ataagcacta gtctatagat gcctcttagg actggtgcct    2678
ggcacagccg cgggacagga ggctgccaca cggaagcaag cagatgaact aatttcattt    2738
caaggcagtt tttaaagaag gcttggaaac agacggcagc acctttcctc taatccagca    2798
aagtgattcc ctgcacacca gagacaagca gagtaacagg atcagtgggt ctaagtgtcc    2858
gagacttaac gaaatagta tttcagctgc aataaagatt gagtttgcaa                2908
```

<210> SEQ ID NO 224
<211> LENGTH: 826
<212> TYPE: PRT
<213> ORGANISM: Pan troglodytes

<400> SEQUENCE: 224

```
Met Trp Ala Leu Cys Ser Leu Leu Arg Ser Ala Ala Gly Arg Thr Met
  1               5                  10                  15

Ser Gln Gly Arg Thr Ile Ser Gln Ala Pro Ala Arg Arg Glu Arg Pro
             20                  25                  30

Arg Lys Asp Pro Leu Arg His Leu Arg Thr Arg Glu Lys Arg Gly Pro
         35                  40                  45

Ser Gly Cys Ser Gly Gly Pro Asn Thr Val Tyr Leu Gln Val Val Ala
     50                  55                  60

Ala Gly Ser Arg Asp Ser Gly Ala Ala Leu Tyr Val Phe Ser Glu Phe
 65                  70                  75                  80

Asn Arg Tyr Leu Phe Asn Cys Gly Glu Gly Ile Gln Arg Leu Met Gln
                 85                  90                  95

Glu His Lys Leu Lys Val Ala Arg Leu Asp Asn Ile Phe Leu Thr Arg
            100                 105                 110

Met His Trp Ser Asn Val Gly Gly Leu Ser Gly Met Ile Leu Thr Leu
        115                 120                 125

Lys Glu Thr Gly Leu Pro Lys Cys Val Leu Ser Gly Pro Pro Gln Leu
    130                 135                 140

Glu Lys Tyr Leu Glu Ala Ile Lys Ile Phe Ser Gly Pro Leu Lys Gly
145                 150                 155                 160

Ile Glu Leu Ala Val Arg Pro His Ser Ala Pro Glu Tyr Glu Asp Glu
                165                 170                 175

Thr Met Thr Val Tyr Gln Ile Pro Ile His Ser Glu Gln Arg Arg Gly
            180                 185                 190

Lys His Gln Pro Trp Gln Ser Pro Glu Arg Pro Leu Ser Arg Leu Ser
        195                 200                 205

Pro Glu Arg Ser Ser Asp Ser Glu Ser Asn Glu Asn Glu Pro His Leu
    210                 215                 220

Pro His Gly Val Ser Gln Arg Arg Gly Val Arg Asp Ser Ser Leu Val
225                 230                 235                 240

Val Ala Phe Ile Cys Lys Leu His Leu Lys Arg Gly Asn Phe Leu Val
                245                 250                 255

Leu Lys Ala Lys Glu Met Gly Leu Pro Val Gly Thr Ala Ala Ile Ala
            260                 265                 270

Pro Ile Ile Ala Ala Val Lys Asp Gly Lys Ser Ile Thr His Glu Gly
        275                 280                 285

Arg Glu Ile Leu Ala Glu Glu Leu Cys Thr Pro Pro Asp Pro Gly Ala
    290                 295                 300
```

```
Ala Phe Val Val Glu Cys Pro Asp Glu Ser Phe Ile Gln Pro Ile
305                 310                 315                 320

Cys Glu Asn Ala Thr Phe Gln Arg Tyr Gln Gly Lys Ala Asp Ala Pro
            325                 330                 335

Val Ala Leu Val Val His Met Ala Pro Glu Ser Val Leu Val Asp Ser
            340                 345                 350

Arg Tyr Gln Gln Trp Met Glu Arg Phe Gly Pro Asp Thr Gln His Leu
            355                 360                 365

Val Leu Asn Glu Asn Cys Ala Ser Val His Asn Leu Arg Ser His Lys
370                 375                 380

Ile Gln Thr Gln Leu Asn Leu Ile His Pro Asp Ile Phe Pro Leu Leu
385                 390                 395                 400

Thr Ser Phe Pro Cys Lys Lys Glu Gly Pro Thr Leu Ser Val Pro Met
            405                 410                 415

Val Gln Gly Glu Cys Leu Leu Lys Tyr Gln Leu Arg Pro Arg Arg Glu
            420                 425                 430

Trp Gln Arg Asp Ala Ile Ile Thr Cys Asn Pro Glu Glu Phe Ile Ile
            435                 440                 445

Glu Ala Leu Gln Leu Pro Asn Phe Gln Gln Ser Val Gln Glu Tyr Arg
450                 455                 460

Arg Ser Ala Gln Asp Gly Pro Ala Pro Ala Glu Lys Arg Ser Gln Tyr
465                 470                 475                 480

Pro Glu Ile Ile Phe Leu Gly Thr Gly Ser Ala Ile Pro Met Lys Ile
            485                 490                 495

Arg Asn Val Ser Ala Thr Leu Val Asn Ile Ser Pro Asp Thr Ser Leu
            500                 505                 510

Leu Leu Asp Cys Gly Glu Gly Thr Phe Gly Gln Leu Cys Arg His Tyr
            515                 520                 525

Gly Asp Gln Val Asp Arg Val Leu Gly Thr Leu Ala Ala Val Phe Val
530                 535                 540

Ser His Leu His Ala Asp His His Thr Gly Leu Leu Asn Ile Leu Leu
545                 550                 555                 560

Gln Arg Glu Arg Ala Leu Ala Ser Leu Gly Lys Pro Phe His Pro Leu
            565                 570                 575

Leu Val Val Ala Pro Asn Gln Leu Lys Ala Trp Leu Gln Gln Tyr His
            580                 585                 590

Asn Gln Cys Gln Glu Val Leu His His Ile Ser Met Ile Pro Ala Lys
            595                 600                 605

Cys Leu Gln Glu Gly Ala Glu Ile Ser Ser Pro Ala Val Glu Arg Leu
610                 615                 620

Ile Ser Ser Leu Leu Arg Thr Cys Asp Leu Glu Glu Phe Gln Thr Cys
625                 630                 635                 640

Leu Val Arg His Cys Lys His Ala Phe Gly Cys Ala Leu Val His Thr
            645                 650                 655

Ser Gly Trp Lys Val Tyr Ser Gly Asp Thr Met Pro Cys Glu Ala
            660                 665                 670

Leu Val Arg Met Gly Lys Asp Ala Thr Leu Leu Ile His Glu Ala Thr
            675                 680                 685

Leu Glu Asp Gly Leu Glu Glu Ala Val Glu Lys Thr His Ser Thr
            690                 695                 700

Thr Ser Gln Ala Ile Ser Val Gly Met Arg Met Asn Ala Glu Phe Ile
705                 710                 715                 720

Met Leu Asn His Phe Ser Gln Arg Tyr Ala Lys Val Pro Leu Phe Ser
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 725 |     |     |     | 730 |     |     |     |     | 735 |     |     |     |     |
| Pro | Asn | Phe | Asn | Glu | Lys | Val | Gly | Val | Ala | Phe | Asp | His | Met | Lys | Val |     |
|     |     |     |     | 740 |     |     |     | 745 |     |     |     | 750 |     |     |     |     |
| Cys | Phe | Gly | Asp | Phe | Ala | Thr | Met | Pro | Lys | Leu | Ile | Pro | Pro | Leu | Lys |     |
|     |     |     | 755 |     |     |     | 760 |     |     |     | 765 |     |     |     |     |     |
| Ala | Leu | Phe | Ala | Gly | Asp | Ile | Glu | Glu | Met | Glu | Glu | Arg | Arg | Glu | Lys |     |
|     |     | 770 |     |     |     | 775 |     |     |     | 780 |     |     |     |     |     |     |
| Arg | Glu | Leu | Arg | Gln | Val | Arg | Ala | Ala | Leu | Leu | Ser | Arg | Glu | Leu | Ala |     |
| 785 |     |     |     | 790 |     |     |     | 795 |     |     |     | 800 |     |     |     |     |
| Gly | Gly | Leu | Glu | Asp | Gly | Glu | Pro | Gln | Gln | Lys | Arg | Ala | His | Thr | Glu |     |
|     |     |     |     | 805 |     |     |     | 810 |     |     |     | 815 |     |     |     |     |
| Glu | Pro | Gln | Ala | Lys | Lys | Val | Arg | Ala | Gln |     |     |     |     |     |     |     |
|     |     |     | 820 |     |     |     | 825 |     |     |     |     |     |     |     |     |     |

<210> SEQ ID NO 225
<211> LENGTH: 2892
<212> TYPE: DNA
<213> ORGANISM: Gorilla gorilla
<220> FEATURE:
<221> NAME/KEY: CDS
<222> LOCATION: (1)..(2478)

<400> SEQUENCE: 225

| atg | tgg | gcg | ctt | tgc | tcg | ctg | ctg | cgg | tcc | gcg | gcc | gga | cgc | acc | atg |     | 48  |
| --- | --- | --- | --- | --- | --- | --- | --- | --- | --- | --- | --- | --- | --- | --- | --- | --- | --- |
| Met | Trp | Ala | Leu | Cys | Ser | Leu | Leu | Arg | Ser | Ala | Ala | Gly | Arg | Thr | Met |     |     |
| 1   |     |     |     | 5   |     |     |     |     | 10  |     |     |     |     | 15  |     |     |     |
| tcg | cag | gga | cgc | acc | ata | tcg | cag | gca | ccc | gcc | cgc | cgc | gag | cgg | ccg |     | 96  |
| Ser | Gln | Gly | Arg | Thr | Ile | Ser | Gln | Ala | Pro | Ala | Arg | Arg | Glu | Arg | Pro |     |     |
|     |     |     | 20  |     |     |     |     | 25  |     |     |     |     | 30  |     |     |     |     |
| cgc | aag | gac | ccg | ctg | cgg | cac | ctg | cgc | acg | cga | gag | aag | cgc | gga | ccg |     | 144 |
| Arg | Lys | Asp | Pro | Leu | Arg | His | Leu | Arg | Thr | Arg | Glu | Lys | Arg | Gly | Pro |     |     |
|     |     | 35  |     |     |     |     | 40  |     |     |     |     | 45  |     |     |     |     |     |
| tcg | ggg | tgc | tcc | ggg | ggc | cca | aac | acc | gtg | tac | ctg | cag | gtg | gtg | gca |     | 192 |
| Ser | Gly | Cys | Ser | Gly | Gly | Pro | Asn | Thr | Val | Tyr | Leu | Gln | Val | Val | Ala |     |     |
|     | 50  |     |     |     |     | 55  |     |     |     |     | 60  |     |     |     |     |     |     |
| gcg | ggt | agc | cgg | gac | tcg | ggc | gcc | gcg | ctc | tac | gtc | ttc | tcc | gag | ttc |     | 240 |
| Ala | Gly | Ser | Arg | Asp | Ser | Gly | Ala | Ala | Leu | Tyr | Val | Phe | Ser | Glu | Phe |     |     |
| 65  |     |     |     |     | 70  |     |     |     |     | 75  |     |     |     |     | 80  |     |     |
| aac | cgg | tat | ctc | ttc | aac | tgt | gga | gaa | ggc | gtt | cag | aga | ctc | atg | cag |     | 288 |
| Asn | Arg | Tyr | Leu | Phe | Asn | Cys | Gly | Glu | Gly | Val | Gln | Arg | Leu | Met | Gln |     |     |
|     |     |     |     | 85  |     |     |     |     | 90  |     |     |     |     | 95  |     |     |     |
| gag | cac | aag | tta | aag | gtt | gtt | cgc | ctg | gac | aac | ata | ttc | ctg | aca | cga |     | 336 |
| Glu | His | Lys | Leu | Lys | Val | Val | Arg | Leu | Asp | Asn | Ile | Phe | Leu | Thr | Arg |     |     |
|     |     |     | 100 |     |     |     |     | 105 |     |     |     |     | 110 |     |     |     |     |
| atg | cac | tgg | tct | aat | gtt | ggg | ggc | tta | agt | gga | atg | att | ctt | act | tta |     | 384 |
| Met | His | Trp | Ser | Asn | Val | Gly | Gly | Leu | Ser | Gly | Met | Ile | Leu | Thr | Leu |     |     |
|     |     | 115 |     |     |     |     | 120 |     |     |     |     | 125 |     |     |     |     |     |
| aag | gaa | acc | ggg | ctt | cca | aag | tgt | gta | ctt | tct | gga | cct | cca | cag | ctg |     | 432 |
| Lys | Glu | Thr | Gly | Leu | Pro | Lys | Cys | Val | Leu | Ser | Gly | Pro | Pro | Gln | Leu |     |     |
|     | 130 |     |     |     |     | 135 |     |     |     |     | 140 |     |     |     |     |     |     |
| gaa | aaa | tac | ctc | gaa | gca | atc | aaa | ata | ttt | tct | ggt | cca | ttg | aaa | gga |     | 480 |
| Glu | Lys | Tyr | Leu | Glu | Ala | Ile | Lys | Ile | Phe | Ser | Gly | Pro | Leu | Lys | Gly |     |     |
| 145 |     |     |     |     | 150 |     |     |     |     | 155 |     |     |     |     | 160 |     |     |
| ata | gaa | ctg | gct | gtg | cgg | ccc | cac | tct | gcc | cca | gaa | tac | gag | gat | gaa |     | 528 |
| Ile | Glu | Leu | Ala | Val | Arg | Pro | His | Ser | Ala | Pro | Glu | Tyr | Glu | Asp | Glu |     |     |
|     |     |     |     | 165 |     |     |     |     | 170 |     |     |     |     | 175 |     |     |     |
| acc | atg | aca | gtt | tac | cag | atc | ccc | ata | cac | agt | gaa | cag | agg | agg | gga |     | 576 |
| Thr | Met | Thr | Val | Tyr | Gln | Ile | Pro | Ile | His | Ser | Glu | Gln | Arg | Arg | Gly |     |     |
|     |     |     | 180 |     |     |     |     | 185 |     |     |     |     | 190 |     |     |     |     |

-continued

```
agg cac caa cca tgg cag agt cca gaa agg cct ctc agc agg ctc agt    624
Arg His Gln Pro Trp Gln Ser Pro Glu Arg Pro Leu Ser Arg Leu Ser
        195                 200                 205 cca gag cga tct tca gac tcc gag tcg aat gaa aat gag cca cac ctt    672
Pro Glu Arg Ser Ser Asp Ser Glu Ser Asn Glu Asn Glu Pro His Leu
    210                 215                 220 cca cat ggt gtt agc cag aga aga ggg gtc agg gac tct tcc ctg gtc    720
Pro His Gly Val Ser Gln Arg Arg Gly Val Arg Asp Ser Ser Leu Val
225                 230                 235                 240 gta gct ttc atc tgt aag ctt cac tta aag aga gga aac ttc ttg gtg    768
Val Ala Phe Ile Cys Lys Leu His Leu Lys Arg Gly Asn Phe Leu Val
            245                 250                 255 ctc aaa gca aag gag atg ggc ctc cca gtt ggg aca gct gcc atc gct    816
Leu Lys Ala Lys Glu Met Gly Leu Pro Val Gly Thr Ala Ala Ile Ala
        260                 265                 270 ccc atc att gct gct gtc aag gac ggg aaa agc atc act cat gaa gga    864
Pro Ile Ile Ala Ala Val Lys Asp Gly Lys Ser Ile Thr His Glu Gly
    275                 280                 285 aga gag att ttg gct gaa gag ctg tgt act cct cca gat cct ggt gct    912
Arg Glu Ile Leu Ala Glu Glu Leu Cys Thr Pro Pro Asp Pro Gly Ala
290                 295                 300 gct ttt gtg gtg gta gaa tgt cca gat gaa agc ttc att caa ccc atc    960
Ala Phe Val Val Val Glu Cys Pro Asp Glu Ser Phe Ile Gln Pro Ile
305                 310                 315                 320 tgt gag aat gcc acc ttt cag agg tac caa gga aag gca gat gcc ccc   1008
Cys Glu Asn Ala Thr Phe Gln Arg Tyr Gln Gly Lys Ala Asp Ala Pro
            325                 330                 335 gtg gcc ttg gtg gtt cac atg gcc cca gaa tct gtg ctt gtg gac agc   1056
Val Ala Leu Val Val His Met Ala Pro Glu Ser Val Leu Val Asp Ser
        340                 345                 350 agg tac cag cag tgg atg gag agg ttt ggg cct gac acc cag cac ttg   1104
Arg Tyr Gln Gln Trp Met Glu Arg Phe Gly Pro Asp Thr Gln His Leu
    355                 360                 365 gtc ctg aat gag aac tgt gcc tca gtt cac aac ctt cgc agc cac aag   1152
Val Leu Asn Glu Asn Cys Ala Ser Val His Asn Leu Arg Ser His Lys
370                 375                 380 att caa acc cag ctc aac ctc atc cac ccg gac atc ttc ccc ctg ctc   1200
Ile Gln Thr Gln Leu Asn Leu Ile His Pro Asp Ile Phe Pro Leu Leu
385                 390                 395                 400 acc agt ttc ccc tgt aag aag gag ggc ccc acc ctc agt gtg ccc atg   1248
Thr Ser Phe Pro Cys Lys Lys Glu Gly Pro Thr Leu Ser Val Pro Met
            405                 410                 415 gtt cag ggt gaa tgc ctc ctc aag tac cag ctc cgt ccc agg agg gaa   1296
Val Gln Gly Glu Cys Leu Leu Lys Tyr Gln Leu Arg Pro Arg Arg Glu
        420                 425                 430 tgg cag agg gat gcc att atc act tgc aat cct gag gaa ttc ata gtt   1344
Trp Gln Arg Asp Ala Ile Ile Thr Cys Asn Pro Glu Glu Phe Ile Val
    435                 440                 445 gag gcg ctg cag ctt ccc aac ttc cag cag agt gtg cag gag tac agg   1392
Glu Ala Leu Gln Leu Pro Asn Phe Gln Gln Ser Val Gln Glu Tyr Arg
450                 455                 460 agg agt gtg cag gac gtc cca gcc cca gca gag aaa aga agt cag tac   1440
Arg Ser Val Gln Asp Val Pro Ala Pro Ala Glu Lys Arg Ser Gln Tyr
465                 470                 475                 480 cca gaa atc atc ttc ctt gga aca ggg tct gcc atc ccc atg aag att   1488
Pro Glu Ile Ile Phe Leu Gly Thr Gly Ser Ala Ile Pro Met Lys Ile
            485                 490                 495 cga aat gtc agt gcc aca ctt gtc aac ata agc ccc gac acg tct ctg   1536
Arg Asn Val Ser Ala Thr Leu Val Asn Ile Ser Pro Asp Thr Ser Leu
        500                 505                 510
```

```
cta ctg gac tgt ggt gag ggc acg ttt ggg cag ctg tgc cgt cat tac    1584
Leu Leu Asp Cys Gly Glu Gly Thr Phe Gly Gln Leu Cys Arg His Tyr
            515                 520                 525 gga gac cag gtg gac agg gtc ctg ggc acc ctg gct gct gtg ttt gtg    1632
Gly Asp Gln Val Asp Arg Val Leu Gly Thr Leu Ala Ala Val Phe Val
    530                 535                 540 tcc cac ctg cac gca gat cac cac acg ggc ttg cta aat atc ttg ctg    1680
Ser His Leu His Ala Asp His His Thr Gly Leu Leu Asn Ile Leu Leu
545                 550                 555                 560 cag aga gaa caa gcc ttg gca tct ttg gga aag ccc ctt cac cct ttg    1728
Gln Arg Glu Gln Ala Leu Ala Ser Leu Gly Lys Pro Leu His Pro Leu
                565                 570                 575 ctg gtg gtt gcc ccc agc cag ctc aaa gcc tgg ctc cag cag tac cac    1776
Leu Val Val Ala Pro Ser Gln Leu Lys Ala Trp Leu Gln Gln Tyr His
            580                 585                 590 aac cag tgc cag gag gtc ctg cac cac atc agt atg att cct gcc aaa    1824
Asn Gln Cys Gln Glu Val Leu His His Ile Ser Met Ile Pro Ala Lys
        595                 600                 605 tgc ctt cag gaa ggg gct gag atc tcc agt cct gca gtg gaa aga ttg    1872
Cys Leu Gln Glu Gly Ala Glu Ile Ser Ser Pro Ala Val Glu Arg Leu
    610                 615                 620 atc agt tcg ctg ttg cga aca tgt gat ttg gaa gag ttt cag acc tgt    1920
Ile Ser Ser Leu Leu Arg Thr Cys Asp Leu Glu Glu Phe Gln Thr Cys
625                 630                 635                 640 ctg gtg cgg cac tgc aag cat gcg ttt ggc tgt gcg ctg gtg cac acc    1968
Leu Val Arg His Cys Lys His Ala Phe Gly Cys Ala Leu Val His Thr
                645                 650                 655 tct ggc tgg aaa gtg gtc tat tcc ggg gac acc atg ccc tgc gag gct    2016
Ser Gly Trp Lys Val Val Tyr Ser Gly Asp Thr Met Pro Cys Glu Ala
            660                 665                 670 ctg gtc cgc atg ggg aaa gat gcc acc ctc ctg ata cat gaa gcc acc    2064
Leu Val Arg Met Gly Lys Asp Ala Thr Leu Leu Ile His Glu Ala Thr
        675                 680                 685 ctg gaa gat ggt ttg gaa gag gaa gca gtg gaa aag aca cac agc aca    2112
Leu Glu Asp Gly Leu Glu Glu Glu Ala Val Glu Lys Thr His Ser Thr
    690                 695                 700 acg tcc caa gcc atc agc gtg ggg atg cgg atg aac gcg gag ttc att    2160
Thr Ser Gln Ala Ile Ser Val Gly Met Arg Met Asn Ala Glu Phe Ile
705                 710                 715                 720 atg ctg aac cac ttc agc cag cgc tat gcc aag gtc ccc ctc ttc agc    2208
Met Leu Asn His Phe Ser Gln Arg Tyr Ala Lys Val Pro Leu Phe Ser
                725                 730                 735 ccc aac ttc aac gag aaa gtg gga gtt gcc ttt gac cac atg aag gtc    2256
Pro Asn Phe Asn Glu Lys Val Gly Val Ala Phe Asp His Met Lys Val
            740                 745                 750 tgc ttt gga gac ttt cca aca atg ccc aag ctg att ccc cca ctg aaa    2304
Cys Phe Gly Asp Phe Pro Thr Met Pro Lys Leu Ile Pro Pro Leu Lys
        755                 760                 765 gcc ctg ttt gcc ggc gac atc gag gag atg gag gag cgc agg gag aag    2352
Ala Leu Phe Ala Gly Asp Ile Glu Glu Met Glu Glu Arg Arg Glu Lys
    770                 775                 780 cgg gag ctg cgg cag gtg cgg gcg gcc ctc ctg tcc ggg gag ctg gca    2400
Arg Glu Leu Arg Gln Val Arg Ala Ala Leu Leu Ser Gly Glu Leu Ala
785                 790                 795                 800 ggc ggc ctg gag gat ggg gag cct cag cag aaa cgg gcc cac aca gag    2448
Gly Gly Leu Glu Asp Gly Glu Pro Gln Gln Lys Arg Ala His Thr Glu
                805                 810                 815 gag cca cag gcc aag aag gtc aga gcc cag tgaagatctg ggagaccctg      2498
Glu Pro Gln Ala Lys Lys Val Arg Ala Gln
```

-continued

```
                        820                 825
aattcagaag gctgtgtgtc ttctgcccca cgcacgcacc cgtatctgcc ctccttgctg    2558
gtagaagctg aagagcacgg tcccccagga ggcagctcag gataggtggt atggagctgt    2618
gccgaggctt aggctcccac ataagcacta gtctataggt gcctggcaca gccgcgggac    2678
aggaggctgc cacacggaag caagcagatg aactaatttc atttcaaggc agttttaaa    2738 gaagtcttgg aaacagacgg cagcaccttt cctctaatcc agcaaagtga ttccctgcac    2798
accagagaca agcagagtaa caggatcact gggtctaagt gtccgagact taacgaaaat    2858
agtatttcag ctgcaataaa gattgagttt gcaa                                2892
```

<210> SEQ ID NO 226
<211> LENGTH: 826
<212> TYPE: PRT
<213> ORGANISM: Gorilla gorilla

<400> SEQUENCE: 226

```
Met Trp Ala Leu Cys Ser Leu Leu Arg Ser Ala Gly Arg Thr Met
 1               5                  10                  15

Ser Gln Gly Arg Thr Ile Ser Gln Ala Pro Ala Arg Arg Glu Arg Pro
                20                  25                  30

Arg Lys Asp Pro Leu Arg His Leu Arg Thr Arg Glu Lys Arg Gly Pro
            35                  40                  45

Ser Gly Cys Ser Gly Gly Pro Asn Thr Val Tyr Leu Gln Val Val Ala
        50                  55                  60

Ala Gly Ser Arg Asp Ser Gly Ala Ala Leu Tyr Val Phe Ser Glu Phe
65                  70                  75                  80

Asn Arg Tyr Leu Phe Asn Cys Gly Glu Gly Val Gln Arg Leu Met Gln
                85                  90                  95

Glu His Lys Leu Lys Val Val Arg Leu Asp Asn Ile Phe Leu Thr Arg
            100                 105                 110

Met His Trp Ser Asn Val Gly Gly Leu Ser Gly Met Ile Leu Thr Leu
        115                 120                 125

Lys Glu Thr Gly Leu Pro Lys Cys Val Leu Ser Gly Pro Pro Gln Leu
    130                 135                 140

Glu Lys Tyr Leu Glu Ala Ile Lys Ile Phe Ser Gly Pro Leu Lys Gly
145                 150                 155                 160

Ile Glu Leu Ala Val Arg Pro His Ser Ala Pro Glu Tyr Glu Asp Glu
                165                 170                 175

Thr Met Thr Val Tyr Gln Ile Pro Ile His Ser Glu Gln Arg Arg Gly
            180                 185                 190

Arg His Gln Pro Trp Gln Ser Pro Glu Arg Pro Leu Ser Arg Leu Ser
        195                 200                 205

Pro Glu Arg Ser Ser Asp Ser Glu Ser Asn Glu Asn Glu Pro His Leu
    210                 215                 220

Pro His Gly Val Ser Gln Arg Arg Gly Val Arg Asp Ser Ser Leu Val
225                 230                 235                 240

Val Ala Phe Ile Cys Lys Leu His Leu Lys Arg Gly Asn Phe Leu Val
                245                 250                 255

Leu Lys Ala Lys Glu Met Gly Leu Pro Val Gly Thr Ala Ala Ile Ala
            260                 265                 270

Pro Ile Ile Ala Ala Val Lys Asp Gly Lys Ser Ile Thr His Glu Gly
        275                 280                 285

Arg Glu Ile Leu Ala Glu Glu Leu Cys Thr Pro Pro Asp Pro Gly Ala
```

-continued

```
            290                 295                 300
Ala Phe Val Val Glu Cys Pro Asp Glu Ser Phe Ile Gln Pro Ile
305                 310                 315                 320
Cys Glu Asn Ala Thr Phe Gln Arg Tyr Gln Gly Lys Ala Asp Ala Pro
                325                 330                 335
Val Ala Leu Val Val His Met Ala Pro Glu Ser Val Leu Val Asp Ser
                340                 345                 350
Arg Tyr Gln Gln Trp Met Glu Arg Phe Gly Pro Asp Thr Gln His Leu
                355                 360                 365
Val Leu Asn Glu Asn Cys Ala Ser Val His Asn Leu Arg Ser His Lys
                370                 375                 380
Ile Gln Thr Gln Leu Asn Leu Ile His Pro Asp Ile Phe Pro Leu Leu
385                 390                 395                 400
Thr Ser Phe Pro Cys Lys Lys Glu Gly Pro Thr Leu Ser Val Pro Met
                405                 410                 415
Val Gln Gly Glu Cys Leu Leu Lys Tyr Gln Leu Arg Pro Arg Arg Glu
                420                 425                 430
Trp Gln Arg Asp Ala Ile Ile Thr Cys Asn Pro Glu Glu Phe Ile Val
                435                 440                 445
Glu Ala Leu Gln Leu Pro Asn Phe Gln Gln Ser Val Gln Glu Tyr Arg
450                 455                 460
Arg Ser Val Gln Asp Val Pro Ala Pro Ala Glu Lys Arg Ser Gln Tyr
465                 470                 475                 480
Pro Glu Ile Ile Phe Leu Gly Thr Gly Ser Ala Ile Pro Met Lys Ile
                485                 490                 495
Arg Asn Val Ser Ala Thr Leu Val Asn Ile Ser Pro Asp Thr Ser Leu
                500                 505                 510
Leu Leu Asp Cys Gly Glu Gly Thr Phe Gly Gln Leu Cys Arg His Tyr
                515                 520                 525
Gly Asp Gln Val Asp Arg Val Leu Gly Thr Leu Ala Ala Val Phe Val
530                 535                 540
Ser His Leu His Ala Asp His His Thr Gly Leu Leu Asn Ile Leu Leu
545                 550                 555                 560
Gln Arg Glu Gln Ala Leu Ala Ser Leu Gly Lys Pro Leu His Pro Leu
                565                 570                 575
Leu Val Val Ala Pro Ser Gln Leu Lys Ala Trp Leu Gln Gln Tyr His
                580                 585                 590
Asn Gln Cys Gln Glu Val Leu His His Ile Ser Met Ile Pro Ala Lys
                595                 600                 605
Cys Leu Gln Glu Gly Ala Glu Ile Ser Ser Pro Ala Val Glu Arg Leu
                610                 615                 620
Ile Ser Ser Leu Leu Arg Thr Cys Asp Leu Glu Glu Phe Gln Thr Cys
625                 630                 635                 640
Leu Val Arg His Cys Lys His Ala Phe Gly Cys Ala Leu Val His Thr
                645                 650                 655
Ser Gly Trp Lys Val Val Tyr Ser Gly Asp Thr Met Pro Cys Glu Ala
                660                 665                 670
Leu Val Arg Met Gly Lys Asp Ala Thr Leu Leu Ile His Glu Ala Thr
                675                 680                 685
Leu Glu Asp Gly Leu Glu Glu Ala Val Glu Lys Thr His Ser Thr
                690                 695                 700
Thr Ser Gln Ala Ile Ser Val Gly Met Arg Met Asn Ala Glu Phe Ile
705                 710                 715                 720
```

-continued

```
Met Leu Asn His Phe Ser Gln Arg Tyr Ala Lys Val Pro Leu Phe Ser
                725                 730                 735

Pro Asn Phe Asn Glu Lys Val Gly Val Ala Phe Asp His Met Lys Val
            740                 745                 750

Cys Phe Gly Asp Phe Pro Thr Met Pro Lys Leu Ile Pro Pro Leu Lys
        755                 760                 765

Ala Leu Phe Ala Gly Asp Ile Glu Met Glu Glu Arg Arg Glu Lys
    770                 775                 780

Arg Glu Leu Arg Gln Val Arg Ala Ala Leu Leu Ser Gly Glu Leu Ala
785                 790                 795                 800

Gly Gly Leu Glu Asp Gly Glu Pro Gln Gln Lys Arg Ala His Thr Glu
                805                 810                 815

Glu Pro Gln Ala Lys Lys Val Arg Ala Gln
            820                 825

<210> SEQ ID NO 227
<211> LENGTH: 844
<212> TYPE: PRT
<213> ORGANISM: Caenorhabditis elegans

<400> SEQUENCE: 227

Met Lys Met Leu Phe Phe Gly Ile Lys Val Ser Arg His Leu Ile Ser
  1               5                  10                  15

Ser Thr Ser Cys Leu Phe Lys Asp Asn Asn Glu Glu Leu Leu Glu Ser
             20                  25                  30

Ile Lys Glu Arg Ile Ala Arg Asn Arg Arg Ile Leu Gln Lys His Ser
         35                  40                  45

Ser Ser His Leu Lys Ala Arg Glu Val Asn Ala Ser Ile Ser Asn Leu
     50                  55                  60

Arg Gln Ser Met Ala Ala Val Gln Lys Lys Gln Lys Ala Ala His Glu
 65                  70                  75                  80

Pro Pro Ala Asn Ser Ile Val Asn Ile Pro Ser Gln Val Ser Ile Glu
                 85                  90                  95

Val Leu Gly Asn Gly Thr Gly Leu Leu Arg Ala Cys Phe Ile Leu Arg
            100                 105                 110

Thr Pro Leu Lys Thr Tyr Met Phe Asn Cys Pro Glu Asn Ala Cys Arg
        115                 120                 125

Phe Leu Trp Gln Leu Arg Ile Arg Ser Ser Val Val Asp Leu Phe
    130                 135                 140

Ile Thr Ser Ala Asn Trp Asp Asn Ile Ala Gly Ile Ser Ser Ile Leu
145                 150                 155                 160

Leu Ser Lys Glu Ser Asn Ala Leu Ser Thr Arg Leu His Gly Ala Met
                165                 170                 175

Asn Ile Lys His Phe Leu Glu Cys Ile Arg Pro Phe Gln Asp Ser Asp
            180                 185                 190

Tyr Gly Ser Cys Lys Tyr Pro Ser Gln Val Glu Glu Arg Pro Tyr Thr
        195                 200                 205

Met Glu Asn Tyr Glu Asp Ala Gly Leu Lys Val Thr Tyr Ile Pro Leu
    210                 215                 220

Ser Pro Pro Leu Asn Ile Gly Ser Asn Asn Glu Lys Ser Lys Asn Val
225                 230                 235                 240

Lys Val Asn Asn Val Asp Ile Ala Phe Leu Ile Glu Met Lys Glu Ala
                245                 250                 255

Ala Arg Arg Ile Asp Thr Met Lys Leu Met Glu Leu Lys Val Pro Lys
```

-continued

```
                260                 265                 270
Gly Pro Leu Ile Gly Lys Leu Lys Ser Gly Glu Ala Val Thr Leu Pro
                275                 280                 285
Asp Gly Arg Thr Ile Gln Pro Asp Gln Val Phe Ser Asp Lys Val
                290                 295                 300
Glu Gly Asp Lys Pro Leu Leu Val Thr Glu Cys Thr Thr Glu Asp
305                 310                 315                 320
His Val Lys Ala Leu Ile Asp Ser Ser Leu Gln Pro Phe Leu Asn
                325                 330                 335
Gly Glu Lys Gln Leu Asp Tyr Met Val His Ile Ser Asp Asp Ala Val
                340                 345                 350
Ile Asn Thr Pro Thr Tyr Arg His Leu Met Glu Lys Leu Asn Asn Pro
                355                 360                 365
Ser Ile Thr His Leu Leu Ile Asn Gly Gly Asn Pro Val Ile Pro Ala
                370                 375                 380
Val Glu Ser Val Tyr Lys His Thr Arg Leu Leu Arg Ser Ile Ala Pro
385                 390                 395                 400
Ser Leu Phe Pro Ala Leu His Pro Ile Asp Trp Ser Gly Ile Ile Thr
                405                 410                 415
Gln Asn Glu Glu Leu Ser Gln Arg Gln Asp Gln Phe Ile Arg Val Ala
                420                 425                 430
Pro Met Gln Arg Tyr Trp Met Arg Arg Gly Ala Ser Phe Asn Glu Glu
                435                 440                 445
Pro Ile Val Asn Asn Leu Leu Ala Ala Glu Pro Glu Leu Ser Asp Lys
                450                 455                 460
Ala Lys Glu Leu Ile Lys Glu Tyr Gln Lys Leu Glu Lys Glu Asn Lys
465                 470                 475                 480
Met Asp Cys Glu Phe Pro Lys Leu Thr Phe Phe Gly Thr Ser Ser Ala
                485                 490                 495
Val Pro Ser Lys Tyr Arg Asn Val Thr Gly Tyr Leu Val Glu Ala Ser
                500                 505                 510
Glu Asn Ser Ala Ile Leu Ile Asp Val Gly Glu Gly Thr Tyr Gly Gln
                515                 520                 525
Met Arg Ala Val Phe Gly Glu Asp Gly Cys Lys Gln Leu Leu Val Asn
                530                 535                 540
Leu Asn Cys Val Leu Ile Thr His Ala His Gln Asp His Met Asn Gly
545                 550                 555                 560
Leu Tyr Thr Ile Ile Ala Arg Arg Lys Glu Ala Phe Glu Ser Leu Gly
                565                 570                 575
Ala Pro Tyr Arg Pro Leu Val Leu Val Cys Asn Arg Asn Val Leu Lys
                580                 585                 590
Pro Met Lys Thr Tyr Ser Ile Cys Phe Glu Asn Ile Glu His Leu Leu
                595                 600                 605
Glu Ile Val Asp Ile Ser Arg Tyr Pro Leu Thr Pro Gly Ser Pro
610                 615                 620
Gly Gly Pro Pro Gly Lys Arg Pro Arg Leu Pro Ser Pro His Leu Pro
625                 630                 635                 640
Pro Ser Arg Asp Val Leu Gln Asp Met Ser Ser Ser Phe Asp Lys Lys
                645                 650                 655
Ala Trp Lys Leu Asp Glu Leu Lys Ala Val Gln Val His His Thr Arg
                660                 665                 670
Met Ala Asn Gly Phe Val Met Arg Val Ala Gly Lys Arg Ile Val Phe
                675                 680                 685
```

```
Ser Gly Asp Thr Lys Pro Cys Asp Leu Leu Val Glu Glu Gly Lys Asp
    690                 695                 700

Ala Asp Val Leu Val His Glu Ser Thr Phe Glu Asp Gly His Glu Val
705                 710                 715                 720

Asp Met Thr Pro Lys Pro Pro Lys Lys Leu Ala Lys Ile Ser Ser Leu
                725                 730                 735

Ala Asp Ala Met Arg Lys Arg His Ser Thr Met Gly Gln Ala Val Asp
                740                 745                 750

Val Gly Lys Arg Met Asn Ala Lys His Ile Ile Leu Thr His Phe Ser
                755                 760                 765

Ala Arg Tyr Pro Lys Val Pro Val Leu Pro Glu Tyr Leu Asp Lys Glu
        770                 775                 780

Asn Ile Gly Val Ala Met Asp Met Leu Arg Val Arg Phe Asp His Leu
785                 790                 795                 800

Pro Leu Val Ser Lys Leu Leu Pro Ile Phe Arg Glu Val Phe Val Ala
                805                 810                 815

Glu Leu Phe Glu Leu Thr Ile Lys Lys Glu Gln Arg Val Leu Lys Asp
                820                 825                 830

Lys Glu Leu Ser Glu Lys Arg Gly Gln Leu Lys Ala
                835                 840

<210> SEQ ID NO 228
<211> LENGTH: 837
<212> TYPE: PRT
<213> ORGANISM: Arabidopsis thaliana

<400> SEQUENCE: 228

Met Glu Asn Asn Glu Ala Thr Asn Gly Ser Lys Ser Ser Ser Asn Ser
1               5                   10                  15

Phe Val Phe Asn Lys Arg Arg Ala Glu Gly Phe Asp Ile Thr Asp Lys
            20                  25                  30

Lys Lys Arg Asn Leu Glu Arg Lys Ser Gln Lys Leu Asn Pro Thr Asn
        35                  40                  45

Thr Ile Ala Tyr Ala Gln Ile Leu Gly Thr Gly Met Asp Thr Gln Asp
    50                  55                  60

Thr Ser Ser Ser Val Leu Leu Phe Phe Asp Lys Gln Arg Phe Ile Phe
65                  70                  75                  80

Asn Ala Gly Glu Gly Leu Gln Arg Phe Cys Thr Glu His Lys Ile Lys
                85                  90                  95

Leu Ser Lys Ile Asp His Val Phe Leu Ser Arg Val Cys Ser Glu Thr
            100                 105                 110

Ala Gly Gly Leu Pro Gly Leu Leu Leu Thr Leu Ala Gly Ile Gly Glu
        115                 120                 125

Glu Gly Leu Ser Val Asn Val Trp Gly Pro Ser Asp Leu Asn Tyr Leu
    130                 135                 140

Val Asp Ala Met Lys Ser Phe Ile Pro Arg Ala Ala Met Val His Thr
145                 150                 155                 160

Arg Ser Phe Gly Pro Ser Ser Thr Pro Asp Pro Ile Val Leu Val Asn
                165                 170                 175

Asp Glu Val Val Lys Ile Ser Ala Ile Ile Leu Lys Pro Cys His Ser
            180                 185                 190

Glu Glu Asp Ser Gly Asn Lys Ser Gly Asp Leu Ser Val Val Tyr Val
        195                 200                 205

Cys Glu Leu Pro Glu Ile Leu Gly Lys Phe Asp Leu Glu Lys Ala Lys
```

-continued

```
                210                 215                 220
Lys Val Phe Gly Val Lys Pro Gly Pro Lys Tyr Ser Arg Leu Gln Ser
225                 230                 235                 240

Gly Glu Ser Val Lys Ser Asp Glu Arg Asp Ile Thr Val His Pro Ser
                245                 250                 255

Asp Val Met Gly Pro Ser Leu Pro Gly Pro Ile Val Leu Leu Val Asp
                260                 265                 270

Cys Pro Thr Glu Ser His Ala Ala Glu Leu Phe Ser Leu Lys Ser Leu
                275                 280                 285

Glu Ser Tyr Tyr Ser Ser Pro Asp Glu Gln Thr Ile Gly Ala Lys Phe
                290                 295                 300

Val Asn Cys Ile Ile His Leu Ser Pro Ser Ser Val Thr Ser Ser Pro
305                 310                 315                 320

Thr Tyr Gln Ser Trp Met Lys Lys Phe His Leu Thr Gln His Ile Leu
                325                 330                 335

Ala Gly His Gln Arg Phe Leu Pro Leu Leu Ile Ile Val Ser His Gln
                340                 345                 350

Lys Thr Val Arg Lys Asn Met Ala Phe Pro Ile Leu Lys Ala Ser Ser
                355                 360                 365

Arg Ile Ala Ala Arg Leu Asn Tyr Leu Cys Pro Gln Phe Phe Pro Ala
370                 375                 380

Pro Gly Phe Trp Pro Ser Gln Leu Thr Asp Asn Ser Ile Ile Asp Pro
385                 390                 395                 400

Thr Pro Ser Asn Lys Phe Asn Leu Arg Pro Val Ala Ile Arg Gly Ile
                405                 410                 415

Asp Arg Ser Cys Ile Pro Ala Pro Leu Thr Ser Ser Glu Val Val Asp
                420                 425                 430

Glu Leu Leu Ser Glu Ile Pro Glu Ile Lys Asp Lys Ser Glu Glu Ile
                435                 440                 445

Lys Gln Phe Trp Asn Lys Gln His Asn Lys Thr Ile Ile Glu Lys Leu
                450                 455                 460

Trp Leu Ser Glu Cys Asn Thr Val Leu Pro Asn Cys Leu Glu Lys Ile
465                 470                 475                 480

Arg Arg Asp Asp Met Glu Ile Val Ile Leu Gly Thr Gly Ser Ser Gln
                485                 490                 495

Pro Ser Lys Tyr Arg Asn Val Ser Ala Ile Phe Ile Asp Leu Phe Ser
                500                 505                 510

Arg Gly Ser Leu Leu Leu Asp Cys Gly Glu Gly Thr Leu Gly Gln Leu
                515                 520                 525

Lys Arg Arg Tyr Gly Leu Asp Gly Ala Asp Glu Ala Val Arg Lys Leu
                530                 535                 540

Arg Cys Ile Trp Ile Ser His Ile His Ala Asp His His Thr Gly Leu
545                 550                 555                 560

Ala Arg Ile Leu Ala Leu Arg Ser Lys Leu Leu Lys Gly Val Thr His
                565                 570                 575

Glu Pro Val Ile Val Val Gly Pro Arg Pro Leu Lys Arg Phe Leu Asp
                580                 585                 590

Ala Tyr Gln Arg Leu Glu Asp Leu Asp Met Glu Phe Leu Asp Cys Arg
                595                 600                 605

Ser Thr Thr Ala Thr Ser Trp Ala Ser Leu Glu Ser Gly Gly Glu Ala
                610                 615                 620

Glu Gly Ser Leu Phe Thr Gln Gly Ser Pro Met Gln Ser Val Phe Lys
625                 630                 635                 640
```

-continued

```
Arg Ser Asp Ile Ser Met Asp Asn Ser Ser Val Leu Leu Cys Leu Lys
            645                 650                 655

Asn Leu Lys Lys Val Leu Ser Glu Ile Gly Leu Asn Asp Leu Ile Ser
        660                 665                 670

Phe Pro Val His Cys Pro Gln Ala Tyr Gly Val Ile Lys Ala
        675                 680                 685

Ala Glu Arg Val Asn Ser Val Gly Glu Gln Ile Leu Gly Trp Lys Met
        690                 695                 700

Val Tyr Ser Gly Asp Ser Arg Pro Cys Pro Glu Thr Val Glu Ala Ser
705                 710                 715                 720

Arg Asp Ala Thr Ile Leu Ile His Glu Ala Thr Phe Glu Asp Ala Leu
            725                 730                 735

Ile Glu Glu Ala Leu Ala Lys Asn His Ser Thr Thr Lys Glu Ala Ile
            740                 745                 750

Asp Val Gly Ser Ala Ala Asn Val Tyr Arg Ile Val Leu Thr His Phe
            755                 760                 765

Ser Gln Arg Tyr Pro Lys Ile Pro Val Ile Asp Glu Ser His Met His
            770                 775                 780

Asn Thr Cys Ile Ala Phe Asp Leu Met Ser Ile Asn Met Ala Asp Leu
785                 790                 795                 800

His Val Leu Pro Lys Val Leu Pro Tyr Phe Lys Thr Leu Phe Arg Asp
            805                 810                 815

Glu Met Val Glu Asp Glu Asp Ala Asp Val Ala Met Asp Asp Leu
            820                 825                 830

Lys Glu Glu Ala Leu
        835

<210> SEQ ID NO 229
<211> LENGTH: 838
<212> TYPE: PRT
<213> ORGANISM: Saccharomyces cerevisiae

<400> SEQUENCE: 229

Met Phe Thr Phe Ile Pro Ile Thr His Pro Thr Ser Asp Thr Lys His
1               5                   10                  15

Pro Leu Leu Val Gln Ser Ala His Gly Glu Lys Tyr Phe Gly
        20                  25                  30

Lys Ile Gly Glu Gly Ser Gln Arg Ser Leu Thr Glu Asn Lys Ile Arg
        35                  40                  45

Ile Ser Lys Leu Lys Asp Ile Phe Leu Thr Gly Glu Leu Asn Trp Ser
    50                  55                  60

Asp Ile Gly Gly Leu Pro Gly Met Ile Leu Thr Ile Ala Asp Gln Gly
65                  70                  75                  80

Lys Ser Asn Leu Val Leu His Tyr Gly Asn Asp Ile Leu Asn Tyr Ile
            85                  90                  95

Val Ser Thr Trp Arg Tyr Phe Val Phe Arg Phe Gly Ile Asp Leu Asn
            100                 105                 110

Asp His Ile Met Lys Asp Lys Glu Val Tyr Lys Asp Lys Ile Ile Ala
        115                 120                 125

Val Lys Ser Phe Asn Val Leu Lys Asn Gly Gly Glu Asp Arg Leu Gly
        130                 135                 140

Val Phe Asp Ser Phe Gln Lys Gly Val Leu Arg Ser Ile Val Ala Lys
145                 150                 155                 160

Met Phe Pro Lys His Ala Pro Thr Asp Arg Tyr Asp Pro Ser Ser Asp
```

-continued

```
                165                  170                  175
Pro His Leu Asn Val Glu Leu Pro Asp Leu Asp Ala Lys Val Glu Val
                180                  185                  190

Ser Thr Asn Tyr Glu Ile Ser Phe Ser Pro Val Arg Gly Lys Phe Lys
            195                  200                  205

Val Glu Glu Ala Ile Lys Leu Gly Val Pro Lys Gly Pro Leu Phe Ala
            210                  215                  220

Lys Leu Thr Lys Gly Gln Thr Ile Thr Leu Asp Asn Gly Ile Val Val
225                  230                  235                  240

Thr Pro Glu Gln Val Leu Glu Asn Glu Arg His Phe Ala Lys Val Leu
                245                  250                  255

Ile Leu Asp Ile Pro Asp Asp Leu Tyr Leu Asn Ala Phe Val Glu Lys
                260                  265                  270

Phe Lys Asp Tyr Asp Cys Ala Glu Leu Gly Met Val Tyr Tyr Phe Leu
            275                  280                  285

Gly Asp Glu Val Thr Ile Asn Asp Asn Leu Phe Ala Phe Ile Asp Ile
            290                  295                  300

Phe Glu Lys Asn Asn Tyr Gly Lys Val Asn His Met Ile Ser His Asn
305                  310                  315                  320

Lys Ile Ser Pro Asn Thr Ile Ser Phe Phe Gly Ser Ala Leu Thr Thr
                325                  330                  335

Leu Lys Leu Lys Ala Leu Gln Val Asn Asn Tyr Asn Leu Pro Lys Thr
            340                  345                  350

Asp Arg Val Phe Ser Lys Asp Phe Tyr Asp Arg Phe Asp Thr Pro Leu
            355                  360                  365

Ser Arg Gly Thr Ser Met Cys Lys Ser Gln Glu Glu Pro Leu Asn Thr
370                  375                  380

Ile Ile Glu Lys Asp Asn Ile His Ile Phe Ser Gln Asn Lys Thr Val
385                  390                  395                  400

Thr Phe Glu Pro Phe Arg Met Asn Glu Glu Pro Met Lys Cys Asn Ile
                405                  410                  415

Asn Gly Glu Val Ala Asp Phe Ser Trp Gln Glu Ile Phe Glu Glu His
            420                  425                  430

Val Lys Pro Leu Glu Phe Pro Leu Ala Asp Val Asp Thr Val Ile Asn
            435                  440                  445

Asn Gln Leu His Val Asp Asn Phe Asn Asn Ser Ala Glu Lys Lys Lys
            450                  455                  460

His Val Glu Ile Ile Thr Leu Gly Thr Gly Ser Ala Leu Pro Ser Lys
465                  470                  475                  480

Tyr Arg Asn Val Val Ser Thr Leu Val Lys Val Pro Phe Thr Asp Ala
                485                  490                  495

Asp Gly Asn Thr Ile Asn Arg Asn Ile Met Leu Asp Ala Gly Glu Asn
            500                  505                  510

Thr Leu Gly Thr Ile His Arg Met Phe Ser Gln Leu Ala Val Lys Ser
            515                  520                  525

Ile Phe Gln Asp Leu Lys Met Ile Tyr Leu Ser Leu His Ala Asp
            530                  535                  540

His His Leu Gly Ile Ile Ser Val Leu Asn Glu Trp Tyr Lys Tyr Asn
545                  550                  555                  560

Lys Asp Asp Glu Thr Ser Tyr Ile Tyr Val Val Thr Pro Trp Gln Tyr
                565                  570                  575

His Lys Phe Val Asn Glu Trp Leu Val Leu Glu Asn Lys Glu Ile Leu
            580                  585                  590
```

-continued

```
Lys Arg Ile Lys Tyr Ile Ser Cys Glu His Phe Ile Asn Asp Ser Phe
            595                 600                 605

Val Arg Met Gln Thr Gln Ser Val Pro Leu Ala Glu Phe Asn Glu Ile
            610                 615                 620

Leu Lys Glu Asn Ser Asn Gln Glu Ser Asn Arg Lys Leu Glu Leu Asp
625                 630                 635                 640

Arg Asp Ser Ser Tyr Arg Asp Val Asp Leu Ile Arg Gln Met Tyr Glu
                645                 650                 655

Asp Leu Ser Ile Glu Tyr Phe Gln Thr Cys Arg Ala Ile His Cys Asp
            660                 665                 670

Trp Ala Tyr Ser Asn Ser Ile Thr Phe Arg Met Asp Glu Asn Asn Glu
            675                 680                 685

His Asn Thr Phe Lys Val Ser Tyr Ser Gly Asp Thr Arg Pro Asn Ile
            690                 695                 700

Glu Lys Phe Ser Leu Glu Ile Gly Tyr Asn Ser Asp Leu Leu Ile His
705                 710                 715                 720

Glu Ala Thr Leu Glu Asn Gln Leu Leu Glu Asp Ala Val Lys Lys Lys
                725                 730                 735

His Cys Thr Ile Asn Glu Ala Ile Gly Val Ser Asn Lys Met Asn Ala
            740                 745                 750

Arg Lys Leu Ile Leu Thr His Phe Ser Gln Arg Tyr Pro Lys Leu Pro
            755                 760                 765

Gln Leu Asp Asn Asn Ile Asp Val Met Ala Arg Glu Phe Cys Phe Ala
            770                 775                 780

Phe Asp Ser Met Ile Val Asp Tyr Glu Lys Ile Gly Glu Gln Gln Arg
785                 790                 795                 800

Ile Phe Pro Leu Leu Asn Lys Ala Phe Val Glu Lys Glu Glu Glu
                805                 810                 815

Glu Asp Val Asp Asp Val Glu Ser Val Gln Asp Leu Glu Val Lys Leu
            820                 825                 830

Lys Lys His Lys Lys Asn
            835

<210> SEQ ID NO 230
<211> LENGTH: 311
<212> TYPE: PRT
<213> ORGANISM: Escherichia coli

<400> SEQUENCE: 230

Met Lys Arg Asp Glu Leu Met Glu Leu Ile Phe Leu Gly Thr Ser Ala
 1               5                  10                  15

Gly Val Pro Thr Arg Thr Arg Asn Val Thr Ala Ile Leu Leu Asn Leu
                20                  25                  30

Gln His Pro Thr Gln Ser Gly Leu Trp Leu Phe Asp Cys Gly Glu Gly
            35                  40                  45

Thr Gln His Gln Leu Leu His Thr Ala Phe Asn Pro Gly Lys Leu Asp
        50                  55                  60

Lys Ile Phe Ile Ser His Leu His Gly Asp His Leu Phe Gly Leu Pro
65                  70                  75                  80

Gly Leu Leu Cys Ser Arg Ser Met Ser Gly Ile Ile Gln Pro Leu Thr
                85                  90                  95

Ile Tyr Gly Pro Gln Gly Ile Arg Glu Phe Val Glu Thr Ala Leu Arg
            100                 105                 110

Ile Ser Gly Ser Trp Thr Asp Tyr Pro Leu Glu Ile Val Glu Ile Gly
```

|   | 115 |   |   |   | 120 |   |   |   | 125 |   |   |   |

Ala Gly Glu Ile Leu Asp Asp Gly Leu Arg Lys Val Thr Ala Tyr Pro
130                 135                 140

Leu Glu His Pro Leu Glu Cys Tyr Gly Tyr Arg Ile Glu Glu His Asp
145                 150                 155                 160

Lys Pro Gly Ala Leu Asn Ala Gln Ala Leu Lys Ala Ala Gly Val Pro
                165                 170                 175

Pro Gly Pro Leu Phe Gln Glu Leu Lys Ala Gly Lys Thr Ile Thr Leu
                180                 185                 190

Glu Asp Gly Arg Gln Ile Asn Gly Ala Asp Tyr Leu Ala Ala Pro Val
                195                 200                 205

Pro Gly Lys Ala Leu Ala Ile Phe Gly Asp Thr Gly Pro Cys Asp Ala
210                 215                 220

Ala Leu Asp Leu Ala Lys Gly Val Asp Val Met Val His Glu Ala Thr
225                 230                 235                 240

Leu Asp Ile Thr Met Glu Ala Lys Ala Asn Ser Arg Gly His Ser Ser
                245                 250                 255

Thr Arg Gln Ala Ala Thr Leu Ala Arg Glu Ala Gly Val Gly Lys Leu
                260                 265                 270

Ile Ile Thr His Val Ser Ser Arg Tyr Asp Asp Lys Gly Cys Gln His
                275                 280                 285

Leu Leu Arg Glu Cys Arg Ser Ile Phe Pro Ala Thr Glu Leu Ala Asn
290                 295                 300

Asp Phe Thr Val Phe Asn Val
305                 310

<210> SEQ ID NO 231
<211> LENGTH: 326
<212> TYPE: PRT
<213> ORGANISM: Synechocystis sp.

<400> SEQUENCE: 231

Met Glu Ile Thr Phe Leu Gly Thr Ser Ser Gly Val Pro Thr Arg Asn
1               5                   10                  15

Arg Asn Val Ser Ser Ile Ala Leu Arg Leu Pro Gln Arg Ala Glu Leu
                20                  25                  30

Trp Leu Phe Asp Cys Gly Glu Gly Thr Gln His Gln Phe Leu Arg Ser
            35                  40                  45

Glu Val Lys Ile Ser Gln Leu Thr Arg Ile Phe Ile Thr His Leu His
        50                  55                  60

Gly Asp His Ile Phe Gly Leu Met Gly Leu Leu Ala Ser Ser Gly Leu
65              70                  75                  80

Ala Gly Ser Gly Gln Gly Ile Glu Ile Tyr Gly Pro Glu Gly Leu Gly
                85                  90                  95

Asp Tyr Leu Glu Ala Cys Cys Arg Phe Ser Ser Thr His Leu Gly Lys
                100                 105                 110

Arg Leu Lys Val His Thr Val Arg Glu Asn Gly Leu Ile Tyr Glu Asp
                115                 120                 125

Lys Asp Phe Gln Val His Cys Gly Leu Leu Lys His Arg Ile Pro Ala
                130                 135                 140

Tyr Gly Tyr Arg Val Glu Glu Lys Gln Arg Pro Gly Arg Phe Asn Val
145                 150                 155                 160

Glu Gln Ala Glu Ala Leu Gly Ile Pro Phe Gly Pro Ile Tyr Gly Gln
                165                 170                 175

```
Leu Lys Gln Gly Lys Thr Val Thr Leu Glu Asp Gly Arg Arg Ile Arg
            180                 185                 190

Gly Gln Asp Leu Cys Glu Pro Glu Pro Gly Arg Lys Phe Val Tyr
            195                 200                 205

Cys Thr Asp Thr Val Phe Cys Glu Glu Ala Ile Ala Leu Ala Gln Glu
210                 215                 220

Ala Asp Leu Leu Val His Glu Ala Thr Phe Ala His Gln Asp Ala Gln
225                 230                 235                 240

Leu Ala Phe Asp Arg Leu His Ser Thr Ser Thr Met Ala Ala Gln Val
            245                 250                 255

Ala Leu Leu Ala Asn Val Lys Gln Leu Ile Met Thr His Phe Ser Pro
            260                 265                 270

Arg Tyr Ala Pro Gly Asn Pro Leu Gln Leu Glu Asn Leu Leu Ala Glu
            275                 280                 285

Ala Gln Ala Ile Phe Pro Asn Thr Arg Leu Ala Arg Asp Phe Leu Thr
            290                 295                 300

Val Glu Ile Pro Arg Arg Thr Ala Asp Pro Ala Ile Ala Met Ser Thr
305                 310                 315                 320

Pro Gln Ala Ser Pro Ala
            325

<210> SEQ ID NO 232
<211> LENGTH: 307
<212> TYPE: PRT
<213> ORGANISM: Methanobacterium thermoautotrophicum

<400> SEQUENCE: 232

Met Met Glu Val Thr Phe Leu Gly Thr Ser Ser Ala Val Pro Ser Lys
  1               5                  10                  15

Asn Arg Asn His Thr Ser Ile Ala Leu Arg Ile Pro Gly Glu Ile Phe
             20                  25                  30

Leu Phe Asp Cys Gly Glu Gly Thr Gln Arg Gln Met Ala Leu Ala Gly
         35                  40                  45

Ile Ser Pro Met Lys Val Thr Arg Ile Phe Ile Thr His Leu His Gly
 50                  55                  60

Asp His Ile Leu Gly Ile Pro Gly Met Ile Gln Ser Met Gly Phe Arg
 65                  70                  75                  80

Gly Arg Glu Glu Pro Leu Asp Ile Tyr Gly Pro Pro Gly Ile His Glu
                 85                  90                  95

Leu His Glu Cys Ile Met Lys Met Gly Tyr Phe Thr Leu Asp Phe Asp
            100                 105                 110

Ile Asn Val His Glu Val Arg Gly Gly Thr Val Val Glu Glu Asp Asp
            115                 120                 125

Tyr Arg Val Thr Ser Ala Pro Ala Ser His Ser Val Phe Asn Leu Ala
130                 135                 140

Tyr Cys Phe Glu Glu Lys Lys Arg Pro Arg Phe Leu Arg Glu Lys Ala
145                 150                 155                 160

Ile Ala Leu Gly Leu Lys Pro Gly Pro Ala Phe Gly Lys Leu His Arg
            165                 170                 175

Gly Ile Pro Val Arg Val Gly Asp Arg Ile Ile Met Pro Glu Glu Val
            180                 185                 190

Leu Gly Ser Pro Arg Lys Gly Val Lys Val Cys Tyr Ser Gly Asp Thr
            195                 200                 205

Arg Pro Cys Glu Ser Val Ile Lys Leu Ala Glu Gly Ala Glu Leu Leu
210                 215                 220
```

```
Ile His Glu Ser Thr Leu Glu Ala Gly Ser Glu Asp Lys Ala Ala Glu
225                 230                 235                 240

Ser Gly His Ser Thr Ala Arg Glu Ala Ala Glu Val Ala Arg Ser Ala
            245                 250                 255

Gly Val Lys Arg Leu Ile Leu Thr His Leu Ser Thr Arg Tyr Lys Arg
        260                 265                 270

Thr Glu Val Ile Leu Glu Ala Ala Arg Gln Val Phe Pro Val Thr Asp
    275                 280                 285

Val Ala Asp Asp Leu Met Thr Val Glu Val Lys Ala Tyr Asp Ser Ser
    290                 295                 300

Pro Asp Ser
305

<210> SEQ ID NO 233
<211> LENGTH: 684
<212> TYPE: PRT
<213> ORGANISM: Homo sapiens

<400> SEQUENCE: 233

Met Ser Ala Ile Pro Ala Glu Glu Ser Asp Gln Leu Leu Ile Arg Pro
1               5                   10                  15

Leu Gly Ala Gly Gln Glu Val Gly Arg Ser Cys Ile Ile Leu Glu Phe
            20                  25                  30

Lys Gly Arg Lys Ile Met Leu Asp Cys Gly Ile His Pro Gly Leu Glu
        35                  40                  45

Gly Met Asp Ala Leu Pro Tyr Ile Asp Leu Ile Asp Pro Ala Glu Ile
    50                  55                  60

Asp Leu Leu Leu Ile Ser His Phe His Leu Asp His Cys Gly Ala Leu
65                  70                  75                  80

Pro Trp Phe Leu Gln Lys Thr Ser Phe Lys Gly Arg Thr Phe Met Thr
                85                  90                  95

His Ala Thr Lys Ala Ile Tyr Arg Trp Leu Leu Ser Asp Tyr Val Lys
            100                 105                 110

Val Ser Asn Ile Ser Ala Asp Asp Met Leu Tyr Thr Glu Thr Asp Leu
        115                 120                 125

Glu Glu Ser Met Asp Lys Ile Glu Thr Ile Asn Phe His Glu Val Lys
    130                 135                 140

Glu Val Ala Gly Ile Lys Phe Trp Cys Tyr His Ala Gly His Val Leu
145                 150                 155                 160

Gly Ala Ala Met Phe Met Ile Glu Ile Ala Gly Val Lys Leu Leu Tyr
                165                 170                 175

Thr Gly Asp Phe Ser Arg Gln Glu Asp Arg His Leu Met Ala Ala Glu
            180                 185                 190

Ile Pro Asn Ile Lys Pro Asp Ile Leu Ile Ile Glu Ser Thr Tyr Gly
        195                 200                 205

Thr His Ile His Glu Lys Arg Glu Glu Arg Glu Ala Arg Phe Cys Asn
    210                 215                 220

Thr Val His Asp Ile Val Asn Arg Gly Gly Arg Gly Leu Ile Pro Val
225                 230                 235                 240

Phe Ala Leu Gly Arg Ala Gln Glu Leu Leu Leu Ile Leu Asp Glu Tyr
                245                 250                 255

Trp Gln Asn His Pro Glu Leu His Asp Ile Pro Ile Tyr Tyr Ala Ser
            260                 265                 270

Ser Leu Ala Lys Lys Cys Met Ala Val Tyr Gln Thr Tyr Val Asn Ala
```

```
                275                 280                 285
Met Asn Asp Lys Ile Arg Lys Gln Ile Asn Ile Asn Asn Pro Phe Val
290                 295                 300
Phe Lys His Ile Ser Asn Leu Lys Ser Met Asp His Phe Asp Asp Ile
305                 310                 315                 320
Gly Pro Ser Val Val Met Ala Ser Pro Gly Met Met Gln Ser Gly Leu
                325                 330                 335
Ser Arg Glu Leu Phe Glu Ser Trp Cys Thr Asp Lys Arg Asn Gly Val
                340                 345                 350
Ile Ile Ala Gly Tyr Cys Val Glu Gly Thr Leu Ala Lys His Ile Met
                355                 360                 365
Ser Glu Pro Glu Ile Thr Thr Met Ser Gly Gln Lys Leu Pro Leu
370                 375                 380
Lys Met Ser Val Asp Tyr Ile Ser Phe Ser Ala His Thr Asp Tyr Gln
385                 390                 395                 400
Gln Thr Ser Glu Phe Ile Arg Ala Leu Lys Pro Pro His Val Ile Leu
                405                 410                 415
Val His Gly Glu Gln Asn Glu Met Ala Arg Leu Lys Ala Ala Leu Ile
                420                 425                 430
Arg Glu Tyr Glu Asp Asn Asp Glu Val His Ile Glu Val His Asn Pro
                435                 440                 445
Arg Asn Thr Glu Ala Val Thr Leu Asn Phe Arg Gly Glu Lys Leu Ala
450                 455                 460
Lys Val Met Gly Phe Leu Ala Asp Lys Lys Pro Glu Gln Gly Gln Arg
465                 470                 475                 480
Val Ser Gly Ile Leu Val Lys Arg Asn Phe Asn Tyr His Ile Leu Ser
                485                 490                 495
Pro Cys Asp Leu Ser Asn Tyr Thr Asp Leu Ala Met Ser Thr Val Lys
                500                 505                 510
Gln Thr Gln Ala Ile Pro Tyr Thr Gly Pro Phe Asn Leu Leu Cys Tyr
                515                 520                 525
Gln Leu Gln Lys Leu Thr Gly Asp Val Glu Glu Leu Glu Ile Gln Glu
                530                 535                 540
Lys Pro Ala Leu Lys Val Phe Lys Asn Ile Thr Val Ile Gln Glu Pro
545                 550                 555                 560
Gly Met Val Val Leu Glu Trp Leu Ala Asn Pro Ser Asn Asp Met Tyr
                565                 570                 575
Ala Asp Thr Val Thr Thr Val Ile Leu Glu Val Gln Ser Asn Pro Lys
                580                 585                 590
Ile Arg Lys Gly Ala Val Gln Lys Val Ser Lys Leu Glu Met His
                595                 600                 605
Val Tyr Ser Lys Arg Leu Glu Ile Met Leu Gln Asp Ile Phe Gly Glu
610                 615                 620
Asp Cys Val Ser Val Lys Asp Ser Ile Leu Ser Val Thr Val Asp
625                 630                 635                 640
Gly Lys Thr Ala Asn Leu Asn Leu Glu Thr Arg Thr Val Glu Cys Glu
                645                 650                 655
Glu Gly Ser Glu Asp Asp Glu Ser Leu Arg Glu Met Val Glu Leu Ala
                660                 665                 670
Ala Gln Arg Leu Tyr Glu Ala Leu Thr Pro Val His
                675                 680

<210> SEQ ID NO 234
```

-continued

```
<211> LENGTH: 693
<212> TYPE: PRT
<213> ORGANISM: Arabidopsis thaliana

<400> SEQUENCE: 234

Met Ala Ser Ser Thr Ser Leu Lys Arg Arg Glu Gln Pro Ile Ser
 1               5                  10                  15

Arg Asp Gly Asp Gln Leu Ile Val Thr Pro Leu Gly Ala Gly Ser Glu
                20                  25                  30

Val Gly Arg Ser Cys Val Tyr Met Ser Phe Arg Gly Lys Asn Ile Leu
            35                  40                  45

Phe Asp Cys Gly Ile His Pro Ala Tyr Ser Gly Met Ala Ala Leu Pro
        50                  55                  60

Tyr Phe Asp Glu Ile Asp Pro Ser Ser Ile Asp Val Leu Leu Ile Thr
 65                  70                  75                  80

His Phe His Ile Asp His Ala Ala Ser Leu Pro Tyr Phe Leu Glu Lys
                 85                  90                  95

Thr Thr Phe Asn Gly Arg Val Phe Met Thr His Ala Thr Lys Ala Ile
                100                 105                 110

Tyr Lys Leu Leu Leu Thr Asp Tyr Val Lys Val Ser Lys Val Ser Val
            115                 120                 125

Glu Asp Met Leu Phe Asp Glu Gln Asp Ile Asn Lys Ser Met Asp Lys
        130                 135                 140

Ile Glu Val Ile Asp Phe His Gln Thr Val Glu Val Asn Gly Ile Lys
145                 150                 155                 160

Phe Trp Cys Tyr Thr Ala Gly His Val Leu Gly Ala Ala Met Phe Met
                165                 170                 175

Val Asp Ile Ala Gly Val Arg Ile Leu Tyr Thr Gly Asp Tyr Ser Arg
            180                 185                 190

Glu Glu Asp Arg His Leu Arg Ala Ala Glu Leu Pro Gln Phe Ser Pro
        195                 200                 205

Asp Ile Cys Ile Ile Glu Ser Thr Ser Gly Val Gln Leu His Gln Ser
    210                 215                 220

Arg His Ile Arg Glu Lys Arg Phe Thr Asp Val Ile His Ser Thr Val
225                 230                 235                 240

Ala Gln Gly Gly Arg Val Leu Ile Pro Ala Phe Ala Leu Gly Arg Ala
                245                 250                 255

Gln Glu Leu Leu Leu Ile Leu Asp Glu Tyr Trp Ala Asn His Pro Asp
            260                 265                 270

Leu His Asn Ile Pro Ile Tyr Tyr Ala Ser Pro Leu Ala Lys Lys Cys
        275                 280                 285

Met Ala Val Tyr Gln Thr Tyr Ile Leu Ser Met Asn Asp Arg Ile Arg
    290                 295                 300

Asn Gln Phe Ala Asn Ser Asn Pro Phe Val Phe Lys His Ile Ser Pro
305                 310                 315                 320

Leu Asn Ser Ile Asp Asp Phe Asn Asp Val Gly Pro Ser Val Val Met
                325                 330                 335

Ala Thr Pro Gly Gly Leu Gln Ser Gly Leu Ser Arg Gln Leu Phe Asp
            340                 345                 350

Ser Trp Cys Ser Asp Lys Lys Asn Ala Cys Ile Ile Pro Gly Tyr Met
        355                 360                 365

Val Glu Gly Thr Leu Ala Lys Thr Ile Ile Asn Glu Pro Lys Glu Val
    370                 375                 380

Thr Leu Met Asn Gly Leu Thr Ala Pro Leu Asn Met Gln Val His Tyr
```

-continued

```
                385                 390                 395                 400
Ile Ser Phe Ser Ala His Ala Asp Tyr Ala Gln Thr Ser Thr Phe Leu
                405                 410                 415

Lys Glu Leu Met Pro Pro Asn Ile Ile Leu Val His Gly Glu Ala Asn
            420                 425                 430

Glu Met Met Arg Leu Lys Gln Lys Leu Leu Thr Glu Phe Pro Asp Gly
        435                 440                 445

Asn Thr Lys Ile Met Thr Pro Lys Asn Cys Glu Ser Val Glu Met Tyr
    450                 455                 460

Phe Asn Ser Glu Lys Leu Ala Lys Thr Ile Gly Arg Leu Ala Glu Lys
465                 470                 475                 480

Thr Pro Asp Val Gly Asp Thr Val Ser Gly Ile Leu Val Lys Lys Gly
                485                 490                 495

Phe Thr Tyr Gln Ile Met Ala Pro Asp Glu Leu His Val Phe Ser Gln
            500                 505                 510

Leu Ser Thr Ala Thr Val Thr Gln Arg Ile Thr Ile Pro Phe Val Gly
        515                 520                 525

Ala Phe Gly Val Ile Lys His Arg Leu Glu Lys Ile Phe Glu Ser Val
    530                 535                 540

Glu Phe Ser Thr Asp Glu Glu Ser Gly Leu Pro Ala Leu Lys Val His
545                 550                 555                 560

Glu Arg Val Thr Val Lys Gln Glu Ser Glu Lys His Ile Ser Leu Gln
                565                 570                 575

Trp Ser Ser Asp Pro Ile Ser Asp Met Val Ser Asp Ser Ile Val Ala
            580                 585                 590

Leu Ile Leu Asn Ile Ser Arg Glu Val Pro Lys Ile Val Met Glu Glu
        595                 600                 605

Glu Asp Ala Val Lys Ser Glu Glu Asn Gly Lys Lys Val Glu Lys
    610                 615                 620

Val Ile Tyr Ala Leu Leu Val Ser Leu Phe Gly Asp Val Lys Leu Gly
625                 630                 635                 640

Glu Asn Gly Lys Leu Val Ile Arg Val Asp Gly Asn Val Ala Gln Leu
                645                 650                 655

Asp Lys Glu Ser Gly Glu Val Glu Ser Glu His Ser Gly Leu Lys Glu
            660                 665                 670

Arg Val Arg Val Ala Phe Glu Arg Ile Gln Ser Ala Val Lys Pro Ile
        675                 680                 685

Pro Leu Ser Ala Ser
    690

<210> SEQ ID NO 235
<211> LENGTH: 779
<212> TYPE: PRT
<213> ORGANISM: Saccharomyces cerevisiae

<400> SEQUENCE: 235

Met Glu Arg Thr Asn Thr Thr Thr Phe Lys Phe Phe Ser Leu Gly Gly
1               5                   10                  15

Ser Asn Glu Val Gly Arg Ser Cys His Ile Leu Gln Tyr Lys Gly Lys
            20                  25                  30

Thr Val Met Leu Asp Ala Gly Ile His Pro Ala Tyr Gln Gly Leu Ala
        35                  40                  45

Ser Leu Pro Phe Tyr Asp Glu Phe Asp Leu Ser Lys Val Asp Ile Leu
    50                  55                  60
```

-continued

```
Leu Ile Ser His Phe His Leu Asp His Ala Ala Ser Leu Pro Tyr Val
 65                  70                  75                  80

Met Gln Arg Thr Asn Phe Gln Gly Arg Val Phe Met Thr His Pro Thr
                 85                  90                  95

Lys Ala Ile Tyr Arg Trp Leu Leu Arg Asp Phe Val Arg Val Thr Ser
            100                 105                 110

Ile Gly Ser Ser Ser Ser Met Gly Thr Lys Asp Glu Gly Leu Phe
        115                 120                 125

Ser Asp Glu Asp Leu Val Asp Ser Phe Asp Lys Ile Glu Thr Val Asp
130                 135                 140

Tyr His Ser Thr Val Asp Val Asn Gly Ile Lys Phe Thr Ala Phe His
145                 150                 155                 160

Ala Gly His Val Leu Gly Ala Ala Met Phe Gln Ile Glu Ile Ala Gly
                165                 170                 175

Leu Arg Val Leu Phe Thr Gly Asp Tyr Ser Arg Glu Val Asp Arg His
            180                 185                 190

Leu Asn Ser Ala Glu Val Pro Pro Leu Ser Ser Asn Val Leu Ile Val
        195                 200                 205

Glu Ser Thr Phe Gly Thr Ala Thr His Glu Pro Arg Leu Asn Arg Glu
210                 215                 220

Arg Lys Leu Thr Gln Leu Ile His Ser Thr Val Met Arg Gly Gly Arg
225                 230                 235                 240

Val Leu Leu Pro Val Phe Ala Leu Gly Arg Ala Gln Glu Ile Met Leu
                245                 250                 255

Ile Leu Asp Glu Tyr Trp Ser Gln His Ala Asp Glu Leu Gly Gly Gly
            260                 265                 270

Gln Val Pro Ile Phe Tyr Ala Ser Asn Leu Ala Lys Lys Cys Met Ser
        275                 280                 285

Val Phe Gln Thr Tyr Val Asn Met Met Asn Asp Asp Ile Arg Lys Lys
290                 295                 300

Phe Arg Asp Ser Gln Thr Asn Pro Phe Ile Phe Lys Asn Ile Ser Tyr
305                 310                 315                 320

Leu Arg Asn Leu Glu Asp Phe Gln Asp Phe Gly Pro Ser Val Met Leu
                325                 330                 335

Ala Ser Pro Gly Met Leu Gln Ser Gly Leu Ser Arg Asp Leu Leu Glu
            340                 345                 350

Arg Trp Cys Pro Glu Asp Lys Asn Leu Val Leu Ile Thr Gly Tyr Ser
        355                 360                 365

Ile Glu Gly Thr Met Ala Lys Phe Ile Met Leu Glu Pro Asp Thr Ile
370                 375                 380

Pro Ser Ile Asn Asn Pro Glu Ile Thr Ile Pro Arg Arg Cys Gln Val
385                 390                 395                 400

Glu Glu Ile Ser Phe Ala Ala His Val Asp Phe Gln Glu Asn Leu Glu
                405                 410                 415

Phe Ile Glu Lys Ile Ser Ala Pro Asn Ile Ile Leu Val His Gly Glu
            420                 425                 430

Ala Asn Pro Met Gly Arg Leu Lys Ser Ala Leu Leu Ser Asn Phe Ala
        435                 440                 445

Ser Leu Lys Gly Thr Asp Asn Glu Val His Val Phe Asn Pro Arg Asn
450                 455                 460

Cys Val Glu Val Asp Leu Glu Phe Gln Gly Val Lys Val Ala Lys Ala
465                 470                 475                 480

Val Gly Asn Ile Val Asn Glu Ile Tyr Lys Glu Glu Asn Val Glu Ile
```

-continued

```
                        485                 490                     495
Lys Glu Glu Ile Ala Ala Lys Ile Glu Pro Ile Lys Glu Glu Asn Glu
                    500                 505                 510

Asp Asn Leu Asp Ser Gln Ala Glu Lys Gly Leu Val Asp Glu Glu
                515                 520                 525

His Lys Asp Ile Val Val Ser Gly Ile Leu Val Ser Asp Lys Asn
            530                 535                 540

Phe Glu Leu Asp Phe Leu Ser Leu Ser Asp Leu Arg Glu His His Pro
545                 550                 555                 560

Asp Leu Ser Thr Thr Ile Leu Arg Glu Arg Gln Ser Val Arg Val Asn
                565                 570                 575

Cys Lys Lys Glu Leu Ile Tyr Trp His Ile Leu Gln Met Phe Gly Glu
                580                 585                 590

Ala Glu Val Leu Gln Asp Asp Arg Val Thr Asn Gln Glu Pro Lys
                595                 600                 605

Val Lys Glu Glu Ser Lys Asp Asn Leu Thr Asn Thr Gly Lys Leu Ile
            610                 615                 620

Leu Gln Ile Met Gly Asp Ile Lys Leu Thr Ile Val Asn Thr Leu Ala
625                 630                 635                 640

Val Val Glu Trp Thr Gln Asp Leu Met Asn Asp Thr Val Ala Asp Ser
                645                 650                 655

Ile Ile Ala Ile Leu Met Asn Val Asp Ser Ala Pro Ala Ser Val Lys
                660                 665                 670

Leu Ser Ser His Ser Cys Asp His Asp His Asn Asn Val Gln Ser
                675                 680                 685

Asn Ala Gln Gly Lys Ile Asp Glu Val Glu Arg Val Lys Gln Ile Ser
            690                 695                 700

Arg Leu Phe Lys Glu Gln Phe Gly Asp Cys Phe Thr Leu Phe Leu Asn
705                 710                 715                 720

Lys Asp Glu Tyr Ala Ser Asn Lys Glu Glu Thr Ile Thr Gly Val Val
                725                 730                 735

Thr Ile Gly Lys Ser Thr Ala Lys Ile Asp Phe Asn Asn Met Lys Ile
                740                 745                 750

Leu Glu Cys Asn Ser Asn Pro Leu Lys Gly Arg Val Glu Ser Leu Leu
                755                 760                 765

Asn Ile Gly Gly Asn Leu Val Thr Pro Leu Cys
            770                 775
```

<210> SEQ ID NO 236
<211> LENGTH: 554
<212> TYPE: PRT
<213> ORGANISM: Synechocystis sp.

<400> SEQUENCE: 236

```
Met Thr Phe Ser Val Pro Thr Gln Gly Lys Ala Phe Ala Asn Ile Ser
1               5                   10                  15

Phe Leu Pro Tyr Gly Val Gly Pro Arg Asp Gly Ile Cys Leu Glu
            20                  25                  30

Leu His Leu Gly Pro Tyr Arg Ile Leu Leu Asp Cys Gly Leu Glu Asp
        35                  40                  45

Leu Thr Pro Leu Leu Ala Ala Asp Pro Gly Thr Val Asp Leu Val Phe
    50                  55                  60

Cys Ser His Ala His Arg Asp His Gly Leu Gly Leu Trp Gln Phe His
65                  70                  75                  80
```

-continued

```
Gln Gln Phe Pro His Ile Pro Ile Leu Ala Ser Glu Val Thr Gln Arg
                85                  90                  95

Leu Leu Pro Leu Asn Trp Pro Asp Glu Phe Val Pro Pro Phe Cys Arg
            100                 105                 110

Val Leu Pro Trp Arg Ser Pro Gln Glu Val Leu Pro Gly Leu Thr Val
        115                 120                 125

Glu Leu Leu Pro Ala Gly His Leu Pro Gly Ala Ala Leu Ile Leu Leu
    130                 135                 140

Glu Tyr His Asn Gly Asp Arg Leu Tyr Arg Val Ile Tyr Thr Gly Asp
145                 150                 155                 160

Tyr Cys Leu Ser His Leu Gln Leu Val Asp Gly Leu Ala Leu Thr Pro
                165                 170                 175

Leu Arg Gly Leu Lys Pro Asp Val Leu Ile Leu Glu Gly His Tyr Gly
            180                 185                 190

Asn Arg Arg Leu Pro His Arg Arg Gln Gln Glu Lys Gln Phe Ile Gln
        195                 200                 205

Ala Ile Glu Thr Val Leu Ala Lys Gly Arg Asn Ile Leu Leu Pro Val
    210                 215                 220

Pro Pro Leu Gly Leu Ala Gln Glu Ile Leu Lys Leu Leu Arg Thr His
225                 230                 235                 240

His Gln Phe Thr Gly Arg Gln Val Asn Leu Trp Ala Gly Glu Ser Val
                245                 250                 255

Ala Arg Gly Cys Asp Ala Tyr Gln Gly Ile Ile Asp His Leu Pro Asp
            260                 265                 270

Asn Val Arg Asn Phe Ala Gln His Gln Pro Leu Phe Trp Asp Asp Lys
        275                 280                 285

Val Tyr Pro His Leu Arg Pro Leu Thr Asp Asp Gln Gly Glu Leu Ser
    290                 295                 300

Leu Ser Ala Pro Ser Ile Val Ile Thr Thr Thr Trp Pro Ala Phe Trp
305                 310                 315                 320

Pro Ser Pro Ala Ala Leu Pro Gly Leu Trp Thr Val Phe Met Pro Gln
                325                 330                 335

Leu Leu Thr Leu Pro Ser Cys Leu Val Asn Phe Ala Trp Gln Asp Leu
            340                 345                 350

Glu Glu Phe Pro Lys Tyr Glu Leu Glu Asp Tyr Leu Leu Ala Asp His
        355                 360                 365

Ser Asp Gly Arg Asn Thr Thr Gln Leu Ile His Asn Leu Arg Pro Gln
    370                 375                 380

His Leu Val Phe Val His Gly Gln Pro Ser Asp Ile Glu Asp Leu Thr
385                 390                 395                 400

Ser Leu Glu Glu Leu Gln Ser Arg Tyr Gln Leu His Ser Pro Ala Ala
                405                 410                 415

Gly Asn Ala Val Ala Leu Pro Ile Gly Asp Arg Phe Val Gln Pro Thr
            420                 425                 430

Pro Pro Pro Gln Ile Tyr Glu Gly Glu Ile His Glu Leu Glu Pro
        435                 440                 445

Asn Lys Gln Ile His His Leu Gly Glu Val Val Ile His Leu Asp Gly
    450                 455                 460

Gln Ile Leu Glu Asn Ser Arg Trp Gly Lys Phe Gly Glu Thr Gly Ile
465                 470                 475                 480

Val Gln Ala Arg Trp Gln Gly Glu Leu Val Leu Arg Gly Ile Ser
                485                 490                 495

Gln Arg Glu Leu Leu Lys Gln Asn Gln Ser Ser Lys Arg Pro Val Asp
```

-continued

```
                    500                 505                 510
Phe Asp Cys Cys Ala Asn Cys Arg His Phe Gln His Tyr His Cys Arg
            515                 520                 525

Asn Pro Val Ser Pro Leu Met Gly Leu Glu Val Arg Ala Asp Gly His
        530                 535                 540

Cys Pro Val Phe Glu Ser Val Ala Ser Ser
545                 550

<210> SEQ ID NO 237
<211> LENGTH: 636
<212> TYPE: PRT
<213> ORGANISM: Methanobacterium thermoautotrophicum

<400> SEQUENCE: 237

Met Val Ser Glu Met Leu Glu Glu Ile Lys Arg Thr Ile Met Gln Arg
  1               5                  10                  15

Leu Pro Glu Arg Val Gln Val Ala Lys Val Phe Glu Gly Pro Glu
                 20                  25                  30

Val Val Ile Tyr Thr Lys Asn Pro Glu Ile Ile Thr Glu Asn Gly Asn
             35                  40                  45

Leu Ile Arg Asp Ile Ala Lys Asp Ile Arg Lys Arg Ile Ile Arg
         50                  55                  60

Ser Asp Arg Ser Val Leu Met Asp Pro Glu Lys Ala Ile Arg Lys Ile
 65                  70                  75                  80

His Glu Ile Val Pro Glu Glu Ala Lys Ile Thr Asn Ile Ser Phe Asp
                 85                  90                  95

Asp Val Thr Cys Glu Val Ile Ile Glu Ala Arg Lys Pro Gly Leu Val
            100                 105                 110

Ile Gly Lys Tyr Gly Ser Thr Ser Arg Glu Ile Val Lys Asn Thr Gly
        115                 120                 125

Trp Ala Pro Lys Ile Leu Arg Thr Pro Pro Ile Ser Ser Glu Ile Ile
130                 135                 140

Glu Arg Ile Arg Arg Thr Leu Arg Lys Asn Ser Lys Glu Arg Lys Lys
145                 150                 155                 160

Ile Leu Gln Gln Leu Gly Asn Arg Ile His Gln Lys Pro Lys Tyr Asp
                165                 170                 175

Asn Asp Trp Ala Arg Leu Thr Ala Met Gly Gly Phe Arg Glu Val Gly
            180                 185                 190

Arg Ser Cys Leu Tyr Leu Gln Thr Pro Asn Ser Arg Val Leu Leu Asp
        195                 200                 205

Cys Gly Val Asn Val Ala Gly Gly Asp Asp Lys Asn Ser Tyr Pro Tyr
    210                 215                 220

Leu Asn Val Pro Glu Phe Thr Leu Asp Ser Leu Asp Ala Val Ile Ile
225                 230                 235                 240

Thr His Ala His Leu Asp His Ser Gly Phe Leu Pro Tyr Leu Tyr His
                245                 250                 255

Tyr Gly Tyr Asp Gly Pro Val Tyr Cys Thr Ala Pro Thr Arg Asp Leu
            260                 265                 270

Met Thr Leu Leu Gln Leu Asp His Ile Asp Ile Ala His Arg Glu Asp
        275                 280                 285

Glu Pro Leu Pro Phe Asn Val Lys His Val Lys Lys Ser Val Lys His
    290                 295                 300

Thr Ile Thr Leu Asp Tyr Gly Glu Val Thr Asp Ile Ala Pro Asp Ile
305                 310                 315                 320
```

```
Arg Leu Thr Leu His Asn Ala Gly His Ile Leu Gly Ser Ala Met Ala
            325                 330                 335

His Leu His Ile Gly Asp Gly Gln His Asn Met Val Tyr Thr Gly Asp
        340                 345                 350

Phe Lys Tyr Glu Gln Ser Arg Leu Leu Glu Ala Ala Ala Asn Arg Phe
    355                 360                 365

Pro Arg Ile Glu Thr Leu Val Met Glu Ser Thr Tyr Gly Gly His Glu
370                 375                 380

Asp Val Gln Pro Ser Arg Asn Arg Ala Glu Lys Glu Leu Val Lys Thr
385                 390                 395                 400

Ile Tyr Ser Thr Leu Arg Arg Gly Gly Lys Ile Leu Ile Pro Val Phe
                405                 410                 415

Ala Val Gly Arg Ala Gln Glu Leu Met Ile Val Leu Glu Glu Tyr Ile
            420                 425                 430

Arg Thr Gly Ile Ile Asp Glu Val Pro Val Tyr Ile Asp Gly Met Ile
        435                 440                 445

Trp Glu Ala Asn Ala Ile His Thr Ala Arg Pro Glu Tyr Leu Ser Lys
    450                 455                 460

Asp Leu Arg Asp Gln Ile Phe His Met Gly His Asn Pro Phe Ile Ser
465                 470                 475                 480

Asp Ile Phe His Lys Val Asn Gly Met Asp Glu Arg Arg Glu Ile Val
                485                 490                 495

Glu Gly Glu Pro Ser Ile Ile Leu Ser Thr Ser Gly Met Leu Thr Gly
            500                 505                 510

Gly Asn Ser Leu Glu Tyr Phe Lys Trp Leu Cys Glu Asp Pro Asp Asn
        515                 520                 525

Ser Leu Val Phe Val Gly Tyr Gln Ala Glu Gly Ser Leu Gly Arg Arg
    530                 535                 540

Ile Gln Lys Gly Trp Lys Glu Ile Pro Leu Lys Asp Glu Asp Asp Lys
545                 550                 555                 560

Met Arg Val Tyr Asn Val Arg Met Asn Ile Lys Thr Ile Glu Gly Phe
                565                 570                 575

Ser Gly His Ser Asp Arg Arg Gln Leu Met Glu Tyr Val Lys Arg Ile
            580                 585                 590

Ser Pro Lys Pro Glu Lys Ile Leu Leu Cys His Gly Asp Asn Tyr Lys
        595                 600                 605

Thr Leu Asp Leu Ala Ser Ser Ile Tyr Arg Thr Tyr Arg Ile Glu Thr
    610                 615                 620

Lys Thr Pro Leu Asn Leu Glu Thr Val Arg Ile Gln
625                 630                 635

<210> SEQ ID NO 238
<211> LENGTH: 1040
<212> TYPE: PRT
<213> ORGANISM: Homo sapiens

<400> SEQUENCE: 238

Met Leu Glu Asp Ile Ser Glu Glu Asp Ile Trp Glu Tyr Lys Ser Lys
  1               5                  10                  15

Arg Lys Pro Lys Arg Val Asp Pro Asn Asn Gly Ser Lys Asn Ile Leu
             20                  25                  30

Lys Ser Val Glu Lys Ala Thr Asp Gly Lys Tyr Gln Ser Lys Arg Ser
         35                  40                  45

Arg Asn Arg Lys Arg Ala Ala Glu Ala Lys Glu Val Lys Asp His Glu
     50                  55                  60
```

```
Val Pro Leu Gly Asn Ala Gly Cys Gln Thr Ser Val Ala Ser Ser Gln
 65                  70                  75                  80

Asn Ser Ser Cys Gly Asp Gly Ile Gln Gln Thr Gln Asp Lys Glu Thr
                 85                  90                  95

Thr Pro Gly Lys Leu Cys Arg Thr Gln Lys Ser Gln His Val Ser Pro
            100                 105                 110

Lys Ile Arg Pro Val Tyr Asp Gly Tyr Cys Pro Asn Cys Gln Met Pro
        115                 120                 125

Phe Ser Ser Leu Ile Gly Gln Thr Pro Arg Trp His Val Phe Glu Cys
    130                 135                 140

Leu Asp Ser Pro Pro Arg Ser Glu Thr Glu Cys Pro Asp Gly Leu Leu
145                 150                 155                 160

Cys Thr Ser Thr Ile Pro Phe His Tyr Lys Arg Tyr Thr His Phe Leu
                165                 170                 175

Leu Ala Gln Ser Arg Ala Gly Asp His Pro Phe Ser Pro Ser Pro
                180                 185                 190

Ala Ser Gly Gly Ser Phe Ser Glu Thr Lys Ser Gly Val Leu Cys Ser
        195                 200                 205

Leu Glu Glu Arg Trp Ser Ser Tyr Gln Asn Gln Thr Asp Asn Ser Val
        210                 215                 220

Ser Asn Asp Pro Leu Leu Met Thr Gln Tyr Phe Lys Lys Ser Pro Ser
225                 230                 235                 240

Leu Thr Glu Ala Ser Glu Lys Ile Ser Thr His Ile Gln Thr Ser Gln
                245                 250                 255

Gln Ala Leu Gln Phe Thr Asp Phe Val Glu Asn Asp Lys Leu Val Gly
            260                 265                 270

Val Ala Leu Arg Leu Ala Asn Asn Ser Glu His Ile Asn Leu Pro Leu
        275                 280                 285

Pro Glu Asn Asp Phe Ser Asp Cys Glu Ile Ser Tyr Ser Pro Leu Gln
        290                 295                 300

Ser Asp Glu Asp Thr His Asp Ile Asp Glu Lys Pro Asp Asp Ser Gln
305                 310                 315                 320

Glu Gln Leu Phe Phe Thr Glu Ser Ser Lys Asp Gly Ser Leu Glu Glu
                325                 330                 335

Asp Asp Asp Ser Cys Gly Phe Phe Lys Lys Arg His Gly Pro Leu Leu
            340                 345                 350

Lys Asp Gln Asp Glu Ser Cys Pro Lys Val Asn Ser Phe Leu Thr Arg
        355                 360                 365

Asp Lys Tyr Asp Glu Gly Leu Tyr Arg Phe Asn Ser Leu Asn Asp Leu
    370                 375                 380

Ser Gln Pro Ile Ser Gln Asn Asn Glu Ser Thr Leu Pro Tyr Asp Leu
385                 390                 395                 400

Ala Cys Thr Gly Gly Asp Phe Val Leu Phe Pro Ala Leu Ala Gly
                405                 410                 415

Lys Leu Ala Ala Ser Val His Gln Ala Thr Lys Ala Lys Pro Asp Glu
            420                 425                 430

Pro Glu Phe His Ser Ala Gln Ser Asn Lys Gln Lys Gln Val Ile Glu
        435                 440                 445

Glu Ser Ser Val Tyr Asn Gln Val Ser Leu Pro Leu Val Lys Ser Leu
        450                 455                 460

Met Leu Lys Pro Phe Glu Ser Gln Val Glu Gly Tyr Leu Ser Ser Gln
465                 470                 475                 480
```

-continued

```
Pro Thr Gln Asn Thr Ile Arg Lys Leu Ser Ser Glu Asn Leu Asn Ala
            485                 490                 495
Lys Asn Asn Thr Asn Ser Ala Cys Phe Cys Arg Lys Ala Leu Glu Gly
            500                 505                 510
Val Pro Val Gly Lys Ala Thr Ile Leu Asn Thr Glu Asn Leu Ser Ser
            515                 520                 525
Thr Pro Ala Pro Lys Tyr Leu Lys Ile Leu Pro Ser Gly Leu Lys Tyr
            530                 535                 540
Asn Ala Arg His Pro Ser Thr Lys Val Met Lys Gln Met Asp Ile Gly
545                 550                 555                 560
Val Tyr Phe Gly Leu Pro Pro Lys Arg Lys Glu Lys Leu Leu Gly
                565                 570                 575
Glu Ser Ala Leu Glu Gly Ile Asn Leu Asn Pro Val Pro Ser Pro Asn
            580                 585                 590
Gln Lys Arg Ser Ser Gln Cys Lys Arg Lys Ala Glu Lys Ser Leu Ser
            595                 600                 605
Asp Leu Glu Phe Asp Ala Ser Thr Leu His Glu Ser Gln Leu Ser Val
            610                 615                 620
Glu Leu Ser Ser Glu Arg Ser Gln Arg Gln Lys Lys Arg Cys Arg Lys
625                 630                 635                 640
Ser Asn Ser Leu Gln Glu Gly Ala Cys Gln Lys Arg Ser Asp His Leu
            645                 650                 655
Ile Asn Thr Glu Ser Glu Ala Val Asn Leu Ser Lys Val Lys Val Phe
            660                 665                 670
Thr Lys Ser Ala His Gly Gly Leu Gln Arg Gly Asn Lys Lys Ile Pro
            675                 680                 685
Glu Ser Ser Asn Val Gly Gly Ser Arg Lys Lys Thr Cys Pro Phe Tyr
            690                 695                 700
Lys Lys Ile Pro Gly Thr Gly Phe Thr Val Asp Ala Phe Gln Tyr Gly
705                 710                 715                 720
Val Val Glu Gly Cys Thr Ala Tyr Phe Leu Thr His Phe His Ser Asp
            725                 730                 735
His Tyr Ala Gly Leu Ser Lys His Phe Thr Phe Pro Val Tyr Cys Ser
            740                 745                 750
Glu Ile Thr Gly Asn Leu Leu Lys Asn Lys Leu His Val Gln Glu Gln
            755                 760                 765
Tyr Ile His Pro Leu Pro Leu Asp Thr Glu Cys Ile Val Asn Gly Val
            770                 775                 780
Lys Val Val Leu Leu Asp Ala Asn His Cys Pro Gly Ala Val Met Ile
785                 790                 795                 800
Leu Phe Tyr Leu Pro Asn Gly Thr Val Ile Leu His Thr Gly Asp Phe
            805                 810                 815
Arg Ala Asp Pro Ser Met Glu Arg Ser Leu Leu Ala Asp Gln Lys Val
            820                 825                 830
His Met Leu Tyr Leu Asp Thr Thr Tyr Cys Ser Pro Glu Tyr Thr Phe
            835                 840                 845
Pro Ser Gln Gln Glu Val Ile Arg Phe Ala Ile Asn Thr Ala Phe Glu
            850                 855                 860
Ala Val Thr Leu Asn Pro His Ala Leu Val Val Cys Gly Thr Tyr Ser
865                 870                 875                 880
Ile Gly Lys Glu Lys Val Phe Leu Ala Ile Ala Asp Val Leu Gly Ser
            885                 890                 895
Lys Val Gly Met Ser Gln Glu Lys Tyr Lys Thr Leu Gln Cys Leu Asn
```

```
                    900                 905                 910
Ile Pro Glu Ile Asn Ser Leu Ile Thr Thr Asp Met Cys Ser Ser Leu
            915                 920                 925

Val His Leu Leu Pro Met Met Gln Ile Asn Phe Lys Gly Leu Gln Ser
    930                 935                 940

His Leu Lys Lys Cys Gly Gly Lys Tyr Asn Gln Ile Leu Ala Phe Arg
945                 950                 955                 960

Pro Thr Gly Trp Thr His Ser Asn Lys Phe Thr Arg Ile Ala Asp Val
                965                 970                 975

Ile Pro Gln Thr Lys Gly Asn Ile Ser Ile Tyr Gly Ile Pro Tyr Ser
            980                 985                 990

Glu His Ser Ser Tyr Leu Glu Met Lys Arg Phe Val Gln Trp Leu Lys
    995                 1000                1005

Pro Gln Lys Ile Ile Pro Thr Val Asn Val Gly Thr Trp Lys Ser Arg
    1010                1015                1020

Ser Thr Met Glu Lys Tyr Phe Arg Glu Trp Lys Leu Glu Ala Gly Tyr
1025                1030                1035                1040

<210> SEQ ID NO 239
<211> LENGTH: 723
<212> TYPE: PRT
<213> ORGANISM: Arabidopsis thaliana

<400> SEQUENCE: 239

Met Ser Asn Thr Val Glu Asp Asp Asp Phe Gln Ile Pro Pro
 1               5                  10                  15

Ser Ser Gln Leu Ser Ile Arg Lys Pro Leu His Pro Thr Asn Ala Asn
            20                  25                  30

Asn Ile Ser His Arg Pro Pro Asn Lys Lys Pro Arg Leu Cys Arg Tyr
        35                  40                  45

Pro Gly Lys Glu Asn Val Thr Pro Pro Ser Pro Asp Pro Asp Leu
    50                  55                  60

Phe Cys Ser Ser Thr Pro His Cys Ile Leu Asp Cys Ile Pro Ser
65                  70                  75                  80

Ser Val Asp Cys Ser Leu Gly Asp Phe Asn Gly Pro Ile Ser Leu
                85                  90                  95

Gly Glu Glu Asp Lys Glu Asp Lys Asp Cys Ile Lys Val Asn Arg
            100                 105                 110

Glu Gly Tyr Leu Cys Asn Ser Met Glu Ala Arg Leu Leu Lys Ser Arg
        115                 120                 125

Ile Cys Leu Gly Phe Asp Ser Gly Ile His Glu Asp Asp Glu Gly Phe
    130                 135                 140

Val Glu Ser Asn Ser Glu Leu Asp Val Leu Ile Asn Leu Cys Ser Glu
145                 150                 155                 160

Ser Glu Gly Arg Ser Gly Glu Phe Ser Leu Gly Lys Asp Asp Ser Ile
                165                 170                 175

Gln Cys Pro Leu Cys Ser Met Asp Ile Ser Ser Leu Ser Glu Glu Gln
            180                 185                 190

Arg Gln Val His Ser Asn Thr Cys Leu Asp Lys Ser Tyr Asn Gln Pro
        195                 200                 205

Ser Glu Gln Asp Ser Leu Arg Lys Cys Glu Asn Leu Ser Ser Leu Ile
    210                 215                 220

Lys Glu Ser Ile Asp Asp Pro Val Gln Leu Pro Gln Leu Val Thr Asp
225                 230                 235                 240
```

-continued

```
Leu Ser Pro Val Leu Lys Trp Leu Arg Ser Leu Gly Leu Ala Lys Tyr
                245                 250                 255

Glu Asp Val Phe Ile Arg Glu Ile Asp Trp Asp Thr Leu Gln Ser
            260                 265                 270

Leu Thr Glu Glu Asp Leu Leu Ser Ile Gly Ile Thr Ser Leu Gly Pro
        275                 280                 285

Arg Lys Lys Ile Val Asn Ala Leu Ser Gly Val Arg Asp Pro Phe Ala
    290                 295                 300

Ser Ser Ala Glu Val Gln Ala Gln Ser His Cys Thr Ser Gly His Val
305                 310                 315                 320

Thr Glu Arg Gln Arg Asp Lys Ser Thr Thr Arg Lys Ala Ser Glu Pro
                325                 330                 335

Lys Lys Pro Thr Ala Asn Lys Leu Ile Thr Glu Phe Phe Pro Gly Gln
            340                 345                 350

Ala Thr Glu Gly Thr Lys Ile Arg Thr Ala Pro Lys Pro Val Ala Glu
        355                 360                 365

Lys Ser Pro Ser Asp Ser Ser Ser Arg Arg Ala Val Arg Arg Asn Gly
    370                 375                 380

Asn Asn Gly Lys Ser Lys Val Ile Pro His Trp Asn Cys Ile Pro Gly
385                 390                 395                 400

Thr Pro Phe Arg Val Asp Ala Phe Lys Tyr Leu Thr Arg Asp Cys Cys
                405                 410                 415

His Trp Phe Leu Thr His Phe His Leu Asp His Tyr Gln Gly Leu Thr
            420                 425                 430

Lys Ser Phe Ser His Gly Lys Ile Tyr Cys Ser Leu Val Thr Ala Lys
        435                 440                 445

Leu Val Asn Met Lys Ile Gly Ile Pro Trp Glu Arg Leu Gln Val Leu
    450                 455                 460

Asp Leu Gly Gln Lys Val Asn Ile Ser Gly Ile Asp Val Thr Cys Phe
465                 470                 475                 480

Asp Ala Asn His Cys Pro Gly Ser Ile Met Ile Leu Phe Glu Pro Ala
                485                 490                 495

Asn Gly Lys Ala Val Leu His Thr Gly Asp Phe Arg Tyr Ser Glu Glu
            500                 505                 510

Met Ser Asn Trp Leu Ile Gly Ser His Ile Ser Ser Leu Ile Leu Asp
        515                 520                 525

Thr Thr Tyr Cys Asn Pro Gln Tyr Asp Phe Pro Lys Gln Glu Ala Val
    530                 535                 540

Ile Gln Phe Val Val Glu Ala Ile Gln Ala Glu Ala Phe Asn Pro Lys
545                 550                 555                 560

Thr Leu Phe Leu Ile Gly Ser Tyr Thr Ile Gly Lys Glu Arg Leu Phe
                565                 570                 575

Leu Glu Val Ala Arg Val Leu Arg Glu Lys Ile Tyr Ile Asn Pro Ala
            580                 585                 590

Lys Leu Lys Leu Leu Glu Cys Leu Gly Phe Ser Lys Asp Asp Ile Gln
        595                 600                 605

Trp Phe Thr Val Lys Glu Glu Ser His Ile His Val Pro Leu
    610                 615                 620

Trp Thr Leu Ala Ser Phe Lys Arg Leu Lys His Val Ala Asn Arg Tyr
625                 630                 635                 640

Thr Asn Arg Tyr Ser Leu Ile Val Ala Phe Ser Pro Thr Gly Trp Thr
                645                 650                 655

Ser Gly Lys Thr Lys Lys Lys Ser Pro Gly Arg Arg Leu Gln Gln Gly
```

```
                        660                 665                 670
Thr Ile Ile Arg Tyr Glu Val Pro Tyr Ser Glu His Ser Ser Phe Thr
        675                 680                 685
Glu Leu Lys Glu Phe Val Gln Lys Val Ser Pro Glu Val Ile Ile Pro
    690                 695                 700
Ser Val Asn Asn Asp Gly Pro Asp Ser Ala Ala Met Val Ser Leu
705                 710                 715                 720
Leu Val Thr

<210> SEQ ID NO 240
<211> LENGTH: 661
<212> TYPE: PRT
<213> ORGANISM: Saccharomyces cerevisiae

<400> SEQUENCE: 240

Met Ser Arg Lys Ser Ile Val Gln Ile Arg Arg Ser Glu Val Lys Arg
  1               5                  10                  15
Lys Arg Ser Ser Thr Ala Ser Ser Thr Ser Glu Gly Lys Thr Leu His
                 20                  25                  30
Lys Asn Thr His Thr Ser Ser Lys Arg Gln Arg Thr Leu Thr Glu Phe
             35                  40                  45
Asn Ile Pro Thr Ser Ser Asn Leu Pro Val Arg Ser Ser Ser Tyr Ser
 50                  55                  60
Phe Ser Arg Phe Ser Cys Ser Thr Ser Asn Lys Asn Thr Glu Pro Val
 65                  70                  75                  80
Ile Ile Asn Asp Asp His Asn Ser Ile Cys Leu Glu Asp Thr Ala
                 85                  90                  95
Lys Val Glu Ile Thr Ile Asp Thr Asp Glu Glu Leu Val Ser Leu
            100                 105                 110
His Asp Asn Glu Val Ser Ala Ile Glu Asn Arg Thr Glu Asp Arg Ile
            115                 120                 125
Val Thr Glu Leu Glu Glu Gln Val Asn Val Lys Val Ser Thr Glu Val
        130                 135                 140
Ile Gln Cys Pro Ile Cys Leu Glu Asn Leu Ser His Leu Glu Leu Tyr
145                 150                 155                 160
Glu Arg Glu Thr His Cys Asp Thr Cys Ile Gly Ser Asp Pro Ser Asn
                165                 170                 175
Met Gly Thr Pro Lys Lys Asn Ile Arg Ser Phe Ile Ser Asn Pro Ser
            180                 185                 190
Ser Pro Ala Lys Thr Lys Arg Asp Ile Ala Thr Ser Lys Lys Pro Thr
        195                 200                 205
Arg Val Lys Leu Val Leu Pro Ser Phe Lys Ile Ile Lys Phe Asn Asn
    210                 215                 220
Gly His Glu Ile Val Val Asp Gly Phe Asn Tyr Lys Ala Ser Glu Thr
225                 230                 235                 240
Ile Ser Gln Tyr Phe Leu Ser His Phe His Ser Asp His Tyr Ile Gly
                245                 250                 255
Leu Lys Lys Ser Trp Asn Asn Pro Asp Glu Asn Pro Ile Lys Lys Thr
            260                 265                 270
Leu Tyr Cys Ser Lys Ile Thr Ala Ile Leu Val Asn Leu Lys Phe Lys
        275                 280                 285
Ile Pro Met Asp Glu Ile Gln Ile Leu Pro Met Asn Lys Arg Phe Trp
    290                 295                 300
Ile Thr Asp Thr Ile Ser Val Val Thr Leu Asp Ala Asn His Cys Pro
```

-continued

```
305                 310                 315                 320
Gly Ala Ile Ile Met Leu Phe Gln Glu Phe Leu Ala Asn Ser Tyr Asp
            325                 330                 335
Lys Pro Ile Arg Gln Ile Leu His Thr Gly Asp Phe Arg Ser Asn Ala
            340                 345                 350
Lys Met Ile Glu Thr Ile Gln Lys Trp Leu Ala Glu Thr Ala Asn Glu
            355                 360                 365
Thr Ile Asp Gln Val Tyr Leu Asp Thr Thr Tyr Met Thr Met Gly Tyr
            370                 375                 380
Asn Phe Pro Ser Gln His Ser Val Cys Glu Thr Val Ala Asp Phe Thr
385                 390                 395                 400
Leu Arg Leu Ile Lys His Gly Lys Asn Lys Thr Phe Gly Asp Ser Gln
            405                 410                 415
Arg Asn Leu Phe His Phe Gln Arg Lys Lys Thr Leu Thr Thr His Arg
            420                 425                 430
Tyr Arg Val Leu Phe Leu Val Gly Thr Tyr Thr Ile Gly Lys Glu Lys
            435                 440                 445
Leu Ala Ile Lys Ile Cys Glu Phe Leu Lys Thr Lys Leu Phe Val Met
    450                 455                 460
Pro Asn Ser Val Lys Phe Ser Met Met Leu Thr Val Leu Gln Asn Asn
465                 470                 475                 480
Glu Asn Gln Asn Asp Met Trp Asp Glu Ser Leu Leu Thr Ser Asn Leu
            485                 490                 495
His Glu Ser Ser Val His Leu Val Pro Ile Arg Val Leu Lys Ser Gln
            500                 505                 510
Glu Thr Ile Glu Ala Tyr Leu Lys Ser Leu Lys Glu Leu Glu Thr Asp
            515                 520                 525
Tyr Val Lys Asp Ile Glu Asp Val Val Gly Phe Ile Pro Thr Gly Trp
    530                 535                 540
Ser His Asn Phe Gly Leu Lys Tyr Gln Lys Lys Asn Asp Asp Asp Glu
545                 550                 555                 560
Asn Glu Met Ser Gly Asn Thr Glu Tyr Cys Leu Glu Leu Met Lys Asn
            565                 570                 575
Asp Arg Asp Asn Asp Asp Glu Asn Gly Phe Glu Ile Ser Ser Ile Leu
            580                 585                 590
Arg Gln Tyr Lys Lys Tyr Asn Lys Phe Gln Val Phe Asn Val Pro Tyr
    595                 600                 605
Ser Glu His Ser Ser Phe Asn Asp Leu Val Lys Phe Gly Cys Lys Leu
    610                 615                 620
Lys Cys Ser Glu Val Ile Pro Thr Val Asn Leu Asn Asn Leu Trp Lys
625                 630                 635                 640
Val Arg Tyr Met Thr Asn Trp Phe Gln Cys Trp Glu Asn Val Arg Lys
            645                 650                 655
Thr Arg Ala Ala Lys
            660
```